United States Patent
Margulies et al.

(10) Patent No.: US 11,639,929 B2
(45) Date of Patent: *May 2, 2023

(54) UNIVERSAL HISTIDINE-TAG BINDING COMPOUNDS AND METHODS OF USE THEREOF AS FLUORESCENT PROBES AND SENSORS

(71) Applicant: YEDA RESEARCH AND DEVELOPMENT CO. LTD., Rehovot (IL)

(72) Inventors: David Margulies, Rehovot, IL (US); Leila Motiei, Rehovot (IL); Naama Lahav, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 433 days.

This patent is subject to a terminal disclaimer.

(21) Appl. No.: 16/783,524

(22) Filed: Feb. 6, 2020

(65) Prior Publication Data

US 2020/0256857 A1    Aug. 13, 2020

Related U.S. Application Data

(63) Continuation-in-part of application No. PCT/IL2019/050639, filed on Jun. 5, 2019, and a
(Continued)

(51) Int. Cl.
*C07D 249/04* (2006.01)
*G01N 33/533* (2006.01)
(Continued)

(52) U.S. Cl.
CPC ......... *G01N 33/533* (2013.01); *C07D 249/04* (2013.01); *G01N 33/582* (2013.01); *G01N 33/6803* (2013.01); *G01N 2570/00* (2013.01)

(58) Field of Classification Search
CPC .... C07D 249/04; C07K 1/13; G01N 33/5005; G01N 33/5008; G01N 33/533; G01N 33/582; G01N 33/6803; G01N 2570/00
See application file for complete search history.

(56) References Cited

U.S. PATENT DOCUMENTS 10,281,459 B2    5/2019 Margulies et al.
10,557,852 B2 *  2/2020 Margulies .......... G01N 33/6803
(Continued)

FOREIGN PATENT DOCUMENTS

WO    WO-0047548 A1 *  8/2000 ........... C07C 217/28
WO    WO 2012/159051 A2    11/2012
WO    WO 2015/166491 A2    11/2015

OTHER PUBLICATIONS

You et al. Multivalent chelators for spatially and temporally controlled protein functionalization. Anal Bioanal Chem 2014, vol. 406, pp. 3345-3357. (Year: 2014).*
(Continued)

*Primary Examiner* — Shafiqul Haq
(74) *Attorney, Agent, or Firm* — Mark S. Cohen; Pearl Cohen Zedek Latzer Baratz LLP

(57) ABSTRACT

This invention is directed to His-tag binding compounds and uses thereof in the preparation of genetically targeted detectable molecules and sensors which can specifically bind tag-labeled proteins. This invention further provides a system comprising recombinant cells decorated with various labels and/or synthetic agents, wherein said labels and/or synthetic agents can be reversibly modified or removed from the cells. Also disclosed herein are methods for decorating and/or modifying the cells and methods for using thereof.

34 Claims, 57 Drawing Sheets

Specification includes a Sequence Listing.

Related U.S. Application Data continuation-in-part of application No. 15/307,011, filed as application No. PCT/IL2015/050441 on Apr. 28, 2015, now Pat. No. 10,557,852.

(60) Provisional application No. 61/985,555, filed on Apr. 29, 2014.

(51) Int. Cl.
*G01N 33/68* (2006.01)
*G01N 33/58* (2006.01)

(56) References Cited

U.S. PATENT DOCUMENTS

| | | |
|---|---|---|
| 2008/0038750 A1 | 2/2008 | Piehler et al. |
| 2011/0091893 A1 | 4/2011 | Heyduk et al. |
| 2014/0038856 A1 | 2/2014 | Gee et al. |
| 2015/0112047 A1* | 4/2015 | Schmidt .............. G01N 33/58 530/395 |

OTHER PUBLICATIONS

Abendroth et al. "DNA-controlled bivalent presentation of ligands for the estrogen receptor" Angewandte Chemie International Edition. Sep. 5, 2011;50(37):8592-6.

Battle et al. "Oligonucleotide-based systems for input-controlled and non-covalently regulated protein binding" Supramolecular chemistry. Dec. 1, 2013;25(12):848-62.

Bausch-Fluck et al. "The in silico human surfaceome" Proceedings of the National Academy of Sciences. Nov. 13, 2018;115(46):E10988-97.

Benincasa et al. "Rapid and reliable detection of antimicrobial peptide penetration into gram-negative bacteria based on fluorescence quenching" Antimicrobial agents and chemotherapy. Aug. 1, 2009;53(8):3501-4.

Berne et al. "Adhesins involved in attachment to abiotic surfaces by Gram-negative bacteria" Microbial Biofilms. Oct. 7, 2015:163-99.

Bi et al. "Enzymatic engineering of live bacterial cell surfaces using butelase 1" Angewandte Chemie International Edition. Jun. 26, 2017;56(27):7822-5.

Bi et al. "Chemical and enzymatic strategies for bacterial and mammalian cell surface engineering" Chemistry—A European Journal. Jun. 7, 2018;24(32):8042-50.

Borisenko et al. "DNA modification of live cell surface" Nucleic acids research. Mar. 1, 2009;37(4):e28-.

Brandman et al. "Feedback loops shape cellular signals in space and time" Science. Oct. 17, 2008;322(5900):390-5.

Cardona et al. "An improved synthesis of a trifurcated newkome-type monomer and orthogonally protected two-generation dendrons" The Journal of organic chemistry. Feb. 22, 2002;67(4):1411.

Chakraborty et al. "Nucleic acid-based nanodevices in biological imaging" Annual Review of Biochemistry. Jun. 2, 2016;85:349-73.

Chen et al. "Synthesis of the Rheb and K-Ras4B GTPases" Angewandte Chemie (International ed. in English). Aug. 16, 2010;49(35):6090.

Chen et al. "Site-specific labeling of cell surface proteins with biophysical probes using biotin ligase" Nature methods. Feb. 2005;2(2):99-104.

Cheng et al. "Metabolic remodeling of cell-surface sialic acids: principles, applications, and recent advances" ChemBioChem. Jan. 1, 2016;17(1):11-27.

Cohen et al. "Probing protein electrostatics with a synthetic fluorescent amino acid" Science (New York, NY). May 31, 2002;296(5573):1700.

Coltharp et al. "Superresolution microscopy for microbiology" Cellular microbiology. Dec. 2012;14(12):1808-18.

Crivici et al. "Molecular and structural basis of target recognition by calmodulin" Annual review of biophysics and biomolecular structure. 1995;24:85.

Dan et al. "DNA nanodevices map enzymatic activity in organelles" Nature nanotechnology. Mar. 2019;14(3):252-9.

Dube et al. "Metabolic oligosaccharide engineering as a tool for glycobiology" Current opinion in chemical biology. Oct. 1, 2003;7(5):616-25.

Dubel et al. "Exploring the limits of bivalency by DNA-based spatial screening" Angewandte Chemie International Edition. Jan. 14, 2019;58(3):907-11.

Dumas et al. "Designing logical codon reassignment—Expanding the chemistry in biology" Chemical science. 2015;6(1):50-69.

Elahipanah et al. "Rewiring gram-negative bacteria cell surfaces with bio-orthogonal chemistry via liposome fusion" Bioconjugate Chemistry. Apr. 20, 2016;27(4):1082-9.

"Fluorophores.org—Database of Fluorescent Dyes, Properties and Applications" download Jul. 9, 2018 from: http://www.fluorophores.org.

Foot et al. "Ubiquitination and the regulation of membrane proteins" Physiological reviews. Jan. 2017;97(1):253-81.

Fujishima et al. "Design of a muitinuclear Zn (II) complex as a new molecular probe for fluorescence imaging of His-tag fused proteins" Chemical communications (Cambridge, England). Jan. 14, 2012;48(4):594.

Fukuda et al. "Aggregation of Alzheimer amyloid beta peptide (1-42) on the multivalent sulfonated suaar interface" Bioconjugate chemistry. Jun. 16, 2010;21(6):1079.

Furst et al. "New techniques for the generation and analysis of tailored microbial systems on surfaces" Biochemistry. May 17, 2018;57(21):3017-26.

Gabrielse et al. "Reversible Re-programing of Cell-Cell Interactions" Angewandte Chemie. May 12, 2014;126(20):5212-6.

Gartner et al. "Programmed assembly of 3-dimensional microtissues with defined cellular connectivity" Proceedings of the National Academy of Sciences. Mar. 24, 2009;106(12):4606-10.

Gautam et al. "Exterior design: strategies for redecorating the bacterial surface with small molecules" Trends in biotechnology. Apr. 1, 2013;31(4):258-67.

Gilbert et al. "Biological engineered living materials: growing functional materials with genetically programmable properties" ACS synthetic biology. Dec. 21, 2018;8(1):1-5.

Goodman et al. "A facile method for reversibly linking a recombinant protein to DNA" ChemBioChem. Jun. 15, 2009;10(9):1551-7.

Govers et al. "High-throughput analysis of the dynamics of recycling cell surface proteins" In Exocytosis and Endocytosis 2008 (pp. 129-146), Humana Press.

Grabchev et al. "A copolymer of 4-N, N-dimethylaminoethylene-N-ally-1, 8-naphthalimide with methylmethacrylate as a selective fluorescent chemosensor in homogeneous systems for metal cations" Journal of Photochemistry and Photobiology A: chemistry. May 30, 2003;158(1):37-43.

Griffin et al. "Specific covalent labeling of recombinant protein molecules inside live cells" Science (New York, NY). Jul. 10, 1998;281(5374):269.

Grunwald et al. "Quantum-yield-optimized fluorophores for site-specific labeling and super-resolution imaging" Journal of the American Chemical Society. Jun. 1, 2011;133(21):8090-3.

Guignet et al. "Reversible site-selective labeling of membrane proteins in live cells" Nature biotechnology. Apr. 2004;22(4):440.

Halo et al. "Selective recognition of protein tetraserine motifs with a cell-permeable, pro-fluorescent bis-boronic acid" Journal of the American Chemical Society. Jan. 21, 2009;131(2):438.

Harris et al. "Protein-binding molecular switches via host-guest stabilized DNA hairpins" Journal of the American Chemical Society. May 25, 2011;133(20):7676-9.

Hauser et al. "A hexahistidine-Zn2+-dye label reveals STIM1 surface exposure" Proceedings of the National Academy of Sciences. Mar. 6, 2007;104(10):3693-7.

Hayashi et al. "Analysis of cell-surface receptor dynamics through covalent labeling by catalyst-tethered antibody" Journal of the American Chemical Society. Apr. 29, 2015;137(16):5372-80.

Hochuli et al. "New metal chelate adsorbent selective for proteins and peptides containing neighbouring histidine residues" Journal of Chromatography A. Jan. 1, 1987;411:177-84.

(56) References Cited

OTHER PUBLICATIONS

Honda et al. "Pyrene excimer-based dual-emission detection of a oligoaspartate tag-fused protein by using a Zn (II)-DpaTyr probe" Chembiochem: a European journal of chemical biology. Aug. 13, 2007;8(12):1370.
Huang et al. "Facile synthesis of multivalent nitrilotriacetic acid (NTA) and NTA conjugates for analytical and drug delivery applications" Bioconjugate chemistry. 2006;17(6):1592.
Huang et al. "Tris-nitrilotriacetic acids of subnanomolar affinity toward hexahistidine tagged molecules" Bioconjugate chemistry. Aug. 3, 2009;20(8):1667-72.
Hurley et al. "Asymmetric regulation of quorum-sensing receptors drives autoinducer-specific gene expression programs in Vibrio cholerae" PLoS genetics. May 26, 2017;13(5):e1006826.
Kamoto et al. "Novel probes showing specific fluorescence enhancement on binding to a hexahistidine tag" Chemistry (Weinheim an der Bergstrasse, Germany). 2008;14(26):8004.
Kim et al. "Supramolecular latching system based on ultrastabie synthetic binding pairs as versatile tools for protein imaging" Nature communications. Apr. 27, 2018;9(1):1-0.
Kubota et al. "Protein recognition using synthetic small-molecular binders toward optical protein sensing in vitro and in live cells" Chemical Society Reviews. 2015;44(13):4454-71.
Lahav-Mankovski et al. "Decorating bacteria with self-assembled synthetic receptors" Nature communications. Mar. 10, 2020;11(1):1-2.
Lang et al. "Cellular incorporation of unnatural amino acids and bioorthogonal labeling of proteins" Chemical reviews. May 14, 2014;114(9):4764-806.
Lata et al. "Specific and stable fluorescence labeling of histidine-tagged proteins for dissecting multi-protein complex formation" Journal of the American Chemical Society. Feb. 22, 2006;128(7):2365-72.
Lata et al. "High-affinity adaptors for switchable recognition of histidine-tagged proteins" Journal of the American Chemical Society. Jul. 27, 2005;127(29):10205.
Lee et al. "Bodipy-diacrylate imaging probes for targeted proteins inside live cells" Chemical communications (Cambridge, England). Apr. 21, 2011;47(15):4508.
Lee et al. "Small-molecule labeling of live cell surfaces for three-dimensional super-resolution microscopy" Journal of the American Chemical Society. Oct. 8, 2014;136(40):14003-6.
Lemmon et al. "Cell signaling by receptor tyrosine kinases" Cell. Jun. 25, 2010;141(7):1117-34.
Link et al. "Presentation and detection of azide functionality in bacterial cell surface proteins" Journal of the American Chemical Society. Sep. 1, 2004;126(34):10598-602.
Mali et al. "Barcoding cells using cell-surface programmable DNA-binding domains" Nature methods. May 2013;10(5):403-6.
Martin et al. "Solvent dependence of the inhibition of intramolecular charge-transfer in N-substituted 1, 8-naphthalimide derivatives as dye lasers" Journal of luminescence. May 1, 1996;68(2-4):157-64.
Melkko et al. "Isolation of high-affinity trypsin inhibitors from a DNA-encoded chemical library" Angewandte Chemie. Jun. 18, 2007;119(25):4755-8.
Moorthy et al. "Perspective: adhesion mediated signal transduction in bacterial pathogens" Pathogens. Mar. 2016;5(1):23.
Motiei et al. "Targeted protein surface sensors as a tool for analyzing small populations of proteins in biological mixtures" Angewandte Chemie. Aug. 25, 2014;126(35):9443-7.
Mukherjee et al. "Design of a DNA-programmed plasminogen activator" Journal of the American Chemical Society. Oct. 22, 2018;140(45):15516-24.
Murata et al. "Construction of a'turn-on' fluorescent probe system for His-tagged proteins" Bioorganic & medicinal chemistry letters. Dec. 1, 2010;20(23):6905.
Nelson et al. "A biosynthetic strategy for re-engineering the *Staphylococcus aureus* cell wall with non-native small molecules" ACS chemical biology. Dec. 17, 2010;5(12):1147-55.

Nissinkorn et al. "Sensing protein surfaces with targeted fluorescent receptors" Chemistry—A European Journal. Nov. 2, 2015;21(45):15981-7.
Nonaka et al. "Selective covalent labeling of tag-fused GPCR proteins on live cell surface with a synthetic probe for their functional analysis" Journal of the American Chemical Society. Jul. 14, 2010;132(27):9301.
Ojida et al. "Oligo-Asp tag/Zn (II) complex probe as a new pair for labeling and fluorescence imaaing of proteins" Journal of the American Chemical Society. Aug. 16, 2006;128(32):10452.
Park et al. "Engineering the surface of therapeutic "living" cells" Chemical reviews. Feb. 28, 2018;118(4):1664-90.
Peng et al. "Engineering a 3D DNA-logic gate nanomachine for bispecific recognition and computing on target cell surfaces" Journal of the American Chemical Society. Jul. 18, 2018;140(31):9793-6.
Pereira et al. "AI-2-mediated signalling in bacteria" FEMS microbiology reviews. Mar. 1, 2013;37(2):156-81.
Peri-Naor et al. "Protein-protein communication and enzyme activation mediated by a synthetic chemical transducer" Journal of the American Chemical Society. Aug. 5, 2015;137(30):9507-10.
Pode et al. "Protein recognition by a pattern-generating fluorescent molecular probe" Nature Nanotechnology. Dec. 2017;12(12):1161-8.
Porchetta A, Ippodrino R, Marini B, Caruso A, Caccuri F, Ricci F. Programmable nucleic acid nanoswitches for the rapid, single-step detection of antibodies in bodily fluids. Journal of the American Chemical Society. Jan. 24, 2018;140(3):947-53.
Qian et al. "Arrays of self-assembled monolayers for studying inhibition of bacterial adhesion" Analytical Chemistry. Apr. 15, 2002;74(8):1805-10.
Rabuka et al. "Noncovalent cell surface engineering: incorporation of bioactive synthetic glycopolymers into cellular membranes" Journal of the American Chemical Society. May 7, 2008;130(18):5947-53.
Ranallo et al. "Antibody-powered nucleic acid release using a DNA-based nanomachine" Nature communications. May 8, 2017;8(1):1-9.
Raulf et al. "Click chemistry facilitates direct labelling and super-resolution imaging of nucleic acids and proteins" RSC advances. 2014;4(57):30462-6.
Reinhardt et al. "Peptide-templated acyl transfer: a chemical method for the labeling of membrane proteins on live cells" Angewandte Chemie International Edition. Sep. 15, 2014;53(38):10237-41.
Riglar et al. "Engineering bacteria for diagnostic and therapeutic applications" Nature Reviews Microbiology. Apr. 2018;16(4):214.
Rosen et al. "Template-directed covalent conjugation of DNA to native antibodies, transferrin and other metal-binding proteins" Nature chemistry. Sep. 2014;6(9):804-9.
Rosenzweig et la. "Multivalent protein binding and precipitation by self-assembling molecules on a DNA pentaplex scaffold" Journal of the American Chemical Society. Apr. 15, 2009;131(14):5020-1.
Rouhanifard et al. "Chemical probing of glycans in cells and organisms" Chemical Society Reviews. 2013;42(10):4284-96.
Saccà et al. "Functionalization of DNA nanostructures with proteins" Chemical Society Reviews. 2011;40(12):5910-21.
Saghatelian et al. "DNA detection and signal amplification via an engineered allosteric enzyme" Journal of the American Chemical Society. Jan. 15, 2003;125(2):344-5.
Saroja et al. "4-Aminophthalimide derivatives as environment-sensitive probes" Journal of Fluorescence. Dec. 1, 1998;8(4):405-10.
Saxon et al. "Cell surface engineering by a modified Staudinger reaction" Science. Mar. 17, 2000;287(5460):2007-10.
Schneider et al. "DNA surface technology: From gene sensors to integrated systems for life and materials sciences" Angewandte Chemie International Edition. Dec. 21, 2018;57(52):16959-67.
Soh et al. "Methodology of reversible protein labeling for ratiometric fluorescent measurement" Molecular bioSystems. Feb. 2006;2(2):128.
Soh N. "Selective Chemical Labeling of Proteins with Small Fluorescent Molecules Based on Metal-Chelation Methodology" Sensors (Basel, Switzerland). Feb. 2008;8(2):1004.

(56) References Cited

OTHER PUBLICATIONS

Spicer et al. "Selective chemical protein modification" Nature communications. Sep. 5, 2014;5(1):1-4.
Spicer et al. "Palladium-mediated cell-surface labeling" Journal of the American Chemical Society. Jan. 18, 2012;134(2):800-3.
Sprengel et al. "Tailored protein encapsulation into a DNA host using geometrically organized supramolecular interactions" Nature communications. Feb. 16, 2017:8(1):1-2.
Szent-Gyorgyi et al. "Fluorogen-activating single-chain antibodies for imaging cell surface proteins" Nature biotechnology. Feb. 2008;26(2):235.
Takaoka et al. "Protein Organic Chemistry and Applications for Labeling and Engineering in Live-Cell Systems" Angewandte Chemie International Edition. Apr. 8, 2013;52(15):4088-106.
Tanaka et al. "Site-specific protein modification on living cells catalyzed by sortase" ChemBioChem. Mar. 25, 2008;9(5):802-7.
Thorley et al. "Super-resolution microscopy: a comparison of commercially available options" In Fluorescence Microscopy Jan. 1, 2014 (pp. 199-212). Academic Press.
Tsukiji et al. "Ligand-directed tosyl chemistry for protein labeling in vivo" Nature chemical biology. May 2009;5(5):341-3.
Vassiliou et al. "Detection of low-affinity adhesion ligands by linking recombinant cell adhesion molecules in uniform orientation to a fluorescently labelled dextran molecule by means of hexahistidine tagging: the case of multimeric CD40" Journal of immunological methods. Jun. 1, 1998;215(1-2):9.
Verbeke et al. "Peptides as quorum sensing molecules: measurement techniques and obtained levels in vitro and in vivo" Frontiers in neuroscience. Apr. 12, 2017;11:183.
Vinkenborg et al. "Aptamer-Based Affinity Labeling of Proteins" Angewandte Chemie International Edition. Sep. 3, 2012;51(36):9176-80.
Wakayama et al. "Chemical labelling for visualizing native AMPA receptors in live neurons" Nature communications. Apr. 7, 2017;8(1):1-4.
Wang et al. "Chemical cell-surface receptor engineering using affinity-guided, multivalent organocatalysts" Journal of the American Chemical Society. Aug. 10, 2011;133(31):12220-8.
Weber et al. "Synthesis and spectral properties of a hydrophobic fluorescent probe: 6-propionyl-2-(dimethylamino) naphthalene" Biochemistry, Jul. 10, 1979;18(14):3075.
Wu et al. "Site-specific chemical modification of recombinant proteins produced in mammalian cells by using the genetically encoded aldehyde tag" Proceedings of the National Academy of Sciences. Mar. 3, 2009;106(9):3000-5.
Xiong et al. "DNA Aptamer-Mediated Cell Targeting" Angewandte Chemie. Jan. 28, 2013;125(5):1512-6.
Xu et al. "Display of Polyhistidine Peptides on the *Escherichia coli* Cell Surface by Using Outer Membrane Protein C as an Anchoring Motif" Applied and Environmental Microbiology. Nov. 1, 1999;65(11):5142-7.
Zhou et al. "Host-guest tethered DNA transducer: ATP fueled release of a protein inhibitor from Cucurbit [7] uril" Journal of the American Chemical Society. Oct. 4, 2017;139(39):13916-21.
Zhou et al. "Reversible regulation of protein binding affinity by a DNA machine" Journal of the American Chemical Society. Jan. 25, 2012;134(3):1416-8.

* cited by examiner

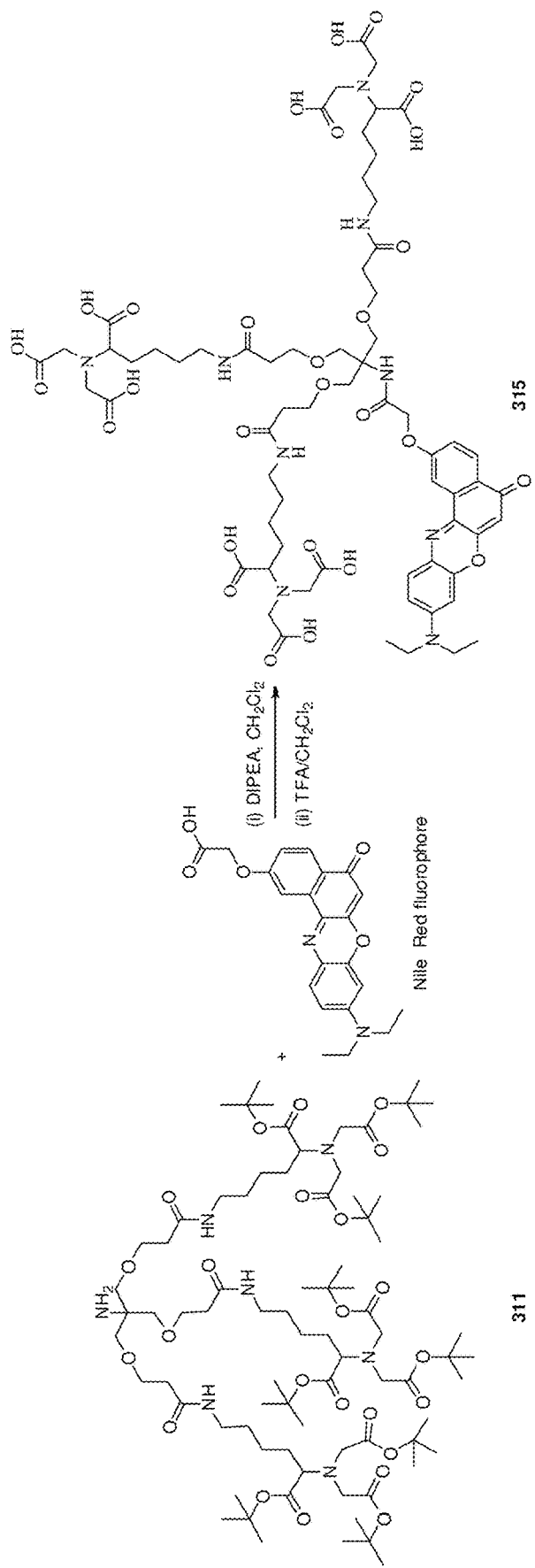
FIGURE 40 - CONTINUE

UNIVERSAL HISTIDINE-TAG BINDING COMPOUNDS AND METHODS OF USE THEREOF AS FLUORESCENT PROBES AND SENSORS

CROSS-REFERENCE TO RELATED APPLICATIONS

This application is a Continuation-in-Part of United-States application Ser. No. 15/307,011, filed Oct. 27, 2016, which is a national stage application, filled under 35 U.S.C § 371, of International Patent Application No. PCT/IL2015/050441, filed Apr. 28, 2015, which claims priority of U.S. Provisional Application Ser. No. 61/985, 555, filed Apr. 29, 2014; and this application is a Continuation-In-Part of International Application Serial No. PCT/IL2019/050639, filed Jun. 5, 2019; each of the above listed documents is hereby incorporated by reference in it's entirety.

SEQUENCE LISTING STATEMENT

The instant application contains a Sequence Listing which has been submitted electronically in ASCII format and is hereby incorporated by reference in its entirety. Said ASCII copy, created on Apr. 23, 2020, is named P-78104-USI-SQL-23APR20_ST25.txt and is 5,587 bytes in size.

FIELD OF THE INVENTION

This invention is directed to His-tag binding compounds and uses thereof in the preparation of genetically targeted detectable molecules and sensors which can specifically bind tag-labeled proteins. This invention further provides a system comprising recombinant cells decorated with various labels and/or synthetic agents, wherein said labels and/or synthetic agents can be reversibly modified or removed from the cells. Also disclosed herein are methods for decorating and/or modifying the cells and methods for using thereof.

BACKGROUND OF THE INVENTION

Fluorescent molecular probes that can label, detect, or image specific proteins serve as a powerful tool for developing in-vitro proteomic assays, for identifying disease biomarkers, as well as for tracking proteins in complex environments.

Fluorescent molecular sensors have become valuable tools in the analytical biosciences owing to their sensitive detection mode, down to the level of a single molecule, the feasibility of naked eye visualization, their versatility, and their small size, which enable them to penetrate the cell membrane and track the rise and fall of various bio-analytes within living cells. Although fluorescent sensors that utilize photo-induced electron transfer (PET), electronic energy transfer (EET) (or fluorescence resonance energy transfer (FRET), and internal charge transfer (ICT) processes have been developed and used to detect various proteins, most of them suffer from a high background signal that complicates their use in complex biochemical mixtures and within cells.

There is a growing interest in developing "genetically targeted fluorescent molecules", namely, small molecule-based fluorescent probes that can bind to short, peptide motifs on the protein of interest and, in doing so, enable the protein's labeling or detection in complex biological environments such as within live cells. Such sensors provide an alternative to using recombinant technology to create a fusion protein comprising the protein of interest with fluorescent proteins (FPs) (e.g., green fluorescent proteins or GFPs) whose large size can interrupt the normal function of many proteins. These genetically targeted probes have already become commercial, for example, the FlAsH— and—ReAsH probes for the selective labeling of tetra-cysteine motifs that are now sold online by Life Technologies.

Genetically encoded fluorescent proteins (FPs) have revolutionized the study of biology by allowing one to track protein expression and localization in living cells at spatial and temporal resolution. This method, however, involves the use of very large protein that can interfere with the normal function of the labeled protein. Over the last few years, it has been demonstrated that this problem can be circumvented by expressing the proteins with a very short peptide sequence to which a small fluorescent molecular sensor, termed "genetically-targeted sensors" can attach. Sensors that can bind to an oligohistidine sequence (i.e. His-tag) with high affinity and can be applied for labeling and detecting a wide range of His-tagged proteins in living cells.

The histidine tag is currently the most widely used tag in protein purification. It is typically composed of six or ten histidine residues fused at the amino or carboxyl terminus of a protein. Recombinant proteins containing a histidine tag are commonly purified on a matrix with nickel(II)-nitrilo-triacetate (Ni-NTA) complexes that are prepared from nickel (II)-activation of nitrilotriacetic acid (NTA). In addition to protein purification, this technology has been used in label-free surface plasmon resonance (SPR) biosensors for bio-molecular interaction analysis that involves histidine-tagged proteins.

Genetic engineering has been used for many years to functionalize the bacterial membrane with heterologous proteins and glycans, which can be used for many applications such as biosensing,[1] biofuel production,[2] and cancer therapeutics.[3] However, this method is limited, since it can be utilized only for genetically encoded molecules. In order to overcome this limitation and incorporate non-genetically encoded small molecules such as fluorescent probes, drugs, and affinity tags, methods for chemical surface display were developed. This research focuses on using "genetically targeted" protein binders for developing a novel method to functionalize the bacterial membrane and utilizing this method for super-resolution imaging and for programing bacterial behavior and response.

A site-specific method for functionalizing the bacterial membrane by using a nitrilotriacetic acid (NTA) derivative that binds outer membrane protein C (OmpC) that was expressed from a clone plasmid in E. coli cells is presented. This approach allows programing a bacterial behavior and response using oligodeoxynucleotide (ODN) small-molecule conjugates. Different modifications on the ODNs such as fluorophores, biotin, and a terminus thiol can each be used to generate bacteria with different properties, for example, bacteria that emit at different colors, bacteria that bind to gold or streptavidin (SA)-coated surfaces, as well as bacteria that interact with specific proteins such as SA. It is also demonstrated how this system could be used to create artificial communication between bacteria and cancer cells, which can open up new possibilities for controlling biological processes.

Another aspect of the invention is the development of a novel, supramolecular approach for creating artificial bacterial receptors. This approach allows decorating the bacterial membrane with different functionalities through high-affinity Ni(II)-NTA interactions. By functionalizing NTA with fluorescent reporters and/or short oligonucleotide (ODN) strands, fluorescent sensors capable of detecting changes on the bacterial membrane were created, as well as systems that can control bacterial behavioral through the addition of complementary ODN inputs. This self-assembly-based approach circumvents the need for different genetic engineering procedures in order to obtain new functions and it also abrogates the need to perform chemical reactions on the bacteria. In addition, by utilizing strand displacement the synthetic receptor can easily be removed, which enables using the same cells over and over again and consequently, changing their properties in a high-throughput manner.

Using these ODN inputs, the ability to fluorescently label the bacteria, modify the membrane with protein binders, and attach the bacteria to solid supports were demonstrated, all in a reversible manner. In addition, this invention demonstrates how the system of the invention can be used to create novel artificial communication between cancer cells and bacteria.

SUMMARY OF THE INVENTION

In some embodiments, this invention is directed to a compound, represented by the structure of formula XI:

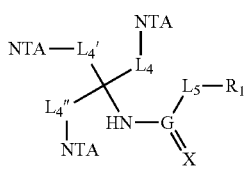

wherein $R_1$ is selected from: H, azide, amine, $C_2$-$C_6$ alkynyl, $C_2$-$C_6$ alkenyl, thioester, disulfide, maleimide, biotin, carboxyl, thiol, triazole, alkylamide, ketone, aldehyde and carbamate;

G=X is absent, or is $CH_2$, C=O, C(O)NH, C=S, C(S)NH, C(O)O, S=O or $SO_2$;

$L_4$, $L_4'$, and $L_4''$ are each independently a substituted or unsubstituted linear or branched alkyl chain of 1-20 carbon atoms, substituted or unsubstituted linear or branched alkyl ether chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl diamide chain of 1-20 carbon atoms, substituted or unsubstituted linear or branched alkyl amine chain of 1-20 carbon atoms or any combination thereof;

$L_5$ is absent, or is a substituted or unsubstituted linear or branched alkyl chain of 1-50 carbon atoms (e.g. ethylene: —$CH_2$—$CH_2$—), substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms or any combination thereof, and NTA is nitrilotriacetic acid or a protected derivative thereof.

In some embodiments, NTA is represented by the structure of fragment (B):

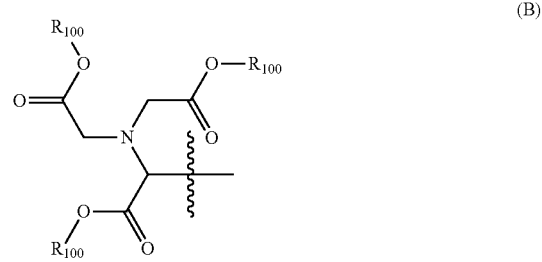

wherein $R_{100}$ is a substituted or unsubstituted linear, branched or cyclic $C_1$-$C_{10}$ alkyl, including: tert-butyl, ethyl, methyl, neo-pentyl, cyclopropyl, and cyclohexyl; benzyl or a substituted or unsubstituted aryl.

In some embodiments, the compound is complexed with at least one metal ion. In some embodiments, the metal ion is Ni(II), Co(II), Co(III) or any combination thereof. In some embodiments, the compound is complexed with three Ni(II) ions.

In some embodiments, the compound is represented by the structure of formula XII:

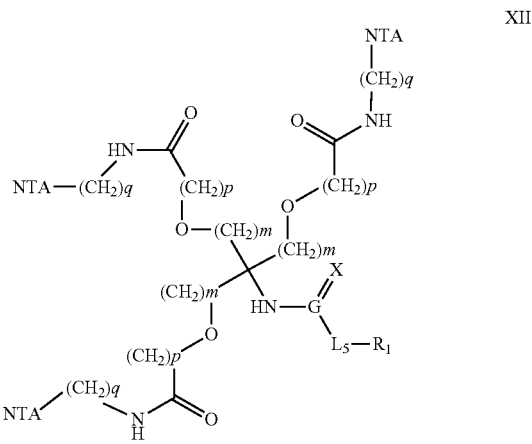

wherein m, p and q are each independently an integer number between 1 and 8. In some embodiments, m is 1, p is 2 and q is 4.

In some embodiments, the compound is represented by the structure of formula XIII:

XIII

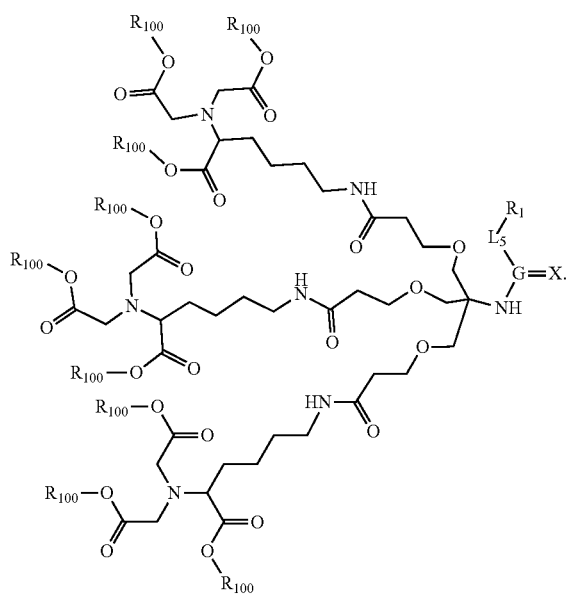

wherein $R_{100}$ is H or a protecting group.

In some embodiments, Rico is H or a substituted or unsubstituted linear, branched or cyclic $C_1$-$C_{10}$ alkyl. In some embodiments. $R_{100}$ is tert-Bu or H; G=X is absent or C=O; $L_5$ is absent or ethylene; $R_1$ is H or maleimide; or any combination thereof. In some embodiments, the compound is represented by the structure of compound 311 or 312 as described hereinbelow. In some embodiments, the compound is represented by the structure of formula XIV as described hereinbelow, wherein n is an integer between 0 and 20. In some embodiments, the compound is represented by the structure of formula XV as described hereinbelow wherein m, p and q are each independently an integer number between 1 and 8. In some embodiments, $R_1$ is H, azide, amine, $C_2$ alkynyl, thioester, biotin or maleimide.

In some embodiments, the compound is further coupled via the $R_1$ moiety to an oligonucleotide, a labeling moiety (e.g fluorescent dye), a peptide, a protein, a small molecule, a solid support, directly or via a first linker. In some embodiments, the first linker comprises a phosphate moiety, a PEG moiety, an alkyl moiety, a thioalkyl moiety or any combination thereof. In some embodiments, the compound is complexed with at least one metal ion selected from: Ni(II), Co(II) and Co(III).

In some embodiments, the oligonucleotide is DNA, RNA or peptide nucleic acid (PNA). In some embodiments, the labeling moiety is a fluorescent dye. In some embodiments, the oligonucleotide is further bound to a labeling moiety, directly or via a third linker. In some embodiments, the third linker comprises a phosphate moiety, a PEG moiety, an alkyl moiety, a thioalkyl moiety or any combination thereof.

In some embodiments, the compound is represented by the structure of formula H:

H

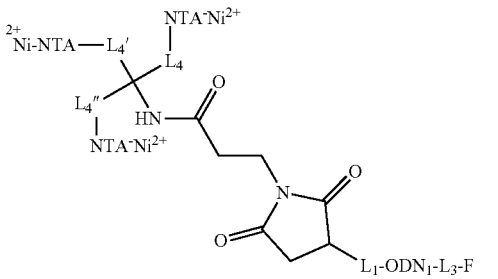

wherein

F is a labeling moiety or absent (e.g., a dye or a dye derivative);

$L_3$ is a third linker or absent;

ODN1 is a first oligonucleotide sequence; and $L_1$ is a first linker or absent.

In some embodiments, F is a fluorescent dye. In some embodiments, F is selected from a group comprising dansyl, fluorescein (6-FAM), FAM, cyanine dyes (e.g. Cy3, Cy5, SCy3, SCy5), sulfoindocyanine, nile red, rhodamine, perylene, fluorenyl, coumarin, 7-methoxycoumarin (Mca), dabcyl, NBD, Nile blue, TAMRA, BODIPY, FITC, Thiazole orange, Quinoline blue, Thiazole red, or derivative thereof; and $L_1$ and $L_3$ each independently comprises a phosphate moiety, a PEG moiety, an alkyl moiety, a thioalkyl moiety or any combination thereof. In some embodiments, the compound is represented by the structure of compounds 100 [CY5-ODN-1], 101 [TAMRA-ODN-1], 102 [ODN-1a], 103 [ODN-1b], or 104 [ODN-1c].

In some embodiments, the compound is coupled via the $R_1$ moiety with a labeling moiety directly. In some embodiments, the compound is represented by the structure of formula XXI:

XXI

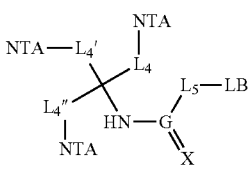

wherein

LB is a labeling moiety; and $L_4$, $L_4'$, and $L_4''$, $L_5$, G=X, and NTA are as defined hereinabove.

In some embodiments, the compound is represented by the structure of formula XXIII:

XXIII

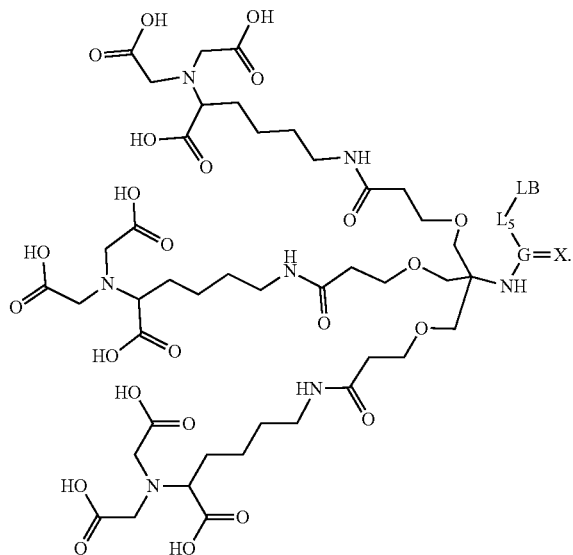

In some embodiments, LB is a fluorescent agent, fluorescent dye, fluorophore, solvatochromic dye, chemiluminescent agent, chromogenic agent, quenching agent, radionucleotide, or a magnetic particle. In some embodiments, the fluorescein dye is selected from: dansyl, fluorescein (6-FAM), FAM, cyanine dyes (e.g. Cy3, Cy5, SCy3, SCy5), sulfoindocyanine, nile red, rhodamine, perylene, fluorenyl, coumarin, 7-methoxycoumarin (Mca), dabcyl, NBD, Nile blue, TAMRA, BODIPY, FITC, Thiazole orange, Quinoline blue, Thiazole red, or a derivative thereof. In some embodiments, the compound is represented by the structure of compounds 313, 314 and 315 as described hereinbelow.

In some embodiments, this invention is directed to a fluorescent probe that can selectively label a His-tagged polypeptide, comprising a compound according to this invention, complexed to at least one metal ion. In some embodiments, the compound is complexed to three Ni(II) ions. In some embodiments, the labeling moiety is a fluorescent dye as described hereinabove. In some embodiments, the compound specifically binds to an oligohistidine sequence (His-tag) of a His-tagged polypeptide to generate a fluorescent signal. In some embodiments, the His-tag sequence consists of at least 6 histidines. In some embodiments, the compound does not perturb living cells function. In some embodiments, the compound is capable of traversing a biological membrane.

In some embodiments, this invention is directed to a method for imaging a His-tagged polypeptide of interest within a cell, said method comprises:

a. expressing said His-tagged polypeptide in a recombinant cell;
b. incubating said recombinant cell with a fluorescent probe according to this invention; and
c. visualizing the fluorescence emission of said fluorescent probe.

In some embodiments, this invention is directed to a method for measuring gene expression of a His-tagged polypeptide of interest in a cell, said method comprises the steps of:

a. expressing a His-tagged polypeptide in a cell;
b. incubating said cell with a fluorescent probe according to this invention; and
c. measuring the fluorescence of said cell;

wherein detection of a fluorescent signal is dependent on the formation of a His-tagged polypeptide:fluorescent probe complex.

In some embodiments, the cell is a living cell. In some embodiments, the fluorescent probe does not perturb living cells function.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 32A shows an embodiment to decorate E. coli with artificial receptors appended with a specific functionality (X). A first molecule X-ODN-1 binds a hexa-histidine tag (His-tag) fused to recombinant OmpC. Recombinant OmpC is inserted into the cell membrane. Reversibility of this process is achieved by subjecting the bacteria to EDTA. A further way to introduce an unnatural recognition motif (Y) to the bacterial surface is adding to the bacteria-bound ODN-1 a complementary strand modified with the desired functionality (Y-ODN-2). Y-ODN-2 can be selectively removed by adding a complementary strand, ODN-3. FIG. 32B shows the structure of X-ODN-1.

FIG. 33A shows fluorescence images of: (i) E. coli expressing His-OmpC incubated with 500 nM of Compound 100 and Ni (II), (ii) Native bacteria (that lack His-tag) incubated with 500 nM of Compound 100 and Ni (II), (iii) E. coli expressing His-OmpC incubated with 500 nM of Compound 100 in the absence of Ni (II), and (iv) E. coli expressing His-OmpC incubated with 500 nM of Cy5-ODN (that lacks the NTA group) and Ni (II). FIG. 33B shows flow cytometry analysis of His-tagged bacteria (yellow) and native bacteria (gray) incubated with Compound 101. FIG. 33C shows fluorescence images of E. coli expressing His-OmpC decorated with Compound 100 in the presence of increasing concentrations of EDTA (0, 5, and 10 mM) (left), and following subsequent addition of Compound 100 in the absence of Ni (II) (right). FIG. 33D shows the growth curve of *E. coli* expressing His-OmpC (black) and of the same bacteria decorated with Compound 101 (red). FIG. 33E shows bright field (top) and fluorescence images (bottom) of bacteria decorated Compound 101 monitored at 0, 12, and 24 hours.

FIG. 34A shows a schematic illustration of the methods used in the experiment. His-tagged bacteria were sequentially modified by attaching them with ectopic molecules. First, cells were attached with—an oligonulcotide comprising TAMRA (TAMRA-ODN-2). Then, this strand was removed by incubating the cells with ODN-3. Then, cells were attached with a compound comprising Cy5 (Cy5-ODN-2). Then Cy5-ODN-2 was detached by incubating the cells with ODN-3. Then, cells were attached with a compound comprising FAM. Then FAM-ODN-2 was detached by incubating the cells with ODN-3. FIG. 34B shows microscopic images of these states by simultaneously observing the emissions of TAMRA, Cy5, and FAM using 590 nm, 700/775 nm, and 510/550 nm emission filters, respectively.

FIG. 35A shows a schematic illustration of the experiment. (i) Different sub-populations of His-tagged cells were incubated with three types of ODN-1: Compound 102, Compound 103, and Compound 104. (ii) cells were incubated with three types of ODN-2: Compound 202, Compound 203, and Compound 204, complementary to Compound 102, Compound 103, and Compound 104, respectively. Compound 202, Compound 203, and Compound 204 were appended with FAM, TAMRA, and Cy5, respectively. FIG. 35B shows a fluorescence overlay image of the labeled mixed population. Bacteria were imaged using 488 nm, 561 nm, and 647 nm excitation lasers and 488/50, 610/60, and 685/50 emission filters. FIG. 35C shows percentages of each sub-population counted and averaged from six different frames. FIG. 35D shows a flow cytometry analysis of the mixed population.

FIG. 36A shows a schematic illustration of an experiment in which modified His-tagged bacteria were treated with Alexa 647-modified streptavidin (Alexa-SA). Left: Bacteria were modified with a duplex generated from ODN-1 and Compound 205. Right: Bacteria were modified with a duplex lacking biotin. FIG. 36B shows Alexa-SA fluorescence in the cells incubated with Alexa 647-modified streptavidin. FIG. 36C shows images recorded following the incubation of the bacteria bound to Alexa-SA with ODN-3. FIG. 36D shows a schematic illustration of an experiment in which decorated bacteria were incubated with KB-cells. Left: Bacteria decorated with a duplex consisting of ODN-1 and TAMRA-labeled Compound 206. Right: Bacteria decorated with a duplex that lacks the folate group. FIG. 36E shows TAMRA-labeling of KB cells incubated with bacteria decorated with folate. FIG. 36F shows fluorescent images obtained after treating the bacteria that are bound to KB cells with ODN-3. FIG. 36G shows that incubating a KB-cell with a duplex consisting of ODN-1 and TAMRA-folate-ODN-2 (Compound 206), in the absence of bacteria, did not lead to fluorescent KB-cell labeling.

FIG. 37A shows microscopic images of: (i) bear gold substrate after incubation with unmodified bacteria, (ii) passivated gold substrate after incubation with unmodified bacteria, and (iii) passivated gold substrate following incubation with bacteria modified with a thiol-modified duplex (ODN-1:Compound 207). FIG. 37B shows the average bacteria count on passivated gold surfaces, which corresponds to an image area of ~0.0165 $mm^2$.

FIG. 38A shows whole bacteria. FIG. 38B shows a transverse cut viewed from the plane of the cell axis.

Figure 1:
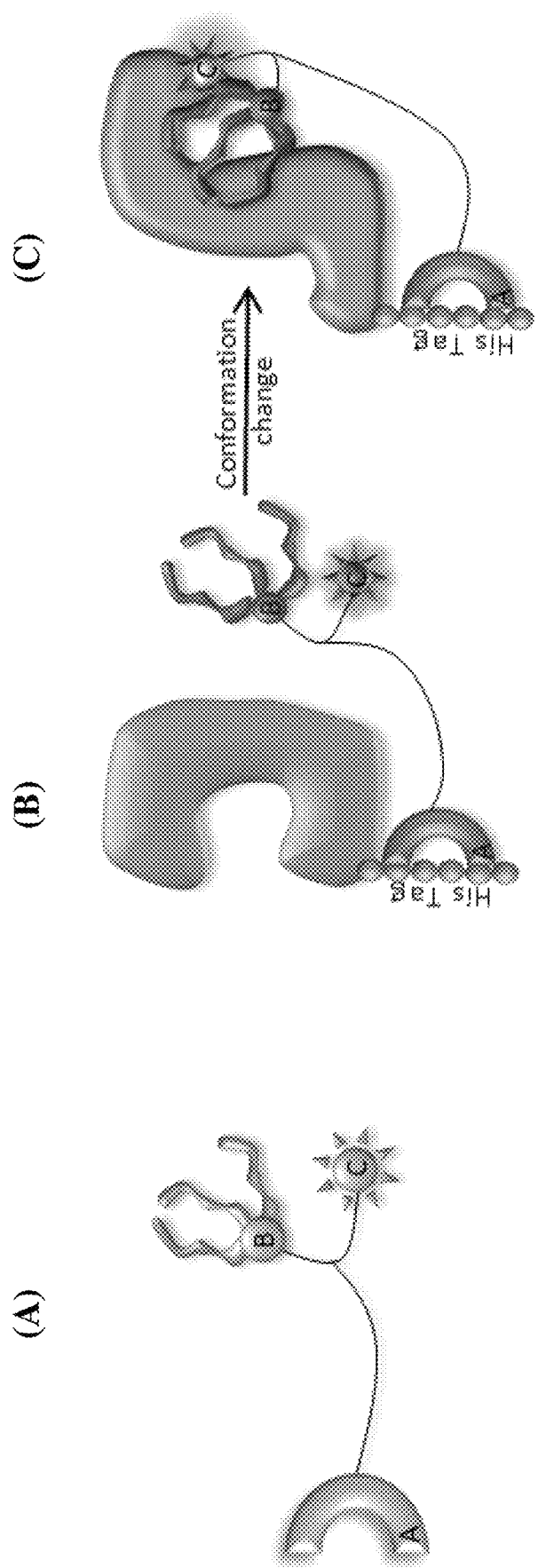
FIG. 1 depicts the design principles of sensors for detecting 3D changes on a protein surface according to this invention. (a): The sensor contains three components: A: A genetically targeted molecule. B: A non-selective protein surface binder. C: A solvatochromic fluorophore. (b) and (c): Preferential binding of the surface receptor (B) to the protein in one of its conformational states (c) induces a change in the fluorescence signal.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The patent of application file contains at least one drawing executed in color. Copies of this patent or patent application publication with color drawings will be provided by the office upon request and payment of the necessary fee.

A. Florescent Molecular Sensor for Targeting Changes in Protein Surfaces

The design of targeted protein surface sensors is based on an approach for enhancing the potency of synthetic protein surface receptors. Specifically, it has been previously shown that when attached to selective protein binders, these receptors exhibit much higher affinity and selectivity toward the surfaces of their protein targets. In this study, this approach is taken a step further and it is demonstrated how it can be used to create compounds, which are fluorescent molecular sensors that respond to dynamic changes that occur on the surfaces of His-tag-labeled proteins. It is further described how combination of flexible linker with a modifiable synthetic receptor enables the design of various compounds that target different regions on the surface of various proteins, and can be used as sensors for tracking protein surface changes.

In one embodiment, this invention is directed to a compound that responds to changes that occur on the surface of a specific protein. In another embodiment, the compound is monomolecular. In another embodiment, the monomolecular compound is a sensor. In another embodiment, the sensor is appended with distinct protein recognition motifs: selective and non-selective. In another embodiment, the compound does not comprise oligonucleotides. In another embodiment, the sensor is a fluorescent sensor that can track changes that occur on the surfaces of a specific protein. In another embodiment the protein is not a homodimer. In another embodiment the protein is labeled with a polypeptide tag. In another embodiment the protein is labeled with a polyhistidine tag (His-tag).

In one embodiment, a "polyhistidine tag" (His-tag) according to this invention comprises at least 2, at least 3, at least 4, at least 5, at least 6, at least 7, at least 8, at least 9, at least 10 histidine residues. In one embodiment, a protein of interest (POI) comprises a polyhistidine tag of this invention, at its N-terminus. In another embodiment, a protein of interest (POI) comprises a polyhistidine tag of this invention, at its C-terminus. In another embodiment, a protein of interest (POI) comprises a polyhistidine tag of this invention, at an internal location of the contiguous amino acid sequence. In another embodiment, the His-tag comprises hexa-histidine peptide (6×His-tag). In another embodiment, the His-tag comprises deca-histidine peptide (10×His-tag).

In another embodiment, this invention is directed to a compound that responds to dynamic changes that occur on the surface of His-tag-labeled proteins. In another embodiment, the protein is any protein known in the art that may be tagged. In another embodiment the protein is calmodulin (CaM), (CaM($Ca^{+2}$)), G protein, or B-cell lymphoma 2 protein (Bcl-2).

The structure of these sensors, which were designed to detect modifications in the surface of proteins, consists of three main components: a genetically targeted section. (a selective binder; e.g., a Tag-binding region) (I), a protein surface receptor (non-selective binder) (II), and a solvatochromic dye (fluorophore) (III). The operating principles of the sensors according to this invention are schematically illustrated in FIG. 1. The genetically targeted section (A) ensures that the sensor will selectively bind a specifically labeled protein (e.g., His-tag labeled protein), regardless of its conformational state. A change in the protein's conformation alters its surface configuration and induces the binding of the protein surface receptor (B). Changes in local environment of the solvatochromic fluorophore (C) lead to the generation of a distinct emission signal. Importantly, through an appropriate choice of protein surface receptors, this approach can be used to track various changes on the surfaces of proteins including a wide range of post-translational modifications (PTMs).

In one embodiment, this invention is directed to a compound that can track changes that occur on the surfaces of a specific protein, said compound comprises:
 a. a selective binder;
 b. a non-selective binder; and
 c. a fluorophore.
In another embodiment, the compound is a monomolecular compound. In another embodiment, the monomolecular compound is a sensor for detecting 3D changes on a protein surface. In another embodiment, the selective binder is a Tag-binding region.

A "Tag binding region" refers to any compound, molecular group, or molecular moiety that can specifically bind with high affinity to a specified peptide motif (i.e., a specific peptide sequence genetically grafted onto a recombinant protein). Non limiting examples for tag binding regions are: FlAsH (for TC tag), ReAsH (for TC tag), Ni-nitrilotriacetic acid (Ni-NTA), bis Ni-NTA, tris-Ni-NTA (for His-tag), etc.

It was decided to first target the most common affinity tag (His-tag) in order to demonstrate the generality of the approach. However, other molecules of this class that can target different types of fusion peptides could also be used as selective binders.

This approach thus circumvents the challenge of selectively recognizing protein surfaces with synthetic agents by bringing a relatively weak and non-selective protein surface receptor (non-selective binder) in the vicinity of the protein of interest (POI). In this way, an intermolecular synthetic receptor-protein interaction becomes intramolecular, which increases the effective molarity of the system and therefore, the receptor's affinity and specificity. This key principle distinguishes such sensors from other probes that can track protein (e.g. CaM) conformational changes or binding interactions, by labeling the protein (e.g. CaM) at specific positions that are sensitive to altered distances between its termini, or by labeling its binding partners, respectively. Here, the combination of a flexible linker with a modifiable synthetic receptor should enable one to design sensor compounds that match different regions on the surfaces of various proteins.

A unique property of the sensors of this invention is that they bind their targets using a dual interaction mode: selective and non-selective. This combination circumvents the need to design a highly specific receptor for the protein's surface or to use natural binding partners (e.g., antibodies, proteins, and peptides) that selectively bind the desired modification. In addition, using this approach the protein does not have to be fluorescently labeled at particular positions, or undergo a significant conformational change.

In one embodiment, this invention is directed to a sensor that can track changes that occur on the surfaces of a specific protein, said sensor comprises:
 a. a selective binder,
 b. a non-selective binder; and
 c. a fluorophore.

The "selective binder" is any compound or derivative that can binds particular protein or protein groups with high affinity and selectivity. In another embodiment, the selective binder is a synthetic inhibitor, a natural ligand or an aptamer that is selective toward a specific protein group, but also broad spectrum which binds particular protein groups with high affinity and selectivity. In another embodiment, the selective protein binder of this invention is any selective protein binder known in the art. In another embodiment, a selective binder is any molecule that can target different type of fusion proteins that contain certain protein tags such as: a polyhistidine tag, (e.g., 6×His-tag, 10×His-tag), tetra cysteine peptide (CCPGCC, TC tag), etc. A "protein tag" refers herein to a peptide sequence genetically grafted onto a recombinant protein. Protein tags include but not limited to: a His-tag, FLAG tag, HA tag, C-myc tag, AviTag, Calmodulin-tag, polyglutamate tag, E-tag, Myc-tag, S-tag, SBP-tag, Softag, Strep-tag, TC tag, V5 tag, VSV-tag, Xpress tag, etc. In one embodiment, the selective binder comprises a "Tag-binding region". In another embodiment, the selective binder is a targeted protein receptor comprising a protein tag binder. In one embodiment, the selective binder comprises a His-tag binder. In another embodiment, the selective binder of this invention comprises Ni-nitrilotriacetic acid (Ni-NTA), bis-Ni-NTA, or tris-Ni-NTA. In another embodiment, the selective binder of this invention comprises a derivative of Ni-nitrilotriacetic acid (Ni-NTA), bis-Ni-NTA, or tris-Ni-NTA, wherein the term "derivative" includes but not limited to alkyl derivatives, amide derivatives, carboxy derivatives, and the like.

A "non-selective binder" which can also be referred to herein as a "protein surface receptor", is a functionalized amino acid sequence or peptide groups that react non-selectively, with complementary protein surfaces based on their size, topology and electrostatic potential. By systematically modifying the non-selective binder's sequence and length one can obtain a library of protein surface binders with distinct physicochemical properties. In one embodiment, the non-selective protein surface binder is a relatively weak binder that varies among the different receptors. In another embodiment, the non-selective binder contains a tripodal peptide group with a large surface area of 750-1500 $Å^2$, typical for synthetic protein surface receptors and protein-protein interaction. Each non-selective binder (e.g. tripodal peptide) is expected to interact differently with the surfaces of distinct proteins of interest (POI). In another embodiment, the non-selective protein surface binder is a peptide. In another embodiment, the non-selective protein surface binder comprises at least one peptide. In another embodiment, the non-selective protein surface binder comprises three peptides. In another embodiment, the non-selective protein surface binder is a tripodal peptides having a surface of 750-1500 $Å^2$. In one embodiment, the non-selective binder comprises at least one hydrophobic peptide (e.g. SEQ ID No. 22). In another embodiment, the non-selective binder comprises at least one negatively charged peptide (e.g., SEQ ID No. 23). In another embodiment, the non-selective binder comprises at least one polar peptide (e.g., SEQ ID No. 24). In another embodiment, the non-selective binder comprises at least one positively charged peptide (e.g., SEQ ID No. 25). In another embodiment, the non-selective binder comprises at least one peptide consisting of positively charged and hydrophobic amino acids (e.g., SEQ ID No. 26). In another embodiment, the non-selective binder comprises at least one peptide consisting of negatively charged and hydrophobic amino acids. In another embodiment, the non-selective binder comprises at least one peptide consisting of polar and hydrophobic amino acids. In another embodiment, the non-selective binder comprises at least one peptide consisting of negatively charged and polar amino acids. In another embodiment, the non-selective binder comprises at least one peptide consisting of positively charged and polar amino acids. In another embodiment, the non-selective binder comprises at least one peptide as listed in FIG. 14 and Table 1.

In some embodiments, the "fluorophore" of this invention comprises a solvatochromic dye. In one embodiment, the solvatochromic dye comprises dansyl, fluorescein (6-FAM), FAM, cyanine dyes (e.g. Cy3, Cy5), sulfoindocyanine, nile red, rhodamine, perylene, fluorenyl, coumarin, 7-methoxy-coumarin (Mca), dabcyl, NBD, Nile blue, Tamra, BODIPY, FITC, Thiazole orange, Quinoline blue, Thiazole red, or derivative thereof. In some embodiments, the solvatochromic dye of this invention is dansyl.

In another embodiment, the sensor further comprises a linker which covalently links between the selective binder and the non-selective binder. In another embodiment, the linker is further covalently attached to the fluorophore. In another embodiment, the fluorophore is attached to the linker in the vicinity of the non-selective binder.

In another embodiment, the linker is hydrophilic linker. In another embodiment, the linker is flexible linker. In another embodiment, the linker is flexible hydrophilic linker. In another embodiment, the linker is a polyethylene glycol (PEG) derivative. In another embodiment, the linker comprises a polyethylene glycol (PEG) moiety. In another embodiment, the linker is a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof.

In one embodiment, this invention is directed to a compound that can track changes that occur on the surfaces of a specific protein, said compound comprises:
  a. a selective binder;
  b. a non-selective binder;
  c. a fluorophore; and
  d. a linker which covalently links between the selective binder and the non-selective binder.

In another embodiment, the compound is a monomolecular compound. In another embodiment, the monomolecular compound is a sensor for detecting 3D changes on a protein surface. In another embodiment, the selective binder is a Tag-binding region.

In one embodiment, this invention is directed to a compound for tracking changes that occur on the surface of a tagged proteins. In another embodiment, the compound comprises a Tag-binding region.

A "tagged-protein" refers to a recombinant protein onto which the specified peptide motif is grafted. Non limiting examples for protein Tags are: His-tag, FLAG tag, HA tag, C-myc tag, AviTag, Calmodulin-tag, polyglutamate tag, E-tag, Myc-tag, S-tag, SBP-tag, Softag, Strep-tag, TC tag, V5 tag, VSV-tag, Xpress tag, etc.

In another embodiment, this invention is directed to a compound that can track changes that occur on the surface of a tagged-protein, said compound comprises:
  a. a selective Tag-binding region;
  b. a non-selective binder, and
  c. a fluorophore.

In another embodiment, the compound is a monomolecular compound. In another embodiment, the monomolecular compound is a sensor for detecting 3D changes on a tagged-protein surface. In another embodiment, the tagged-protein is a His-tagged protein. In another embodiment, the Tag-binding region comprises Ni-nitrilotriacetic acid (Ni-NTA) groups (i.e., mono-Ni-NTA, bis-Ni-NTA, or tris-Ni-NTA). In another embodiment, the Tag-binding region comprises three Ni-NTA groups (tris-Ni-NTA).

Figure 2:
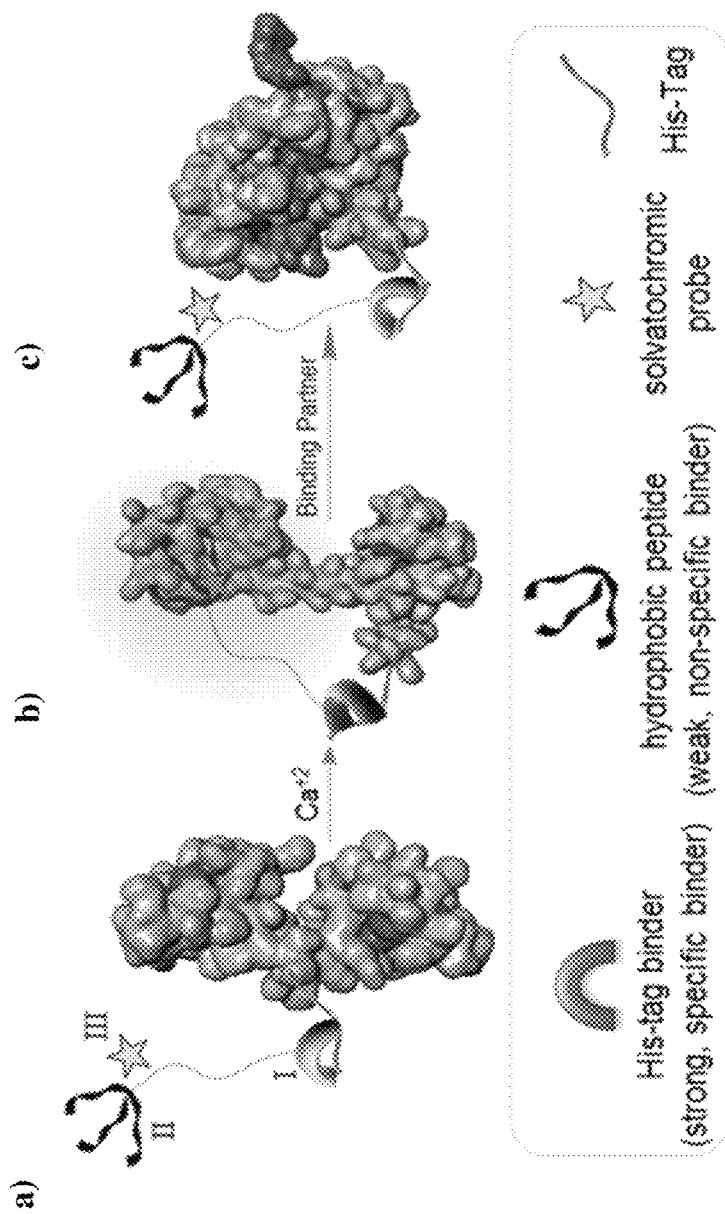
FIG. 2 depicts the operating principles of a targeted protein surface sensor consisting of a His-tag binder (I), a protein surface receptor (II), and a solvatochromic probe (III). The binding of calcium ions to His-CaM (a) promotes the exposure of a hydrophobic cleft on the surface of His-CaM($Ca^{+2}$) and a consequent interaction with the sensor's hydrophobic receptor (b). Changes in the molecular environment of the solvatochromic probe result in enhanced emission. A binding partner, such as the M13 peptide, can also be sensed by the system owing to the formation of a His-CaM($Ca^{+2}$)-M13 complex (c), which triggers the release of the protein-bound receptor.

There are two main limitations of existing genetically targeted molecules and sensors. The first limitation is the lack of a simple and easily applicable method for targeting His-tags, which are most prevalent genetically fused peptide motifs. The second limitation is the inability of such sensors to track changes that occur on the surfaces of proteins. These limitations are circumvented by the development of (1) a universal building block for preparing various His-tag-binders and sensors as described herein below. In the following step (2) the His-tag binder is attached to a protein surface receptor, and the resulting sensor (FIG. 1) can track changes that occur on the surfaces of proteins, e.g. the exposure of a hydrophobic cleft resulting from the binding of calmodulin (CaM) to calcium ions (FIG. 2). This is the first method that enables tracking changes on the surfaces of specific proteins using fluorescent molecular sensors and hence, this invention could lead to the realization of various other sensors that can track important post-translational modifications.

In one embodiment, this invention is directed to a compound for tracking changes that occur on the surface of a His-tag labeled protein.

In another embodiment, this invention is directed to a compound that can track changes that occur on the surfaces of a His-tagged protein, said compound comprises:
 a. a His-tag binder;
 b. a non-selective binder and
 c. a fluorophore.

In another embodiment, the compound is a monomolecular compound. In another embodiment, the monomolecular compound is a sensor for detecting 3D changes on a His-tag labeled protein surface.

The first component of the sensor (1), is a His-tag binder. The His-tag binder is a synthetic agent that can selectively bind to a polyhistidine tag fused to the POI (e.g., 6×His-tag, 10×His-tag). The role of this binder is to ensure that the sensor will bind to the His-tagged POI with high affinity and selectivity (FIG. 2, state a). The second component of the sensor (II) is a branched peptide receptor, whose sequence and length can be adjusted to obtain preferential affinity toward a specific domain on the protein's surface. In the exemplary case of His-tagged Calmodulin (His-CaM), this receptor should consist of a hydrophobic peptide that matches the exposed hydrophobic region on His-CaM(Ca$^+$$_2$).

The third part of the sensor (III) is an environmentally sensitive fluorophore introduced in the vicinity of the receptor, which should enable the system to fluoresce when the receptor binds the solvent-exposed hydrophobic patch (FIG. 2, State b). This fluorescence should be eliminated in the presence of a binding partner, which interacts with this region and displaces the protein-surface receptor (FIG. 2, state c).

Considering that a polyhistidine peptide (His-tag) is the most common affinity tag and that high-throughput methodologies for sensing protein modifications and binding interactions are needed, it is believed that by choosing appropriate recognition elements and by systematically modifying the receptors' structures, various protein surfaces could be detected by using the technology of this invention. Accordingly, the approach presented here is general, and by systematically screening various peptide sequences, one can, in principle, identify a wide range of protein surface binders and use them to track diverse protein structural modifications such as post-translational modifications (PTMs).

By selecting, in one embodiment, His-tagged CaM as a protein target, it is herein demonstrated how this approach could be used to track protein surface modifications that result from structural changes or binding interactions. In addition, it is shown in another embodiment, how such sensors could be further applied to detect dephosphorylating of an unlabeled calmodulin-dependent protein kinase II (CaMKII), as well as, in another embodiment, sense the interaction between the His-tagged B cell 2 lymphoma protein and its natural binder—Bax (His-Bcl-2-Bax).

a. Non-Selective protein surface binder ("non-selective binder") of sensors of the invention.

In one embodiment, this invention is directed to a sensor that can track changes that occur on the surface of a protein, said sensor comprises a selective binder, a non-selective binder and a fluorophore.

In one embodiment, the non-selective binder is a relatively weak binder that varies among the different receptors. In one embodiment, the non-selective protein surface binder is a branched peptide receptor, whose sequence and length can be adjusted to obtain preferential affinity towards a specific domain on the protein of interest (POI)'s surface. In another embodiment, the non-selective binder contains a tripodal peptide group with a large surface area of 750-1500 Å$^2$, typical for synthetic protein surface receptors and protein-protein interaction. Each non-selective binder (e.g. tripodal peptide) is expected to interact differently with the surfaces of distinct proteins of interest (POI).

In one embodiment, the non-selective binder, of the sensor according to this invention, comprises a peptide tripod, represented by the structure of formula A:

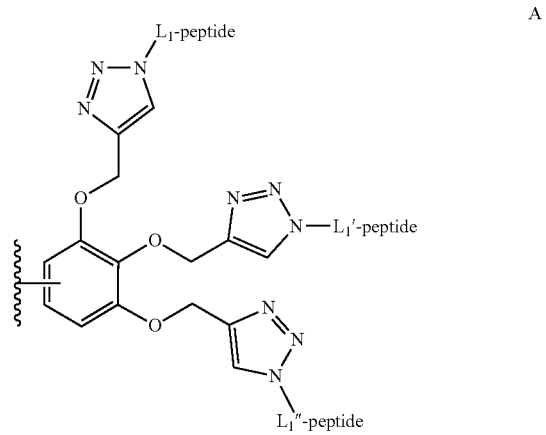

wherein each of $L_1$, $L_1'$ and $L_1''$ is independently a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof; and wherein the peptide comprises any 2-20 amino acid peptide (hydrophobic, polar, charged or combination thereof).

In one embodiment, the non-selective protein surface binder of the sensor according to this invention comprises a peptide tripod, represented by the structure of formula B:

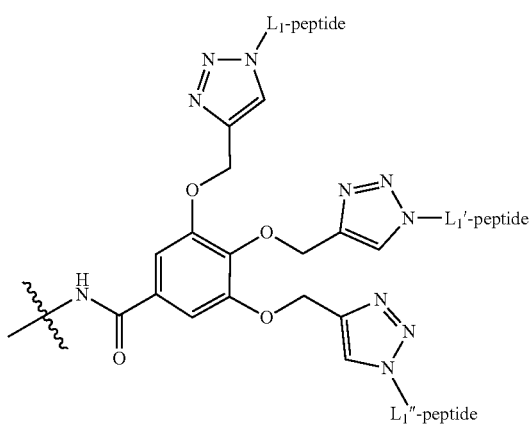

B wherein $L_1$, $L_1'$ and $L_1''$ and "peptide" are as defined above.

In some embodiments the non-selective protein surface binder of the sensor according to this invention comprises a tripod molecule represented the structure of formula C:

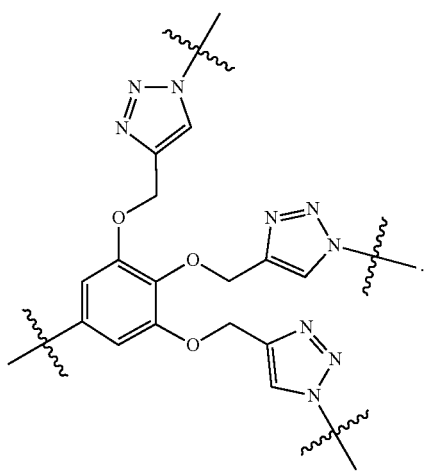

C

In another embodiment, each of $L_1$, $L_1'$ and $L_1''$ of formula (A) and/or (B) is independently a linear alkyl chain of 2-10 carbon atoms. In another embodiment, each of $L_1$, $L_1'$ and $L_1''$ is n-propyl.

In another embodiment, the peptides comprised in the non-selective binder and in formula (A) and/or (B) possess between 2 to 30 amino acid sequences. In another embodiment, the peptides possess between 4 to 15 amino acid sequences. In another embodiment, the peptides possess between 2 to 20 amino acid sequences. In another embodiment, the peptides possess between 3 to 10 amino acid sequences. In another embodiment, the peptide comprises between 3 to 8 amino acids. In another embodiment, the peptides are the same. In another embodiment, the peptides are different. In another embodiment, the peptides comprise hydrophobic amino acids. In another embodiment, the peptide is SEQ ID No. 22. In another embodiment, the peptides comprise polar amino acids. In another embodiment, the peptide is SEQ ID No. 24. In another embodiment, the peptides comprise negatively charged amino acids. In another embodiment, the peptide is SEQ ID No. 23. In another embodiment, the peptides comprise positively charged amino acids. In another embodiment, the peptide is SEQ ID No. 25. In another embodiment, the peptides comprise combination of hydrophobic and negatively charged amino acids. In another embodiment, the peptides comprise combination of hydrophobic and positively charged amino acids. In another embodiment, the peptide is SEQ ID No. 26. In another embodiment, the peptides comprise combination of hydrophobic and polar amino acids. In another embodiment, the peptides comprise combination of polar and negatively charged amino acids. In another embodiment, the peptides comprise combination of polar and positively charged amino acids. In another embodiment the peptides are as described in Table 1, 1A and FIG. 14.

In another embodiment the peptide includes amino acid sequence interrupted by a solvatochromic dye. In another embodiment the peptide includes amino acid sequence, wherein one of the amino acids is substituted with a solvatochromic dye. In another embodiment, the solvatochromic dye is covalently bonded to a lysine residue (K). In another embodiment, the solvatochromic dye is covalently bonded to the backbone of the peptide tripod of formula (A) and/or (B). In another embodiment, the solvatochromic dye is covalently bonded to the linker, which covalently links between the selective, and the non-selective binders. In another embodiment, the solvatochromic dye is covalently bonded to the linker, in the vicinity of the non-selective binder.

According to this invention, the phrase "in the vicinity of the non-selective binder" refers to a distance between the dye and the non-selective binder that is shorter than the distance between the dye and the selective binder. In one embodiment, the distance between the dye and the non-selective binder is less than 15 Å; or in another embodiment, less than 10 Å; or in another embodiment, less than 5 Å; wherein the distance is calculated between the dye atom that is attached to the linker and the non-selective binder aryl ring.

b. Selective Protein Binder of Sensors of the Invention.

In one embodiment, this invention is directed to a sensor that can track changes that occur on the surface of proteins, said sensor comprises a selective binder, a non-selective binder and a fluorophore.

A selective protein binder is referred in this invention to an aptamer, a natural ligand, a synthetic group, or a peptide which binds a specific protein with high affinity and selectivity.

In some embodiments the sensor of this invention comprises at least one selective protein binder. In another embodiment, the selective protein binder of this invention is any selective protein binder known in the art.

In another embodiment, the selective protein binder is marimastat, ethacrynic acid, bisethacrynic acid, complexed nitrilotriacetic acid (NTA), complexed bis NTA, complexed tris-NTA, Ni-nitrilotriacetic acid (Ni-NTA), bis Ni-NTA, tris-Ni-NTA, PDGF-BB, heparin, FGF aptamer, estrogen, DNA aptamer, RNA aptamer, peptide aldehyde, estrogen, suberoylanilidehydroxamic acid (SAHA), or a peptide binder. In another embodiment, the complexed NTA, complexed bis-NTA, complexed tris NTA is a nickel or cobalt complex.

In another embodiment, a selective binder comprises a Tag-binding region.

In another embodiment, a selective binder is any molecule that can target different type of affinity tags, such as polyhistidine tag (HHHHHH, His-tag), or tetra cysteine peptide (CCPGCC, TC tag). In another embodiment, the selective binder is FlAsH probe. In another embodiment, the selective binder is ReAsH probe.

A "polyhistidine-tag" commonly known as "His-tag" is an amino acid motif in proteins that typically consists of at least six histidine residues, often at the N- or C-terminus of the protein. It is also known as hexa histidine-tag, 6×His-tag, His6 tag, by the US trademarked name HIS TAG, and most commonly as His-Tag.

In one embodiment, the selective binder is a His-tag binder. In another embodiment, the selective protein binder of this invention comprises Ni-nitrilotriacetic acid (Ni-NTA), bis-Ni-NTA, or tris-Ni-NTA. In another embodiment, the selective protein binder of this invention comprises a derivative of Ni-nitrilotriacetic acid (Ni-NTA), bis-Ni-NTA, or tris-Ni-NTA, wherein the term "derivative" includes but not limited to alkyl derivatives, amide derivatives, amine derivatives, carboxy derivatives, and the like. In another embodiment, the His-Tag binder comprises a derivative of tris-Ni-nitrilotriacetic acid (tris-Ni-NTA). In another embodiment, a derivative of bis-Ni-nitrilotriacetic acid (bis-Ni-NTA). In another embodiment, a derivative of mono-Ni-nitrilotriacetic acid (Ni-NTA). In another embodiment, the His-tag binder is any monomolecular compound which comprises three Ni-NTA moieties (i.e., tris-Ni-NTA).

In one embodiment, the His-tag binder comprised in the sensor of the invention is represented by the structure of formula D:

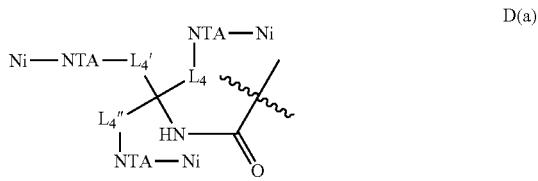

D wherein each of $L_4$, $L_4'$, and $L_4''$ is independently a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof; and M is a metal ion.

In one embodiment, M is cobalt (Co). In another embodiment, M is nickel (Ni). In another embodiment, M is Ni(II). In another embodiment, M is Co(II). In another embodiment, M is Co(III). In another embodiment, each of $L_4$, $L_4'$, and $L_4''$ is independently a combination of alkyl ether and alkyl amide (i.e., alkylether-alkylamide). In another embodiment, each of $L_4$, $L_4'$, and $L_4''$ is independently —$(CH_2)_n$—NHCO—$(CH_2)_m$—O—$(CH_2)_l$—, wherein n, m and l are each independently an integer between 1 and 6. In another embodiment, n is 4, m is 2 and l is 1. In another embodiment, each of $L_4$, $L_4'$, and $L_4''$ is —$(CH_2)_4$—NHCO—$(CH_2)_2$—O—$CH_2$—. In another embodiment, each of $L_4$, $L_4'$, and $L_4''$ is represented by the following structure:

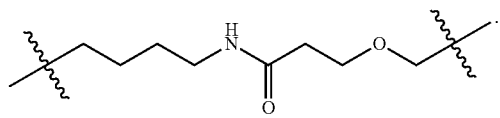 [SMILES: *CCCCNC(=O)CCOC*]

In another embodiment, the His-tag binder comprised in the sensor of the invention is represented by the structure of formula D(a):

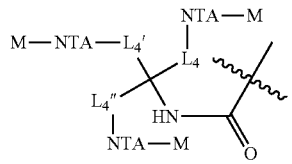

D(a)

wherein each of $L_4$, $L_4'$, and $L_4''$ is independently a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof.

In another embodiment, each of $L_4$, $L_4'$, and $L_4''$ is independently is a combination of alkyl ether and alkyl amide (i.e., alkylether-alkylamide). In another embodiment, each of $L_4$, $L_4'$, and $L_4''$ is independently —$(CH_2)_n$—NHCO—$(CH_2)_m$—O—$(CH_2)_l$—, wherein n, m and l are each independently an integer between 1 and 6. In another embodiment, n is 4, m is 2 and l is 1. In another embodiment, each of $L_4$, $L_4'$, and $L_4''$ is —$(CH_2)_4$—NHCO—$(CH_2)_2$—O—$CH_2$—. In another embodiment, each of $L_4$, $L_4'$, and $L_4''$ is represented by the following structure:

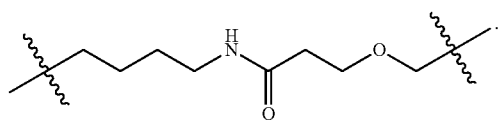 [SMILES: *CCCCNC(=O)CCOC*]

In another embodiment, the His-tag binder comprised in the sensor of the invention is represented by the structure of formula E:

E

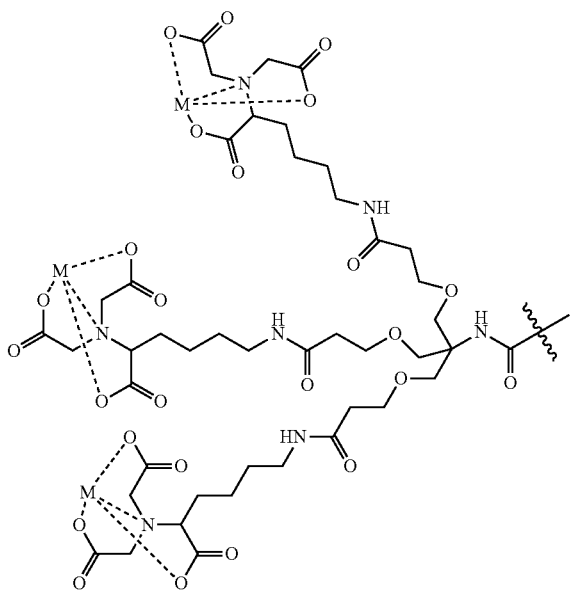

wherein M is a metal ion.

In one embodiment, M is cobalt (Co). In another embodiment, M is nickel (Ni). In another embodiment, M is Ni(II). In another embodiment, M is Co(II). In another embodiment, M is Co(III).

In another embodiment, the His-tag binder comprised in the sensor of the invention is represented by the structure of formula F:

F

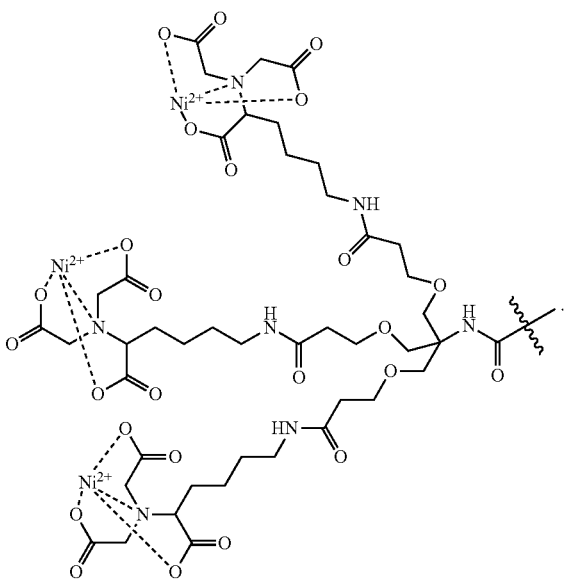

c. Fluorophore of Sensors of the Invention.

In one embodiment, this invention is directed to a sensor that can track changes that occur on the surface of proteins, said sensor comprises a selective binder, a non-selective binder and a fluorophore.

The fluorophore is an environmentally sensitive probe, introduced in the vicinity of the protein surface receptor, which should enable the system to fluoresce when the protein surface receptor (non-selective binder) binds the POI. This fluorescence should be eliminated in the presence of a binding partner, which either interacts with this region and displaces the protein-bound surface receptor, or induces a conformational change in the protein, which results in the dissociation of the protein surface receptor.

Accordingly, and in one embodiment, the sensor is labeled with a fluorophore, which may be attached directly to the non-selective binder or in the vicinity of it. In one embodiment, the fluorophore is covalently attached directly to the non-selective binder. In another embodiment, the fluorophore is covalently attached to the linker, which covalently links the selective binder with the non-selective binder. In another embodiment, the fluorophore is covalently attached to the linker, in the vicinity of the non-selective binder. In another embodiment, the fluorophore is covalently attached to the linker, in a position that is closer to the non-selective binder than to the selective binder.

In some embodiments, the fluorophore of this invention is a solvatochromic dye. Solvatochromic fluorophores display sensitivity to the polarity of the local environment. These molecules exhibit a low quantum yield in aqueous solution, but become highly fluorescent in nonpolar solvents or when bound to hydrophobic sites in proteins or membranes. In certain embodiments, solvatochromic fluorophores include 2-propionyl-6-dimethylaminonaphthalene (PRODAN) (Weber et al. *Biochemisry,* 1979, 18, 3075-3078; Cohen et al. *Science* 2002, 296, 1700-1703), 4-dimethylamino phthalimide (4-DMAP) (Saroja et al. *J. Fluoresc.* 1998, 8, 405-410), and 4-amino-1,8-naphthalimide derivatives (Grabchev et al. *J. Photochem. Photobiol., A* 2003, 158, 37-43; Martin et al. *J. Lumin.* 1996, 68, 157-146). In another embodiment, the solvatochromic dye is dansyl, fluorescein (6-FAM), FAM, cyanine dyes (e.g. Cy3. Cy5), sulfoindocyanine, nile red, rhodamine, perylene, fluorenyl, coumarin, 7-methoxycoumarin (Mca), dabcyl, NBD, Nile blue, Tamra, BODIPY, FITC, Thiazole orange, Quinoline blue, Thiazole red, or derivative thereof. In some embodiments, the solvatochromic dye of this invention is dansyl. In another embodiment, the fluorophore is dansyl.

In some embodiments, the fluorophore of this invention is a fluorescent dye. In another embodiment, the fluorescent dye is substituted or unsubstituted anthracene; substituted or unsubstituted nile red; substituted or unsubstituted dansyl; substituted or unsubstituted fluorenyl; substituted or unsubstituted naphthalene; substituted or unsubstituted tetracene; substituted or unsubstituted perylene; substituted or unsubstituted pyrene substituted or unsubstituted fluorescein; substituted or unsubstituted rhodamine; substituted or unsubstituted cyanine, substituted or unsubstituted coumarin; substituted or unsubstituted NBD; substituted or unsubstituted Nile blue; substituted or unsubstituted Tamra; substituted or unsubstituted BODIPY; or any other fluorescent dye known in the art and/or disclosed in http://www.fluorophores.org which is incorporated herein by reference. In another embodiment, the fluorescent dye of this invention is anthracene, naphthalene, fluorenyl, dansyl, nile red, fluorescein, rhodamine, perylene, cyanine, Cy3, Cy5, coumarin, NBD, Nile blue, Tamra, BODIPY, FITC, Thiazole orange, Quinoline blue, Thiazole red, derivative thereof, or combination thereof. In another embodiment, the fluorescent dye of this invention is substituted by one to three substituents. In another embodiment the fluorescent dye is substituted by alkyl, alkenyl, haloalkyl, aryl, O-aryl, —(CH$_2$)n-aryl, cycloalkyl, O-cycloalkyl, CF$_3$, F, I, Br, Cl, NO$_2$, CN, N(Z)$_2$, COOH, CO—Z, NHCOZ, CONHZ, (CH$_2$)$_n$NH$_2$, (CH$_2$)$_n$NH—Z, S—Z, SH, O—Z, (CH$_2$)$_n$OH, (CH$_2$)$_n$COOH, or OH; wherein Z is H, alkyl, haloalkyl, dihaloalkyl, trihaloalkyl, aryl, phenyl or halogen and n is between 0 and 8. In another embodiment n is between 1 and 6.

In another embodiment, the fluorophore is attached to the non-selective binder of said sensor. In another embodiment, the fluorophore is in the vicinity of the non-selective binder of said sensor. In another embodiment, the fluorophore is attached to the linker of said sensor.

d. Linker of Sensors of the Invention.

In one embodiment, this invention is directed to a sensor that can track changes that occur on the surface of proteins, said sensor comprises a selective binder, a non-selective binder and a fluorophore. In another embodiment, the sensor further comprises a linker that covalently links the selective binder and the non-selective binder. In another embodiment, the fluorophore is attached to the linker.

In another embodiment, the linker is hydrophilic linker. In another embodiment, the linker is flexible linker. In another embodiment the linker is flexible hydrophilic linker. In another embodiment, the linker is a polyethylene glycol (PEG) derivative, wherein the term "derivative" includes but not limited to alkyl derivatives, amine derivatives, amide derivatives, carboxy derivatives, and the like. In another embodiment, the linker comprises polyethylene glycol (PEG) moiety. In another embodiment, the linker is a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof. In another embodiment, the linker is a combination of linear or branched alkyl ether chain of 2-50 carbon atoms and substituted linear or branched alkyl diamide chain of 2-50 carbon atoms.

In another embodiment, the linker is represented by the following structure:

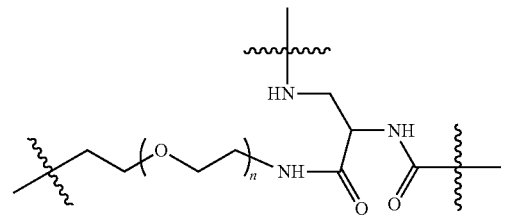

wherein n is an integer number between 1 and 10.

In another embodiment, n is 3.

In another embodiment, the linker is represented by the following structure:

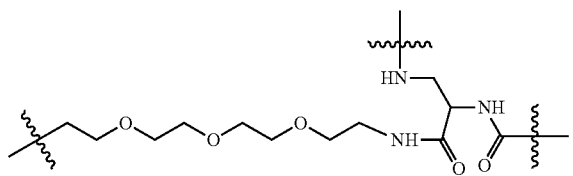 [SMILES: *CCOCCOCCOCCNC(=O)C(CN*)NC(*)=O]

e. Molecular Structure of Sensors of the Invention.

In one embodiment, this invention is directed to a compound that can track changes that occur on the surface of proteins, said compound comprises a selective binder, a non-selective binder and a fluorophore. In another embodiment, the compound is monomolecular compound. In another embodiment, the monomolecular compound is a sensor for tracking changes that occur on the surface of proteins.

In another embodiment, the sensor is represented by the structure of formula I:

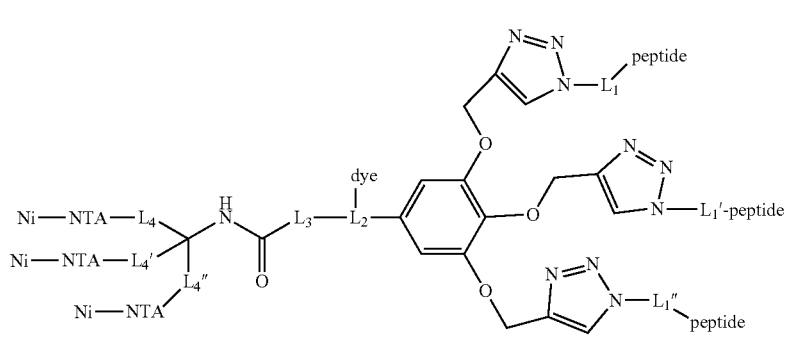

wherein each of $L_1$, $L_1'$ and $L_1''$ is independently a first linker, wherein each of said first linker is independently a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof;

L₂ is a second linker, wherein said second linker is a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof;

L₃ is a third linker, wherein said third linker is a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof;

each of L₄, L₄', and L₄" is independently a fourth linker, wherein each of said fourth linkers is a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof;

Ni-NTA is nickel complex of nitrilotriacetic acid, "dye" is solvatochromic dye, e.g. dansyl, and "peptide" is any peptide comprising 2-15 amino acids.

In one embodiment, each of L₁, L₁' and L₁" is independently a linear alkyl chain of 2-5 carbon atoms, L₂ is a substituted alkyl diamide, L₃ is a linear alkylether, and each of L₄, L₄', and L₄" is independently a combination of a linear alkyl ether and linear alkyl amide.

In another embodiment, the peptide comprises 3-8 amino acids. In another embodiment, the peptide is a hydrophobic peptide. In another embodiment, the peptide is SEQ ID No. 22. In another embodiment, the peptide comprises both hydrophobic and positively charged amino acids. In another embodiment, the peptide is SEQ ID No. 26. In another embodiment, the peptides are the same. In another embodiment, the peptides are different.

In another embodiment, the sensor is represented by the structure of formula II:

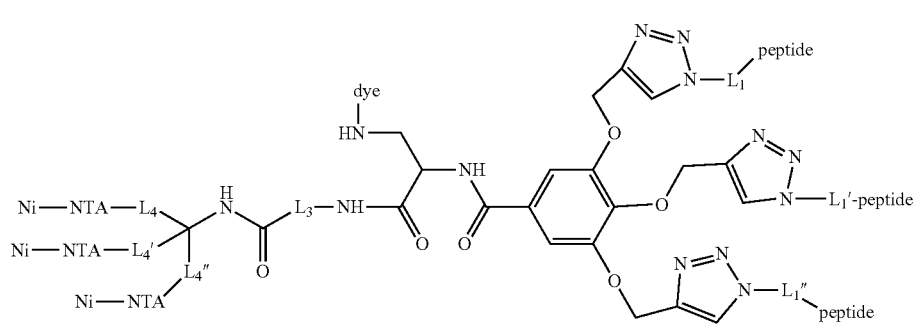

wherein
each of L₁, L₁' and L₁" is independently a first linker, wherein each of said first linker is independently a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof;

L₃ is a third linker, wherein said third linker is a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof;

each of L₄, L₄', and L₄" is independently a fourth linker, wherein each of said fourth linkers is independently a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof;

Ni-NTA is nickel complex of nitrilotriacetic acid, "dye" is solvatochromic dye, e.g. dansyl, and "peptide" is any peptide comprising 2-15 amino acids.

In one embodiment, each of L₁, L₁' and L₁" is independently a linear alkyl chain of 2-6 carbon atoms, L₃ is polyethylene glycol, and each of L₄, L₄', and L₄" is independently combination of a linear alkyl ether and linear alkyl amide of 3-10 carbon atoms (i.e., alkylether-alkylamide).

In another embodiment, the peptide comprises 3-8 amino acids. In another embodiment, the peptide is a hydrophobic peptide. In another embodiment, the peptide is SEQ ID No. 22. In another embodiment, the peptide comprises both hydrophobic and positively charged amino acids. In another embodiment, the peptide is SEQ ID No. 26.

In another embodiment, the sensor is represented by the structure of formula III:

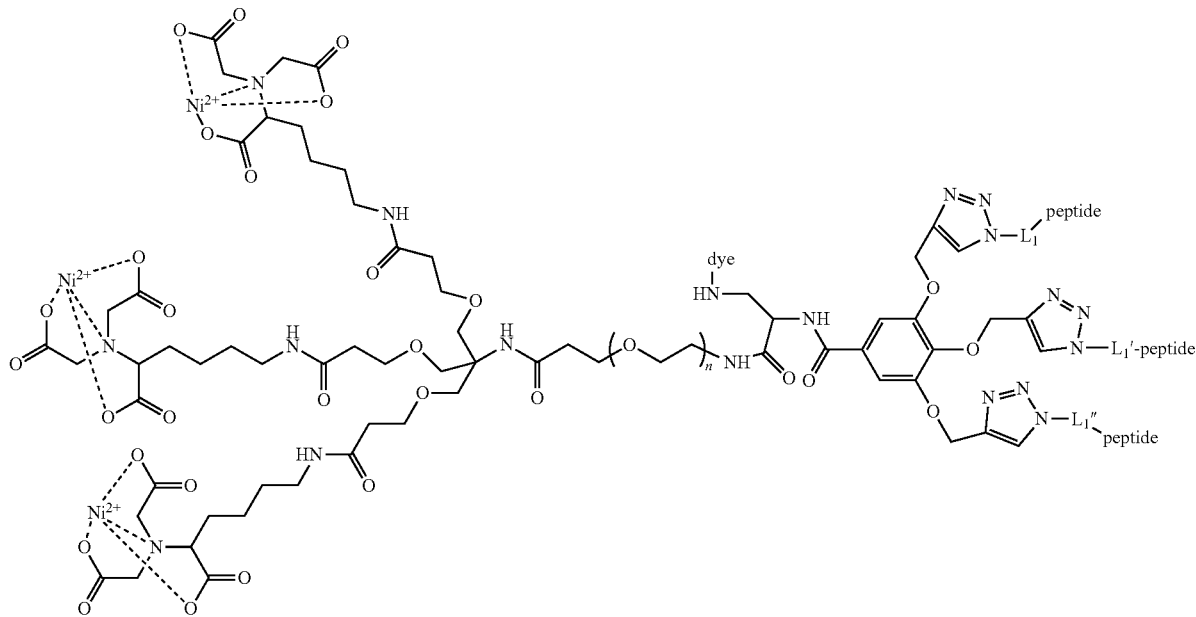

III wherein
each of $L_1$, $L_1'$ and $L_1''$ is independently a first linker, wherein each of said first linkers is a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof;
n is an integer number between 1 and 20;

Ni-NTA is nickel complex of nitrilotriacetic acid, "dye" is solvatochromic dye, e.g. dansyl, and "peptide" is any peptide comprising 2-15 amino acids.

In one embodiment, each of $L_1$, $L_1'$ and $L_1''$ is independently a linear alkyl chain of 2-6 carbon atoms. In another embodiment, each of $L_1$, $L_1'$ and $L_1''$ is propyl. In another embodiment, n is 3.

In another embodiment, the peptide comprises 3-8 amino acids. In another embodiment, the peptide is a hydrophobic peptide. In another embodiment, the peptide is SEQ ID No. 22. In another embodiment, the peptide comprises both hydrophobic and positively charged amino acids. In another embodiment, the peptide is SEQ ID No. 26.

In another embodiment, the sensor is represented by the structure of formula IV:

IV
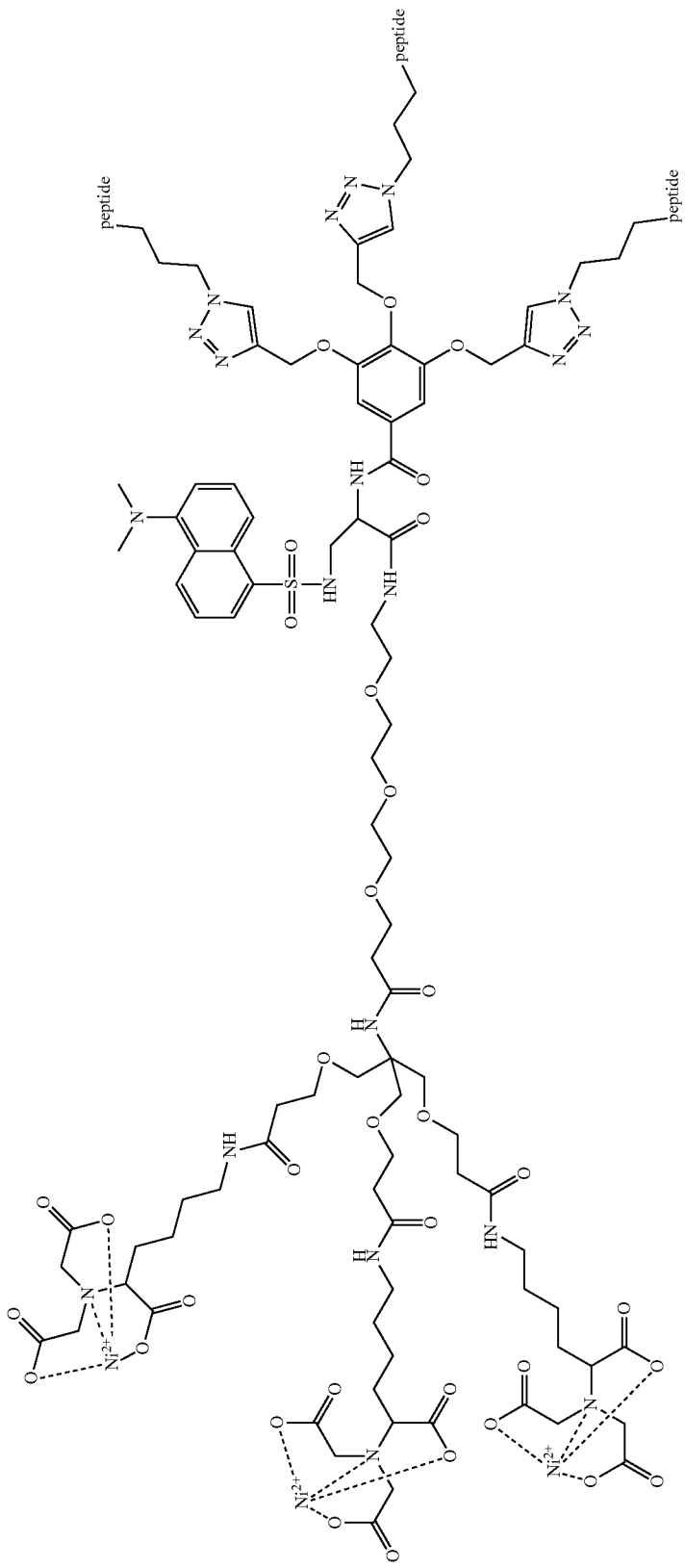

wherein "peptide" can be any peptide comprising 2-20 amino acids.

f. Specific Embodiments for Sensors of the Invention

In one embodiment, $L_1$ of formula I, II, III, (A) or (B) is a substituted or unsubstituted linear or branched alkyl chain of 2-50 carbon atoms. In another embodiment, unsubstituted linear alkyl chain of 2-50 carbon atoms. In another embodiment, unsubstituted linear alkyl chain of 2-6 carbon atoms. In another embodiment, $L_1$ is propyl. In another embodiment, $L_1$ is a substituted or unsubstituted linear or branched alkyl ether chain of 2-50 carbon atoms. In another embodiment, substituted or unsubstituted linear or branched alkyl phosphate chain of 2-50 carbon atoms. In another embodiment, substituted or unsubstituted linear or branched alkyl amide chain of 2-50 carbon atoms. In another embodiment, substituted or unsubstituted linear or branched alkyl diamide chain of 2-50 carbon atoms. In another embodiment, substituted or unsubstituted linear or branched alkyl amine chain of 2-50 carbon atoms. In another embodiment, $L_1$ is any combination of substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, and substituted or unsubstituted linear or branched alkyl amine chain of 2-50 carbon atoms.

In one embodiment, $L_1'$ of formula I, II, III, (A) or (B) is a substituted or unsubstituted linear or branched alkyl chain of 2-50 carbon atoms. In another embodiment, unsubstituted linear alkyl chain of 2-50 carbon atoms. In another embodiment, unsubstituted linear alkyl chain of 2-6 carbon atoms. In another embodiment, $L_1'$ is propyl. In another embodiment, $L_1'$ is a substituted or unsubstituted linear or branched alkyl ether chain of 2-50 carbon atoms. In another embodiment, substituted or unsubstituted linear or branched alkyl phosphate chain of 2-50 carbon atoms. In another embodiment, substituted or unsubstituted linear or branched alkyl amide chain of 2-50 carbon atoms. In another embodiment, substituted or unsubstituted linear or branched alkyl diamide chain of 2-50 carbon atoms. In another embodiment, substituted or unsubstituted linear or branched alkyl amine chain of 2-50 carbon atoms. In another embodiment, $L_1'$ is any combination of substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, and substituted or unsubstituted linear or branched alkyl amine chain of 2-50 carbon atoms.

In one embodiment, $L_1''$ of formula I, II, III, (A) or (B) is a substituted or unsubstituted linear or branched alkyl chain of 2-50 carbon atoms. In another embodiment, unsubstituted linear alkyl chain of 2-50 carbon atoms. In another embodiment, unsubstituted linear alkyl chain of 2-6 carbon atoms. In another embodiment, $L_1''$ is propyl. In another embodiment, $L_1''$ is a substituted or unsubstituted linear or branched alkyl ether chain of 2-50 carbon atoms. In another embodiment, substituted or unsubstituted linear or branched alkyl phosphate chain of 2-50 carbon atoms. In another embodiment, substituted or unsubstituted linear or branched alkyl amide chain of 2-50 carbon atoms. In another embodiment, substituted or unsubstituted linear or branched alkyl diamide chain of 2-50 carbon atoms. In another embodiment, substituted or unsubstituted linear or branched alkyl amine chain of 2-50 carbon atoms. In another embodiment, $L_1''$ is any combination of substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, and substituted or unsubstituted linear or branched alkyl amine chain of 2-50 carbon atoms.

In one embodiment, $L_1$, $L_1'$ and $L_1''$ are different. In another embodiment, $L_1$, $L_1'$ and $L_1''$ are the same. In another embodiment, $L_1$ and $L_1'$ are the same and $L_1''$ is different. In another embodiment, $L_1$ and $L_1''$ are the same and $L_1'$ is different. In another embodiment, $L_1'$ and $L_1''$ are the same and $L_1$ is different.

In one embodiment, $L_2$ of formula I is a substituted or unsubstituted linear or branched alkyl diamide chain of 2-50 carbon atoms. In another embodiment, substituted alkyl diamide chain of 2-50 carbon atoms. In another embodiment, substituted linear alkyl diamide of 2-6 carbon atoms, wherein substitutions include: one or more groups selected from halogen, hydroxy, hydroxyalkyl, alkoxy, haloalkyl, carbonyl, amido, alkylamido, dialkylamido, nitro, cyano, amino, alkylamino, dialkylamino, carboxyl, thiol, thioalkyl and the like. In another embodiment, $L_2$ is In another embodiment, $L_2$ is a substituted or unsubstituted linear or branched alkyl ether chain of 2-50 carbon atoms. In another embodiment, substituted or unsubstituted linear or branched alkyl phosphate chain of 2-50 carbon atoms. In another embodiment, substituted or unsubstituted linear or branched alkyl amide chain of 2-50 carbon atoms. In another embodiment, substituted or unsubstituted linear or branched alkyl chain of 2-50 carbon atoms. In another embodiment, substituted or unsubstituted linear or branched alkyl amine chain of 2-50 carbon atoms. In another embodiment, $L_2$ is any combination of substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, and substituted or unsubstituted linear or branched alkyl amine chain of 2-50 carbon atoms.

In one embodiment, $L_3$ of formula I or II is a substituted or unsubstituted linear or branched alkyl ether chain of 2-50 carbon atoms. In another embodiment, unsubstituted linear alkyl ether chain of 2-20 carbon atoms. In another embodiment, unsubstituted linear alkyl ether chain of 2-8 carbon atoms. In another embodiment, $L_3$ is $(CH_2CH_2O)_n$, wherein n is an integer between 1 and 10. In another embodiment, n is 3. In another embodiment, $L_3$ is polyethylene glycol (PEG). In another embodiment, $L_3$ is a substituted or unsubstituted linear or branched alkyl chain of 2-50 carbon atoms. In another embodiment, substituted or unsubstituted linear or branched alkyl phosphate chain of 2-50 carbon atoms. In another embodiment, substituted or unsubstituted linear or branched alkyl amide chain of 2-50 carbon atoms. In another embodiment, substituted or unsubstituted linear or branched alkyl diamide chain of 2-50 carbon atoms. In another embodiment, substituted or unsubstituted linear or branched alkyl amine chain of 2-50 carbon atoms. In another embodiment, $L_3$ is any combination of substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, and substituted or unsubstituted linear or branched alkyl amine chain of 2-50 carbon atoms.

In one embodiment, $L_4$ of formula I, II, (D) or D(a) is a combination of substituted or unsubstituted linear or branched alkyl ether chain of 2-50 carbon atoms and substituted or unsubstituted linear or branched alkyl amide chain of 2-50 carbon atoms. In another embodiment, a combination of unsubstituted linear alkyl ether chain of 2-50 carbon atoms and unsubstituted linear alkyl amide chain of 2-50 carbon atoms. In another embodiment, the unsubstituted linear alkyl ether chain is of 2-6 carbon atoms. In another embodiment, the unsubstituted linear alkyl amide chain is of 2-6 carbon atoms. In another embodiment, $L_4$ is a combination of a linear alkyl ether and linear alkyl amide of 3-10 carbon atoms (i.e., alkylether-alkylamide). In another embodiment, $L_4$ is —$(CH_2)_n$—NHCO—$(CH_2)_m$—O—$(CH_2)_l$—, wherein n, m and l are each independently an integer between 1 and 6. In another embodiment, $L_4$ is —$(CH_2)_4$—NHCO—$(CH_2)_2$—O—$CH_2$—. In another embodiment, $L_4$ is represented by the following structure:

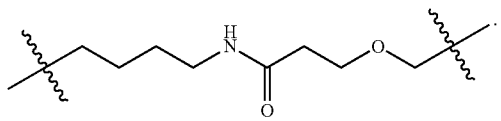 [SMILES: *CCCCNC(=O)CCOC*]

In another embodiment, $L_4$ is a substituted or unsubstituted linear or branched alkyl ether chain of 2-50 carbon atoms. In another embodiment, substituted or unsubstituted linear or branched alkyl chain of 2-50 carbon atoms. In another embodiment, substituted or unsubstituted linear or branched alkyl phosphate chain of 2-50 carbon atoms. In another embodiment, substituted or unsubstituted linear or branched alkyl amide chain of 2-50 carbon atoms. In another embodiment, substituted or unsubstituted linear or branched alkyl diamide chain of 2-50 carbon atoms. In another embodiment, substituted or unsubstituted linear or branched alkyl amine chain of 2-50 carbon atoms. In another embodiment, $L_4$ is any combination of substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, and substituted or unsubstituted linear or branched alkyl amine chain of 2-50 carbon atoms.

In one embodiment, $L_4'$ of formula I, II, (D) or D(a) is a combination of substituted or unsubstituted linear or branched alkyl ether chain of 2-50 carbon atoms and substituted or unsubstituted linear or branched alkyl amide chain of 2-50 carbon atoms. In another embodiment, a combination of unsubstituted linear alkyl ether chain of 2-50 carbon atoms and unsubstituted linear alkyl amide chain of 2-50 carbon atoms. In another embodiment, the unsubstituted linear alkyl ether chain is of 2-6 carbon atoms. In another embodiment, the unsubstituted linear alkyl amide chain is of 2-6 carbon atoms. In another embodiment, $L_4'$ is a combination of a linear alkyl ether and linear alkyl amide of 3-10 carbon atoms (i.e., alkylether-alkylamide). In another embodiment, $L_4'$ is —$(CH_2)_n$—NHCO—$(CH_2)_m$—O—$(CH_2)_l$—, wherein n, m and l are each independently an integer between 1 and 6. In another embodiment, $L_4'$ is —$(CH_2)_4$—NHCO—$(CH_2)_2$—O—$CH_2$—. In another embodiment, $L_4'$ is represented by the following structure:

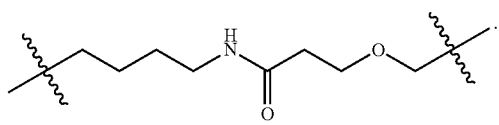 [SMILES: *CCCCNC(=O)CCOC*]

In another embodiment, $L_4'$ is a substituted or unsubstituted linear or branched alkyl ether chain of 2-50 carbon atoms. In another embodiment, substituted or unsubstituted linear or branched alkyl chain of 2-50 carbon atoms. In another embodiment, substituted or unsubstituted linear or branched alkyl phosphate chain of 2-50 carbon atoms. In another embodiment, substituted or unsubstituted linear or branched alkyl amide chain of 2-50 carbon atoms. In another embodiment, substituted or unsubstituted linear or branched alkyl diamide chain of 2-50 carbon atoms. In another embodiment, substituted or unsubstituted linear or branched alkyl amine chain of 2-50 carbon atoms. In another embodiment, $L_4'$ is any combination of substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, and substituted or unsubstituted linear or branched alkyl amine chain of 2-50 carbon atoms.

In one embodiment, $L_4''$ of formula I, II, (D) or D(a) is a combination of substituted or unsubstituted linear or branched alkyl ether chain of 2-50 carbon atoms and substituted or unsubstituted linear or branched alkyl amide chain of 2-50 carbon atoms. In another embodiment, a combination of unsubstituted linear alkyl ether chain of 2-50 carbon atoms and unsubstituted linear alkyl amide chain of 2-50 carbon atoms. In another embodiment, the unsubstituted linear alkyl ether chain is of 2-6 carbon atoms. In another embodiment, the unsubstituted linear alkyl amide chain is of 2-6 carbon atoms. In another embodiment, $L_4''$ is a combination of a linear alkyl ether and linear alkyl amide of 3-10 carbon atoms (i.e., alkylether-alkylamide). In another embodiment, $L_4''$ is —$(CH_2)_n$—NHCO—$(CH_2)_m$—

O—(CH$_2$)$_l$—, wherein n, m and l are each independently an integer between 1 and 6. In another embodiment, L$_4$" is —(CH$_2$)$_4$—NHCO—(CH$_2$)$_2$—O—CH$_2$—. In another embodiment, L$_4$" is represented by the following structure:

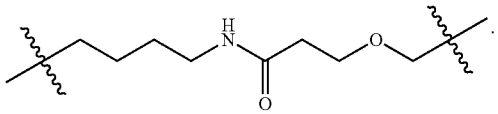 [SMILES: *CCCCNC(=O)CCOC*]

In another embodiment, L$_4$" is a substituted or unsubstituted linear or branched alkyl ether chain of 2-50 carbon atoms. In another embodiment, substituted or unsubstituted linear or branched alkyl chain of 2-50 carbon atoms. In another embodiment, substituted or unsubstituted linear or branched alkyl phosphate chain of 2-50 carbon atoms. In another embodiment, substituted or unsubstituted linear or branched alkyl amide chain of 2-50 carbon atoms. In another embodiment, substituted or unsubstituted linear or branched alkyl diamide chain of 2-50 carbon atoms. In another embodiment, substituted or unsubstituted linear or branched alkyl amine chain of 2-50 carbon atoms. In another embodiment, L$_4$" is any combination of substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, and substituted or unsubstituted linear or branched alkyl amine chain of 2-50 carbon atoms.

In one embodiment, L$_4$, L$_4$' and L$_4$" are different. In another embodiment, L$_4$, L$_4$' and L$_4$" are the same. In another embodiment, L$_4$ and L$_4$' are the same and L$_4$" is different. In another embodiment, L$_4$ and L$_4$" are the same and L$_4$' is different. In another embodiment, L$_4$' and L$_4$" are the same and L$_4$ is different.

In one embodiment, "dye" of formula I, II or III is a solvatochromic dye. In another embodiment, a fluorophore. In another embodiment, dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, Tamra, BODIPY, FITC, Thiazole orange, Quinoline blue, Thiazole red, or derivative thereof. In another embodiment, dansyl. In another embodiment, fluorescein (6-FAM). In another embodiment, FAM. In another embodiment, cyanine dyes (e.g. Cy3, Cy5). In another embodiment, sulfoindocyanine. In another embodiment, nile red. In another embodiment, rhodamine. In another embodiment, perylene. In another embodiment, fluorenyl. In another embodiment, coumarin. In another embodiment, 7-methoxycoumarin (Mca). In another embodiment, dabcyl. In another embodiment, NBD. In another embodiment, Nile blue. In another embodiment, Tamra. In another embodiment, BODIPY. In another embodiment, a derivative of any one of dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, Tamra, BODIPY, FITC, Thiazole orange, Quinoline blue, or Thiazole red.

In one embodiment, "peptide" of formula I, II, III, IV, (A) or (B) is any peptide comprising between 2 to 30 amino acid sequence. In another embodiment, the peptides possess between 4 to 15 amino acid sequences. In another embodiment, the peptides possess between 2 to 20 amino acid sequences. In another embodiment, the peptides possess between 3 to 10 amino acid sequences. In another embodiment, the peptide comprises 3-8 amino acids. In another embodiment, the peptide comprises 4 amino acids. In another embodiment, the peptide comprises 6 amino acids. In another embodiment, the peptides comprise hydrophobic amino acids. In another embodiment, the peptide is SEQ ID No. 22. In another embodiment, the peptides comprise polar amino acids. In another embodiment, the peptide is SEQ ID No. 24. In another embodiment, the peptides comprise negatively charged amino acids. In another embodiment, the peptide is SEQ ID No. 23. In another embodiment, the peptides comprise positively charged amino acids. In another embodiment, the peptide is SEQ ID No. 25. In another embodiment, the peptides comprise combination of hydrophobic and negatively charged amino acids. In another embodiment, the peptides comprise combination of hydrophobic and positively charged amino acids. In another embodiment, the peptide is SEQ ID No. 26. In another embodiment, the peptides comprise combination of hydrophobic and polar amino acids. In another embodiment, the peptides comprise combination of polar and negatively charged amino acids. In another embodiment, the peptides comprise combination of polar and positively charged amino acids. In another embodiment the peptides are as described in Table 1, 1A and FIG. 14.

In another embodiment, n of formula III is an integer number between 1 and 20. In another embodiment, between 2 and 10. In another embodiment, between 1 and 8. In another embodiment, 2. In another embodiment, 3. In another embodiment, 4. In another embodiment, 5. In another embodiment, 6. In another embodiment, 7.

g. Applications of Sensor Compounds of the Invention.

Protein surface recognition by synthetic receptors is an important research direction in the areas of bioorganic and medicinal chemistry, particularly due to the ability of such receptors to disrupt the interactions between two proteins.

Herein, it is demonstrated how the attachment of protein surface receptors to genetically targeted molecules (e.g., His-tag binding compounds) can afford fluorescent sensors that respond to changes in the surfaces of affinity-labelled proteins, upon binding to metal ions, small molecules, and protein partners. It is herein demonstrated how combination of flexible linker with a modifiable synthetic receptor enables the design of various sensors that match different regions on the surface of various proteins.

In one embodiment, this invention is directed to a method of detecting changes in a protein surface using a sensor of the invention, or in another embodiment, to a method of detecting conformational changes of a protein of interest using a sensor of the invention; or in another embodiment, to a method of sensing binding interactions of a protein of interest using a sensor of the invention.

The ability to detect changes in protein surfaces opens up new possibilities for using sensors according to this invention, to identify binding partners (FIG. 2, state c). Unlike enzyme inhibitors that can be readily detected by enzymatic assays, identifying molecules that interact with protein surfaces is generally complicated by the need to use antibodies and stepwise protocols, or special techniques such as fluorescence anisotropy or SPR.

In one embodiment, this invention is directed to a method of detecting protein modifications and binding interactions, which are difficult to sense using the current available probes, using a sensor of the invention. In another embodiment, the protein is labeled. In another embodiment, a protein is labeled with any tag known in the art. In another embodiment the protein is labeled with a polyhistidine tag (His-tag). In another embodiment, said polyhistidine tag (His-tag) comprises a 6×His-tag. In another embodiment, said polyhistidine tag (His-tag) comprises a 10×His-tag. In another embodiment, a protein is labeled with a FLAG-tag. In another embodiment, a FLAG-tag label is a multi-FLAG tag. In another embodiment, a FLAG tag is a dimmer (2×). In another embodiment, a FLAG tag is a 3× tag. In another embodiment, a protein is labeled with a c-myc tag. In another embodiment, said label does not interfere with a protein's tertiary structure. In another embodiment, said label does not interfere with a proteins quaternary structure. Each possibility comprises an embodiment of this invention.

In one embodiment, a protein to be labeled comprises any protein known in the art, wherein a tagged-protein may be encoded by a nucleic acid sequence. In another embodiment the protein is calmodulin (CaM), G protein or B-cell lymphoma 2 protein (Bcl-2).

The terms "polypeptide", "protein", "polypeptide of interest" and "protein of interest (POI)" are used interchangeably having all the same meanings and qualities. In some embodiments, a "polypeptide" or "protein" as used herein encompasses native polypeptides (either degradation products, fractions thereof, or recombinant polypeptides, or any combination thereof). In some embodiments, modifications include, but are not limited to N terminus modification, C terminus modification, and residue modification. In certain embodiments, a polypeptide or protein may comprise a fraction of the wild-type polypeptide or protein. In some embodiments, a polypeptide or protein may comprise a mutated amino acid sequence.

In one embodiment, this invention is directed to a method of identifying a binding partner of protein of interest (POI), said method comprises:
 a. incubating a sensor according to this invention with a tagged POI in solution, wherein said sensor comprises a tag binding region;
 b. measuring the fluorescence intensity of said solution;
 c. adding a test compound to said solution;
 d. remeasuring the fluorescence intensity of said solution; and
 e. determining binding of said test compound to said tagged POI based on a change in fluorescence intensity, wherein decreased fluorescent intensity indicates binding of said test compound;
 thereby identifying said binding partner for said POI.

In another embodiment, said tagged-POI comprises an affinity tag. In another embodiment, said tagged-POI comprises any tag known in the art. Non limiting examples for tag are: His-tag, FLAG tag, HA tag, C-myc tag, AviTag, Calmodulin-tag, polyglutamate tag, E-tag, Myc-tag, S-tag, SBP-tag, Softag, Strep-tag, TC tag, V5 tag, VSV-tag, Xpress tag, etc. In another embodiment, said tagged-POI comprises a polyhistidine tag (His-tag). In another embodiment, said polyhistidine tag (His-tag) comprises a δ×His-tag. In another embodiment, said polyhistidine tag (His-tag) comprises a 10×His-tag. In another embodiment, said polyhistidine tag (His-tag) comprises at least six histidine residues. In another embodiment, said tagged-POI comprises a FLAG-tag. In another embodiment, a FLAG-tag label is a multi-FLAG tag. In another embodiment, a FLAG tag is a dimmer (2×). In another embodiment, a FLAG tag is a 3×tag. In another embodiment, said tagged-POI comprises a c-myc tag. In another embodiment, said tag does not interfere with a protein's tertiary structure. In another embodiment, said tag does not interfere with a proteins quaternary structure.

In another embodiment, said POI is calmodulin (CaM). In another embodiment, said POI is calmodulin-$Ca^{2+}$ (CaM ($Ca^{2+}$)). In another embodiment, said POI is B-cell lymphoma 2 protein (Bcl-2).

In another embodiment, the solution further comprises proteins that tend to engage in non-specific interactions. In another embodiment, the proteins that tend to engage in non-specific interactions are selected from, IgG, IgA, Avidine, Insulin, SAv, BSA, GST-P1, HSA, AGP.

In another embodiment, the binding partner is a protein. In another embodiment, the binding partner is a peptide. In another embodiment, the binding partner is a synthetic molecule. In another embodiment, the binding partner is a small molecule. In another embodiment, the binding partner is a drug. Each possibility comprises an embodiment of this invention.

In one embodiment, this invention is directed to a method of identifying binding partners of protein of interest (POI) in a complex environment, said method comprises:
 a. incubating a sensor according to this invention with a tagged POI in solution, wherein said sensor comprises a tag binding region;
 b. measuring the fluorescence intensity of said solution;
 c. adding a complex environment comprising a test compound to said solution;
 d. remeasuring the fluorescence intensity of said solution; and
 e. determining binding of said test compound in complex environment to said tagged POI based on a change in fluorescence intensity, wherein decreased fluorescent intensity indicates binding of said test compound;
thereby identifying a binding partner for said POI in a complex environment.

In another embodiment, said tagged-POI comprises an affinity tag. In another embodiment, said tagged-POI comprises any tag known in the art. In another embodiment, said tagged-POI comprises a polyhistidine tag (His-tag). In another embodiment, said polyhistidine tag (His-tag) comprises a 6×His-tag. In another embodiment, said polyhistidine tag (His-tag) comprises a 10×His-tag. In another embodiment, said tagged-POI comprises a FLAG-tag. In another embodiment, a FLAG-tag label is a multi-FLAG tag. In another embodiment, a FLAG tag is a dimmer (2×). In another embodiment, a FLAG tag is a 3×tag. In another embodiment, said tagged-POI comprises a c-myc tag. In another embodiment, said tag does not interfere with a protein's tertiary structure. In another embodiment, said tag does not interfere with a proteins quaternary structure.

In another embodiment, said POI is calmodulin (CaM). In another embodiment, said POI is calmodulin-$Ca^{2+}$ (CaM ($Ca^{2+}$)). In another embodiment, said POI is B-cell lymphoma 2 protein (Bcl-2).

In another embodiment, the binding partner is a protein. In another embodiment, the binding partner is a peptide. In another embodiment, the binding partner is a synthetic molecule. In another embodiment, the binding partner is a small molecule. In another embodiment, the binding partner is a drug. Each possibility comprises an embodiment of this invention.

In one embodiment, this invention is directed to a method of measuring gene expression of a His-tagged polypeptide in a cell, said method comprising the steps of:

a. expressing a His-tagged polypeptide in a cell;
b. incubating the cell with a sensor according to this invention; and
c. measuring the fluorescence of said cell;
wherein detection of a fluorescent signal is dependent on the formation of a His-tagged polypeptide:sensor complex.

In another embodiment, said His-tagged polypeptide comprises a polyhistidine-tag. In another embodiment, said sensor comprises a tag-binding region. In another embodiment, said sensor comprises a fluorophore according to this invention. In another embodiment, said fluorophore comprises a solvatochromic dye. In another embodiment, said solvatochromic dye is dansyl. In another embodiment, said fluorescence is measured over time. In another embodiment, said measuring is of a live cell. In another embodiment, said measuring of is a fixed cell. In one embodiment, said cell is a human cell. In another embodiment, said cell is a recombinant primary culture cell. In another embodiment, said cell is a tissue culture cell.

In one embodiment, this invention is directed to a method of localizing a His-tagged polypeptide of interest within a cell, said method comprises the steps of:
a. expressing said His-tagged polypeptide in a recombinant cell;
b. incubating said recombinant cell with a sensor according to this invention; and
c. visualizing the fluorescence emission of said sensor.

In one embodiment, said recombinant cell is fixed using any method known in the art, prior to the incubating step. In another embodiment, the sensor passively crosses the plasma membrane of a live cell. In another embodiment, the sensor is micro-injected into a live cell. In another embodiment, the sensor is derivatized in a way that allows its crossing of the plasma membrane of a live cell. In another embodiment, said visualizing is observing under a microscope. In one embodiment, a fluorescent microscope is used to detect and localize the fluorescent signal. In another embodiment, a fluorescent microscope with a plate reader or the ability to record images at multiple locations over time is used to detect and localize the fluorescent signal.

In one embodiment, this invention is directed to a method of identifying the phosphorylation state of calmodulin-dependent protein kinase II (CaMKII) using a complex of His-tag labeled CaM($Ca^{2+}$) and a sensor according to this invention, said method comprises:
a. incubating a sensor according to this invention, with a His-tag labeled CaM($Ca^{2+}$), thereby forming said complex of His-tag labeled CaM($Ca^{2+}$) and said sensor,
b. recording the fluorescence response of said complex to addition of CaMKII in an unknown state (i.e., either phosphorylated or dephosphorylated);
wherein a decrease in the fluorescence response is indicative of CaMKII in a phosphorylated state (i.e., p-CaMKII), and increase in the fluorescence response is indicative of CaMKII in a dephosphorylated state (CaMKII).

In one embodiment, this invention is directed to a method of detecting changes that occur in the surface of a His-tag labeled protein using a sensor according to this invention, said method comprises incubating said sensor with said His-tag labeled protein, wherein an enhancement in the optical signal of said sensor is indicative of a bound sensor-protein complex, which is indicative of a specific conformational state of said protein. In another embodiment, the optical signal is fluorescence emission. In another embodiment, the His-tag labeled protein is a His-CaM. In another embodiment, the His-tag labeled protein is a His-CaM ($Ca^{2+}$). In another embodiment, the His-tag labeled protein is a His-Bcl-2.

In one embodiment, this invention is directed to a method of identifying a compound that binds to a His-tag labeled protein of interest (His-tag-POI), said method comprises:
a. incubating a sensor according to this invention, with said His-tag labeled protein of interest (His-tag-POI) in solution, wherein said sensor comprises a tag binding region;
b. measuring the fluorescence intensity of said solution;
c. adding a test compound to said solution;
d. remeasuring the fluorescence intensity of said solution; and
e. determining binding of said test compound to said His-tag-POI based on a change in fluorescence intensity, wherein decreased fluorescent intensity indicates binding of said test compound;
thereby identifying a compound that binds said His-tag-POI.

In another embodiment, the POI is calmodulin (CaM). In another embodiment, said POI is calmodulin-$Ca^{2+}$ (CaM ($Ca^{2+}$)). In another embodiment, said POI is B-cell lymphoma 2 protein (Bcl-2).

In another embodiment, the solution further comprises proteins that tend to engage in non-specific interactions. In another embodiment, the proteins that tend to engage in non-specific interactions are selected from IgG, IgA, Avidine, Insulin, SAv, BSA, GST-P1, HSA, AGP.

In another embodiment, the test compound is a protein. In another embodiment, the test compound is a peptide. In another embodiment, the test compound is a synthetic molecule. In another embodiment, the test compound is a small molecule. In another embodiment, the test compound is a drug. Each possibility comprises an embodiment of this invention.

In one embodiment, this invention is directed to a method of identifying a compound that binds to a protein of interest (POI), said method comprises:
a. incubating a sensor according to this invention, with a protein of interest labeled with a histidine tag (His-tag-POI) in solution;
b. measuring the fluorescence intensity of said solution;
c. adding a test compound to said solution;
d. remeasuring the fluorescence intensity of said solution; and
e. determining binding of said test compound to said His-tag-POI based on a change in fluorescence intensity, wherein decreased fluorescent intensity indicates binding of said test compound;
thereby identifying a compound that binds said POI.

In another embodiment, the POI is calmodulin (CaM). In another embodiment, said POI is calmodulin-$Ca^{2+}$ (CaM ($Ca^{2+}$)). In another embodiment, said POI is B-cell lymphoma 2 protein (Bcl-2).

In another embodiment, the solution further comprises proteins that tend to engage in non-specific interactions. In another embodiment, the proteins that tend to engage in non-specific interactions are selected from—IgG, IgA, Avidine, Insulin, SAv, BSA, GST-P1, HSA, AGP.

In another embodiment, the test compound is a protein. In another embodiment, the test compound is a peptide. In another embodiment, the test compound is a synthetic molecule. In another embodiment, the test compound is a small molecule. In another embodiment, the test compound is a drug.

B. Universal His-Tag Binding Compounds.

In one embodiment, this invention is directed to a universal building block for preparing various His-tag-binding compounds and genetically targeted sensors.

The His-tag binding compound (or building block) according to this invention, comprises three nitrilotriacetic acid (NTA) units that upon complexation with nickel (II) or other metal ions, can bind an oligohistidine sequence of a polypeptide (His-tag) with low nanomolar affinities. The compound of the invention, also comprises an auxiliary unit ($R_1$, as described herein below), a functional group, that enables one to modify it using a wide range of functionalities. This building block is general for various protein binders, DNA binders and sensors, and can be easily modified through the auxiliary unit to bind to various synthetic agents, labeling moieties, solid support, oligonucleotides and detectable groups.

This invention is therefore directed to a universal His-tag binding compounds as well as to their building blocks and precursors, that upon complexation with metal ions (e.g., Ni(II), Co(II), or Co(III)) can selectively bind histidine-tags of various labeled proteins with nanomolar affinities. Therefore, the His tag binding compounds, and their building blocks and precursors according to this invention, are useful in the preparation of various fluorescent probes and genetically targeted sensors for various applications as described herein below.

In one embodiment, the compound, is represented by the structure of formula XI:

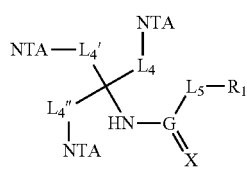

XI wherein $R_1$ is selected from: H, azide, amine, $C_2$-$C_6$ alkynyl, $C_2$-$C_6$ alkenyl, thioester, disulfide, maleimide, biotin, carboxyl, thiol, triazole, alkylamide, ketone, aldehyde and carbamate;

or $R_1$ is selected from:

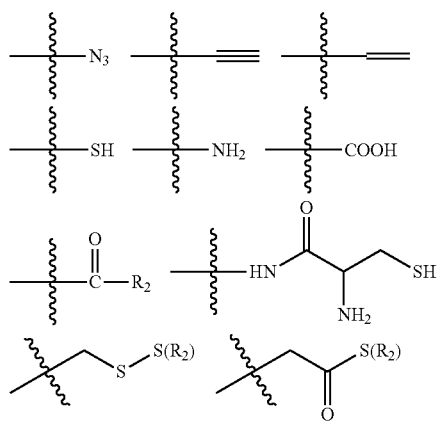

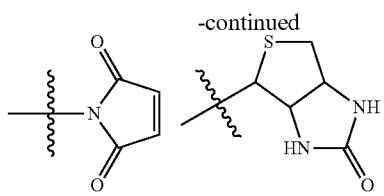

wherein $R_2$ is hydrogen, substituted or unsubstituted linear or branched $C_1$-$C_{12}$ alkyl, substituted or unsubstituted linear or branched $C_1$-$C_{12}$ arylalkyl or benzyl; G=X is absent, or is $CH_2$, C=O, C(O)NH, C=S. C(S)NH, C(O)O, S=O or $SO_2$; $L_4$, $L_4'$, and $L_4''$ are each independently a substituted or unsubstituted linear or branched alkyl chain of 1-20 carbon atoms, substituted or unsubstituted linear or branched alkyl ether chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl diamide chain of 1-20 carbon atoms, substituted or unsubstituted linear or branched alkyl amine chain of 1-20 carbon atoms or any combination thereof;

$L_5$ is absent, or is a substituted or unsubstituted linear or branched alkyl chain of 1-50 carbon atoms (e.g. ethylene: —$CH_2$—$CH_2$—), substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms or any combination thereof; and NTA is nitrilotriacetic acid or a protected derivative thereof.

In another embodiment, the compound is represented by the structure of formula XII:

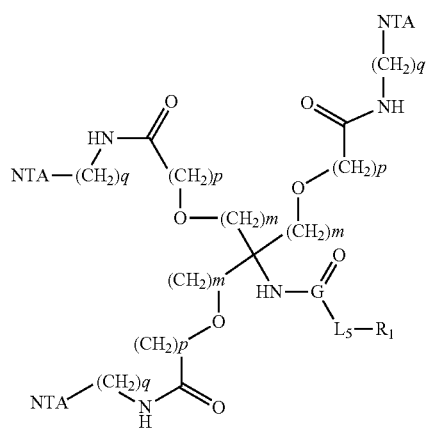

XII wherein $R_1$ is selected from: H, azide, amine, $C_2$-$C_6$ alkynyl, $C_2$-$C_6$ alkenyl, thioester, disulfide, maleimide, biotin, carboxyl, thiol, triazole, alkylamide, ketone, aldehyde and carbamate;

or $R_1$ is selected from:

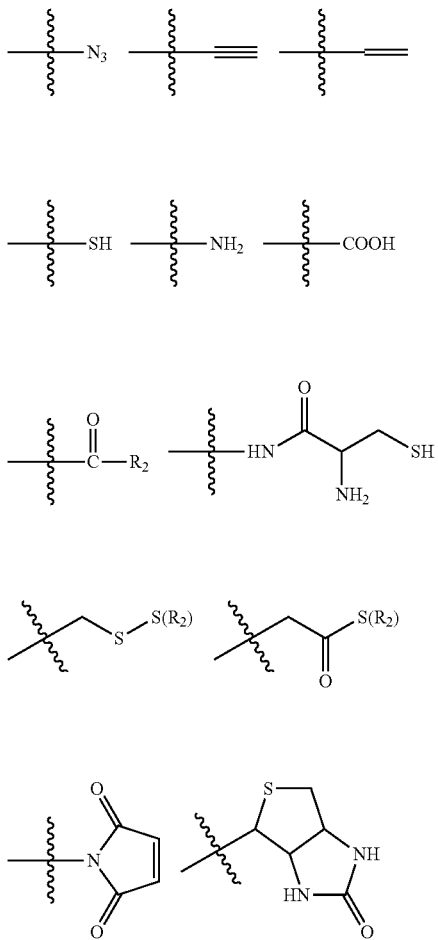

wherein
- $R_2$ is hydrogen, substituted or unsubstituted linear or branched $C_1$-$C_{12}$ alkyl, substituted or unsubstituted linear or branched $C_1$-$C_{12}$ arylalkyl or benzyl;
- m, p and q are each independently an integer number between 1 and 8; and
- G=X is absent, or is $CH_2$, C=O, C(O)NH, C=S, C(S)NH, C(O)O, S=O or $SO_2$;
- $L_5$ is absent or is a substituted or unsubstituted linear or branched alkyl chain of 1-50 carbon atoms (e.g. ethylene: —$CH_2$—$CH_2$—), substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms or any combination thereof; and
- NTA is nitrilotriacetic acid or a protected derivative thereof.

In another embodiment, the compound is represented by the structure of formula XIII:

XIII

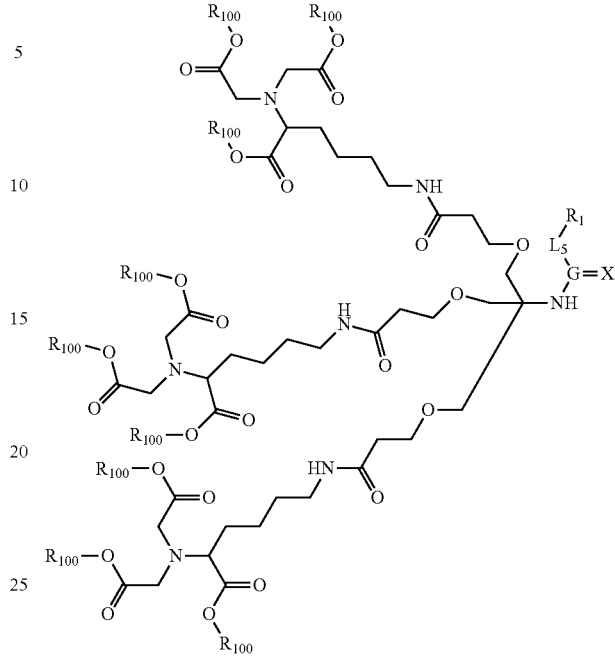

wherein
- $R_{100}$ is a protecting group;
- $R_1$ is selected from: H, azide, amine, $C_2$-$C_6$ alkynyl, $C_2$-$C_6$ alkenyl, thioester, disulfide, maleimide, biotin, carboxyl, thiol, triazole, alkylamide, ketone, aldehyde and carbamate;
- or $R_1$ is selected from:

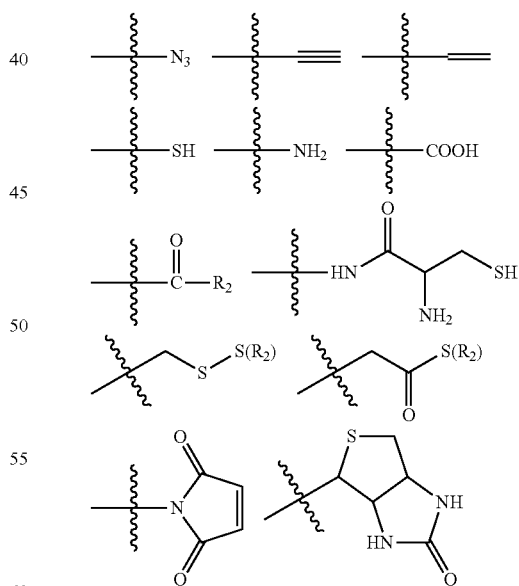

wherein
- $R_2$ is hydrogen, substituted or unsubstituted linear or branched $C_1$-$C_{12}$ alkyl, substituted or unsubstituted linear or branched $C_1$-$C_{12}$ arylalkyl or benzyl;
- G=X is absent, or is $CH_2$, C=O, C(O)NH, C=S, C(S)NH, C(O)O, S=O or $SO_2$;

$L_5$ is absent or is a substituted or unsubstituted linear or branched alkyl chain of 1-50 carbon atoms (e.g. ethylene: —$CH_2$—$CH_2$—), substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms or any combination thereof.

In another embodiment, the compound is represented by the structure of formula XIV:

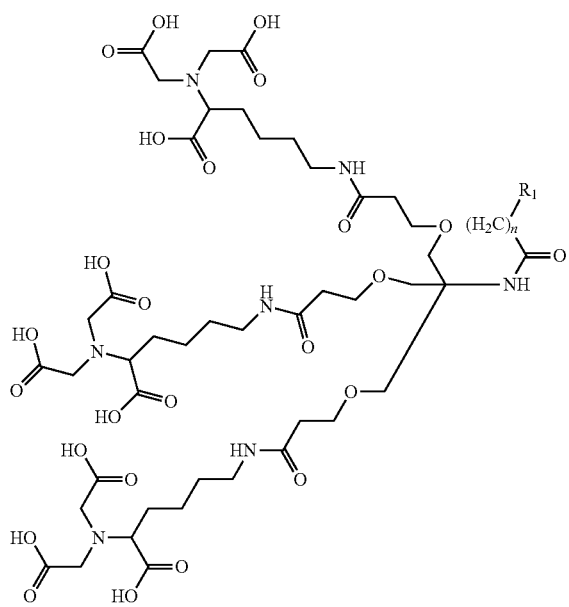

XIV wherein $R_1$ is selected from: H, azide, amine, $C_2$-$C_6$ alkynyl, $C_2$-$C_6$ alkenyl, thioester, disulfide, maleimide, biotin, carboxyl, thiol, triazole, alkylamide, ketone, aldehyde and carbamate;

or $R_1$ is selected from:

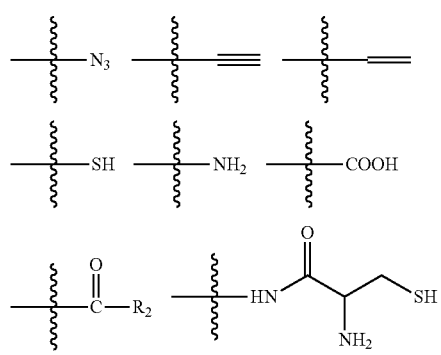

-continued

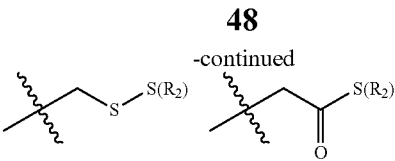

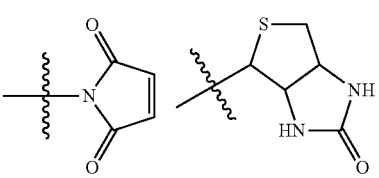

wherein $R_2$ is hydrogen, substituted or unsubstituted linear or branched $C_1$-$C_{12}$ alkyl, substituted or unsubstituted linear or branched $C_1$-$C_{12}$ arylalkyl or benzyl; and n is an integer between 0 and 20 (e.g., 2).

In another embodiment, the compound is represented by the structure of formula XV:

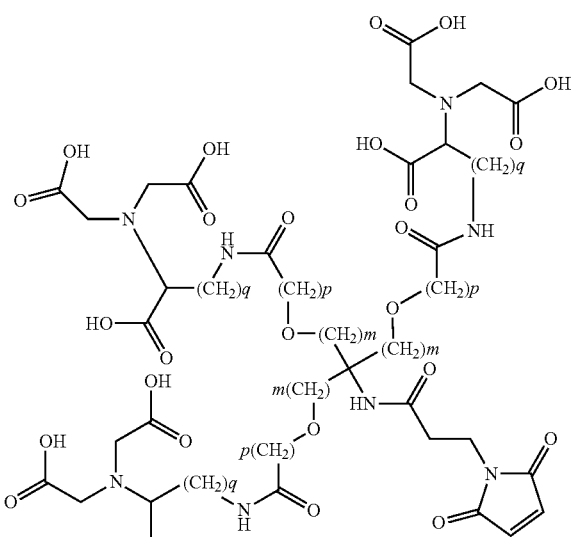

XV wherein m, p and q are each independently an integer number between 1 and 8.

In another embodiment, the compound is represented by the structure of formula XVI:

XVI

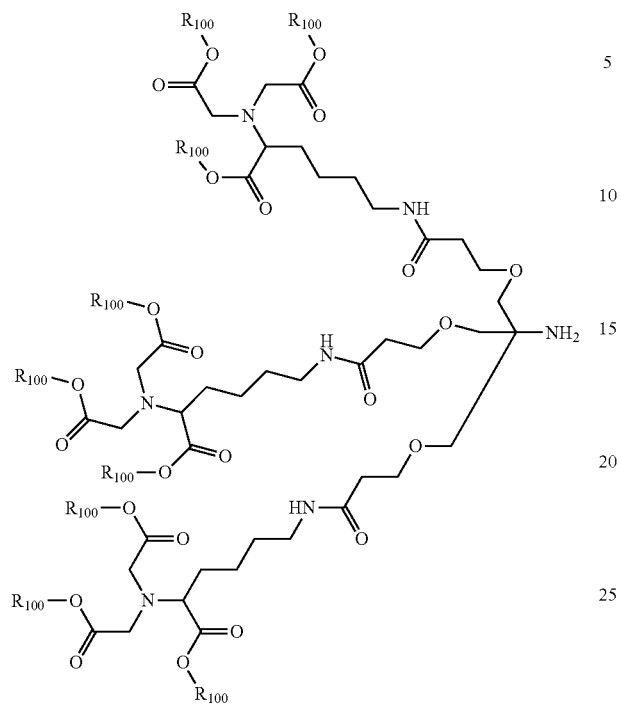

wherein $R_{100}$ is H or a protecting group.

In some embodiments, upon complexation to a metal ion, compound of formula XI-XVI can selectively bind an oligohistidine sequence of various His-tagged polypeptides and proteins. In some embodiments, the metal ion is cobalt (Co). In some embodiments, the metal ion is nickel (Ni). In some embodiments, the metal ion is Ni(II). In some embodiments, the metal ion is Co(II). In some embodiments, the metal ion is Co(III).

Specific Embodiments for His-Tag Binding Compounds of the Invention

In some embodiments, the compound according to this invention is a His-tag binding compound. In some embodiments, the compound according to this invention is a His-tag binding compound precursor.

In one embodiment, $R_1$ of formula XI-XIV is a functional group. In some embodiments, $R_1$ of compound of formula XI-XIV is H. In some embodiments, $R_1$ is azide. In some embodiments, $R_1$ is amine. In some embodiments, $R_1$ is $C_2$-$C_6$ alkynyl. In some embodiments, $R_1$ is $C_2$-$C_6$ alkenyl. In some embodiments, $R_1$ is ketone. In some embodiments, $R_1$ is aldehyde. In some embodiments, $R_1$ is thioester. In some embodiments, $R_1$ is disulfide. In some embodiments, $R_1$ is maleimide. In some embodiments, $R_1$ is biotin. In some embodiments, $R_1$ is carboxyl. In some embodiments, $R_1$ is thiol. In some embodiments, $R_1$ is triazole. In some embodiments, $R_1$ is alkylamide. In some embodiments, $R_1$ is carbamate. In some embodiments, $R_1$ is

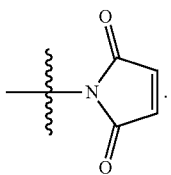 [SMILES: *N1C(=O)C=CC1=O]

In some embodiments, $R_1$ is

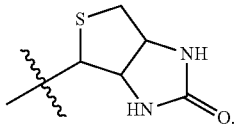 [SMILES: *C1SCC2NC(=O)NC21]

In some embodiments, $R_1$ is

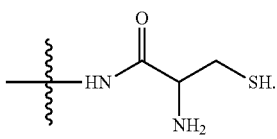

In some embodiments, $R_1$ is

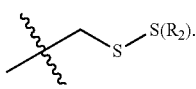

In some embodiments, $R_1$ is

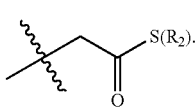

In one embodiment, $R_2$ of formula XI-XIV is a hydrogen. In another embodiment, substituted or unsubstituted linear or branched arylalkyl. In another embodiment, unsubstituted linear arylalkyl. In another embodiment, benzyl (i.e., —$CH_2$-Ph). In another embodiment, substituted or unsubstituted linear or branched $C_1$-$C_{12}$ alkyl. In another embodiment, unsubstituted linear $C_1$-$C_6$ alkyl. In another embodiment, methyl. In another embodiment, propyl. In another embodiment, ethyl. In another embodiment, t-Butyl. In another embodiment, hexyl. In another embodiment, $C_1$-$C_{12}$ haloalkyl. In another embodiment, $CF_3$.

In some embodiments, NTA of compound of formula XI and XII, is nitrilotriacetic acid. In some embodiments, NTA is a protected derivative of nitrilotriacetic acid. Non limiting examples for protecting groups of carboxylic acids include but are not limited to: methyl esters, benzyl esters, tert-butyl esters, esters of 2,6-disubstituted phenols (e.g. 2,6-dimethylphenol, 2,6-diisopropylphenol, 2,6-di-tert-butylphenol), silyl esters, orthoesters, and oxazoline; each represents a separate embodiment according to this invention.

In some embodiments NTA is represented by the structure of fragment (A):

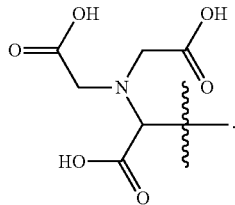
(A)

In some embodiments, NTA or a protected derivative of NTA is represented by the structure of fragment (B):

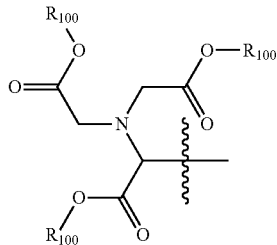
(B)

wherein $R_{100}$ is H or a protecting group.

In some embodiments, a protected derivative of NTA is represented by the structure of fragment (B):

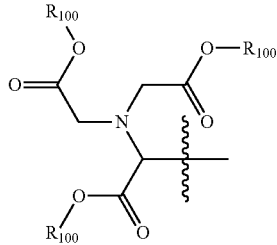
(B)

wherein $R_{100}$ is a protecting group.

In some embodiments, Rice of fragment (B), is H. In some embodiments, $R_{100}$ of fragment (B), is a protecting group. In some embodiments, $R_{100}$ of fragment (B), is a substituted or unsubstituted linear, branched or cyclic $C_1$-$C_{10}$ alkyl. In some embodiments, $R_{100}$ is an unsubstituted linear, branched or cyclic $C_1$-$C_{10}$ alkyl. In some embodiments, $R_{100}$ is H. In some embodiments, $R_{100}$ is tert-butyl. In some embodiments, $R_{100}$ is iso-propyl. In some embodiments, $R_{100}$ is ethyl. In some embodiments, $R_{100}$ is methyl. In some embodiments, $R_{100}$ is neo-pentyl. In some embodiments, $R_{100}$ is cyclopropyl. In some embodiments, $R_{100}$ is cyclohexyl. In some embodiments, $R_{100}$ is a substituted linear, branched or cyclic $C_1$-$C_{10}$ alkyl. In some embodiments, $R_{100}$ is benzyl. In some embodiments, $R_{100}$ is a substituted or unsubstituted aryl.

In some embodiments, a protected derivative of NTA is represented by the structure of fragment (C):

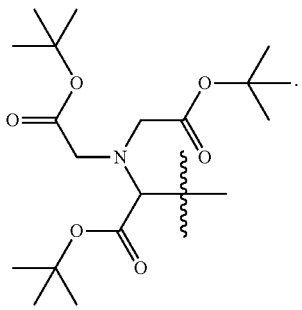
(C)

In some embodiments, the compound according to this invention is a His-tag binding compound precursor. In some embodiments, $R_{100}$ of fragment (B) is tert-Bu, G=X is absent, $L_5$ is absent, $R_1$ is H, or any combination thereof, each represents a separate embodiment according to this invention.

In some embodiments, G=X of compound of formula XI-XIII is absent. In some embodiment, G=X is C=O. In some embodiment, G=X is $CH_2$. In some embodiment, G=X is C(O)NH. In some embodiment, G=X is C(S)NH. In some embodiment, G=X is C(O)O. In some embodiment, G=X is C=S. In some embodiment, G=X is S=O In some embodiment, G=X is $SO_2$.

In some embodiments, each of $L_4$, $L_4'$, and $L_4''$ of the structure of formula XI, is independently a substituted or unsubstituted linear or branched alkyl chain of 1-20 carbon atoms, substituted or unsubstituted linear or branched alkyl ether chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl diamide chain of 1-20 carbon atoms, substituted or unsubstituted linear or branched alkyl amine chain of 1-20 carbon atoms or any combination thereof; each represents a separate embodiment according to this invention. In some embodiments, each of $L_4$, $L_4'$, and $L_4''$ is a combination of alkyl ether and alkyl amide (i.e., alkylether-alkylamide). In another embodiment, each of $L_4$, $L_4'$, and $L_4''$ is independently —$(CH_2)_q$—NHCO—$(CH_2)_p$—O—$(CH_2)_m$—, wherein q, p and m are each independently an integer between 1 and 8. In another embodiment, q is 4, p is 2 and m is 1. In another embodiment, each of $L_4$, $L_4'$, and $L_4''$ is —$(CH_2)_4$—NHCO—$(CH_2)_2$—O—$CH_2$—. In another embodiment, each of $L_4$, $L_4'$, and $L_4''$ is represented by the following structure:

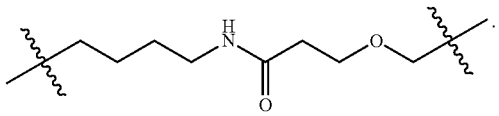 [SMILES: *CCCCNC(=O)CCOC*]

In one embodiment, $L_4$, $L_4'$ and $L_4''$ are different. In another embodiment, $L_4$, $L_4'$ and $L_4''$ are the same. In another embodiment, $L_4$ and $L_4'$ are the same and $L_4''$ is different. In another embodiment, $L_4$ and $L_4''$ are the same and $L_4'$ is different. In another embodiment, $L_4'$ and $L_4''$ are the same and $L_4$ is different.

In some embodiments, $L_5$ of the structures of formulas XI-XIII is absent. In other embodiments, $L_5$ is a substituted or unsubstituted linear or branched alkyl chain of 1-50 carbon atoms. In other embodiments, $L_5$ is a linear alkyl of 2-6 carbon atoms. In other embodiments, $L_5$ is ethylene. In other embodiments, $L_5$ is propylene. In other embodiments, $L_5$ is butylene. In other embodiments, $L_5$ is methylene. In other embodiments, $L_5$ is $(CH_2)_n$, wherein n is an integer between 1 and 8; in some embodiments n is 1, 2, 3, 4, 5, 6, 7, or 8; each is a separate embodiment according to this invention. In other embodiments, $L_5$ is —$CH_2$—$CH_2$—. In other embodiments, $L_5$ is a substituted or unsubstituted linear or branched alkyl ether chain of 1-50 carbon atoms. In other embodiments, $L_5$ is substituted or unsubstituted linear or branched alkyl phosphate chain of 1-50 carbon atoms. In other embodiments, $L_5$ is substituted or unsubstituted linear or branched alkyl amide chain of 1-50 carbon atoms. In other embodiments, $L_5$ is substituted or unsubstituted linear or branched alkyl diamide chain of 1-50 carbon atoms. In other embodiments, $L_5$ is substituted or unsubstituted linear or branched alkyl amine chain of 1-50 carbon atoms. In other embodiments, $L_5$ is any combination of the embodiments above.

In another embodiment, m of the structure of formula XII or XV is 1. In another embodiment, m is 2. In another embodiment, m is 3. In another embodiment, m is 4.

In another embodiment, p of the structure of formula XII or XV is 1. In another embodiment, p is 2. In another embodiment, p is 3. In another embodiment, p is 4.

In another embodiment, q of the structure of formula XII or XV is 1. In another embodiment, q is 2. In another embodiment, q is 3. In another embodiment, q is 4. In another embodiment, q is 5. In another embodiment, q is 6.

In another embodiment, m is 1, p is 2 and q is 4.

In another embodiment, n of the structure of formula XIV is 1. In another embodiment, n is 2. In another embodiment, n is 3. In another embodiment, n is 4.

In one embodiment, this invention is directed to a His-tag binding compound of formula XI-XIV, coupled through the $R_1$ moiety to an oligonucleotide, a peptide, a protein, a labeling moiety, a drug, a solid support, a small molecule, or any combination thereof. In one embodiment, this invention is directed to a His-tag binding compound of formula XV, coupled through the maleimide moiety to an oligonucleotide, a peptide, a protein, a labeling moiety, a drug, a solid support, a small molecule, or any combination thereof. In one embodiment, this invention is directed to a His-tag binding compound of formula XVI, coupled through the $NH_2$ moiety to an oligonucleotide, a peptide, a protein, a labeling moiety, a drug, a solid support, a small molecule, or any combination thereof. In another embodiment, the oligonucleotide is DNA. In another embodiment, the oligonucleotide is RNA. In another embodiment, the labeling moiety is as described hereinbelow. In another embodiment, the labeling moiety is a fluorescent dye. Examples of fluorescent dyes include but are not limited to: dansyl, fluorescein (6-FAM), FAM, cyanine dyes (e.g. Cy3, Cy5), sulfoindocyanine, SCy5, Nile red, rhodamine, perylene, fluorenyl, coumarin, 7-methoxycoumarin (Mca), dabcyl, NBD, Nile blue, TAMRA, BODIPY, FITC, Thiazole orange, Quinoline blue, Thiazole red, or derivative thereof. In another embodiment, the dye is FITC. In another embodiment, the dye is Nile Red. In another embodiment, the dye is SCy5. In another embodiment, the labeling moiety is a solvatochromic dye. In another embodiment, the small molecule is a therapeutically active molecule.

C. Fluorescent Probes for Sensing and Imaging Comprising His-Tag Binding Compounds of the Invention.

In some embodiments, this invention if directed to a compound according to this invention, or a derivative thereof, coupled to a labeling moiety as described hereinbelow. In some embodiments, the labeling moiety is a fluorescent dye. In some embodiments, the labeling moiety is covalently bound to the compound. In some embodiments, the labeling moiety is covalently bound to the compound via a first linker. In some embodiments, the compound is further complexed with at least one metal ion. In some embodiments, upon complexation to at least one metal ion, the compound can selectively bind histidine-tags of various labeled proteins, thereby becoming a His-tag binding compound. In some embodiments, the His-tag binding compound is a molecular probe for fluorescence sensing and imaging. In some embodiments, the His-tag binding compound is a fluorescent probe. In some embodiments, the His-tag binding compound does not perturb living cells function. In some embodiments, the His-tag binding compound is capable of traversing a biological membrane. In some embodiments, the His-tag binding compound is a genetically targeted sensor.

In some embodiments, this invention if directed to a small molecule probe for fluorescence sensing and imaging, comprising a His-tag binding compound according to this invention, or a derivative thereof, complexed to at least one metal ion.

In some embodiments, this invention if directed to a genetically targeted sensor, comprising a His-tag binding compound according to this invention, or a derivative thereof. In some embodiments, the sensor comprises a His-tag binding compound according to this invention, or derivative thereof, and a labeling moiety bound thereto. In some embodiments, the labeling moiety is a fluorescent dye. In some embodiments, the compound is complexed to at least one metal ion. In some embodiments, the metal ion is selected from: Ni(II), Co(II) and Co(III).

In some embodiment, this invention is directed to a fluorescent probe, comprising a compound according to this invention as described hereinabove and a fluorescent dye bound thereto, directly or via a first linker, wherein the compound is complexed to at least one metal ion.

In some embodiments, the His-tag binding compound which is coupled through $R_1$ to a labeling moiety is represented by the structure of formula XXI-XXIII as described herein below.

In some embodiment, this invention is directed to a compound, represented by the structure of formula XXI:

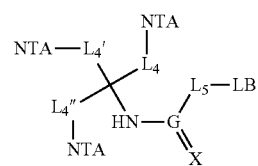

XXI wherein $L_4$, $L_4'$, and $L_4''$ are each independently a substituted or unsubstituted linear or branched alkyl chain of 1-20 carbon atoms, substituted or unsubstituted linear or branched alkyl ether chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl diamide chain of 1-20 carbon atoms, substituted or unsubstituted linear or branched alkyl amine chain of 1-20 carbon atoms or any combination thereof;

$L_5$ is absent or is a substituted or unsubstituted linear or branched alkyl chain of 1-50 carbon atoms (e.g. ethylene: —$CH_2$—$CH_2$—), substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms or any combination thereof;

G=X is absent, or is $CH_2$, C=O, C(O)NH, C=S, C(S)NH, C(O)O, S=O or $SO_2$;

LB is a labeling moiety; and

NTA is nitrilotriacetic acid or a protected derivative thereof.

In some embodiment, the compound is represented by the structure of formula XXII:

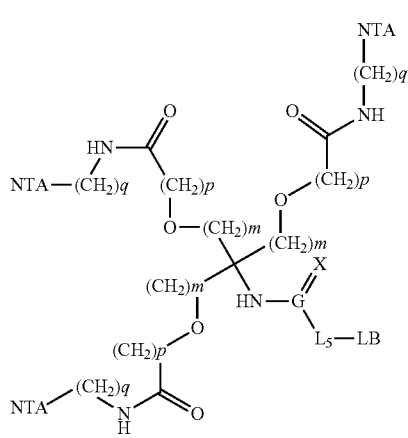

XXII wherein m, p and q are each independently an integer between 1 and 8;

$L_5$ is absent or is a substituted or unsubstituted linear or branched alkyl chain of 1-50 carbon atoms (e.g. ethylene: —$CH_2$—$CH_2$—), substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms or any combination thereof;

G=X is absent, or is $CH_2$, C=O, C(O)NH, C=S, C(S)NH, C(O)O, S=O or $SO_2$;

LB is a labeling moiety; and

NTA is nitrilotriacetic acid or a protected derivative thereof.

In some embodiment, the compound is represented by the structure of formula XXIII:

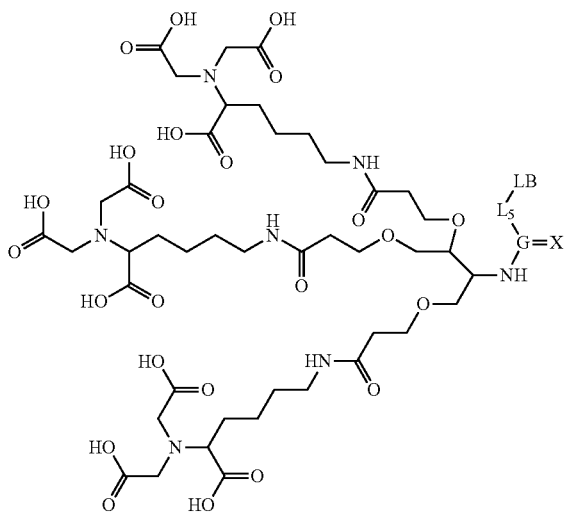

XXIII wherein $L_5$ is absent or is a substituted or unsubstituted linear or branched alkyl chain of 1-50 carbon atoms (e.g. ethylene: —$CH_2$—$CH_2$—), substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms or any combination thereof;

G=X is absent, or is $CH_2$, C=O, C(O)NH, C=S, C(S)NH, C(O)O, S=O or $SO_2$;

LB is a labeling moiety.

In some embodiment, the compound is represented by the structure of compounds 313, 314 and 315:

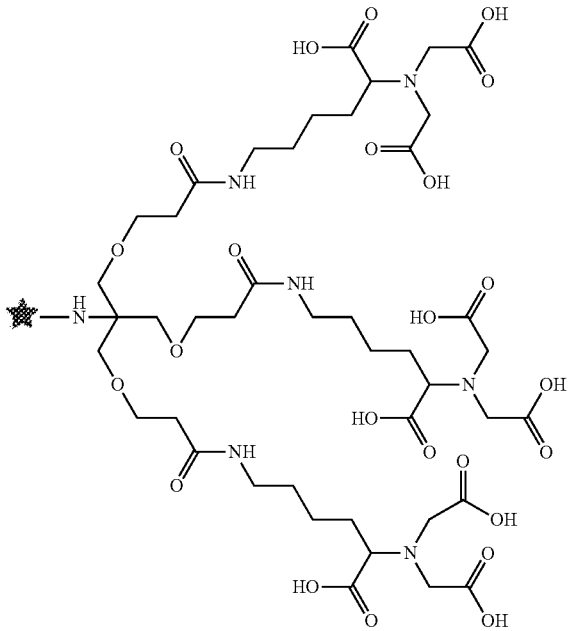

-continued

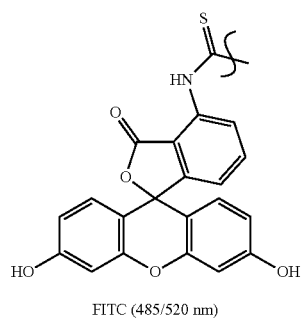

FITC (485/520 nm)
314

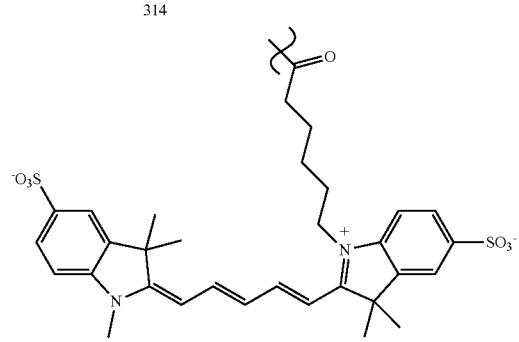

SCy5 (640/675 nm)
313

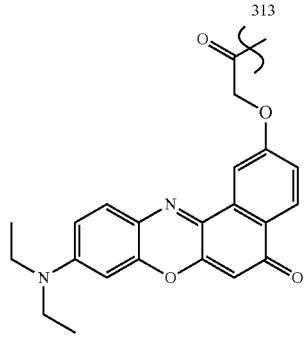

Nile Red (560/630 nm)
315

In some embodiments, upon complexation to at least one metal ion, compound of formula XXI-XXIII, and compounds 313, 314 and 315 can selectively bind His-tags of various labeled proteins, thereby becoming a fluorescent probe or a molecular probe for fluorescence sensing and imaging. In some embodiments, the compound is a genetically targeted sensor. In some embodiments, the metal ion is cobalt (Co). In some embodiments, the metal ion is nickel (Ni). In some embodiments, the metal ion is Ni(II). In some embodiments, the metal ion is Co(II). In some embodiments, the metal ion is Co(III). In some embodiments, the compound is complexed to three; two; one metal ions; each is a separate embodiment according to this invention. In some embodiments, the compound is complexed to three Ni(II) ions.

In some embodiments, LB comprises labeling moiety as described hereinbelow for labeling moiety. In some embodiments, LB is a fluorescent dye. In some embodiment LB comprises a fluorescent dye. Examples of fluorescent dyes include but are not limited to: dansyl, fluorescein (6-FAM), FAM, cyanine dyes (e.g. Cy3, Cy5), sulfoindocyanine, SCy5, nile red, rhodamine, perylene, fluorenyl, coumarin, 7-methoxycoumarin (Mca), dabcyl, NBD, Nile blue, TAMRA, BODIPY, FITC, Thiazole orange, Quinoline blue, Thiazole red, or derivative thereof. In some embodiments, LB comprises FITC, Nile Red or SCy5. In some embodiments, LB comprises the following structures:

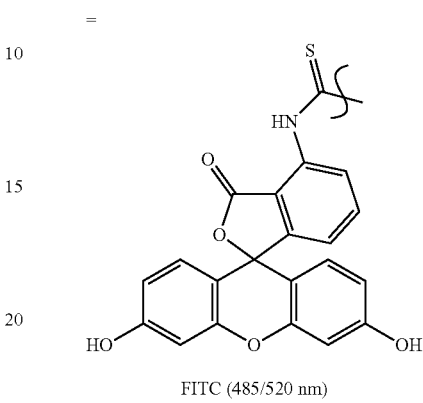

FITC (485/520 nm)

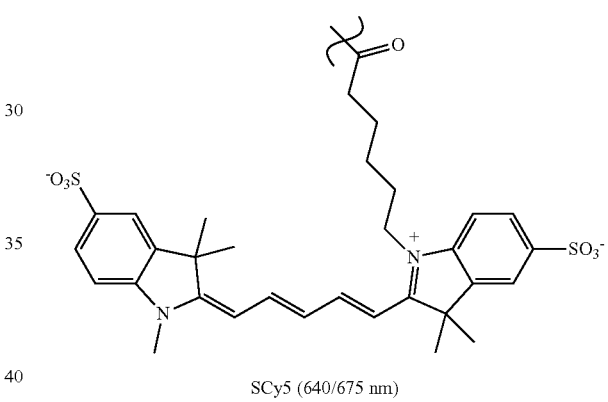

SCy5 (640/675 nm)

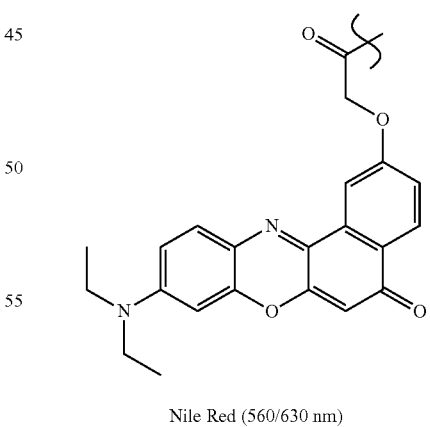

Nile Red (560/630 nm)

In some embodiments, the His-tag binding compound of formula XI-XVI, described hereinabove, is coupled through the $R_1$ moiety to a labeling moiety. In some embodiments, the His-tag binding compound which is coupled through $R_1$ to a labeling moiety is represented by the structure of compounds 313, 314 and 315:

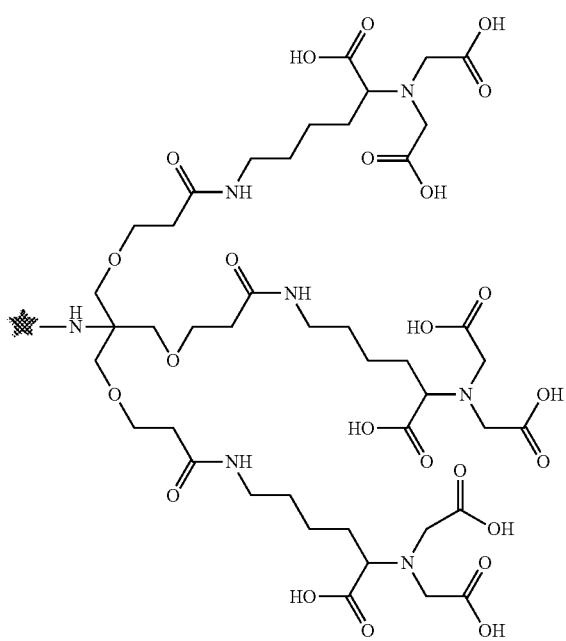

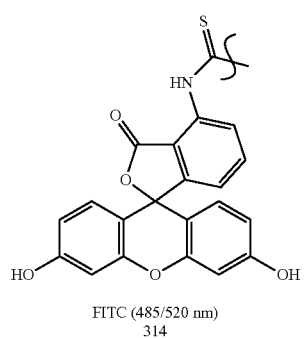

FITC (485/520 nm)
314

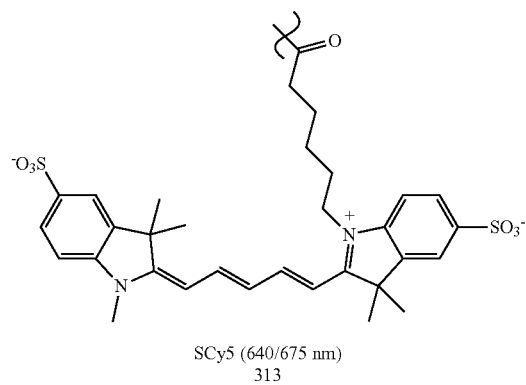

SCy5 (640/675 nm)
313

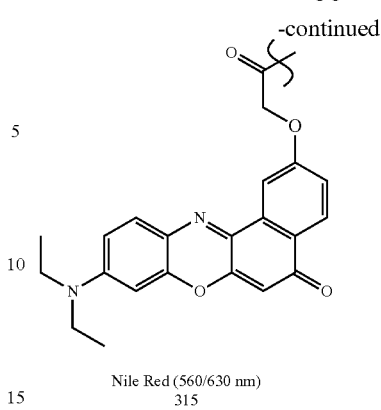

Nile Red (560/630 nm)
315

In one embodiment, this invention is directed to a His-tag binding compound of formula XI-XVI as described herein above, coupled to an oligonucleotide. In some embodiments, the compound is covalently bound to the oligonucleotide through the $R_1$ moiety. In some embodiments, the compound is covalently bound to the oligonucleotide through the $R_1$ moiety via a first linker, which links the $R_1$ moiety with the 3' or 5' end of the oligonucleotide. In some embodiment, the compound is further covalently bound to a fluorophore directly or via a third linker, which links the fluorophore with the 3' or 5' end of the oligonucleotide. In some embodiment, the compound is a fluorescent probe. In some embodiment, the compound is a genetically targeted sensor.

In some embodiments, the His-tag binding compound which is coupled through $R_1$ to an oligonucleotide is represented by the structure of the first compound (X-ODN-1) as described herein below in section D (Artificial receptors and recombinant cells comprising thereof).

In some embodiments, the His-tag binding compound which is coupled through $R_1$ to an oligonucleotide is represented by the structure of formula J:

$$F\text{-}L_3\text{-}ODN1\text{-}L_1\text{-}Y_1 \tag{J}$$

wherein
F is a labeling moiety (e.g., fluorescent dye) or absent;
$L_3$ is a third linker or absent;
ODN1 is a first oligonucleotide sequence;
$L_1$ is a first linker or absent; and
Y is a His-tag binding compound.

In some embodiments, the His-tag binding compound is a derivative of compound XI-XVI as described hereinabove.

In some embodiments, the His-tag binding compound which is coupled through $R_1$ to an oligonucleotide is represented by the structure of formula H:

H

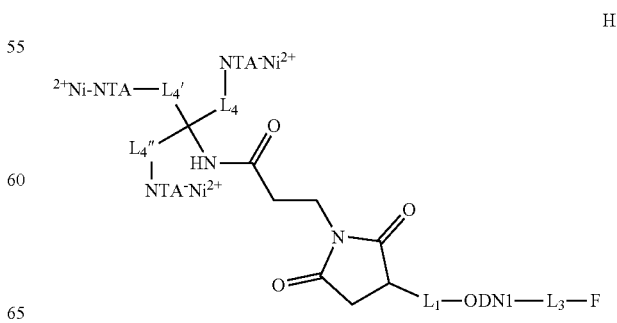

wherein

F is a labeling moiety or absent (e.g., a fluorescent dye);

$L_3$ is a third linker or absent;

ODN1 is a first oligonucleotide sequence;

$L_1$ is a first linker or absent;

$L_4$, $L_4'$, and $L_4''$ are each independently a substituted or unsubstituted linear or branched alkyl chain of 1-20 carbon atoms, substituted or unsubstituted linear or branched alkyl ether chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl diamide chain of 1-20 carbon atoms, substituted or unsubstituted linear or branched alkyl amine chain of 1-20 carbon atoms, or any combination thereof; and NTA is nitrilotriacetic acid.

In some embodiments, the His-tag binding compound which is coupled through $R_1$ to an oligonucleotide is represented by the structure of formula H(a):

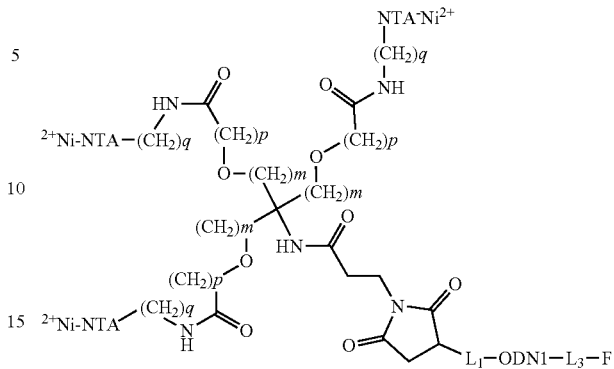

wherein

F is a labeling moiety or absent (e.g., a fluorescent dye);

$L_3$ is a third linker or absent;

ODN1 is a first oligonucleotide sequence;

$L_1$ is a first linker or absent;

m, p and q are each independently an integer number between 1 and 8; and

NTA is nitrilotriacetic acid.

In some embodiments, the His-tag binding compound which is coupled through $R_1$ to an oligonucleotide is represented by the structure of formula H(b):

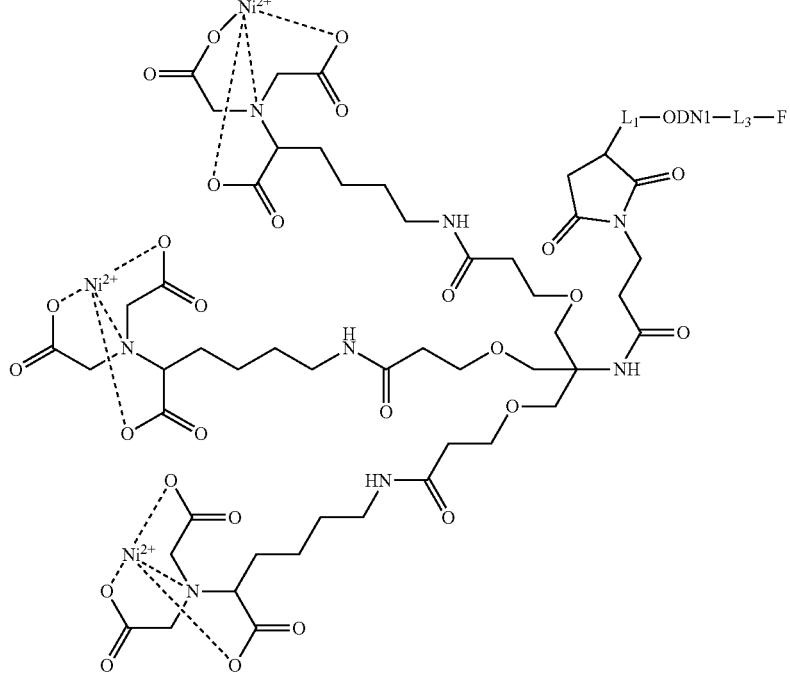

wherein

F is a labeling moiety or absent (e.g., a dye or a dye derivative);

$L_a$ is a third linker or absent;

ODN1 is a first oligonucleotide sequence; and $L_1$ is a first linker or absent.

In some embodiments, the His-tag binding compound which is coupled through $R_1$ to an oligonucleotide is represented by the structure of the nickel complexes of the following compounds:

Compound 100
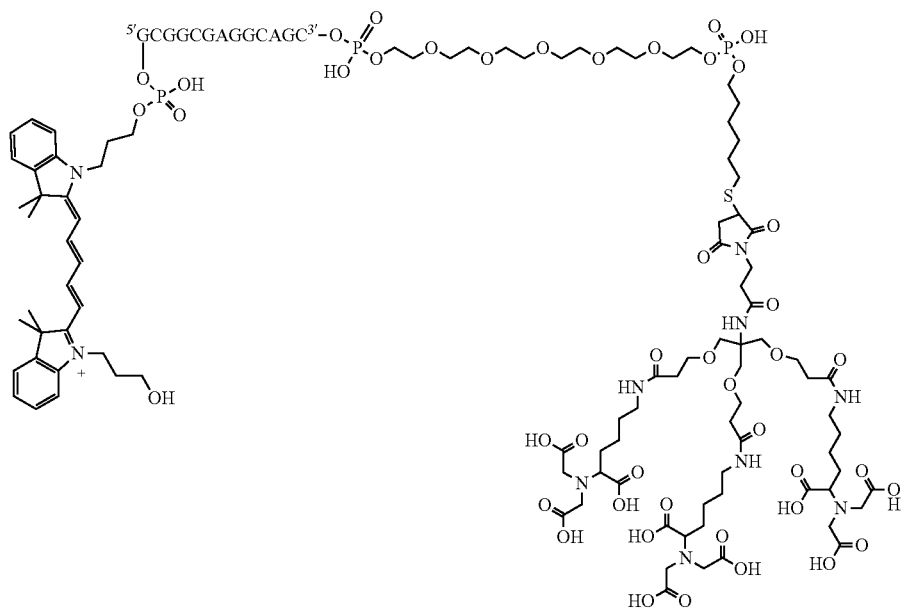
[CY5-ODN-1]
Compound 101
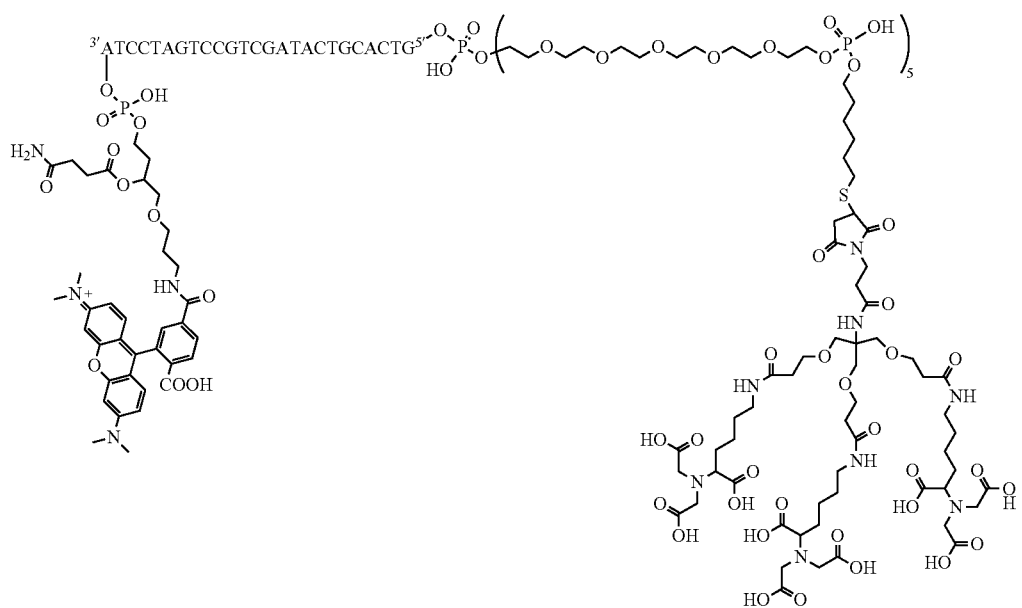
[TAMRA-ODN-1]

Compound 102
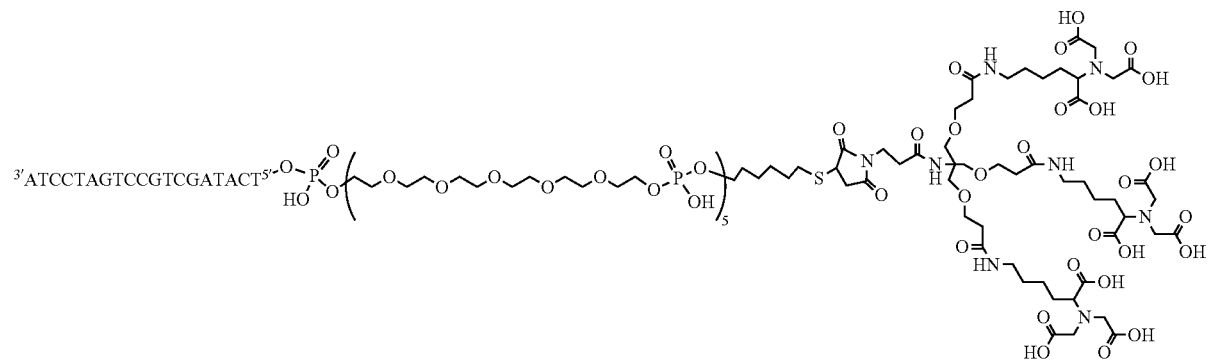
[ODN-1a]
Compound 103
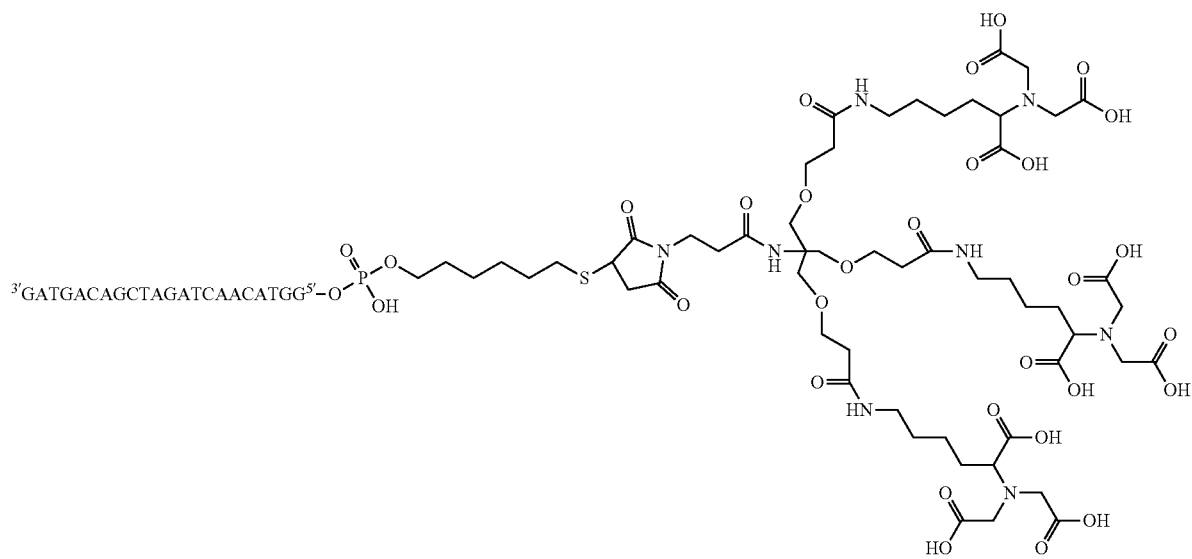
[ODN-1b]

Compound 104

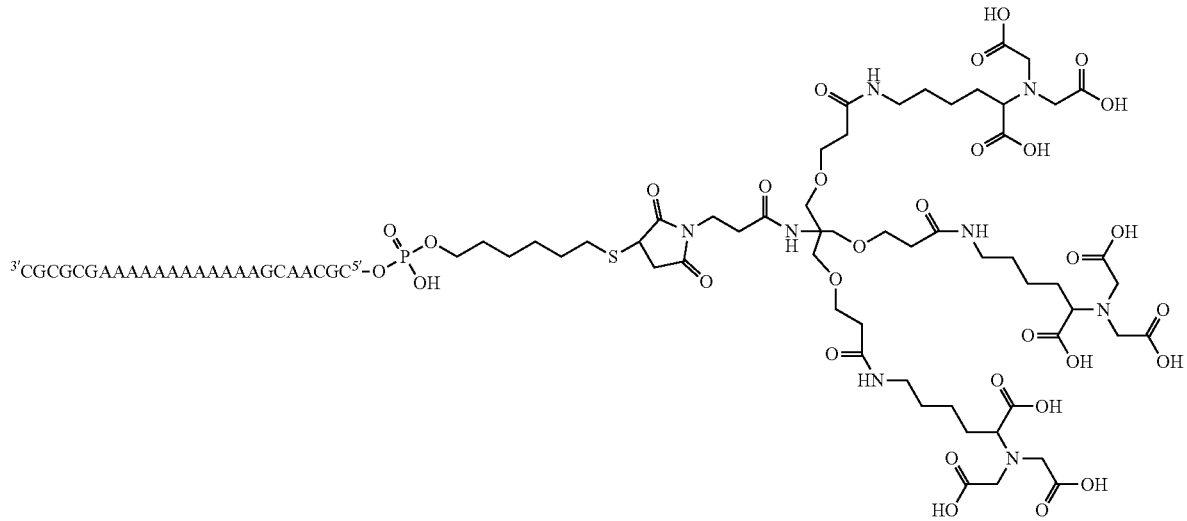

[ODN-1c]

In some embodiments, $Y_1$ of formulas J comprises Ni-nitrilotriacetic acid (Ni-NTA), bis-Ni-NTA, or tris-Ni-NTA. In some embodiments, $Y_1$ comprises a derivative of Ni-nitrilotriacetic acid (Ni-NTA), bis-Ni-NTA, or tris-Ni-NTA, wherein the term "derivative" includes but not limited to alkyl derivatives, amide derivatives, amine derivatives, carboxy derivatives, and the like. In some embodiments, $Y_1$ comprises a derivative of tris-Ni-nitrilotriacetic acid (tris-Ni-NTA), a derivative of bis-Ni-nitrilotriacetic acid (bis-Ni-NTA), a derivative of mono-Ni-nitrilotriacetic acid (Ni-NTA); each represents a separate embodiment according to this invention. In some embodiments, $Y_1$ comprises any monomolecular compound which comprises three Ni-NTA moieties (i.e., tris-Ni-NTA). In some embodiments, $Y_1$ is represented by the structure of formulas D, D(a), D(b), G, G(a), G(b) as described herein below. In some embodiments, $Y_1$ comprises the structure of formulas D, D(a), D(b), G, G(a), G(b) as described herein below.

In some embodiments, $L_1$ of formulas J, H, H(a), and H(b) is a first linker. In some embodiments, $L_1$ is absent. In some embodiments, $L_1$ is bound to the 3' end of ODN1. In some embodiments, $L_1$ is bound to the 5' end of ODN1. In some embodiments, $L_1$ is bound to $Y_1$ through an amide bond, an ester bond, a phosphate bond, an ether bond, a thioether bond, each represents a separate embodiment according to this invention. In some embodiments, $L_1$ is as defined for "first linker" hereinbelow.

In some embodiments, ODN1 of formulas J, H, H(a), and H(b) is a first oligonucleotide sequence. In some embodiments, ODN1 is directly bound to $Y_1$, through an amide bond, an ester bond, a phosphate bond, an ether bond, each represents a separate embodiment according to this invention. In some embodiments, ODN1 is directly bound to F, through an amide bond, an ester bond, a phosphate bond, an ether bond, a thioether bond, each represents a separate embodiment according to this invention. In some embodiments, ODN1 is directly bound to F, through a phosphate moiety.

In some embodiments, $L_3$ of formulas J, H, H(a), and H(b) is a third linker. In some embodiments, L is absent. In some embodiments, $L_3$ is bound to the 3' end of ODN1. In some embodiments, $L_3$ is bound to the 5' end of ODN1. In some embodiments, $L_3$ is bound to F through an amide bond, an ester bond, a phosphate bond, an ether bond, a thioether bond, each represents a separate embodiment according to this invention. In some embodiments, $L_3$ is as defined for "third linker" hereinbelow.

In some embodiments, each of $L_1$, $L_4'$, and $L_4''$ of the structure of formula H, is independently a substituted or unsubstituted linear or branched alkyl chain of 1-20 carbon atoms, substituted or unsubstituted linear or branched alkyl ether chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl diamide chain of 1-20 carbon atoms, substituted or unsubstituted linear or branched alkyl amine chain of 1-20 carbon atoms or any combination thereof; each represents a separate embodiment according to this invention. In some embodiments, each of $L_4$, $L_4'$, and $L_4''$ is a combination of alkyl ether and alkyl amide (i.e., alkylether-alkylamide). In another embodiment, each of $L_4$, $L_4'$, and $L_4''$ is independently —$(CH_2)_q$—NHCO—$(CH_2)_p$—O—$(CH_2)_m$—, wherein q, p and m are each independently an integer between 1 and 8. In another embodiment, q is 4, p is 2 and m is 1. In another embodiment, each of $L_4$, $L_4'$, and $L_4''$ is —$(CH_2)_4$—NHCO—$(CH_2)_2$—O—$CH_2$—. In another embodiment, each of $L_4$, $L_4'$, and $L_4''$ is represented by the following structure:

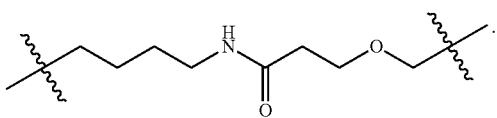 [SMILES: *CCCCNC(=O)CCOC*]

In one embodiment, $L_4$, $L_4'$ and $L_4''$ are different. In another embodiment, $L_4$, $L_4'$ and $L_4''$ are the same. In another embodiment, $L_4$ and $L_4'$ are the same and $L_4''$ is different. In another embodiment, L$_4$ and L$_4$" are the same and L$_4$' is different. In another embodiment, L$_4$' and L$_4$" are the same and L$_4$ is different.

In some embodiments, F of formulas J, H, H(a), and H(b) is a labeling moiety as defined for "labeling moieties" hereinbelow. In some embodiments, F is absent. In some embodiments, F is a fluorescent dye. Examples of fluorescent dyes include but are not limited to: dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, TAMRA, BODIPY, FITC, Thiazole orange, Quinoline blue, Thiazole red, or derivative thereof. In some embodiments, F is a dye derivative. In some embodiments, a labeling moiety is bound to ODN1 through an amide bond, an ester bond, a phosphate bond, an ether bond, a thioether bond; each represents a separate embodiment according to this invention. In some embodiments, a labeling moiety F is bound to L$_3$ through an amide bond, an ester bond, a phosphate bond, an ether bond, a thioether bond; each represents a separate embodiment according to this invention.

As used herein, "labeling moieties" or "labels" are chemical or biochemical moieties useful for labeling a compound. Such labeling moieties include fluorescent agents, chemiluminescent agents, chromogenic agents, quenching agents, radionucleotides, enzymes, substrates, cofactors, inhibitors, nanoparticles, magnetic particles, and other moieties known in the art. Labels are capable of generating a measurable signal and may be covalently or noncovalently joined to a his-tag compound according to this invention. In some embodiments, the labeling moieties are covalently bound to the compounds of the invention. In some embodiments, the labeling moieties are covalently bound to the compounds of the invention through a linker or a spacer.

In illustrative embodiments, the compounds according to this invention, may be labeled with a "fluorescent dye" or a "fluorophore." As used herein, a "fluorescent dye" or a "fluorophore" is a chemical group that can be excited by light to emit fluorescence. Some fluorophores may be excited by light to emit phosphorescence. Dyes may include acceptor dyes that are capable of quenching a fluorescent signal from a fluorescent donor dye. In some embodiments, the dye is selected from: dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, TAMRA, BODIPY, FITC, Thiazole orange, Quinoline blue, Thiazole red, or a derivative thereof. Non limiting examples of Dyes that may be used in the disclosed compounds, system and methods include, but are not limited to, the following dyes and/or dyes sold under the following trade names: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-Hydroxy Tryptamine (HAT); 5-ROX (carboxy-X-rhodamine); 6-Carboxyrhodamine 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue™; Calcium Crimson™, Calcium Green; Calcium Orange; Calcofluor White; Cascade Blue™; Cascade Yellow; Catecholamine; CCF2 (GeneBlazer); CFDA; CFP-Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.18; Cy3.5™; Cy3™; Cy5.18; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF;

Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; NED™; Nitrobenzoxadidole; Noradrenaline; Nuclear Fast Red; Nuclear Yellow; Nylosan Brilliant Iavin EBG; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; TET™; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3: TriColor (PE-Cy5); TRITC TetramethylRodamineIsoThioCyanate; True Blue; TruRed; Ultralite; Uranine B; Uvitex SFC; VIC®; wt GFP; WW 781; X-Rhodamine; XRITC: Xylene Orange; Y66F; Y66H; Y66W; Yellow GFP; YFP; YO-PRO-1; YO-PRO-3; YOYO-1; YOYO-3; and salts thereof; each is a separate embodiment according to this invention.

Fluorescent dyes or fluorophores may include derivatives that have been modified to facilitate conjugation to another reactive molecule. As such, fluorescent dyes or fluorophores may include amine-reactive derivatives such as isothiocyanate derivatives and/or succinimidyl ester derivatives of the fluorophore.

In some embodiments, the labeling moiety on the compounds according to the invention, is a quencher. Quenching may include dynamic quenching (e.g., by FRET), static quenching, or both. Illustrative quenchers may include Dabcyl. Illustrative quenchers may also include dark quenchers, which may include black hole quenchers sold under the tradename "BHQ" (e.g., BHQ-0, BHQ-1, BHQ-2, and BHQ-3, Biosearch Technologies, Novato, Calif.). Dark quenchers also may include quenchers sold under the tradename "QXL™" (Anaspec, San Jose, Calif.). Dark quenchers also may include DNP-type non-fluorophores that include a 2,4-dinitrophenyl group.

The labels can be conjugated to the compounds according to this invention directly, or indirectly through linkers or spacers, by a variety of techniques. In some embodiments, the labeling moiety is a fluorescent agent, fluorescent dye, fluorophore, solvatochromic dye, chemiluminescent agent, chromogenic agent, quenching agent, radionucleotide, or a magnetic particle; each is a separate embodiment according to this invention.

In some embodiments, the His-tag binding compound which is coupled through the $R_1$ moiety to a labeling moiety is a fluorescent probe. In some embodiments, the His-tag binding compound which is coupled through the $R_1$ moiety to a labeling moiety is a genetically targeted sensor.

In some embodiments, this invention is directed to a fluorescent probe, comprising the compound of formula XI-XVI, wherein said compound is covalently bound to a labeling moiety. In some embodiments, the compound is covalently bound to the labeling moiety through the $R_1$ moiety, directly or via a first linker. In some embodiments, the compound is complexed to at least one metal ion. In some embodiments, the metal ion is Ni(II). In some embodiments, the fluorescent probe is a genetically targeted sensor.

In one embodiment, this invention is directed to a fluorescent probe, comprising the compound of formula XI-XVI, wherein said compound is covalently bound to a labeling moiety through a first linker, which links between the $R_1$ moiety of said compound and said labeling moiety. In some embodiments, the compound is complexed to at least one metal ion. In some embodiments, the metal ion is Ni(II). In some embodiments, the fluorescent probe is a genetically targeted sensor.

In one embodiment, this invention is directed to a fluorescent probe, comprising a compound of formula XI-XV, covalently bound to an oligonucleotide through a first linker, which links between the $R_1$ moiety of said compound and said oligonucleotide. In some embodiments, the compound is further bound to a labeling moiety. In some embodiments, the labeling moiety is bound to the oligonucleotide. In some embodiments, the labeling moiety is bound to the oligonucleotide via a third linker. In some embodiments, the compound is complexed to at least one metal ion. In some embodiments, the metal ion is Ni(II).

In another embodiment, the labeling moiety is a fluorescent dye.

In another embodiment, the compound is coupled through the $R_1$ moiety to an oligonucleotide, a peptide, a protein, a labeling moiety, a drug, a solid support, or a small molecule via a first linker.

a. A First Linker

In some embodiments, the His-tag binding compound or precursor of the invention, is coupled through the $R_1$ moiety to an oligonucleotide, a peptide, a protein, a labeling moiety, a drug, a solid support, or a small molecule via a first linker. In some embodiments, the first linker comprises a phosphate moiety, a PEG moiety, an alkyl moiety, a thioalkyl moiety or any combination thereof; each represents a separate embodiment according to the invention. In some embodiments, the first linker is covalently bound to the 3' end of the oligonucleotide. In some embodiments, the first linker is covalently bound to the 5' end of the oligonucleotide. In some embodiments, the first linker is covalently bound to the oligonucleotide, a peptide, a protein, a labeling moiety, a drug, a solid support, a small molecule through an amide bond, an ester bond, a phosphate bond, an ether bond, a thioether bond; each represents a separate embodiment according to this invention. In some embodiments, the first linker is covalently bound to the oligonucleotide through a phosphate moiety.

b. A Third Linker

In some embodiments, the His-tag binding compound of the invention, coupled through the $R_1$ moiety to an oligonucleotide, a peptide, a protein, a labeling moiety, a drug, a solid support, or a small molecule, directly or via a first linker, is further coupled to a labeling moiety directly or via a third linker. In some embodiments, the labeling moiety is a fluorescent dye. In some embodiments, the third linker comprises a phosphate moiety, a PEG moiety, an alkyl moiety, a thioalkyl moiety or any combination thereof; each represents a separate embodiment according to the invention. In some embodiments, the third linker is covalently bound to the 3' end of the oligonucleotide. In some embodiments, the third linker is covalently bound to the 5' end of the oligonucleotide. In some embodiments, the third linker is covalently bound to the oligonucleotide, a peptide, a protein, a labeling moiety, a drug, a solid support, or a small molecule through an amide bond, an ester bond, a phosphate bond, an ether bond, a thioether bond; each represents a separate embodiment according to this invention. In some embodiments, the second linker is covalently bound to the oligonucleotide through a phosphate moiety.

In some embodiments, the first and/or the third linker is any chemical fragment which comprises at least one segment of a commercially available phosphoramidite spacer derivative. Phosphoramidite compounds are used as reactive agents for linking oligonucleotides according to this invention with other moieties, e.g., the binder of this invention, the labeling moiety, the synthetic agents, etc. Non limiting examples of such phosphoramidite derivatives, useful for linking oligonucleotides with other moieties include:

branched alkyl ether chain of 1-20 carbon atoms, oligoethylene glycol, polyethylene glycol (PEG), oligopropylene glycol, polypropylene glycol (PPG), substituted or unsubstituted linear or branched thioalkyl chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl ester of 1-20 carbon atoms, substituted or unsubstituted linear or branched alkyl diamide chain of 2-10 carbon atoms, substituted or unsubstituted linear or branched alkyl triazole of 1-20 carbon atoms, substituted or unsubstituted linear or branched alkyl amine chain of 1-20 carbon atoms or any combination thereof; each represents a separate embodiment according to this invention.

In some embodiments, the first and/or the third linker comprises at least one polyethyleneglycol (PEG) moiety. In some embodiments, the first and/or the third linker, comprises at least one phosphate moiety. In some embodiments, the first and/or the third linker, comprises at least one alkyl ether moiety. In some embodiments, the first and/or the third linker, comprises at least one alkyl diamide moiety. In some embodiments, the first and/or the third linker, comprises at least one alkyl moiety. In some embodiments, the first and/or the third linker, comprises at least one thioalkyl moiety. In some embodiments, the first and/or the third linker, comprises at least one polyethyleneglycol (PEG) moiety, at least one phosphate moiety, at least one thioalkyl moiety, at least one alkyl moiety, or any combination thereof.

In some embodiments, the first and/or the third linker is represented by the following formula:

—[(CH$_2$O)$_k$—PO$_3$H]$_l$(CH$_2$)$_w$—S— wherein k and l are each independently an integer number between 0 and 10; and w is an integer number between 1 and 10.

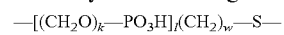

Spacer Phosphoramidite 9

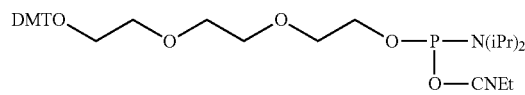

Spacer Phosphoramidite 18

Spacer C12 CE Phosphoramidite

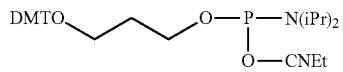

Amino-Modifier Serinol Phosphoramidite

Spacer Phosphoramidite C3

In some embodiments, the first and/or the third linker is a substituted or unsubstituted linear or branched alkyl chain of 1-20 carbon atoms, substituted or unsubstituted linear or In some embodiments, k is 0. In some embodiments, k is 6. In some embodiments, k is 1, 2, 3, 4, 5, 7, 8, 9, 10; each is a separate embodiment according to this invention.

In some embodiments, l is 0. In some embodiments, l is 1. In some embodiments, l is 5. In some embodiments, l is 2, 3, 4, 6, 7, 8, 9, 10; each is a separate embodiment according to this invention.

In some embodiments, w is 6. In some embodiments, w is 1, 2, 3, 4, 5, 7, 8, 9, 10; each is a separate embodiment according to this invention.

An "alkyl" or "alkylene" group refers, in one embodiment, to a saturated aliphatic hydrocarbon, including straight-chain and branched-chain. In one embodiment, the alkyl group has 1-20 carbons. In another embodiment, the alkyl has 1-12 carbons. In another embodiment, the alkyl group has 1-7 carbons. In another embodiment, the alkyl group has 1-5 carbons. In another embodiment, the alkyl group has 1-6 carbons. In another embodiment, the alkyl group has 1-4 carbons. The alkyl group may be unsubstituted or substituted by one or more groups selected from halogen, hydroxy, hydroxyalkyl, alkoxy, haloalkyl, carbonyl, amido, alkylamido, dialkylamido, nitro, cyano, amino, alkylamino, dialkylamino, carboxyl, thiol and thioalkyl. In another embodiment, the alkyl is —$(CH_2)_6$—. In another embodiment, the alkyl is —$(CH_2)_2$—. In another embodiment, the alkyl is —$(CH_2)_3$—. In another embodiment, the alkyl is —$CH_2$—. In another embodiment, the alkyl is —$CH_2$—$CH(CH_2$—$OH)$—$(CH_2)_4$—. In another embodiment, the alkyl is —$CH_2$—$CH(CH_2$—$OH)$—. In some embodiments the alkyl of this invention is optionally substituted and optionally interrupted by a heteroatom consisting of O, N, P, S or combination thereof.

A "haloalkyl" group refers, in another embodiment, to an alkyl group as defined above, which is substituted by one or more halogen atoms, e.g. by F, Cl, Br or I.

A "hydroxyl" group refers, in another embodiment, to an OH group. It is understood by a person skilled in the art that when $R_1$, $R_2$ or $R_3$ in the compounds of the present invention is OR, then R is not OH.

In one embodiment, the term "halogen" or "halo" refers to a halogen, such as F, Cl, Br or I.

An "alkynyl" refers to unsaturated hydrocarbon which comprises at least one carbon-carbon triple bond. In one embodiment, the alkynyl group has 2-20 carbons. In another embodiment, the alkynyl has 2-12 carbons. In another embodiment, the alkynyl has 2-6 carbons. In another embodiment, the alkynyl has 2 carbons.

An "arylalkyl" group refers to an alkyl bound to an aryl, wherein alkyl and aryl are as defined above. An example of an aralkyl group is a benzyl group.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like. In one embodiment, the aryl group is a 4-8 membered ring. In another embodiment, the aryl group is a 4-12 membered ring(s). In another embodiment, the aryl group is a 6 membered ring. In another embodiment, the aryl group is a 5 membered ring. In another embodiment, the aryl group is 2-4 fused ring system.

An "alkyl ether" of this invention refers to an alkyl as defined above interrupted by one or more oxygen atoms. In another embodiment, alkyl ether refers to a PEG (poly ethylene glycol). In one embodiment, the alkylether has 1-6 carbon atoms. In another embodiment, the alkylether has 1-12 carbon atoms. In another embodiment, the alkylether has 1-20 carbon atoms. In another embodiment, the alkylether has 3 carbon atoms. In another embodiment, the alkylether has 4 carbon atoms. In another embodiment, the alkylether has 2-5 carbon atoms. In another embodiment, the alkylether has 2 carbon atoms. In another embodiment, the alkylether is —$CH_2$—$CH_2$—O—$CH_2$—.

An "alkyl amine" of this invention refers to an alkyl as defined above which has an amine moiety within the carbon atom chain. In another embodiment, alkyl amine refers to $(CH_2)_n$—NH—. In another embodiment, the amine moiety is at one end of the carbon chain. In another embodiment, the amine moiety is within the backbone of the carbon chain. In another embodiment, the alkyl amine is a substituted or unsubstituted linear or branched alkyl of 1-6 carbon atoms which has an amine moiety at one end. In another embodiment, the alkyl amine is a substituted or unsubstituted linear or branched alkyl of 1-12 carbon atoms which has an amine moiety at one end. In another embodiment, the alkyl amine is a substituted or unsubstituted linear or branched alkyl of 1-3 carbon atoms which has an amine moiety at one end.

An "alkyl amide" of this invention refers to an alkyl as defined above which has an amide moiety at one end. In another embodiment, alkyl amide refers to $(CH_2)_n$—NHC(O). In another embodiment, alkyl amide refers to $(CH_2)_n$—C(O)NH wherein n is an integer between 1 and 10. In another embodiment, the alkyl amide is a substituted or unsubstituted linear or branched alkyl of 1-6 carbon atoms which has an amide moiety at one end. In another embodiment, the alkyl amide is a substituted or unsubstituted linear or branched alkyl of 1-12 carbon atoms which has an amide moiety at one end. In another embodiment, the alkyl amide is a substituted or unsubstituted linear or branched alkyl of 1-3 carbon atoms which has an amide moiety at one end. In another embodiment, the alkyl amide is —$(CH_2)_6$—NHC(O). In another embodiment, the alkyl amide is —$(CH_2)_2$—NHC(O). In another embodiment, the alkyl amide is —$CH_2$—NHC(O). In another embodiment, the alkyl amide is —$CH_2$—$CH(CH_2$—$OH)$—$(CH_2)_4$—NHC(O). In another embodiment, the alkyl amide is —$CH_2$—$CH(CH_2$—$OH)$—NHC(O).

An "alkyl di-amide" of this invention refers to an alkyl as defined above which is interrupted by two amide moieties. In one embodiment, alkyl di-amide refers to $(CH_2)_n$—NHC(O)—$(CH_2)_m$—NHC(O) wherein n is an integer between 1 and 10. In another embodiment, the alkyl di-amide is a substituted or unsubstituted linear or branched alkyl of 1-6 carbon atoms which has an amide moiety at one end of the carbon chain and another amide moiety inside the backbone of the chain. In another embodiment, the alkyl di-amide is a substituted or unsubstituted linear or branched alkyl of 2-12 carbon atoms which has two amide moieties within the carbon chain. In another embodiment, the alkyl di-amide is a substituted or unsubstituted linear or branched alkyl of 2-6 carbon atoms which has two amide moieties within the carbon chain. In another embodiment, the alkyl di-amide is a substituted or unsubstituted linear or branched alkyl of 1-20 carbon atoms which has two amide moieties within the carbon chain. In another embodiment, the alkyl di-amide is —$CH_2$—$CH(CH_2OH)$—NHC(O)—$(CH_2)_2$—NHC(O)—. In another embodiment, the alkyl di-amide is —NHC(O)—$(CH_2)_2$—NHC(O)—.

An "alkyl triazole" of this invention refers to an alkyl as defined above which has a triazole moiety at one end. In one embodiment, alkyl triazole refers to $(CH_2)_n$-triazole wherein n is an integer between 1 and 10. In another embodiment n is 3. In another embodiment, the alkyl triazole is a substituted or unsubstituted linear or branched alkyl of 1-6 carbon atoms which has a triazole moiety at one end. In another embodiment, the alkyl triazole has 1-12 carbon atoms. In another embodiment, the alkyl triazole has 1-3 carbon atoms.

The term "substituted" refer to substitutions that include one or more groups selected from: halogen, hydroxy, hydroxyalkyl, alkoxy, haloalkyl, carbonyl, amido, alkylamido, dialkylamido, nitro, cyano, amino, alkylamino, dialkylamino, carboxyl, thiol, thioalkyl and the like.

In another embodiment, a "subject" refers to a mammal, a human, a female or a male.

The terms "comprises" and variations thereof do not have a limiting meaning where these terms appear in the description and claims.

Unless otherwise specified, "a," "an," "the," and "at least one" are used interchangeably and mean one or more than one.

Figure 3:
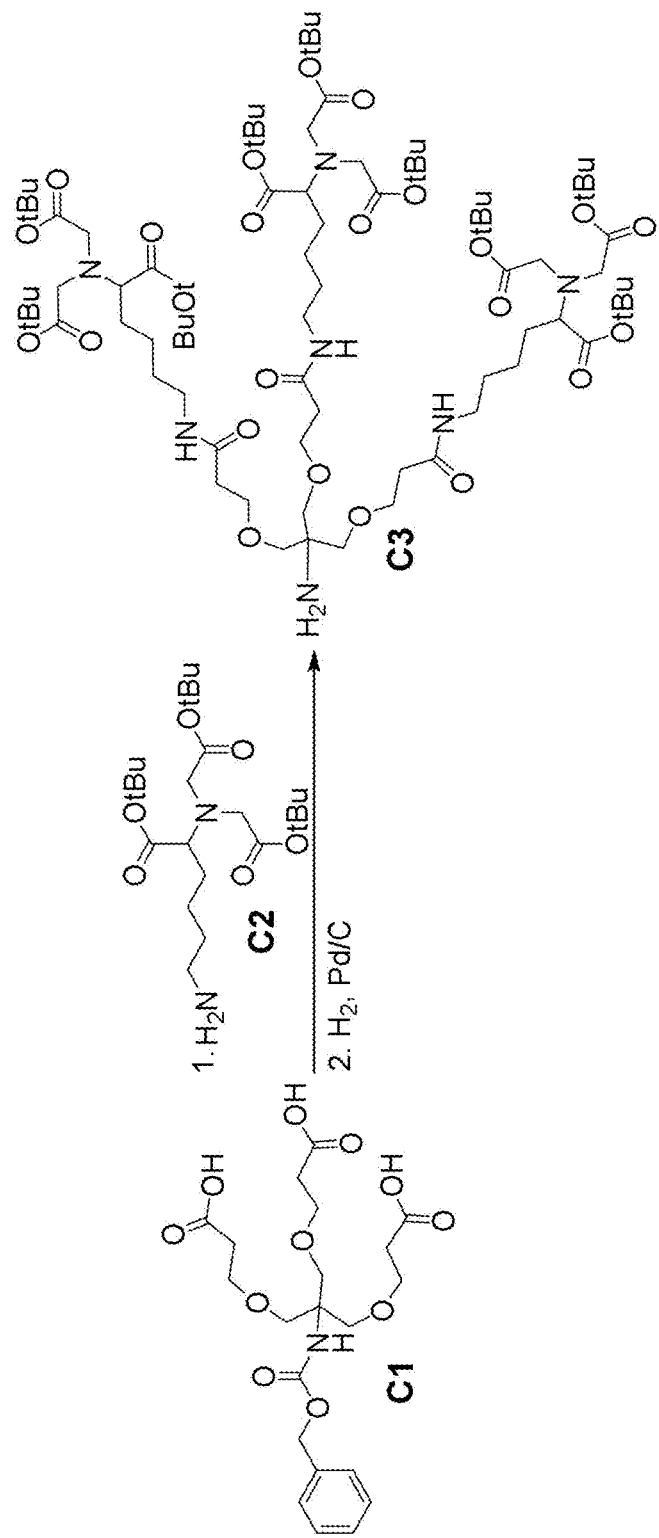
FIG. 3 depicts a synthetic scheme of the synthesis of a His-tag binder comprising tri-Nitrilotriacetic Acid (C3).

In one embodiment, this invention is further directed to the process for the preparation of a compound according to this invention, as described in Example 1, and FIG. 3. In another embodiment, this invention is directed to the process for the preparation of a compound, as described in Example 2 and FIGS. 6-10. In another embodiment, this invention is directed to the process for the preparation of a compound, as described in Example 3 and FIG. 11. In another embodiment, this invention is directed to the process for the preparation of a compound, as described in Example 13. In another embodiment, this invention is directed to the process for the preparation of a compound, as described in FIG. 39.

Figure 40:
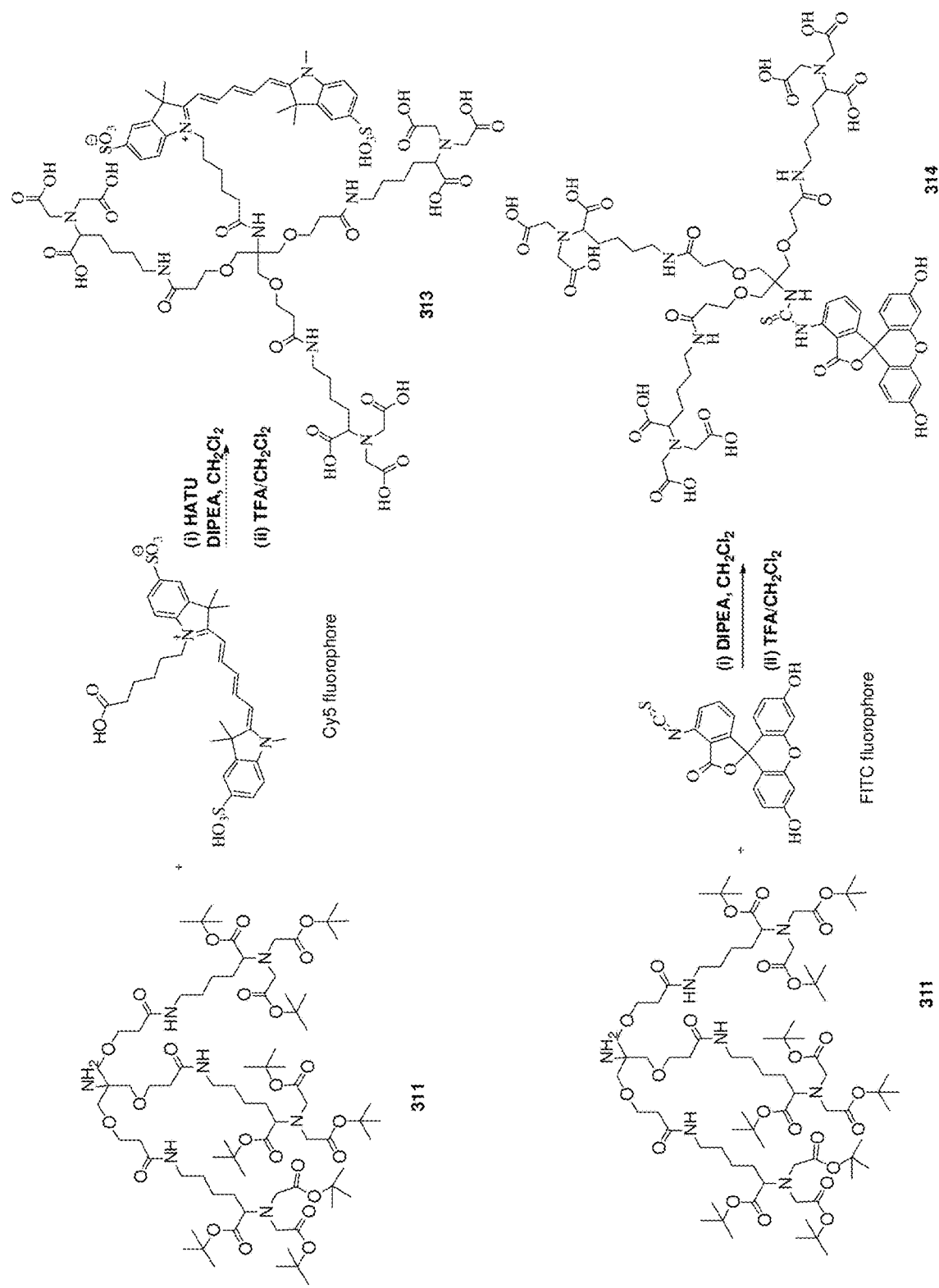
FIG. 40 shows the synthetic details of fluorophore coupling to His-tag binding compounds according to this invention.
Figure 41:
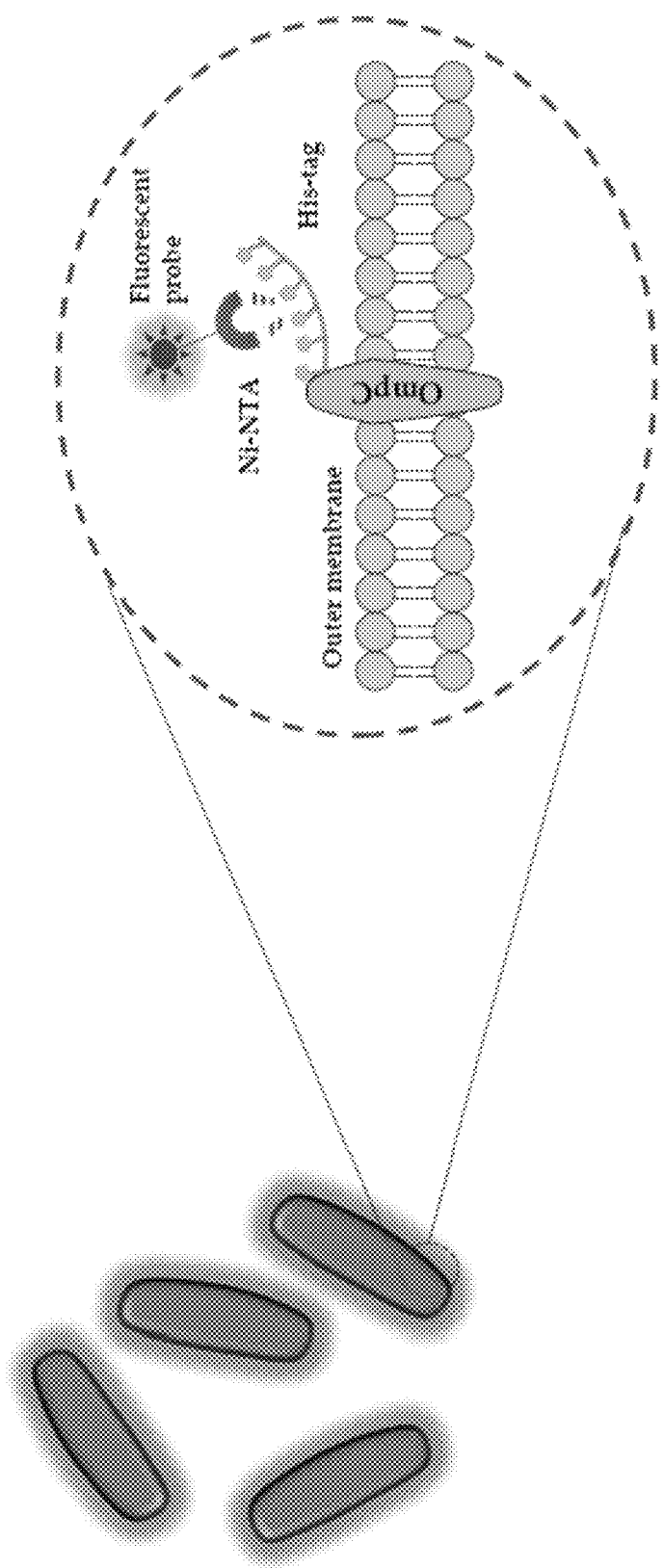
FIG. 41 shows a graphical illustration of the design of fluorescent probes comprising His-tag binding compounds according to this invention.
Figure 42:
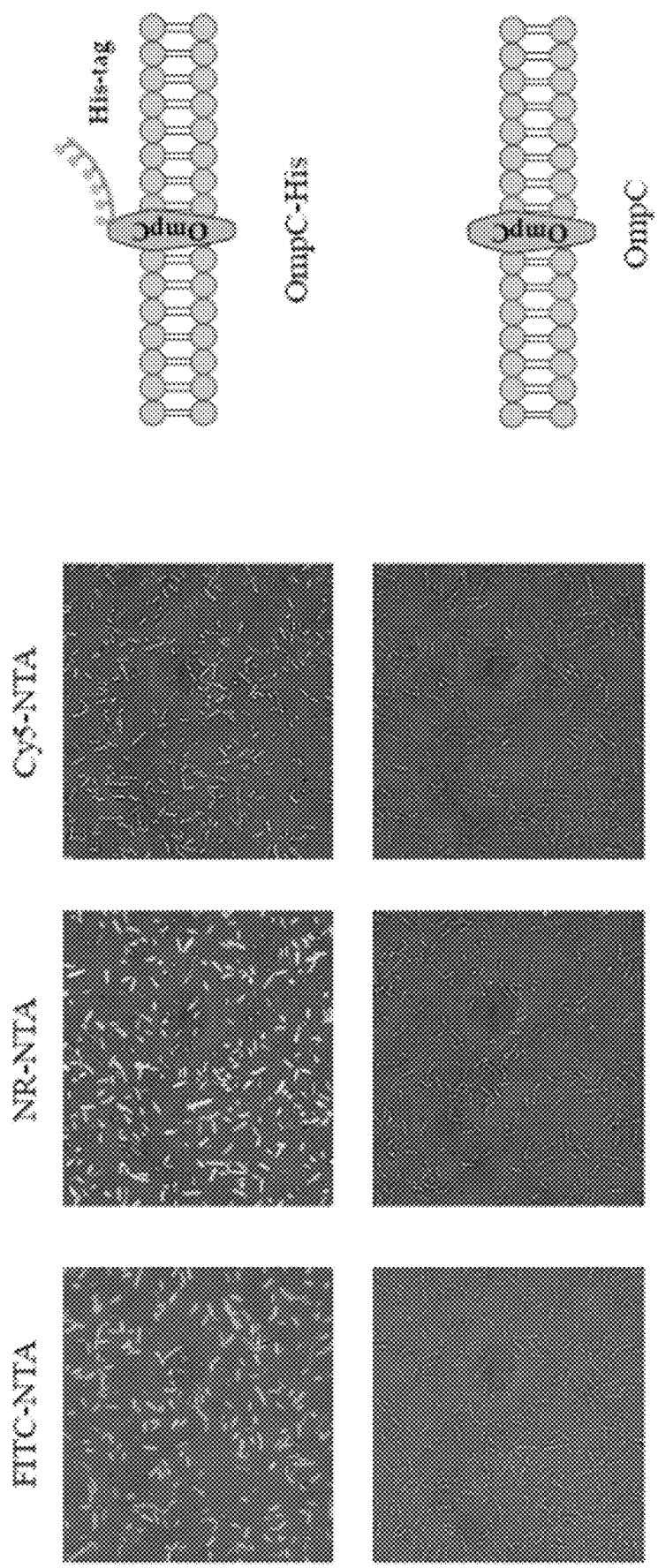
FIG. 42 shows fluorescence images of *E. coli* expressing His-OmpC (top) and OmpC (bottom) after incubation with 314 (FITC-NTA), 315 (NR-NTA) and 313 (Cy5-NTA).
Figure 43:
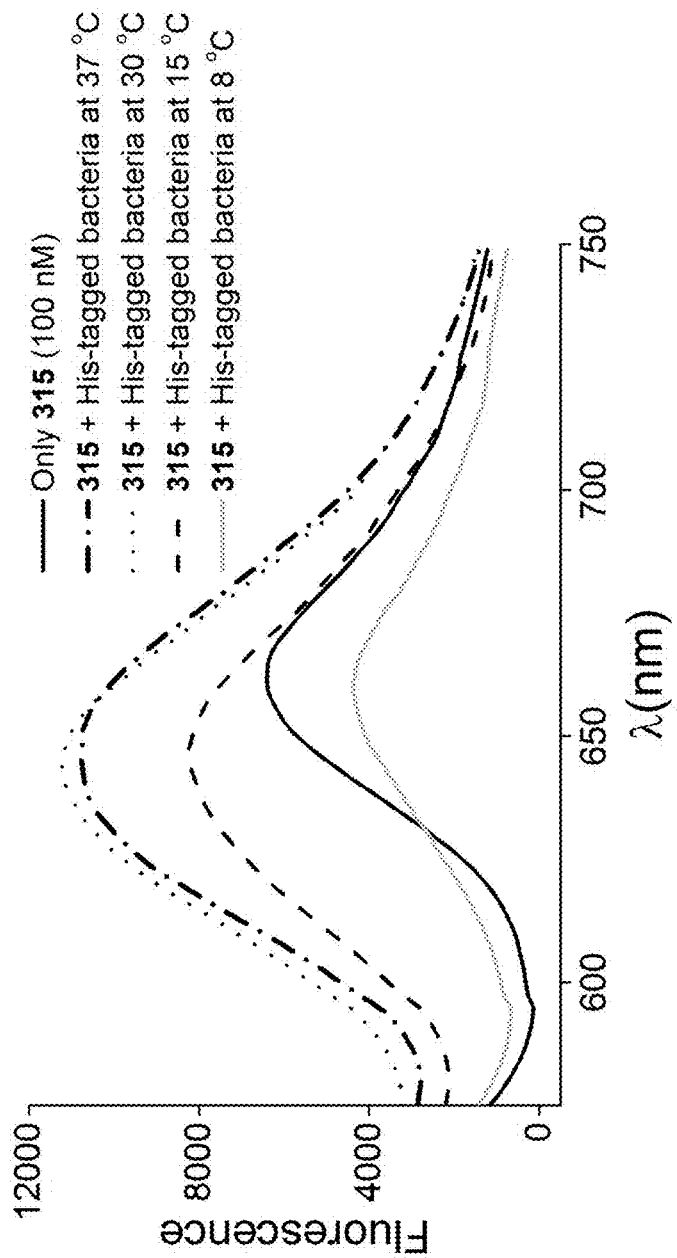
FIG. 43 shows the changes in the fluorescence response of a pre-incubated sample of 315 and $NiCl_2$ after addition of His-tagged bacteria expressed at different temperatures.
Figure 44:
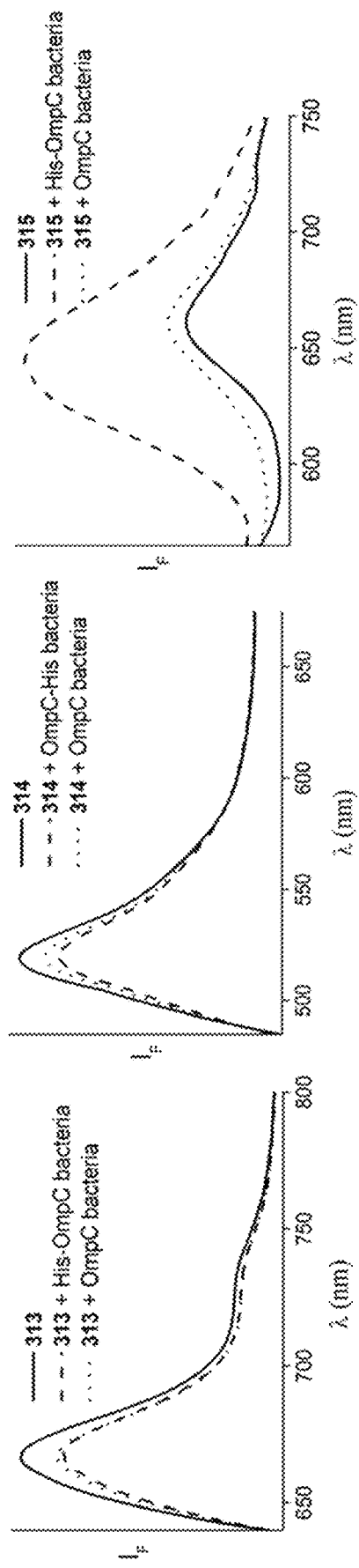
FIG. 44 shows fluorescence responses of probes 313-315 to His-OmpC and OmpC bacteria expressed at 30° C.
Figure 45:
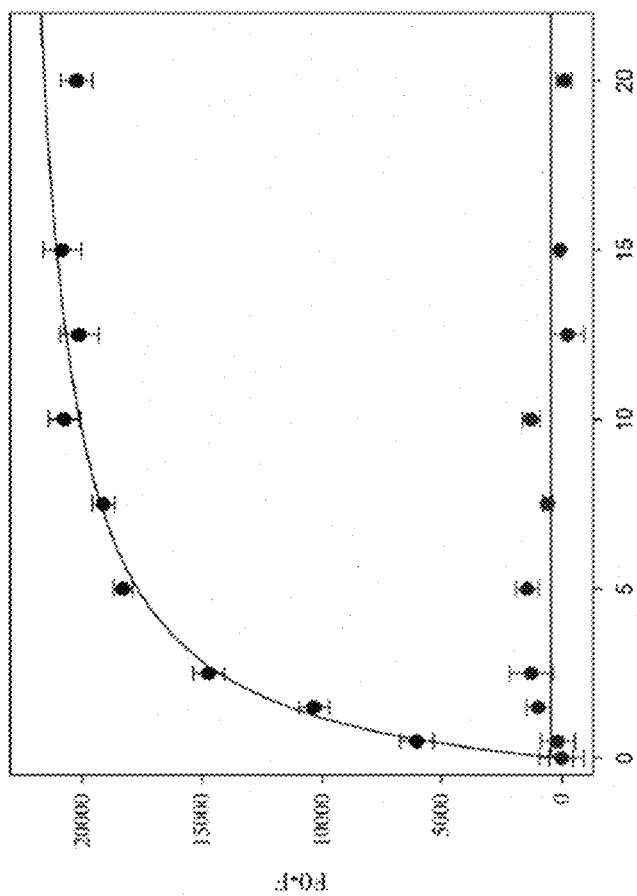
FIG. 45 depicts the changes in the fluorescence of a fluorescein-labeled His-tag peptide (5 nM) upon addition of increasing concentrations of NR-NTA (Compound 315). $NiCl_2$ was tested as a negative control.

In another embodiment, this invention is directed to the process for the preparation of a compound, attached to a fluorescent dye, as described in FIG. 40.

Figure 4:
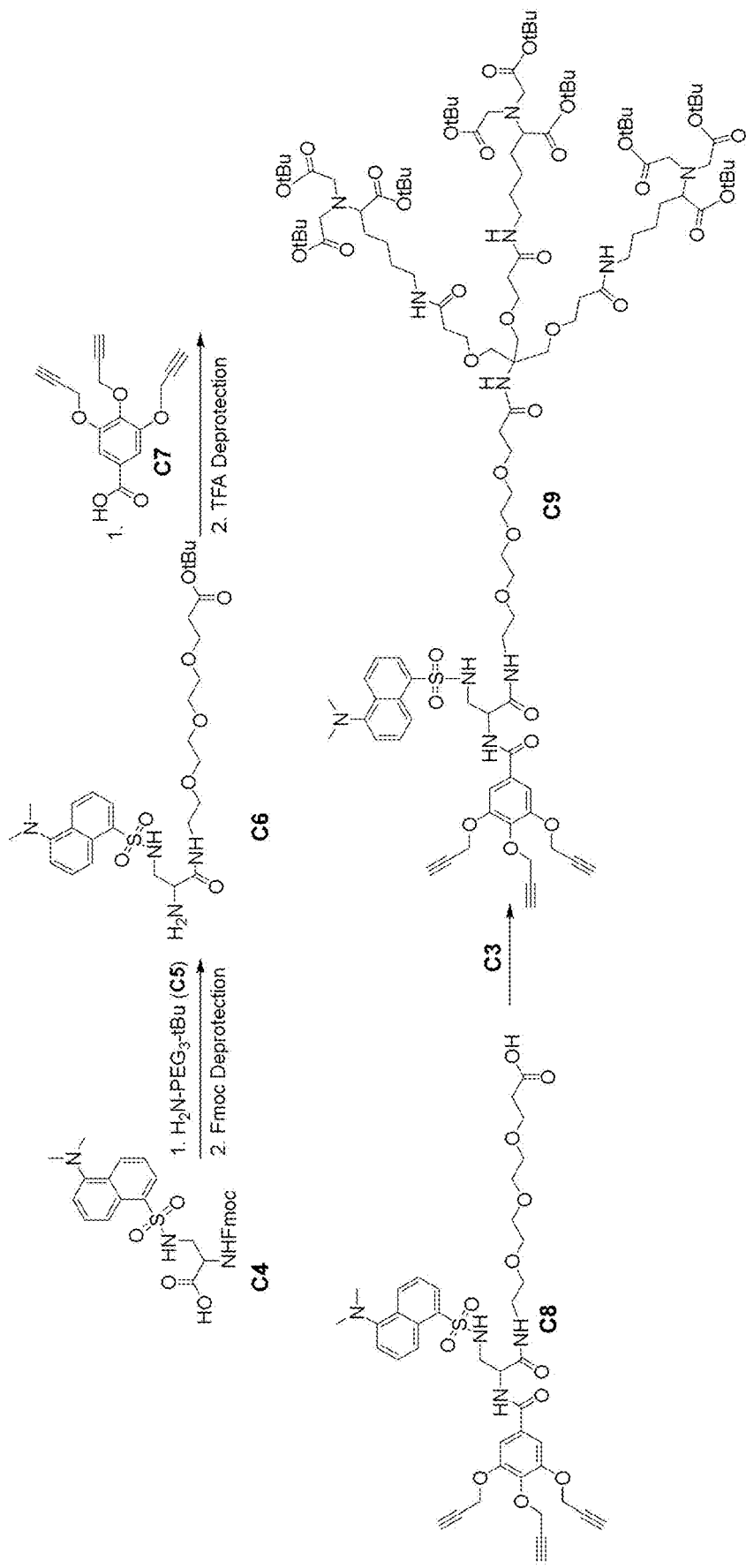
FIG. 4 depicts a synthetic scheme of the synthesis of compound C9.
Figure 5:
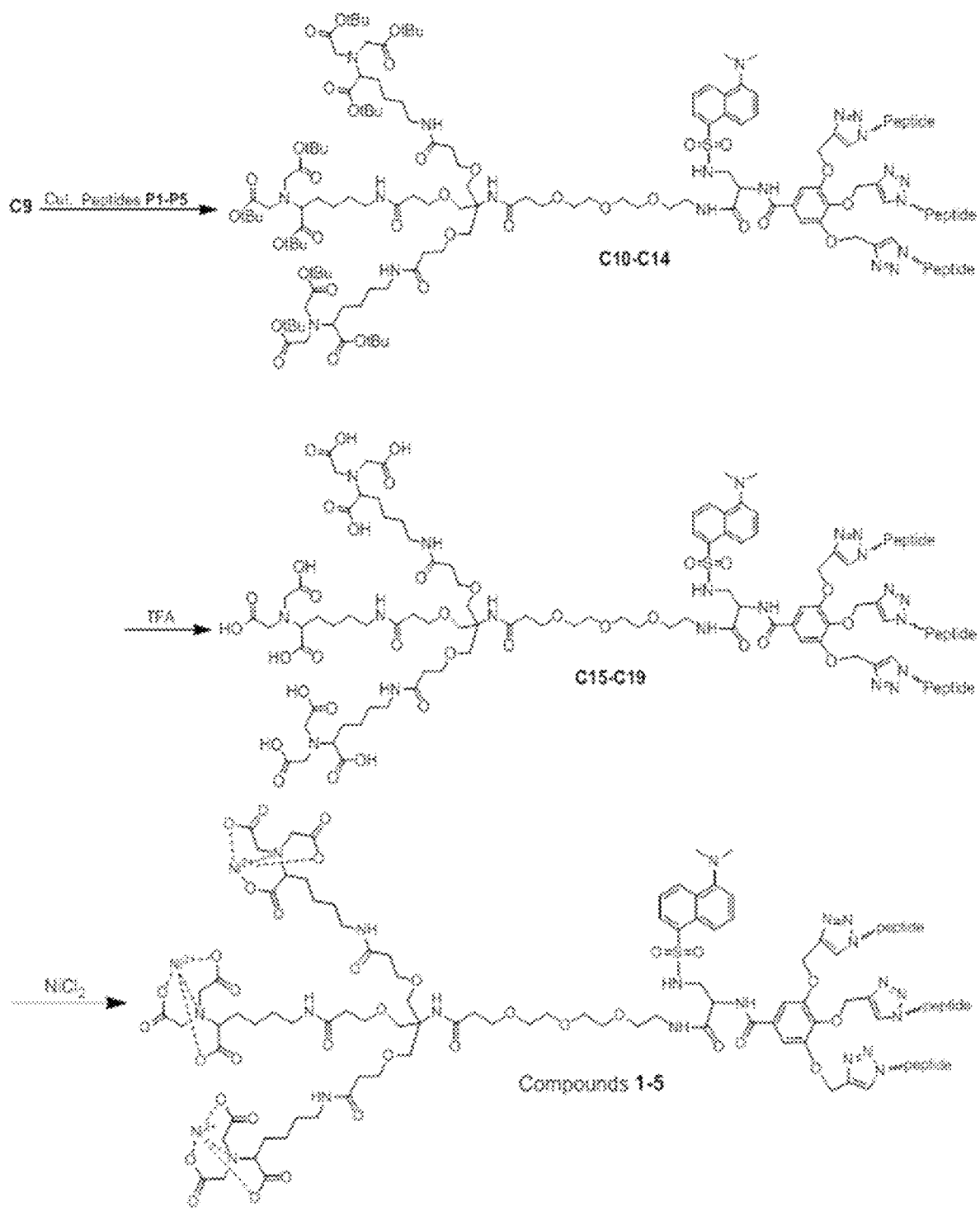
FIG. 5 depicts a synthetic scheme of the synthesis of compounds 1-5.
Figure 6:
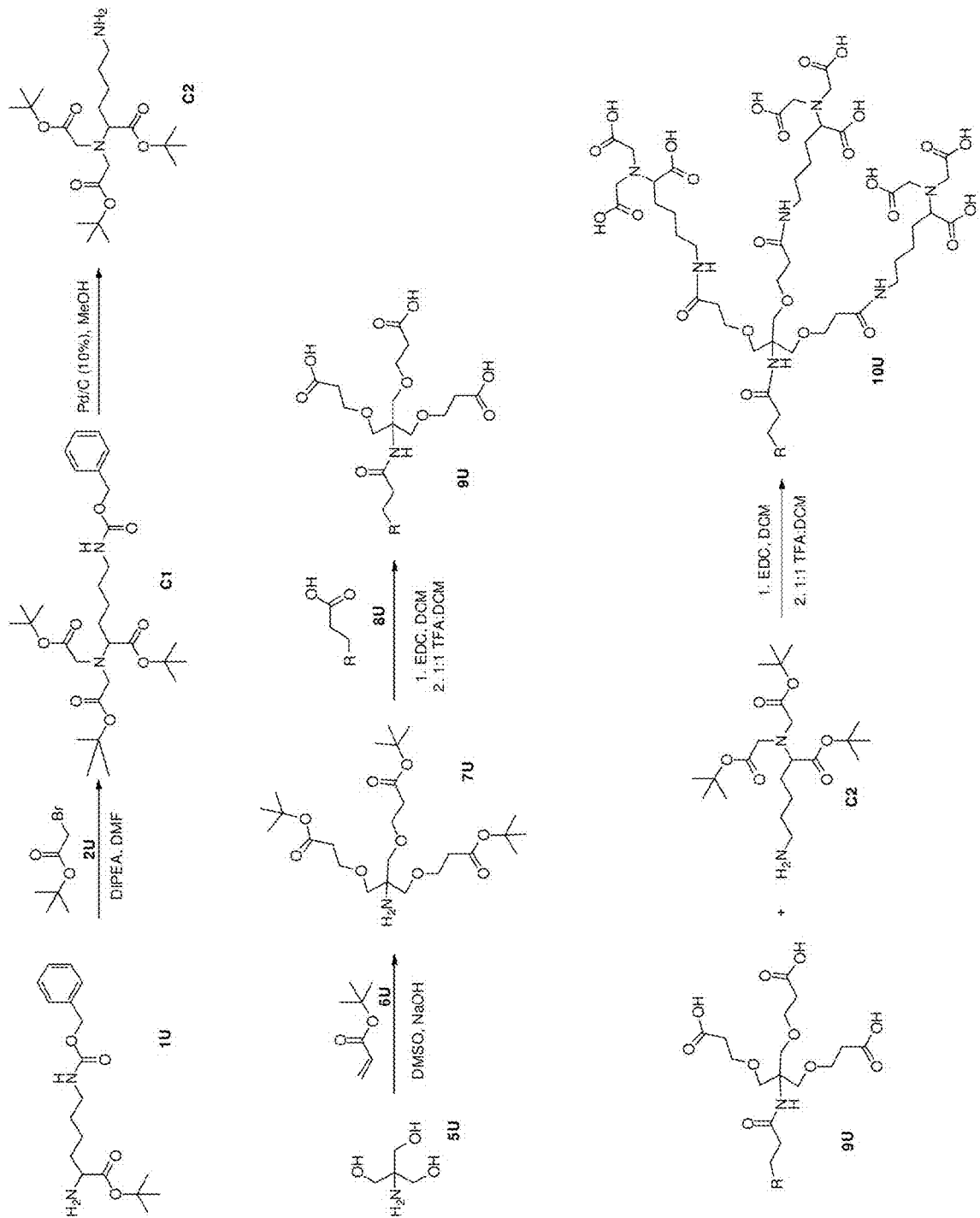
FIG. 6 depicts a synthetic scheme for preparing a variety of modified tri NTA compounds (10u) whose complex with Ni(II) can selectively bind His Tags.
Figure 14:
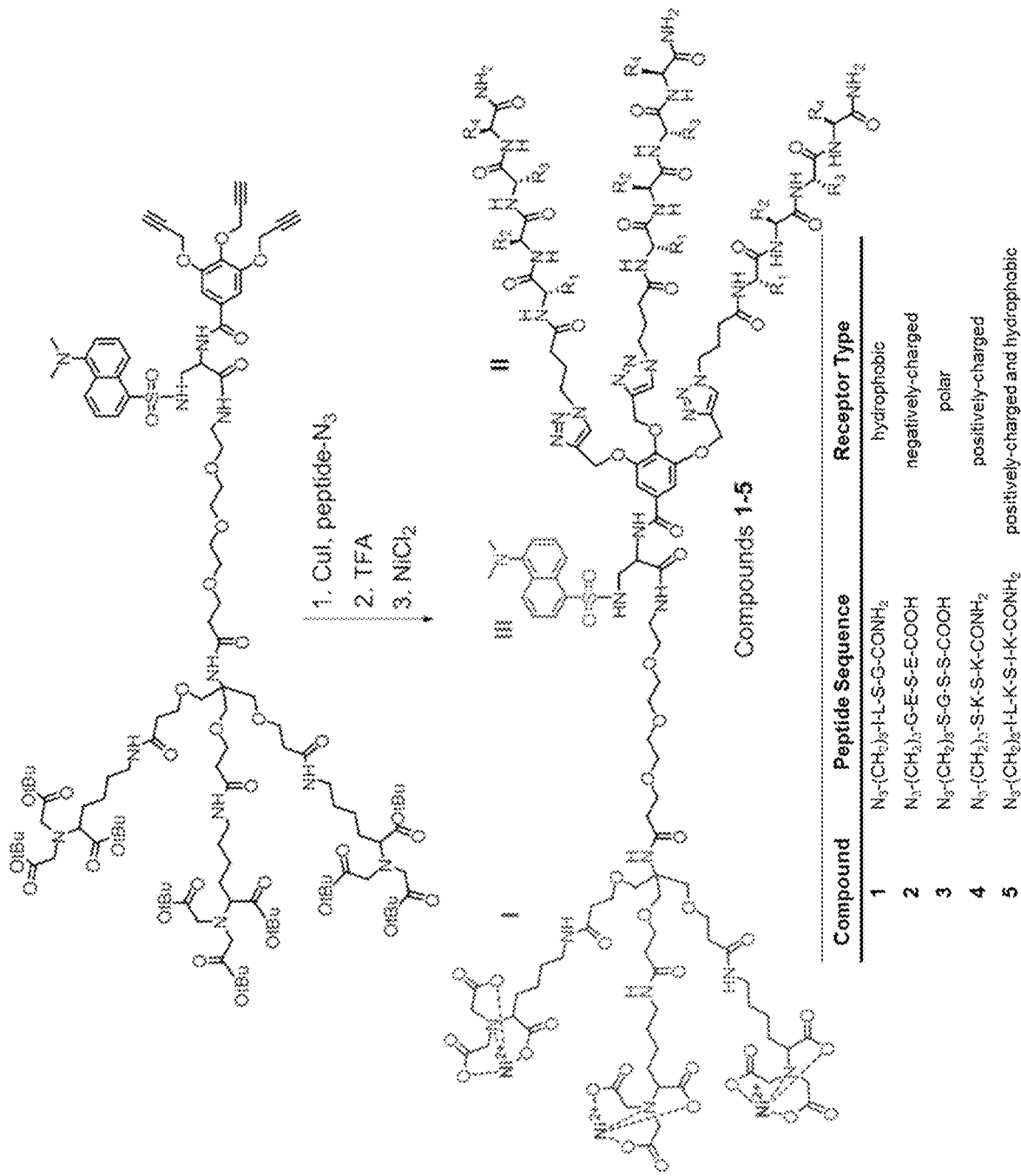
FIG. 14 depicts a method for preparing different protein surface sensors comprising a tri-$Ni^{+2}$-NTA complex (I), a tripodal peptide receptor (II), and a dansyl group (III), which serve as a His-tag binder, a protein surface receptor, and a solvatochromic probe, respectively.

In another embodiment, this invention is directed to the process for the preparation of a compound attached to a protein surface receptor according to this invention, as described in Example 1 and FIGS. 4-5 and 14.

Figure 10:
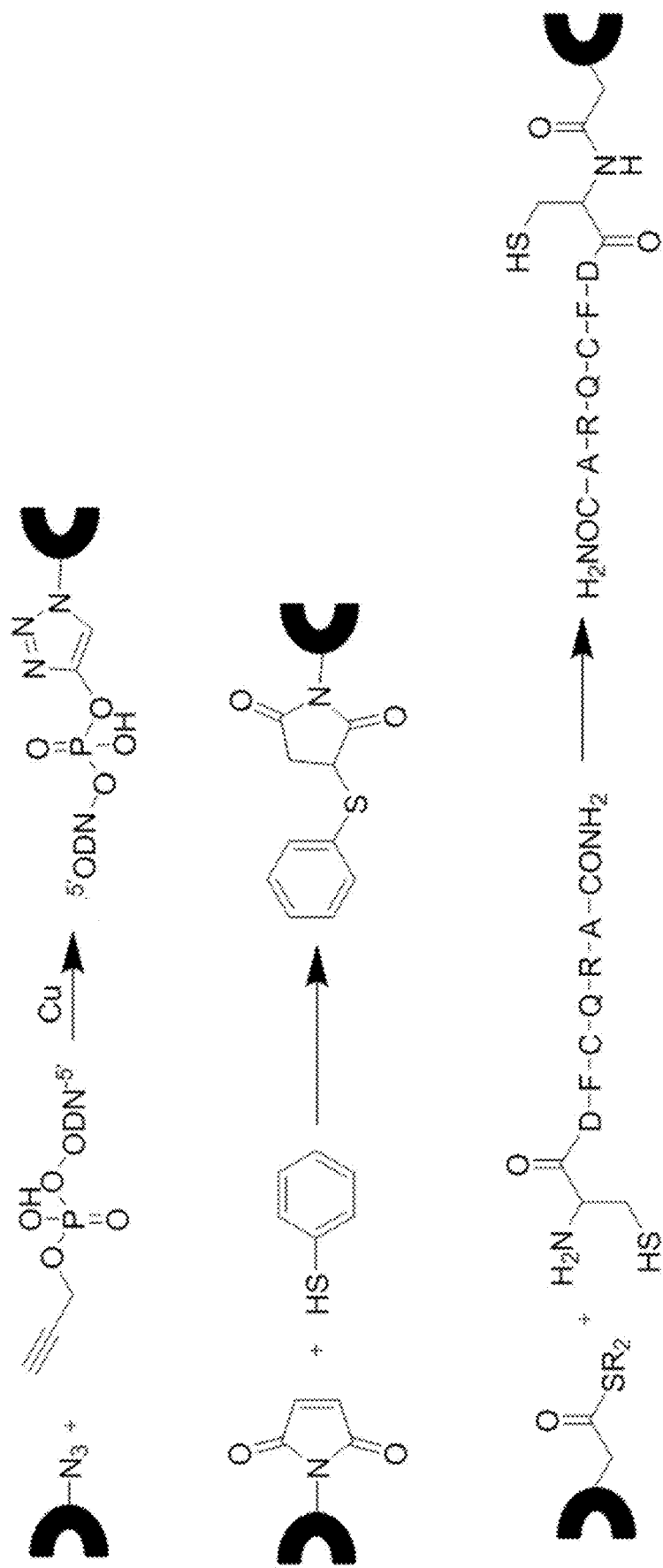
FIG. 10 depicts specific examples for modifying His-tag binding compounds of the invention to oligonucleotides (top), to small molecules (middle), and to peptides (bottom).
Figure 11:
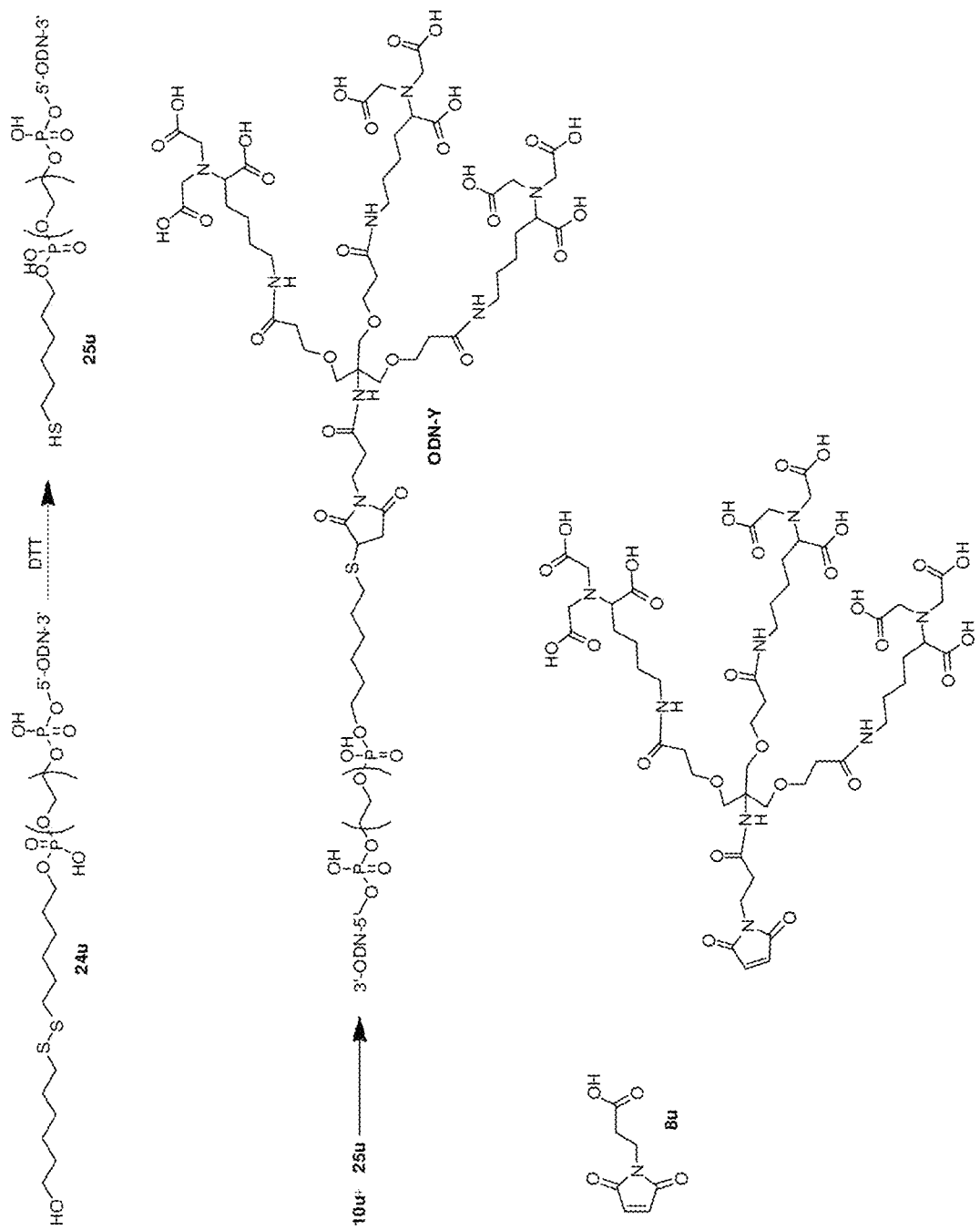
FIG. 11 depicts a synthetic scheme for an ODN modified with specific His-tag compound of the invention (ODN-Y), as well as the structures of a Maleimidopropionic acid (compound 8u), which was used to prepare the maleimide-modified His-tag binding compound (10u).

In another embodiment, this invention is directed to the process for the preparation of a compound, attached to an oligonucleotide, as described in Example 3 and FIGS. 10 and 11.

In another embodiment, this invention is directed to the process for the preparation of a compound, attached to a small molecule, as described in Example 2 and FIG. 10.

In another embodiment, this invention is directed to the process for the preparation of a compound, attached to a peptide, as described in Example 2 and FIG. 10.

Applications of His-Tag Binding Compounds of the Invention.

Upon complexation with at least one metal ion, the compound described herein above, which comprise tri-NTA group, can selectively bind a His-tagged labeled polypeptides inside living (in vivo) and/or fixed cells (in-vitro). Because the His-tag binding compounds and their precursors according to this invention can bear various functional groups, these tri-NTA derivatives can be easily attached to various detectable probes. In one embodiment, functional groups are at position $R_1$ of compounds of formulas XI-XVI as described above. In another embodiment, derivatives may be attached by using, for example, the 'click' chemistry, amide coupling, thiol-maleimide conjugation, etc. Such probes, (e.g. fluorescent probes) therefore, could be easily generated and complexed with metal ions to detect or label His-tagged proteins (e.g. within cells). Owing to the simple conjugation methods (e.g., 'click' chemistry, amide coupling, thiol-maleimide conjugation, etc.), this approach should enable one to attach various synthetic agents (e.g., fluorescent dyes, small molecules, peptides, oligonucleotides (e.g., DNA, RNA), solid support and the like), to the compounds of this invention, which will enable bringing these synthetic agents into close proximity of His-tagged polypeptides and proteins targeted by the His-tag-binding compounds comprising the specific agents.

Accordingly, the compounds according to this invention may be engineered to comprise a variety of synthetic agents, labeling moieties and/or detectable groups. These synthetic agents, labeling moieties and/or detectable groups can be covalently bound to the compound, either directly or through linkers as described hereinabove.

According to this invention, the term "synthetic agent" refers to any chemical moiety, which provides a chemical or biological function to the system, or to the cell, to which it is attached. In some embodiments, synthetic agent refers to any chemical moiety, which is capable of binding to various extracellular signals such as ions, small molecules, proteins, and cells, and can control the response of cells to their surroundings. In some embodiments, a synthetic agent refers to any chemical moiety, which has a chemical, physical or biological effect on the cell to which it is attached. In some embodiments, a synthetic agent refers to any chemical moiety, which has a biological effect on a living organism, a tissue or a cell (also referred herein as "a bioactive moiety"). In some embodiments, a biological effect comprises affecting the growth, the survival, the replication, the differentiation, the transcriptome, the proteome, or the function of a cell. In some embodiments, synthetic agent refers to any chemical moiety, which can bind, either covalently or non-covalently, to a solid support, and/or to an abiotic surface (also referred herein as "a surface binder"). In some embodiments, a synthetic agent refers an artificial receptor appended with a specific functionality. In some embodiments, a synthetic agent refers to any chemical moiety, which provides the cell, system or compound to which it is attached, with a specific functionality (e.g., fluorescence, therapeutic effect, solid surface binding capability, specific cell targeting, etc.).

In some embodiments, the synthetic agent is a detectable group as described herein below. In some embodiments, the detectable group is a labeling moiety. In some embodiments, the labeling moiety is a dye. In some embodiments, the dye is a fluorescent dye. In some embodiments, the fluorescent dye is selected from a group consisting of: dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, TAMRA, BODIPY, FITC, Thiazole orange, Quinoline blue, Thiazole red, or a derivative thereof.

In some embodiments, the synthetic agent is a therapeutically active agent. In some embodiments, the therapeutically active agent is a drug. In some embodiments, the therapeutically active agent is selected from: anticancer agents, DNA-interacting molecules, cholesterol-lowering compounds, antibiotics, anti-AIDS molecules, each represents a separate embodiment according to the invention.

In some embodiments, the synthetic agent is a is an oligonucleotide, a nucleic acid construct, an antisense, a plasmid, a polynucleotide, an amino acid, a peptide, a polypeptide, a hormone, a steroid, an antibody, an antigen, a radioisotope, a chemotherapeutic agent, a toxin, an anti-inflammatory agent, a growth factor or any combination thereof; each represents a separate embodiment according to the invention.

In some embodiments, the synthetic agent is a molecular marker. In some embodiments, the synthetic agent is an adhesion molecule. In some embodiments, synthetic agent is a cancer cell binder. In some embodiments, "cancer cell binder" refers to any chemical moiety capable of interacting with proteins expressed by cancer cells. In some embodiments, "cancer cell binder" refers to a protein binder capable of interacting with proteins expressed by cancer cells. In some embodiments, the synthetic agent is a protein ligand. In some embodiments, the synthetic agent is a protein binder. In some embodiments, the synthetic agent is a protein receptor. In some embodiments, the synthetic agent is a drug. In some embodiments, the synthetic agent is an anticancer agent. In some embodiments, the synthetic agent is a growth factor. In some embodiments, the synthetic agent is a surface binder. In some embodiments, the synthetic agent is an abiotic surface binder. In some embodiments, the surface binder is a functional group capable of binding a solid surface or a solid support.

In some embodiments, the synthetic agent is a protein binder. In some embodiments, a "protein binder" refers to any biological research reagent which binds to a specific target protein. Non limiting examples of protein binders known in the art include: drugs, folate, biotin, marimastat, ethacrynic acid, bisethacrynic acid, Ni-nitrilotriacetic acid (Ni-NTA), bis Ni-NTA, tris-Ni-NTA, PDGF-BB, heparin, FGF aptamer, estrogen, DNA aptamer, RNA aptamer, peptide aldehyde, estrogen, suberoylanilidehydroxamic acid (SAHA), or a peptide binder; each represents a separate embodiment according to this invention.

In some embodiments, the synthetic agent is a molecular marker. In some embodiments, the synthetic agent is an angiogenic factor. In some embodiments, the synthetic agent is a cytokine. In some embodiments, the synthetic agent is a hormone. In some embodiments, the synthetic agent is a DNA molecule. In some embodiments, the synthetic agent is a siRNA molecule. In some embodiments, the synthetic agent is an oligosaccharide.

In some embodiments, the synthetic agent is a protein receptor. In some embodiments, the synthetic agent is a protein binder. In some embodiments, the synthetic agent is an immune activator. In some embodiments, the synthetic agent is an immune suppressor. In some embodiments, the synthetic agent is a small molecule. In some embodiments, the small molecule is a drug.

In some embodiments, the synthetic agent is a surface binder. In some embodiments, the synthetic agent is an abiotic surface binder. In some embodiments, the synthetic agent is a binder for abiotic surfaces. In some embodiments, the synthetic agent is an agent capable of binding to solid support. In some embodiments, the surface binder is capable of binding a surface. According to this invention, a "surface binder" is any chemical moiety, or functional group, that is capable of binding solid surfaces. In some embodiments, the binding is covalent, electrostatic, van der Waals or any combination thereof, each is a separate embodiment. In some embodiments, attachment of the surface binder to the surface comprises covalent bond, coordination bond, polar bond, van der Waals bond or any combination thereof.

In some embodiments, the surface binder comprises a functional moiety capable of binding a surface. According to this aspect and in some embodiments, the surface binder comprises a thiol end group (SH) or an end group comprising a sulfur-sulfur bond (—S—S—). Such bonds are capable of binding to a noble metal. For example, thiol or —S—S— moieties binds strongly to gold surfaces and to other noble metal surface including but not limited to silver, platinum and palladium. Thiols and —S—S— bonds also bind to semiconductor surfaces such as GaAs etc. In some embodiments, the surface binder comprises a thiol group (HS). In some embodiments, the surface binder is a $C_1$-$C_{20}$ thioalkyl. In some embodiments, the surface binder is a $C_2$-$C_8$ thioalkyl. In some embodiments, the surface binder is a thiohexyl. In some embodiments, attachment of the surface binder to a surface comprise silicon chemistry. According to this aspect and in some embodiments, the surface is or comprises silicon. In some embodiments, the surface comprises silicon oxide. In some embodiments, the silicon oxide surface comprises glass or quartz. In some embodiments, the surface comprises silicon coated by a silicon oxide layer. According to this aspect and in some embodiments, the surface binder comprises a functional group capable of binding to silicon oxide. In some embodiments, the functional group comprises silicon atom. In some embodiments, the functional group comprises silicon bonded to a halogen atom. In some embodiments, the halogen atom is Cl, Br, F or I. In one embodiment the silicon-halogen functional group comprise Si-trichloride, Si-tribromide, Si-dichloride, Si dibromide. In some embodiments, the functional group comprises Si bonded to oxygen atom. In some embodiments, the functional group comprises Si bonded to two or three oxygen atoms. In some embodiments, the functional group of the surface binder comprises Si-halogen bond and upon reaction with the surface, the halogen atom is replaced by an oxygen atom, and bonding to the surface occurs. In some embodiments, the surface binder comprises a pyridine moiety.

In some embodiments, the synthetic agent is a detectable group as described herein below.

"Detectable group" as used herein refers to any atom or molecule that can be engineered into the His-tag binding compound to aid in the detection of the His-tag binding compounds without significantly destroying the His-tag binding compound's ability to react with a target sequence. The His-tag binding compound may be substituted at one or more positions to add a signal generating detectable group(s). Preferably, the His-tag binding compound is substituted at the $R_1$ position of compounds of formulas I-V described above.

Inclusion of more than one detectable group is also within the scope of this invention. The selection of a detectable group may be made based on the ease of the protocol for engineering the detectable group into the compound, and on the end use of the compound.

Examples of detectable groups include fluorescent groups, phosphorescent groups, luminescent groups, spin labels, photosensitizers, photocleavable moieties, chelating centers, heavy atoms, radioactive isotopes, isotopes detectable by nuclear magnetic resonance, paramagnetic atoms, and combinations thereof.

Typically, a detectable group generates a detectable signal that can be readily monitored. Examples of detectable signals that can be monitored include fluorescence, fluorescence anisotropy, time-resolved luminescence, phosphorescence amplitude and anisotropy, electron spin resonance (ESR), singlet oxygen production, hydroxy radical-mediated protein inactivation, metal-ion sensing, X-ray scattering, radioactivity, nuclear magnetic resonance spectroscopy of the attached isotope, and enhanced relaxivity of protons in the immediate vicinity of a paramagnetic species.

Other modifying groups that aid in the use of the His-tag binding compound of the invention may also be incorporated. For example, the compound may be substituted at one or more positions to add a solid phase binding group or a cross linking group. Preferably, the compound is substituted with a solid phase binding group at the $R_1$ position of compounds of formulas XI-XVI described above. The compound may be further coupled to a solid phase. In another embodiment, the compound may be substituted at one or more positions to add an oligonucleotide of any length (e.g., DNA or RNA). Preferably, the compound is substituted with an oligonucleotide at the $R_1$ position of compounds of formulas XI-XVI described above. The compound may be further coupled to another oligonucleotide which is bound to a synthetic agent, including but not limited to: drug, selective protein binder, fluorophore, etc.

In one embodiment, the His-tag binding compound is capable of traversing a biological membrane. The small size of the His-tag binding compound can contribute toward the ability of the His-tag binding compound to traverse a biological membrane.

A His-tag binding compound that is unable to traverse a biological membrane may be derivatized. In one embodiment, a His-tag binding compound may be derivatized by addition of groups that enable or enhance the ability of the His-tag binding compound to traverse a biological membrane. In another embodiment, derivatization of the His-tag binding compound does not significantly alter the ability of the His-tag binding compound to subsequently react with the target sequence. In another embodiment, a His-tag binding compound may be derivatized transiently. In such instances, after traversing the membrane, the derivatizing group is eliminated to regenerate the original His-tag binding compound. Examples of derivatization methods that increase membrane traversability include esterification of phenols, ether formation with acyloxyalkyl groups, and reduction of chromophores to uncharged leuco compounds.

In some embodiments, the His-tag binding compound, engineered to comprise a detectable group, may be nearly or completely undetectable until it specifically reacts with a target sequence (i.e., with a His-tag peptide motif). Such engineered His-tag binding compound can be particularly useful because it provides a means to specifically and accurately detect the presence of the His-tag binding compound/target sequence complex with very little background signal.

Also within the scope of this invention is a His-tag binding compound that may be detectable before and after it specifically reacts with a target sequence to form the His-tag binding compound/target sequence complex. In such instances, it is preferable if the detectable signal of the His-tag binding compound can be differentiated from the detectable signal of the complex. For example, if the detectable signal of the His-tag binding compound is a fluorescent signal, it would be preferable if the fluorescence of the complex is red-shifted or blue-shifted relative to the detectable signal produced by the His-tag binding compound alone.

The His-tag binding compound may also lack a detectable signal, both before and even after specifically reacting with a target sequence. These His-tag binding compounds can be useful in many techniques that do not require a detectable signal, or that use other methods of detection. These His-tag binding compounds may be useful when the goal is to attach a polypeptide to a solid substrate, or cross-link two polypeptides.

In one embodiment, use of His-tag binding compounds according to this invention may provide a means to detect proteins of interest, wherein it may be advantageous to express these proteins of interest as His-tagged fusion proteins instead of expressing the protein as a fusion protein with a very large fluorescent protein (FP) attached to it. A His-tag binding compound of this invention, coupled to a synthetic agent and/or detectable group, (e.g. a fluorescent dye or oligonucleotide), may then be used to target the protein of interest (See FIGS. 1 and 2, FIG. 32A, and FIG. 41). Such His-tag targeted fluorescent agent is expected to fluoresce upon binding to the targeted His-tagged protein, which may serve as a genetically targeted probe. In one embodiment, the His-tag binding compound is coupled to a protein surface receptor according to this invention. In another embodiment, the His-tag binding compound is coupled to a fluorescent dye. In another embodiment, the His-tag binding compound is coupled to an oligonucleotide.

In one embodiment, this invention is directed to a His-tag binding compound for use as a genetically targeted probe; or in another embodiment, for use as a fluorescent probe; or in another embodiment, for use in imaging of a His-tagged polypeptide of interest within a cell; or in another embodiment, for use in the detection of a protein of interest (POI) in its native environment; or in another embodiment, for use in measuring gene expression of a His-tagged polypeptide of interest (POI) in a living and/or fixed cells; or in another embodiment, for the localization of a POI in a living and/or fixed cells; or in another embodiment, for use as an artificial receptor, capable of binding a His-tagged protein; or in another embodiment, for use in decorating a cell with a synthetic agent; or in another embodiment, for use in adhering a first cell to a second cell; or in another embodiment, for use in adhering a cell to a surface; or in another embodiment, for use in inducing luminescence in a cell; or in another embodiment, for use in binding a cell to a protein of interest (POI).

In another embodiment, the His-tag binding compound is coupled to a fluorescent dye. In another embodiment, the His-tag binding compound is coupled to an oligonucleotide. In another embodiment, the His-tag binding compound is coupled to a protein surface receptor. In another embodiment, the His-tag binding compound is a sensor according to this invention. In another embodiment, the His-tag binding compound is a fluorescent probe.

In another embodiment, the His-tag binding compound is a genetically targeted probe. In another embodiment, the fluorescently-tagged His-tag binding compound is a genetically targeted probe.

In another embodiment, said His-tag binding compound according to this invention is covalently linked to a fluorophore, directly or via a linker, thereby obtaining said fluorescently tagged His-tag binding compound. In another embodiment, said His-tag binding compound is linked to a fluorophore through the $R_1$ moiety of compounds of formulas XI-XVI. In another embodiment, said $R_1$ of compounds of formulas XI-XVI are linked to said fluorophore through a linker, wherein said linker is as described herein above for compounds according to this invention.

In one embodiment, a fluorophore comprises a solvatochromic dye. Solvatochromic fluorophores display sensitivity to the polarity of the local environment. These molecules exhibit a low quantum yield in aqueous solution but become highly fluorescent in nonpolar solvents or when bound to hydrophobic sites in proteins or membranes. In certain embodiments, solvatochromic fluorophores include 2-propionyl-6-dimethylaminonaphthalene (PRODAN) (Weber et al. *Biochemistry* 1979, 18, 3075-3078; Cohen et al. *Science* 2002, 296, 1700-1703), 4-dimethylamino phthalimide (4-DMAP) (Saroja et al. *J. Fluoresc.* 1998, 8, 405-410), and 4-amino-1,8-naphthalimide derivatives (Grabchev et al. *J. Photochem. Photobiol.*, A 2003, 158, 37-43; Martin et al. *J. Lumin.* 1996, 68, 157-146). In another embodiment, the solvatochromic fluorophore is selected from: fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, Tamra, BODIPY, FITC, Thiazole orange, Quinoline blue, and Thiazole red. In another embodiment, said solvatochromic dye is dansyl.

In one embodiment, fluorescence emission is measured over time. In another embodiment, fluorescence emission is measure before and after a His-binding compound is incubated with a His-tagged polypeptide or a cell comprising a His-tagged polypeptide. In another embodiment, said measuring is of a live cell. In another embodiment, said measuring of is a fixed cell. In another embodiment, said measuring is of a cell supernatant.

In one embodiment, a cell is a mammalian cell. In another embodiment, a cell is a rat, a mouse, a dog, or a human cell. In another embodiment, a cell is a yeast cell. In another embodiment, a cell is a tissue culture cell-line cell. In another embodiment, a cell is a primary culture cell from a transgenic mammal. In another embodiment, a cell is a recombinant cell. In yet another embodiment, a cell comprises a nucleic acid encoding a His-tagged polypeptide of interest. In another embodiment, a cell expresses a His-tagged polypeptide of interest. In another embodiment a cell secretes a His-tagged polypeptide of interest. Each possibility comprises an embodiment of this invention.

In one embodiment, this invention is directed to a method for imaging a His-tagged polypeptide of interest (POI) within a cell, said method comprising the steps of:
  a. expressing said His-tagged polypeptide in a recombinant cell;
  b. incubating said recombinant cell with a fluorescent probe according to this invention; and
  c. visualizing the fluorescence emission of said fluorescent probe.

In one embodiment, said recombinant cell is fixed using any method known in the art, prior to the incubating step. In another embodiment, the fluorescent probe passively crosses the plasma membrane of a live cell. In another embodiment, the fluorescent probe is micro-injected into a live cell. In another embodiment, the fluorescent probe is derivatized in a way that allows its crossing of the plasma membrane of a live cell. In another embodiment, said visualizing is observing under a microscope. In one embodiment, a fluorescent microscope is used to detect and localize the fluorescent signal. In another embodiment, a fluorescent microscope with a plate reader or the ability to record images at multiple locations over time is used to detect and localize the fluorescent signal. In another embodiment, the fluorescent probe is a genetically targeted sensor.

In one embodiment, this invention is directed to a method of labeling a protein of interest (POI) in complex environment using a fluorescent probe, said method comprises:
  a. expressing a His-tagged POI in a complex environment;
  b. incubating the His-tagged POI with a fluorescent probe according to this invention; and
  c. measuring the fluorescence emission of said fluorescent probe:His-tagged POI complex;
wherein detection of a fluorescent signal is dependent on the formation of said fluorescent probe:His-tagged POI complex.

In another embodiment, said fluorescent probe is a His-tag binding compound according to this invention coupled to a fluorescent dye or a fluorophore.

The term "complex environment" refers, in one embodiment, to an environment that comprises large proteins that tend to engage in non-specific interactions such as serum albumin (e.g., BSA and HSA). In another embodiment, the complex environment comprises-, IgG, IgA, Avidine, Insulin, SAv, BSA, GST-P1, HSA, AGP or any combination thereof. In another embodiment, the complex environment is an environment that stabilizes the POI. In another embodiment, the complex environment is the native environment of the POI.

In one embodiment, this invention is directed to a method of identifying a protein of interest (POI) in complex environment using a fluorescent probe according to this invention, said method comprising:
  a. expressing a His-tagged POI in a complex environment;
  b. incubating the His-tagged POI with a fluorescent probe according to this invention; and
  c. measuring the fluorescence emission of said fluorescent probe:His-tagged POI complex;
wherein detection of a fluorescent signal is dependent on the formation of said fluorescent probe:His-tagged POI complex.

In one embodiment, this invention is directed to a method of measuring gene expression of a His-tagged polypeptide of interest (POI) in a cell said method comprising the steps of:
  a. expressing a His-tagged polypeptide of interest in a cell;
  b. incubating the cell with a fluorescent probe according to this invention; and
  c. measuring the fluorescence of said cell;
wherein detection of a fluorescent signal is dependent on the formation of a His-tagged polypeptide:fluorescent probe complex.

In another embodiment, the His-tagged polypeptide is a cell surface receptor and measuring comprising use of a fluorescent cell sorter. In another embodiment, the His-tagged polypeptide is secreted from the cells, and said measuring involves collecting the cell supernatant and measuring the fluorescence of the supernatant. In yet another embodiment, a method of measuring gene expressing comprises a further step of homogenizing a cell comprising a His-tagged polypeptide at a given time point, incubating the fluorescent probe with the cell homogenate, and measuring the resultant fluorescence. In another embodiment, a plate reader is used to measure the fluorescence of an array of cells. In another embodiment, a low density array is used. Each possibility comprises an embodiment of the invention. Methods for measuring fluorescence are well known in the art.

In one embodiment, a His-tagged polypeptide comprises a polyhistidine tag. A "polyhistidine tag" (His-tag) according to this invention comprises at least 2, at least 3, at least 4, at least 5, at least 6, at least 7, at least 8, at least 9, at least 10 histidine residues. In one embodiment, a protein of interest (POI) comprises a polyhistidine tag of this invention, at its N-terminus. In another embodiment, a protein of interest (POI) comprises a polyhistidine tag of this invention, at its C-terminus. In another embodiment, a protein of interest (POI) comprises a polyhistidine tag of this invention, at an internal location of the contiguous amino acid sequence. In another embodiment, the His-tag comprises hexa-histidine peptide (6×His-tag). In another embodiment, the His-tag comprises deca-histidine peptide (10×His-tag).

D. Artificial Receptors and Recombinant Cells Comprising Thereof a. System for Decorating Cell Membranes In some embodiments, disclosed herein is a system comprising:

a. a recombinant cell ectopically expressing a polypeptide, wherein said polypeptide comprises a membranal anchoring domain and an extracellular binding domain,
b. a first compound comprising a first oligonucleotide (ODN-1) covalently bound to a binder, either directly or through a first linker, said binder comprising affinity to said extracellular binding domain,
c. a second compound comprising a second oligonucleotide (ODN-2) covalently bound to a synthetic agent, either directly or through a second linker, wherein said second oligonucleotide is complementary to said first oligonucleotide.

In some embodiments, the polypeptide is bound to the first compound, the second compound is bound to the first compound, or combination thereof; each represent a separate embodiment according to the invention. In some embodiments, when incubated together, the polypeptide, the first compound, and the second compound, form a complex, in which the polypeptide is attached to the first compound and the first compound is attached to the second compound. In some embodiments, the first compound is attached to the second compound via the hybridization of the first oligonucleotide to the second oligonucleotide. In some embodiments, the first compound is attached to the polypeptide via coordination of said binder to said extracellular binding domain of said polypeptide. In some embodiments, the first compound is attached to the polypeptide via coordination of said binder to an affinity tag comprised in said extracellular binding domain of said polypeptide. In some embodiments, the polypeptide is a cell surface proteins (CSPs). In some embodiments, the polypeptide is an outer membrane protein C (OmpC). In some embodiments, the polypeptide is a receptor tyrosine kinase (RTK).

In some embodiments, the system does not perturb said cell's function. In some embodiments, the system can be reversibly modified. In some embodiments, the recombinant cell is selected from: eukaryotes, prokaryotes, mammalian cells, plant cells, human cells, and bacteria. In some embodiments, the bacteria comprise E. coli. In some embodiments, the membranal anchoring domain comprises a transmembranal protein or a part of it, an artificial polypeptide, or a combination thereof. In some embodiments, the transmembranal protein comprises an outer membrane protein C (OmpC); receptor tyrosine kinases (RTKs); Ion channel linked receptors; Enzyme-linked receptors; G protein-coupled receptors or any combination thereof; each represents a separate embodiment according to this invention. In some embodiments, the extracellular domain comprises an affinity tag. In some embodiments, the affinity tag comprises a poly-histidine peptide (6×-His-tag, 10×-His-tag, His-tag), a tetra cysteine peptide (CCPGCC, TC tag), or a combination thereof. In some embodiments, the binder comprises a His-tag specific binder. In some embodiments, the binder comprises a moiety represented by the structure of formula C, D, D(a), D(b), E, E(a), E(b), G, G(a), or G(b). In some embodiments, the first compound is represented by the structure of formula J, H, H(a) and H(b) and compounds 100-104. In some embodiments, the second compound is represented by the structure of formula K and compounds 200-207. In some embodiments, the first linker comprises at least one polyethyleneglycol (PEG) moiety, at least one phosphate moiety, at least one thioalkyl moiety or any combination thereof. In some embodiments, the first compound further comprises a labeling moiety. In some embodiments, the labeling moiety is a fluorescent dye. In some embodiments, the synthetic agent of said second compound comprises a molecular marker, a labeling moiety, a fluorescent dye, an adhesion molecule, a cancer cell binder, a protein binder, a protein ligand, an anticancer agent, a surface binder (e.g., an abiotic surface binder), a growth factor, an angiogenic factor, a cytokine, a hormone, a DNA molecule, a siRNA molecule, an oligosaccharide, a protein receptor, an immune activator, an immune suppressor, a small molecule, a drug, or a derivative therefore, or any combination thereof; each represents a separate embodiment according to this invention. In some embodiments, the second compound further comprises a second labeling moiety. In some embodiments, the second labeling moiety comprises a fluorescent dye. In some embodiments, the system further comprises a third compound comprising a third oligonucleotide (ODN-3), wherein said third oligonucleotide is complementary to said second oligonucleotide. In some embodiments, the third oligonucleotide comprises higher affinity to said second oligonucleotide than the affinity of said second oligonucleotide to said first oligonucleotide.

b. A Kit for Decorating Cell Membranes

In some embodiments, this invention relates to a kit comprising:
a. a recombinant cell ectopically expressing a polypeptide according to this invention, wherein said polypeptide comprises a membranal anchoring domain and an extracellular binding domain, said extracellular binding domain bound to
b. a first compound according to this invention, comprising a first oligonucleotide (ODN-1) covalently bound to a binder according to this invention, either directly or through a first linker, said binder comprises affinity to said extracellular binding domain, and
c. a second compound according to this invention, comprising a second oligonucleotide (ODN-2) covalently bound to a synthetic agent, either directly or through a second linker, wherein said second oligonucleotide is complementary to said first oligonucleotide In some embodiments, the polypeptide is bound to the first compound, the second compound is bound to the first compound, or combination thereof; each represent a separate embodiment according to the invention. In some embodiments, when incubated together, the polypeptide, the first compound, and the second compound, form a complex, in which the polypeptide is attached to the first compound and the first compound is attached to the second compound. In some embodiments, the complex can be reversibly modified. In some embodiments, the first compound is attached to the second compound via the hybridization of the first oligonucleotide to the second oligonucleotide. In some embodiments, the first compound is attached to the polypeptide via coordination of said binder to said extracellular binding domain of said polypeptide. In some embodiments, the first compound is attached to the polypeptide via coordination of said binder to an affinity tag comprised in said extracellular binding domain of said polypeptide. In some embodiments, the polypeptide is a cell surface proteins (CSPs). In some embodiments, the polypeptide is an outer membrane protein C (OmpC). In some embodiments, the polypeptide is a receptor tyrosine kinase (RTK). In some embodiments, the polypeptide is an ion channel linked receptor. In some embodiments, the polypeptide is an enzyme-linked receptor. In some embodiments, the polypeptide is a G protein-coupled receptor.

In some embodiments, the kit further comprises a third compound comprising a third oligonucleotide (ODN-3), wherein said third oligonucleotide is complementary to said second oligonucleotide. In some embodiments, the third oligonucleotide comprises higher affinity to said second oligonucleotide than the affinity of said second oligonucleotide to said first oligonucleotide. In some embodiments, the recombinant cell is selected from: eukaryotes, prokaryotes, mammalian cells, plant cells, human cells, and bacteria. In some embodiments, the bacteria comprise E. coli. In some embodiments, the membranal anchoring domain comprises a transmembranal protein or a part of it, an artificial polypeptide, or a combination thereof. In some embodiments, the transmembranal protein comprises an outer membrane protein C (OmpC); receptor tyrosine kinases (RTKs); Ion channel linked receptors; Enzyme-linked receptors; G protein-coupled receptors or any combination thereof; each represents a separate embodiment according to this invention. In some embodiments, the extracellular domain comprises an affinity tag. In some embodiments, the affinity tag comprises a poly-histidine peptide (6×-His-tag, 10×-His-tag, His-tag), a tetra cysteine peptide (CCPGCC, TC tag), or a combination thereof. In some embodiments, the binder comprises a His-tag specific binder. In some embodiments, the binder comprises a moiety represented by the structure of formula C, D, D(a), D(b), E, E(a), E(b), G, G(a), or G(b). In some embodiments, the first compound is represented by the structure of formula J, H, H(a) and H(b) and compounds 100-104. In some embodiments, the second compound is represented by the structure of formula K and compounds 200-207. In some embodiments, the first linker comprises at least one polyethyleneglycol (PEG) moiety, at least one phosphate moiety, at least one thioalkyl moiety or any combination thereof. In some embodiments, the first compound further comprises a labeling moiety. In some embodiments, the labeling moiety is a fluorescent dye. In some embodiments, the synthetic agent of said second compound comprises a molecular marker, a labeling moiety, a fluorescent dye, an adhesion molecule, a cancer cell binder, a protein binder, a protein ligand, an anticancer agent, a surface binder (e.g., an abiotic surface binder), a growth factor, an angiogenic factor, a cytokine, a hormone, a DNA molecule, a siRNA molecule, an oligosaccharide, a protein receptor, an immune activator, an immune suppressor, a small molecule, a drug, or a derivative therefore, or any combination thereof; each represents a separate embodiment according to this invention. In some embodiments, the second compound further comprises a second labeling moiety. In some embodiments, the second labeling moiety comprises a fluorescent dye.

c. Artificial Receptor

In some embodiments, disclosed herein is an artificial receptor, capable of binding a His-tagged protein, comprising:

a. a first compound comprising a first oligonucleotide (ODN-1) bound to a His-tag binder, either directly or through a first linker, said His-tag binder comprises a moiety represented by the structure of formula E:

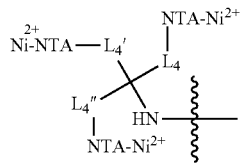

E wherein $L_4$, $L_4'$, and $L_4''$ is each independently a substituted or unsubstituted linear or branched alkyl chain of 1-20 carbon atoms, substituted or unsubstituted linear or branched alkyl ether chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl diamide chain of 1-20 carbon atoms, substituted or unsubstituted linear or branched alkyl amine chain of 1-20 carbon atoms or any combination thereof, and b. a second compound comprising a second oligonucleotide (ODN-2) covalently bound to a synthetic agent, either directly or through a second linker, said second oligonucleotide is complementary to said first oligonucleotide.

In some embodiments, the artificial receptor does not perturb the function of a living cell. In some embodiments, the receptor can be reversibly modified. In some embodiments, the binder comprises a moiety represented by the structure of formula C, D, D(a), D(b), E(a), E(b), G, G(a), or G(b) as described herein below; each represents a separate embodiment according to this invention. In some embodiments, the first compound is represented by the structure of formula J, H, H(a) and H(b) and compounds 100-104. In some embodiments, the second compound is represented by the structure of formula K and compounds 200-207. In some embodiments, the first linker comprises at least one polyethyleneglycol (PEG) moiety, at least one phosphate moiety, at least one thioalkyl moiety or any combination thereof. In some embodiments, the first compound further comprises a labeling moiety. In some embodiments, the labeling moiety is a fluorescent dye. In some embodiments, the synthetic agent of said second compound comprises a molecular marker, a labeling moiety, a fluorescent dye, an adhesion molecule, a cancer cell binder, a protein binder, a protein ligand, an anticancer agent, a surface binder (e.g., an abiotic surface binder), a growth factor, an angiogenic factor, a cytokine, a hormone, a DNA molecule, a siRNA molecule, an oligosaccharide, a protein receptor, an immune activator, an immune suppressor, a small molecule, a drug, or a derivative therefore, or any combination thereof; each represents a separate embodiment according to this invention. In some embodiments, the second compound further comprises a second labeling moiety. In some embodiments, the second labeling moiety comprises a fluorescent dye. In some embodiments, the artificial receptor further comprises a third compound comprising a third oligonucleotide (ODN-3), wherein said third oligonucleotide is complementary to said second oligonucleotide. In some embodiments, the third oligonucleotide comprises higher affinity to said second oligonucleotide than the affinity of said second oligonucleotide to said first oligonucleotide.

In some embodiments, the first compound is further attached to a polypeptide comprising a His-tag affinity tag, via the binding of said His-tag binder of the first compound, to the His-tag affinity tag of the polypeptide.

In some embodiments, the second compound is bound to the first compound. In some embodiments, when incubated together, the first compound, and the second compound, form a double helix complex, in which the first oligonucleotide is bound to the second oligonucleotide.

In some embodiments, a complex comprising the polypeptide, the first compound, and the second compound, wherein the polypeptide is attached to the first compound and the first compound is attached to the second compound, is termed herein an "artificial receptor", "synthetic receptor", "artificial receptor system", or "synthetic receptor system". In some embodiments, expressing a polypeptide in a cell and attaching to it a first compound, and in some embodiments, a second compound, is termed "decorating" a cell. In some embodiments, the terms "decorating", "modifying" and "coating" are used herein interchangeably, having all the same meanings.

d. Recombinant Cells

In some embodiments, disclosed herein is a recombinant cell ectopically expressing a polypeptide, wherein said polypeptide comprises a membranal anchoring domain and an extracellular binding domain, said extracellular binding domain bound to a. a first compound comprising a first oligonucleotide (ODN-1) covalently bound to a binder, either directly or through a first linker, said binder comprising affinity to said extracellular binding domain, b. a second compound comprising a second oligonucleotide (ODN-2) covalently bound to a synthetic agent, either directly or through a second linker, wherein said second oligonucleotide is complementary to said first oligonucleotide.

In some embodiments, the recombinant cell is selected from a group comprising eukaryotes, prokaryotes, mammalian cells, plant cells, human cells, and bacteria. In some embodiments, a mammalian or a human cell is selected from a group comprising epithelial cells, Brunner's gland cells in duodenum, insulated goblet cells of respiratory and digestive tracts, stomach, foveolar cells, chief cells, parietal cells, pancreatic acinar cells, Paneth cells of small intestine, Type II pneumocyte of lung, club cells of lung, barrier cells, type i pneumocytes, gall bladder epithelial cells, centroacinar cells, intercalated duct cells, intestinal brush border cells, hormone-secreting cells, enteroendocrine cells, K cells, L cells, I cells, G cells, enterochromaffin cells, enterochromaffin-like cells, N cells, S cells, D cells, Mo cells, thyroid gland cells, thyroid epithelial cells, parafollicular cells, parathyroid gland cells, parathyroid chief cells, oxyphil cells, pancreatic islets, alpha cells, beta cells, delta cells, epsilon cells, PP cells, salivary gland mucous cells, salivary gland serous cells, Von Ebner's gland cells in tongue, mammary gland cells, lacrimal gland cells, ceruminous gland cells in ear, eccrine sweat gland dark cells, eccrine sweat gland clear cells, apocrine sweat gland cells, gland of moll cells in eyelid, sebaceous gland cells, Bowman's gland cells in nose, hormone-secreting cells, anterior/intermediate pituitary cells, corticotropes, gonadotropes, lactotropes, melanotropes, somatotropes, thyrotropes, magnocellular neurosecretory cells, parvocellular neurosecretory cells, chromaffin cells, keratinocytes, epidermal basal cells, melanocytes, trichocytes, medullary hair shaft cells, cortical hair shaft cells, cuticular hair shaft cells, huxley's layer hair root sheath cells, Henle's layer hair root sheath cells, outer root sheath hair cells, surface epithelial cells of cornea, tongue, mouth, nasal cavity, distal anal canal, distal urethra, and distal vagina, basal cells, intercalated duct cells, striated duct cells, lactiferous duct cells, ameloblast, auditory inner hair cells of organ of Corti, auditory outer hair cells of organ of Corti, basal cells of olfactory epithelium, primary sensory neurons, Merkel cells of epidermis, olfactory receptor neuron, pain-sensitive primary sensory neurons, photoreceptor cells of retina in eye, proprioceptive primary sensory neurons, touch-sensitive primary sensory neurons, chemoreceptor glomus cells of carotid body cells, outer hair cells of vestibular system of ear, inner hair cells of vestibular system of ear, taste receptor cells of taste bud, neuron cells, interneurons, basket cells, cartwheel cells, Stellate cells, Golgi cells, granule cells, Lugaro cells, unipolar brush cells, Martinotti cells, chandelier cells, Cajal-Retzius cells, double-bouquet cells, neuroglia form cells, retina horizontal cells, amacrine cells, spinal interneuron, renshaw cells, spindle neurons, fork neurons, pyramidal cells, place cells, grid cells, speed cells, head direction cells, Betz cells, stellate cells, boundary cells, bushy cells, Purkinje cells, medium spiny neurons, astrocytes, oligodendrocytes, ependymal cells, tanycytes, pituicytes, adipocytes, white fat cells, brown fat cells, liver lipocytes, cells of the adrenal cortex, cells of the zona glomerulosa, cells of the zona fasciculata, cells of the zona reticularis, theca interna cells of ovarian follicle, granulosa lutein cells, theca lutein cells, leydig cells of testes, seminal vesicle cells, prostate gland cells, bulbourethral gland cells, Bartholin's gland cells, gland of littre cells, uterus endometrium cells, juxtaglomerular cells, macula densa cells of kidney, peripolar cells of kidney, mesangial cells of kidney, parietal epithelial cells, podocytes, proximal tubule brush border cells, loop of Henle thin segment cells, kidney distal tubule cells, kidney collecting duct cells, principal cells, intercalated cells, transitional epithelium, duct cells, efferent ducts cells, epididymal principal cells, epididymal basal cells, endothelial cells, planum semilunatum epithelial cells of vestibular system of ear, organ of Corti interdental epithelial cells, loose connective tissue fibroblasts, corneal fibroblasts, tendon fibroblasts, bone marrow reticular tissue fibroblasts, other nonepithelial fibroblasts, pericytes, hepatic stellate cells, nucleus pulposus cells of intervertebral disc, hyaline cartilage chondrocytes, fibrocartilage chondrocytes, elastic cartilage chondrocytes, osteoblast/osteocytes, osteoprogenitor cells, hyalocyte of vitreous body of eye, stellate cells of perilymphatic space of ear, pancreatic stellate cells, red skeletal muscle cells, white skeletal muscle cells, intermediate skeletal muscle cells, nuclear bag cells of muscle spindle, nuclear chain cells of muscle spindle, myosatellite cells, cardiac muscle cells, cardiac muscle cells, node cells, Purkinje fiber cells, smooth muscle cells, myoepithelial cells of iris, myoepithelial cells of exocrine glands, erythrocytes, megakaryocytes, platelets, monocytes, connective tissue macrophage, epidermal Langerhans cells, osteoclast, dendritic cells, microglial cells, neutrophil granulocytes, eosinophil granulocytes, basophil granulocytes, hybridoma cells, mast cells, helper T cells, suppressor T cells, cytotoxic T cells, natural killer T cells, B cells, natural killer cells, reticulocytes, hematopoietic stem cells and committed progenitors for the blood and immune system, oogonium/oocytes, spermatids, spermatocytes, spermatogonium cells, spermatozoon, and interstitial kidney cells.

In some embodiments, a prokaryote comprises a microbial cell such as bacteria, e.g., Gram-positive or Gram-negative bacteria. In some embodiments, the bacteria comprise Gram-negative bacteria or Negativicutes that stain negative in Gram stain. In some embodiments, the bacteria comprise gram-positive bacteria, gram-negative bacteria, or archaea.

In some embodiments, Gram-negative bacteria comprise *Acinetobacter calcoaceticus, Actinobacillus actinomyvcetemcomitans, Aeromonas hydrophila, Alcaligenes xylosoxidans, Bacteroides, Bacteroides fragilis, Bartonella bacilliformis, Bordetella* spp., *Borrelia burgdorferi, Branhamella catarrhalis, Brucella* spp., *Campylobacter* spp., *Chalmydia pneumoniae, Chlamydia psittaci. Chlamydia trachomatis, Chromobacterium violaceum, Citrobacter* spp., *Eikenella corrodens, Enterobacter aerogenes, Escherichia coli, Flavobacterium meningosepticum. Fusobacterium* spp., *Haemophilus influenzae, Haemophilus* spp., *Helicobacter*

*pylori, Klebsiella* spp., *Legionella* spp., *Leptospira* spp., *Morarella catarrhalis, Morganella morganii, Mycoplasma pneumoniae, Neisseria gonorrhoeae, Neisseria meningitidis, Pasteurella multocida, Plesiomonas shigelloides, Prevotella* spp., *Proteus* spp., *Providencia rettgeri, Pseudomonas aeruginosa, Pseudomonas* spp., *Rickettsia prowazekii, Rickettsia rickettsii, Rochalimaea* spp., *Salmonella* spp., *Salmonella typhi, Serratia marcescens, Shigella* spp., *Treponema carateum, Treponema pallidum, Treponema pallidum endemicum, Treponema pertenue, Veillonella* spp., *Vibrio cholerae, Vibrio vulnificus, Yersinia enterocolitica., Yersinia pestis.*

In some embodiments, the bacteria comprise gammaproteobacteria (e.g. *Escherichia coli, pseudomonas, vibrio* and *klebsiella*) or Firmicutes (belonging to class Negativicutes that stain negative in Gram stain).

In some embodiments, Gram-positive bacteria comprise *Actinomyces* spp., *Bacillus anthracis, Bifidobacterium* spp., *Clostridium botulinum, Clostridium perfringens, Clostridium* spp., *Clostridium tetani, Corynebacterium diphtheriae, Corynebacterium jeikeium, Enterococcus faecalis, Enterococcus faecium, Erysipelothrix rhusiopathiae, Eubacterium* spp., *Gardnerella vaginalis, Gemella morbillorum, Leuconostoc* spp., *Mycobacterium abcesss, Mycobacterium avium* complex, *Mycobacterium chelonae, Mycobacterium fortuitum, Mycobacterium haemophilium, Mycobacterium kansasii, Mycobacterium leprae, Mycobacterium marimm, Mycobacterium scrofulaceum, Mycobacterium smegmatis, Mycobacterium terrae, Mycobacterium tuberculosis, Mycobacterium ulcerans, Nocardia* spp. *Peptococcus niger, Peptostreptococcus* spp., *Propionibacterium* spp., *Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdunensis, Staphylococcus saccharolyticus, Staphylococcus saprophyticus. Staphylococcus schleiferi, Staphylococcus simulans, Staphylococcus warneri, Staphylococcus xylosus, Streptococcus agalactiae* (group B *streptococcus*), *Streptococcus anginosus, Streptococcus bovis, Streptococcus canis, Streptococcus equi, Streptooccus milleri, Streptococcus mitior, Streptococcus mutans, Streptococcus pneumoniae, Streptococcus pyogenes* (group A *streptococcus*), *Streptococcus salivarius, Streptococcus sanguis.*

In some embodiments the bacteria is a species selected from the group consisting of *Escherichia, Shigella, Salmonella, Erwinia, Yersinia, Bacillus, Vibrio, Legionella, Pseudomonas, Neisseria, Bordetella, Helicobacter, Listeria, Agrobacterium, Staphylococcus, Streptococcus, Enterococcus. Clostridium, Corynebacterium, Mycobacterium, Treponema, Borrelia, Francisella, Brucella, Campylobacter, Klebsiella, Frankia, Bartonella, Rickettsia, Shewanella, Serratia, Enterobacter, Proteus, Providencia, Brochothrix,* and *Brevibacterium.*

In some embodiments, an oligonucleotide encoding the polypeptide is incorporated in an expression vector. In some embodiments, an oligonucleotide encoding the polypeptide is incorporated in a viral vector. An expression or viral vector can be introduced to the cell by any of the following: transfection, electroporation, infection, or transduction. In other embodiments, the polypeptide is encoded by an mRNA polynucleotide which is delivered for example by electroporation. In one embodiment, methods of electroporation comprise flow electroporation technology.

A skilled artisan would appreciate that the term "vector" encompasses a nucleic acid molecule capable of transporting another nucleic acid to which it has been linked. One type of vector is a "plasmid", which encompasses a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. A skilled artisan would appreciate that the terms "plasmid" and "vector" may be used interchangeably having all the same qualities and meanings. In one embodiment, the term "plasmid" is the most commonly used form of vector. However, the disclosure presented herein is intended to include such other forms of expression vectors, such as viral vectors (e.g., replication defective retroviruses, lentivirus, adenoviruses and adeno-associated viruses), which serve equivalent functions. Additionally, some viral vectors are capable of targeting a particular cell type either specifically or non-specifically.

The recombinant expression vectors disclosed herein comprise a nucleic acid in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, a skilled artisan would appreciate that the term "operably linked" may encompass nucleotide sequences of interest linked to the regulatory sequence(s) in a manner that allows for expression of the nucleotide sequence (e.g., in an in vitro transcription/translation system or in a host cell when the vector is introduced into the host cell). A skilled artisan would appreciate that term "regulatory sequence" may encompass promoters, enhancers and other expression control elements (e.g., polyadenylation signals). Such regulatory sequences are described, for example, in Goeddel; GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors disclosed here may be introduced into host cells to thereby produce proteins or peptides, including fusion proteins or peptides, encoded by nucleic acids as described herein. For example, an expression vector comprises a nucleic acid encoding a polypeptide comprising a membranal anchoring domain and an extracellular binding domain.

Another embodiment disclosed herein pertains to host cells into which a recombinant expression vector disclosed here has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

For stable transfection of mammalian cells, it is known that, depending upon the expression vector and transfection technique used, only a small fraction of cells may integrate the foreign DNA into their genome the remainder of the DNA remains episomal. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the polypeptide or can be introduced on a separate vector. Cells stably transfected with the introduced nucleic acid can be identified by drug selection (e.g., cells that have incorporated the selectable marker gene will survive, while the other cells die). In another embodiment the transfected cells are identified by the induction of expression of an endogenous reporter gene. In another embodiment the transfected cells are identified by the expression of the polypeptide.

A skilled artisan would appreciate that there are several methods in the art to identify recombinant cells expressing the polypeptide. In some embodiments, the expression of the mRNA encoding the polypeptide can be measured by RT-PCR. In some embodiments, the insertion of a DNA encoding the polypeptide can be identified by DNA gene sequencing. In some embodiments, expression of the polypeptide can be detected by an antibody, for example by Western blotting or ELISA. In some embodiments, the expression of a His-tag on the cell membrane can be detected by a labeled His-tag binder, for example by any of the binders disclosed herein, or by any other His-tag binder available.

In some embodiments, the cell's function is not disturbed by the presence of the polypeptide, the first, and the second compound on its surface. In some embodiments, the cell can be reversibly modified. In some embodiments, the membranal anchoring domain comprises a transmembranal protein or a part of it, an artificial polypeptide, or a combination thereof. In some embodiments, the transmembranal protein comprises an outer membrane protein C (OmpC); receptor tyrosine kinases (RTKs); Ion channel linked receptors; Enzyme-linked receptors; G protein-coupled receptors or any combination thereof; each represents a separate embodiment according to this invention. In some embodiments, the extracellular domain comprises an affinity tag. In some embodiments, the affinity tag comprises a poly-histidine peptide (6×-His-tag, 10×-His-tag, His-tag), a tetra cysteine peptide (CCPGCC, TC tag), or a combination thereof. In some embodiments, the binder comprises a His-tag specific binder. In some embodiments, the binder comprises a moiety represented by the structure of formula C, D, D(a), D(b), E, E(a), E(b), G, G(a), or G(b), as described herein below; each is a separate embodiment. In some embodiments, the first compound is represented by the structure of formula J, H, H(a) and H(b) and compounds 100-104. In some embodiments, the second compound is represented by the structure of formula K and compounds 200-207. In some embodiments, the first linker comprises at least one polyethyleneglycol (PEG) moiety, at least one phosphate moiety, at least one thioalkyl moiety or any combination thereof. In some embodiments, the first compound further comprises a labeling moiety. In some embodiments, the labeling moiety is a fluorescent dye. In some embodiments, the synthetic agent of said second compound comprises a molecular marker, a labeling moiety, a fluorescent dye, an adhesion molecule, a cancer cell binder, a protein binder, a protein ligand, an anticancer agent, a surface binder (e.g., an abiotic surface binder), a growth factor, an angiogenic factor, a cytokine, a hormone, a DNA molecule, a siRNA molecule, an oligosaccharide, a protein receptor, an immune activator, an immune suppressor, a small molecule, a drug, or a derivative therefore, or any combination thereof; each represents a separate embodiment according to this invention. In some embodiments, the second compound further comprises a second labeling moiety. In some embodiments, the second labeling moiety comprises a fluorescent dye.

e. Membranal Anchoring Domain

In some embodiments, the polypeptide according to this invention is a Cell Surface Protein (CSP). In some embodiments, the transmembranal protein comprises an outer membrane protein C (OmpC); receptor tyrosine kinases (RTKs); Ion channel linked receptors; Enzyme-linked receptors; G protein-coupled receptors or any combination thereof; each represents a separate embodiment according to this invention.

In some embodiments, the polypeptide comprises a membranal anchoring domain. In some embodiments, a membranal anchoring domain comprises a polypeptide that, when expressed in a cell, it attaches to the cell membrane. In some embodiments, a membranal anchoring domain comprises at least one end emerging to the extracellular side. In some embodiments, the membranal anchoring domain comprises a transmembranal protein. In some embodiments, the membranal anchoring domain comprises a transmembranal fragment of a protein. In some embodiments, the protein comprises a protein expressed in the recombinant cell. In some embodiments, the protein comprises a cell not expressed in the recombinant cell. In some embodiments, the anchoring domain comprises an artificial polypeptide.

A skilled artisan would appreciate that a membrane anchoring can be selected to be stably expressed in the recombinant cell. For example, the membrane anchoring domain can comprise a protein that is abundantly expressed in the recombinant cell. In some embodiments, the membrane anchoring comprises a protein or a part of it, known to be abundantly expressed on the membrane of the recombinant cell. Thus, a membrane anchoring can be chosen to be a protein abundantly expressed on the recombinant cell membrane.

In some embodiments, a membrane anchoring comprises outer membrane protein C (OmpC) or a part thereof. In some embodiments, the transmembranal protein comprises an outer membrane protein C (OmpC); receptor tyrosine kinases (RTKs); Ion channel linked receptors; Enzyme-linked receptors; G protein-coupled receptors, a part thereof or any combination thereof; each represents a separate embodiment according to this invention. In some embodiments, a membrane anchoring comprises a polypeptide comprising at least 80% homology to any of SEQ ID NO.: 13, 16, or 21.

f. Extracellular Binding Domain

In some embodiments, the extracellular domain comprised in the recombinant polypeptide comprises an affinity tag. In some embodiments, the binder comprises affinity to a specific affinity tag in the extracellular binding domain.

In some embodiments, an affinity tag comprises a protein tag. In some embodiments, an affinity tag comprises an epitope tag. In some embodiments, an affinity tag comprises a peptide tag. In some embodiments, an affinity tag comprises a combination of a number of tags.

In some embodiments, affinity tags are enzymatically modified, for example they are biotinylated by biotin ligase. In some embodiments, affinity tags are chemically modified. In some embodiments, expression of a tag does not interfere with the cell functions. In some embodiments, an affinity tag can be removed by specific proteolysis. In some embodiments, tags are removed by TEV protease, Thrombin, Factor Xa or Enteropeptidase.

In some embodiments, an affinity tag is selected from a group comprising AviTag, C-tag, Calmodulin-tag, polyglutamate tag, E-tag, FLAG-tag, HA-tag, His-tag, 5-10 histidines bound by a nickel or cobalt chelate (HHHHHH), Myc-tag, NE-tag, Rho1D4-tag, S-tag, SBP-tag, Softag 1, Softag 3, Spot-tag, Strep-tag, TC tag, Ty tag, V5 tag, VSV-tag, Xpress tag, Isopeptag, SpyTag, SnoopTag, SnoopTagJr, DogTag, SdyTag, BCCP (Biotin Carboxyl Carrier Protein), Glutathione-S-transferase-tag, Green fluorescent protein-tag, HaloTag, SNAP-tag, CLIP-tag, Maltose binding protein-tag, Nus-tag, Thioredoxin-tag, Fc-tag, Designed Intrinsically Disordered tags containing disorder promoting amino acids (P, E, S, T, A, Q, G, . . . ), and Carbohydrate Recognition Domain or CRDSAT-tag; each represents a separate embodiment.

In some embodiments, an affinity tag comprises a poly-histidine peptide comprising 6 histidine residues (6×-His-tag). In some embodiments, an affinity tag comprises a poly-histidine peptide comprising 10 histidine residues (10×-His-tag). In some embodiments, an affinity tag comprises a tetra cysteine peptide (CCPGCC, TC tag).

In some embodiments, more than one type of extracellular binding domain or affinity tag is used. A skilled artisan would recognize using more than one type of extracellular binding domain allows decorating the cell with more than one type of receptor. For example, a first extracellular binding domain and a second extracellular binding domain can be co-expressed in a recombinant cell. The recombinant cell is then incubated with a first and a second binder, wherein the first binder binds the first extracellular binding domain and the second binder binds the second extracellular binding domain. Thus, the first and the second binders will be bound to the same recombinant cell.

g. The First Compound (X-ODN-1)

In some embodiments, the first compound, of the system, the artificial receptor, the recombinant cell, and the methods according to this invention (i.e., X-ODN-1) comprises:

a. a first oligonucleotide (ODN-1),
b. a binder which comprises affinity to a tagged polypeptide,
c. optionally a first linker which links the first oligonucleotide with the binder,
d. optionally a labeling moiety; and
e. optionally a third linker which links the first oligonucleotide with the labeling moiety.

In some embodiments, the first oligonucleotide is directly bound to the binder. In other embodiments, the first oligonucleotide is bound to the binder through a first linker. In some embodiments, the first oligonucleotide is directly bound to the labeling moiety. In other embodiments, the first oligonucleotide is bound to the labeling moiety through a third linker.

In some embodiments, the first compound of the system, the artificial receptor, the recombinant cell, and the methods according to this invention (i.e., X-ODN-1) is represented by the structure of formula J:

wherein
F is a labeling moiety (e.g., a dye or a dye derivative) or absent;
$L_3$ is a third linker or absent;
ODN1 is a first oligonucleotide sequence;
$L_1$ is a first linker or absent; and
$Y_1$ is a binder.

In some embodiments, the first compound of the system, the artificial receptor, the recombinant cell, and the methods according to this invention (i.e., X-ODN-1) is represented by the structure of formula H:

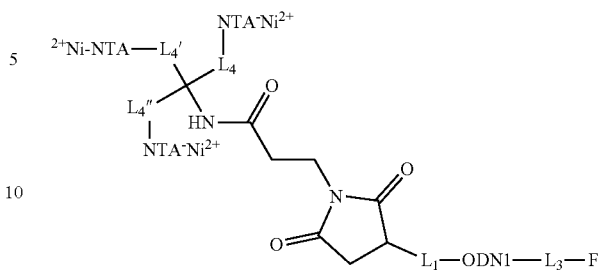

wherein
F is a labeling moiety or absent (e.g., a dye or a dye derivative);
$L_3$ is a third linker or absent;
ODN1 is a first oligonucleotide sequence,
$L_1$ is a first linker or absent;
$L_4$, $L_4'$, and $L_1''$ are each independently a substituted or unsubstituted linear or branched alkyl chain of 1-20 carbon atoms, substituted or unsubstituted linear or branched alkyl ether chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl diamide chain of 1-20 carbon atoms, substituted or unsubstituted linear or branched alkyl amine chain of 1-20 carbon atoms, or any combination thereof.

In some embodiments, the first compound of the system, the artificial receptor, the recombinant cell, and the methods according to this invention (i.e., X-ODN-1) is represented by the structure of formula H(a):

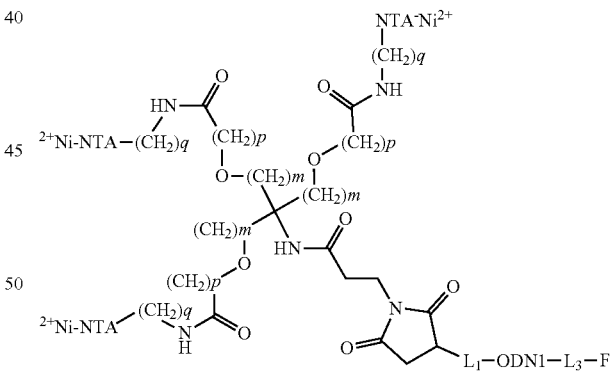

wherein
F is a labeling moiety or absent (e.g., a dye or a dye derivative);
$L_3$ is a third linker or absent;
ODN1 is a first oligonucleotide sequence;
$L_1$ is a first linker or absent;
m, p and q are each independently an integer number between 1 and 8.

In some embodiments, the first compound of the system, the artificial receptor, the recombinant cell, and the methods according to this invention (i.e., X-ODN-1) is represented by the structure of formula H(b):

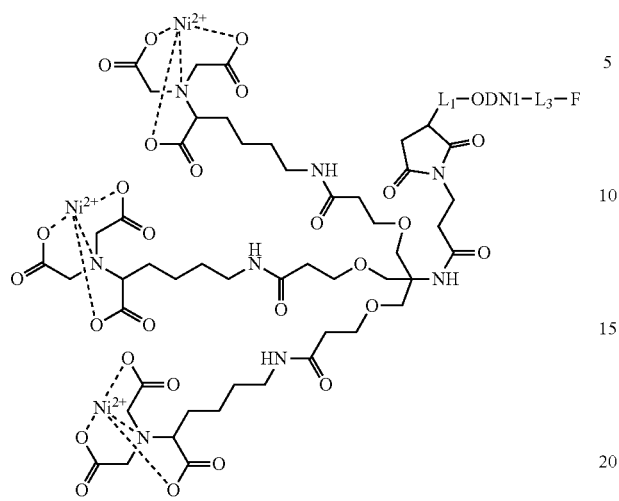

wherein
- F is a labeling moiety or absent (e.g., a dye or a dye derivative);
- $L_3$ is a third linker or absent;
- ODN1 is a first oligonucleotide sequence; and
- $L_1$ is a first linker or absent.

In some embodiments, the first compound of the system, the artificial receptor, the recombinant cell, and the methods according to this invention (i.e., X-ODN-1) is represented by the structure of the nickel complexes of the following compounds:

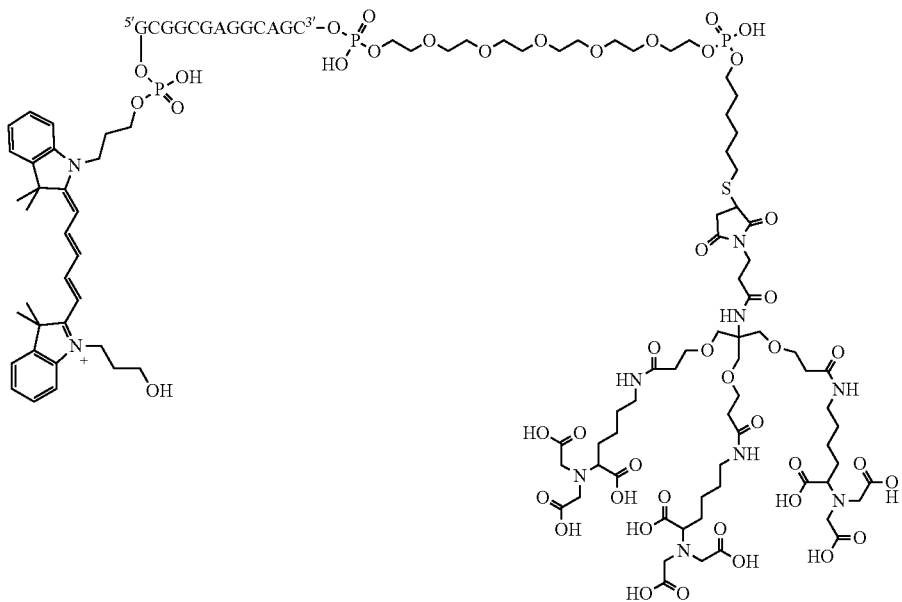

Compound 100

[CY5-ODN-1]

Compound 101
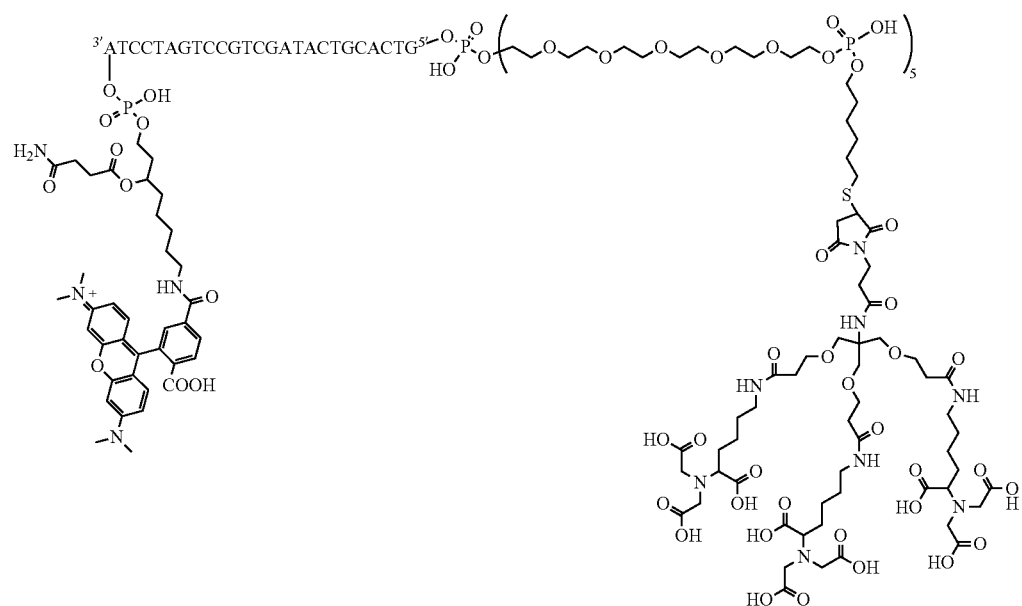
[TAMRA-ODN-1]
Compound 102
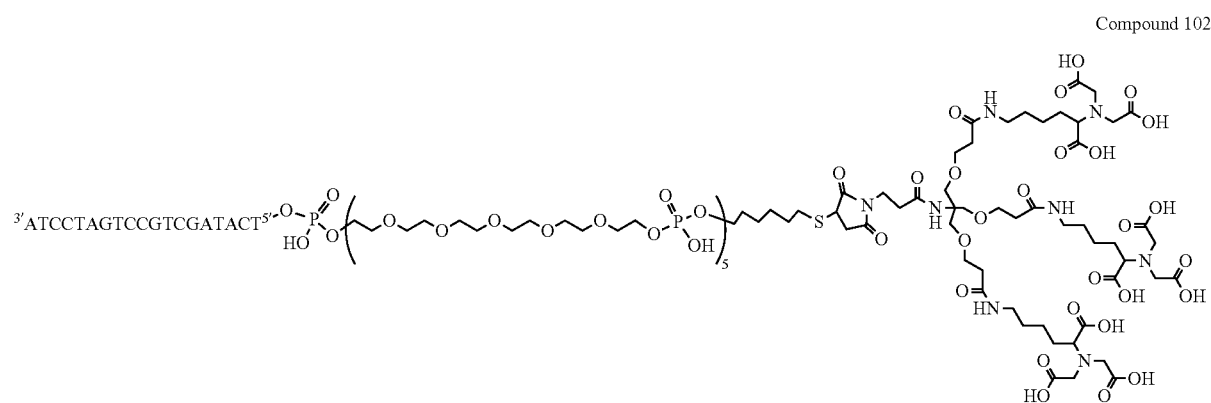
[ODN-1a]

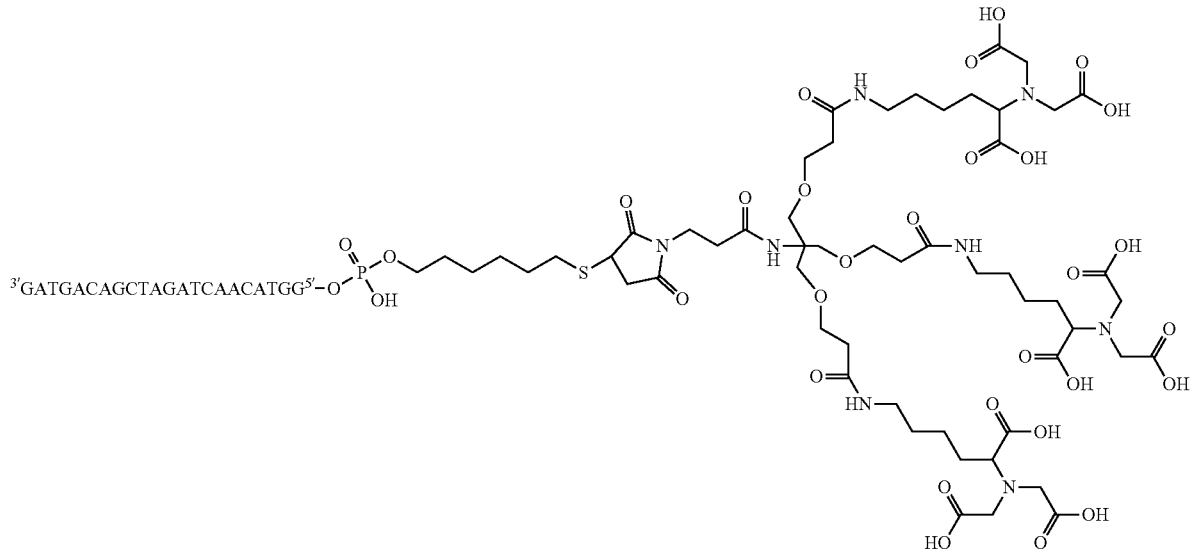

[ODN-1b]

Compound 103

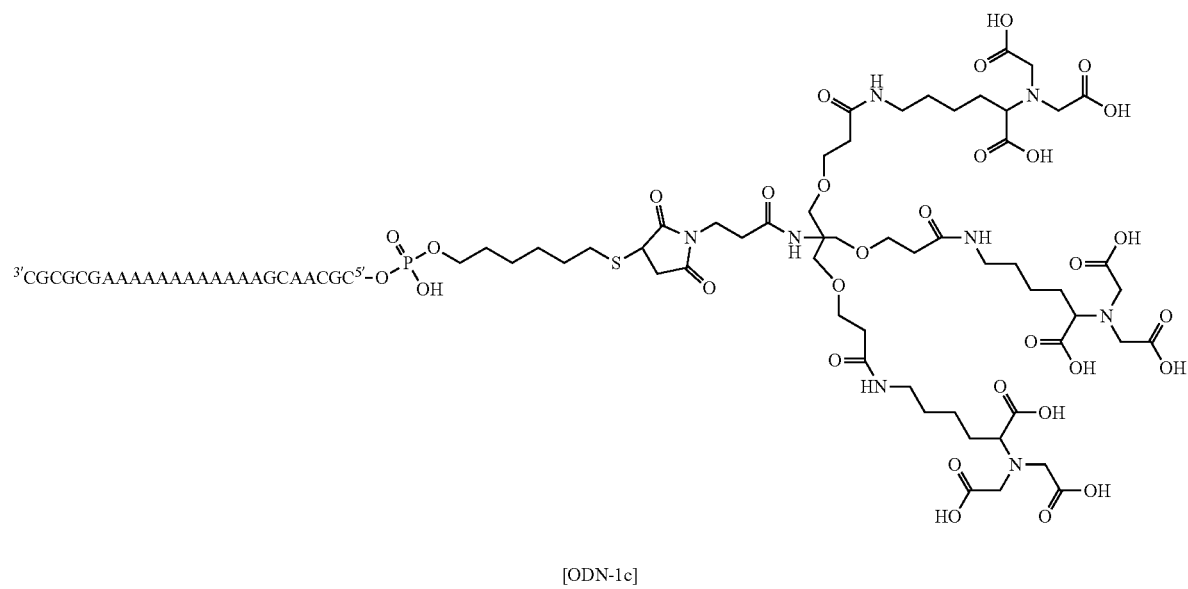

[ODN-1c]

Compound 104

In some embodiments, $Y_1$ of formulas J is a binder. In some embodiments, $Y_1$ is an aptamer, a natural ligand, a synthetic group, or a peptide which binds a specific protein with high affinity and selectivity. In some embodiments, $Y_1$ comprises any selective protein binder known in the art. In another embodiment, $Y_1$ comprises marimastat, ethacrynic acid, bisethacrynic acid, complexed nitrilotriacetic acid (NTA), complexed bis NTA, complexed tris-NTA, Ni-nitrilotriacetic acid (Ni-NTA), bis Ni-NTA, tris-Ni-NTA, PDGF-BB, heparin, FGF aptamer, estrogen, DNA aptamer, RNA aptamer, peptide aldehyde, estrogen, suberoylanilide-hydroxamic acid (SAHA), or a peptide binder. In another embodiment, the complexed NTA, complexed bis-NTA, complexed tris NTA is a nickel or cobalt complex. In some embodiments, $Y_1$ comprises a Tag-binding region. In some embodiments, $Y_1$ comprises any molecule that can target different type of affinity tags, such as poly-histidine peptide (HHHHHH, His-tag), or tetra cysteine peptide (CCPGCC, TC tag). In another embodiment, $Y_1$ comprises FlAsH probe. In another embodiment, Y comprises ReAsH probe. In some embodiments, $Y_1$ comprises a His-tag binder. In some embodiments, $Y_1$ is a His-tag binder. In some embodiments, $Y_1$ comprises Ni-nitrilotriacetic acid (Ni-NTA), bis-Ni-NTA, or tris-Ni-NTA. In some embodiments, $Y_1$ comprises a derivative of Ni-nitrilotriacetic acid (Ni-NTA), bis-Ni-NTA, or tris-Ni-NTA, wherein the term "derivative" includes but not limited to alkyl derivatives, amide derivatives, amine derivatives, carboxy derivatives, and the like. In some embodiments, $Y_1$ comprises a derivative of tris-Ni-nitrilotriacetic acid (tris-Ni-NTA), a derivative of bis-Ni-nitrilotriacetic acid (bis-Ni-NTA), a derivative of mono-Ni-nitrilotriacetic acid (Ni-NTA); each represents a separate embodiment according to this invention. In some embodiments, $Y_1$ comprises any monomolecular compound which comprises three Ni-NTA moieties (i.e., tris-Ni-NTA). In some embodiments, $Y_1$ is represented by the structure of formulas D, D(a), D(b), G, G(a), G(b) as described herein below. In some embodiments, $Y_1$ comprises the structure of formulas D, D(a), D(b), G, G(a), G(b) as described herein below.

In some embodiments, $L_1$ of formulas J, H, H(a), and H(b) is a first linker. In some embodiments, $L_1$ is absent. In some embodiments, $L_1$ is bound to the 3' end of ODN1. In some embodiments, $L_1$ is bound to the 5' end of ODN1. In some embodiments, $L_1$ is bound to $Y_1$ through an amide bond, an ester bond, a phosphate bond, an ether bond, a thioether bond, each represents a separate embodiment according to this invention. In some embodiments, $L_1$ is as defined for the "first linker" hereinbelow.

In some embodiments, ODN1 of formulas J, H, H(a), and H(b) is a first oligonucleotide sequence. In some embodiments, ODN1 is directly bound to $Y_1$, through an amide bond, an ester bond, a phosphate bond, an ether bond, each represents a separate embodiment according to this invention. In some embodiments, ODN1 is directly bound to F, through an amide bond, an ester bond, a phosphate bond, an ether bond, a thioether bond, each represents a separate embodiment according to this invention. In some embodiments, ODN1 is directly bound to F, through a phosphate moiety.

In some embodiments, $L_3$ of formulas J, H, H(a), and H(b) is a third linker. In some embodiments, $L_3$ is absent. In some embodiments, $L_3$ is bound to the 3' end of ODN1. In some embodiments, $L_3$ is bound to the 5' end of ODN1. In some embodiments, $L_3$ is bound to F through an amide bond, an ester bond, a phosphate bond, an ether bond, a thioether bond, each represents a separate embodiment according to this invention. In some embodiments, $L_3$ is as defined for the "third linker" hereinbelow.

In some embodiments, F of formulas J, H, H(a), and H(b) is a labeling moiety. In some embodiments, F is absent. In some embodiments, F is a dye. Examples of dyes include but are not limited to: dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, TAMRA, BODIPY, FITC or derivative thereof. In some embodiments, F is a dye derivative. In some embodiments, a labeling moiety is bound to ODN1 through an amide bond, an ester bond, a phosphate bond, an ether bond, a thioether bond; each represents a separate embodiment according to this invention. In some embodiments, a labeling moiety F is bound to $L_3$ through an amide bond, an ester bond, a phosphate bond, an ether bond, a thioether bond; each represents a separate embodiment according to this invention.

h. Linkers ($L_1$ and $L_3$)

In some embodiments, the first compound of the system, the artificial receptor, the recombinant cell, and the methods according to this invention (i.e., X-ODN-1) comprises:
a. a first oligonucleotide (ODN-1)
b. a binder which comprises affinity to the extracellular binding domain of said polypeptide,
c. optionally a first linker which links the first oligonucleotide with the binder
d. optionally a labeling moiety, and
e. optionally a third linker which links the first oligonucleotide with the labeling moiety.

The terms "linker" or "spacer" are used interchangeably, and refer to a chemical fragment that connects between the 5' or the 3' end of an oligonucleotide according to this invention, and other chemical moieties of the system of the invention (e.g., binder, labeling moiety or a dye, synthetic agent, etc). In some embodiments, the linker is covalently bound to the oligonucleotide through a phosphate moiety.

i. A first linker ($L_1$)

In some embodiments, the first compound (X-ODN-1) of the system, the artificial receptor, the recombinant cell, and the methods according to the invention, comprises a first linker, which links the first oligonucleotide with the binder. In some embodiments, the first linker is covalently bound to the 3' end of the first oligonucleotide (ODN-1). In some embodiments, the first linker is covalently bound to the 5' end of the first oligonucleotide. In some embodiments, the first linker is covalently bound to the binder through an amide bond, an ester bond, a phosphate bond, an ether bond, a thioether bond; each represents a separate embodiment according to this invention. In some embodiments, the first linker is covalently bound to the first oligonucleotide through an amide bond, an ester bond, a phosphate bond, an ether bond, a thioether bond, each represents a separate embodiment according to this invention. In some embodiments, the first linker is covalently bound to the first oligonucleotide through a phosphate moiety.

In some embodiments, the first linker of the system, the artificial receptor, the recombinant cell, and the methods, and/or $L_1$ according to formula J, H, H(a), and H(b) is any chemical fragment which comprises at least one segment of a commercially available phosphoramidite spacer derivative. Phosphoramidite compounds are used as reactive agents for linking oligonucleotides according to this invention with other moieties, e.g., the binder of this invention, the labeling moiety, the synthetic agents, etc. Non limiting examples of such phosphoramidite derivatives, useful for linking oligonucleotides with other moieties include:

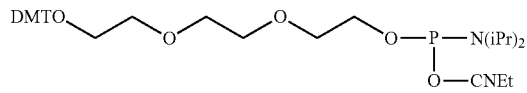

Spacer Phosphoramidite 9

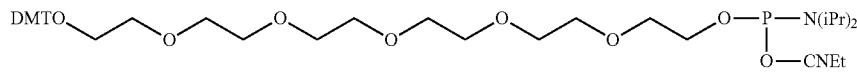

Spacer Phosphoramidite 18

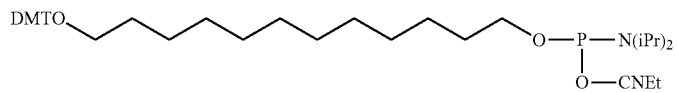

Spacer C12 CE Phosphoramidite

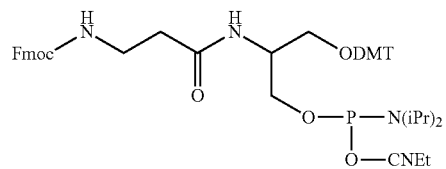

Amino-Modifier Serinol Phosphoramidite

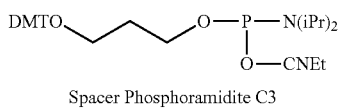

Spacer Phosphoramidite C3

-continued

In some embodiments, the first linker of the system, the artificial receptor, the recombinant cell, and the methods, and/or $L_1$ according to formula J, H, H(a), and H(b) is a substituted or unsubstituted linear or branched alkyl chain of 1-20 carbon atoms, substituted or unsubstituted linear or branched alkyl ether chain of 1-20 carbon atoms, oligoethylene glycol, polyethylene glycol (PEG), oligopropylene glycol, polypropylene glycol (PPG), substituted or unsubstituted linear or branched thioalkyl chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl ester of 1-20 carbon atoms, substituted or unsubstituted linear or branched alkyl diamide chain of 2-10 carbon atoms, substituted or unsubstituted linear or branched alkyl triazole of 1-20 carbon atoms, substituted or unsubstituted linear or branched alkyl amine chain of 1-20 carbon atoms or any combination thereof; each represents a separate embodiment according to this invention.

In some embodiments, the first linker of the system, the artificial receptor, the recombinant cell, and the methods, and/or $L_1$ according to formula J, H, H(a), and H(b) comprises at least one polyethyleneglycol (PEG) moiety. In some embodiments, the first linker, and/or $L_1$ comprises at least one phosphate moiety. In some embodiments, the first linker, and/or $L_1$ comprises at least one alkyl ether moiety. In some embodiments, the first linker, and/or $L_1$ comprises at least one alkyl diamide moiety. In some embodiments, the first linker, and/or $L_1$ comprises at least one alkyl moiety. In some embodiments, the first linker, and/or $L_1$ comprises at least one thioalkyl moiety. In some embodiments, the first linker, and/or $L_1$ comprises at least one polyethyleneglycol (PEG) moiety, at least one phosphate moiety, at least one thioalkyl moiety, at least one alkyl moiety, or any combination thereof.

In some embodiments, the first linker of the system, the artificial receptor, the recombinant cell, and the methods, and/or $L_1$ according to formula J, H, H(a), and H(b) is represented by the following formula:

wherein
k and l are each independently an integer number between 0 and 10; and
w is an integer number between 1 and 10.

In some embodiments, k is 0. In some embodiments, k is 6. In some embodiments, k is 1, 2, 3, 4, 5, 7, 8, 9, 10; each is a separate embodiment according to this invention.

In some embodiments, l is 0. In some embodiments, l is 1. In some embodiments, l is 5. In some embodiments, l is 2, 3, 4, 6, 7, 8, 9, 10; each is a separate embodiment according to this invention.

In some embodiments, w is 6. In some embodiments, w is 1, 2, 3, 4, 5, 7, 8, 9, 10; each is a separate embodiment according to this invention.

j. A Third Linker ($L_3$)

In some embodiments, the first compound (X-ODN-1) of the system, the artificial receptor, the recombinant cell, and the methods comprises a third linker, which links the first oligonucleotide with the labeling moiety. In some embodiments, the third linker is absent. In some embodiments, the third linker is bound to the 3' end of ODN-1. In some embodiments, the third linker is bound to the 5' end of ODN-1. In some embodiments, the third linker is a part of a commercially available phosphoramidite dye derivative. In some embodiments, the third linker is bound to the labeling moiety through an amide bond, an ester bond, a phosphate bond, an ether bond, a thioether bond; each represents a separate embodiment according to this invention. In some embodiments, the third linker is bound to ODN-1 through an amide bond, an ester bond, a phosphate bond, an ether bond, a thioether bond; each represents a separate embodiment according to this invention. In some embodiments, the third linker is covalently bound to the first oligonucleotide through a phosphate moiety.

In some embodiments, the third linker of the system, the artificial receptor, the recombinant cell, and the methods and/or $L_3$ according to formula J, H, H(a), and H(b), is a substituted or unsubstituted linear or branched alkyl chain of 1-20 carbon atoms, substituted or unsubstituted linear or branched alkyl ether chain of 1-20 carbon atoms, oligoethylene glycol, polyethylene glycol (PEG), oligopropylene glycol, polypropylene glycol (PPG), substituted or unsubstituted linear or branched thioalkyl chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl ester of 1-20 carbon atoms, substituted or unsubstituted linear or branched alkyl diamide chain of 2-10 carbon atoms, substituted or unsubstituted linear or branched alkyl triazole of 1-20 carbon atoms, substituted or unsubstituted linear or branched alkyl amine chain of 1-20 carbon atoms or any combination thereof; each is a separate embodiment according to this invention.

In some embodiments, the third linker of the system, the artificial receptor, the recombinant cell, and the methods, and/or L according to formula J, H, H(a), and H(b) comprises at least one polyethyleneglycol (PEG) moiety. In some embodiments, the third linker, and/or $L_3$ comprises at least one phosphate moiety. In some embodiments, the third linker, and/or $L_3$ comprises at least one alkyl ether moiety. In some embodiments, the third linker, and/or $L_3$ comprises at least one alkyl diamide moiety. In some embodiments, the third linker, and/or $L_3$ comprises at least one alkyl moiety. In some embodiments, the third linker, and/or $L_3$ comprises at least one thioalkyl moiety. In some embodiments, the third linker, and/or $L_3$ comprises at least one polyethyleneglycol (PEG) moiety, at least one phosphate moiety, at least one thioalkyl moiety, at least one alkyl moiety, or any combination thereof.

In some embodiments, the third linker of the system, the artificial receptor, the recombinant cell, and the methods, and/or $L_3$ according to formula J, H, H(a), and H(b) is represented by the following formula:

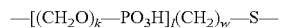

wherein
k and l are each independently an integer number between 0 and 10; and
w is an integer number between 1 and 10.

In some embodiments, k is 0. In some embodiments, k is 6. In some embodiments, k is 1, 2, 3, 4, 5, 7, 8, 9, 10; each is a separate embodiment according to this invention.

In some embodiments, l is 0. In some embodiments, l is 1. In some embodiments, l is 5. In some embodiments, l is 2, 3, 4, 6, 7, 8, 9, 10; each is a separate embodiment according to this invention.

In some embodiments, w is 6. In some embodiments, w is 1, 2, 3, 4, 5, 7, 8, 9, 10; each is a separate embodiment according to this invention.

k. Binder ($Y_1$)

In some embodiments, a binder of the system, the artificial receptor, the recombinant cell, and the methods according to this invention is an aptamer, a natural ligand, a synthetic group, or a peptide, which binds a specific protein with high affinity and selectivity.

In some embodiments, the binder of the system, the artificial receptor, the recombinant cell, and the methods of this invention is any selective protein binder known in the art. In another embodiment, the selective protein binder comprises marimastat, ethacrynic acid, bisethacrynic acid, complexed nitrilotriacetic acid (NTA), complexed bis NTA, complexed tris-NTA, Ni-nitrilotriacetic acid (Ni-NTA), bis Ni-NTA, tris-Ni-NTA, PDGF-BB, heparin, FGF aptamer, estrogen, DNA aptamer, RNA aptamer, peptide aldehyde, estrogen, suberoylanilidehydroxamic acid (SAHA), or a peptide binder. In another embodiment, the complexed NTA, complexed bis-NTA, complexed tris NTA is a nickel or cobalt complex.

In some embodiments, the binder comprises a Tag-binding region.

In some embodiments, the binder is any molecule that can target different type of affinity tags, such as poly-histidine peptide (HHHHHH, His-tag), or tetra cysteine peptide (CCPGCC, TC tag). In another embodiment, the binder is FlAsH probe. In another embodiment, the binder is ReAsH probe.

In some embodiments, the selective binder is a His-tag binder. In some embodiments, the binder of this invention comprises Ni-nitrilotriacetic acid (Ni-NTA), bis-Ni-NTA, or tris-Ni-NTA. In some embodiments, the binder of this invention comprises a derivative of Ni-nitrilotriacetic acid (Ni-NTA), bis-Ni-NTA, or tris-Ni-NTA, wherein the term "derivative" includes but not limited to alkyl derivatives, amide derivatives, amine derivatives, carboxy derivatives, and the like In some embodiments, the His-Tag binder comprises a derivative of tris-Ni-nitrilotriacetic acid (tris-Ni-NTA), a derivative of bis-Ni-nitrilotriacetic acid (bis-Ni-NTA), a derivative of mono-Ni-nitrilotriacetic acid (Ni-NTA); each represents a separate embodiment according to this invention. In some embodiments, the His-tag binder is any monomolecular compound which comprises three Ni-NTA moieties (i.e., tris-Ni-NTA).

In some embodiments, the binder according to this invention is a His-tag binder.

In some embodiments, the His-tag binder comprised in the system, the artificial receptor, the recombinant cell, and the methods of the invention comprises a moiety represented by the structure of Formula C:

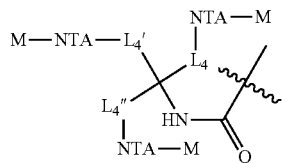

C wherein $L_4$, $L_4'$, and $L_4''$ are each independently a substituted or unsubstituted linear or branched alkyl chain of 1-20 carbon atoms, substituted or unsubstituted linear or branched alkyl ether chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl diamide chain of 1-20 carbon atoms, substituted or unsubstituted linear or branched alkyl amine chain of 1-20 carbon atoms or any combination thereof; and M-NTA is a metal complex of nitrilotriacetic acid.

In some embodiments, M is a metal ion. In some embodiments, M is cobalt (Co).

In some embodiments, M is nickel (Ni). In some embodiments, M is Ni(II). In some embodiments, M is Co(II). In some embodiments, M is Co(III).

In some embodiments, the His-tag binder comprised in the system, the artificial receptor, the recombinant cell, and the methods of the invention comprises a moiety represented by the structure of formula D:

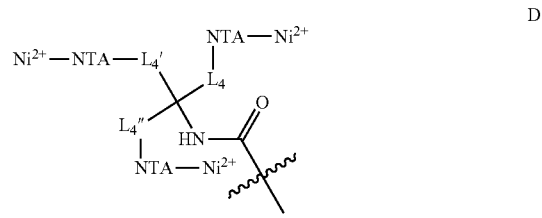

D wherein $L_4$, $L_4'$, and $L_4''$ are each independently a substituted or unsubstituted linear or branched alkyl chain of 1-20 carbon atoms, substituted or unsubstituted linear or branched alkyl ether chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl diamide chain of 1-20 carbon atoms, substituted or unsubstituted linear or branched alkyl amine chain of 1-20 carbon atoms or any combination thereof.

In another embodiment, the His-tag binder comprised in the system, the artificial receptor, the recombinant cell, and the methods of the invention comprises a moiety represented by the structure of formula D(a):

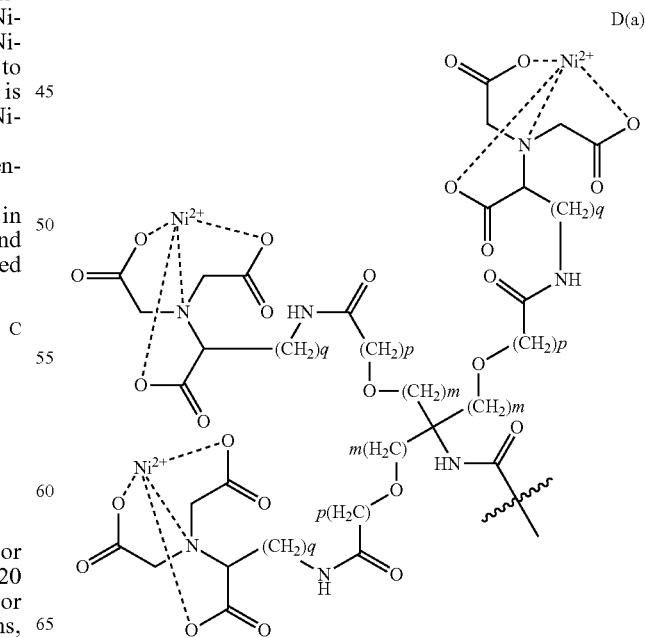

D(a)

wherein m, p and q are each independently an integer number between 1 and 8.

In another embodiment, the His-tag binder comprised in the system, the artificial receptor, the recombinant cell, and the methods of the invention comprises a moiety represented by the structure of formula D(b):

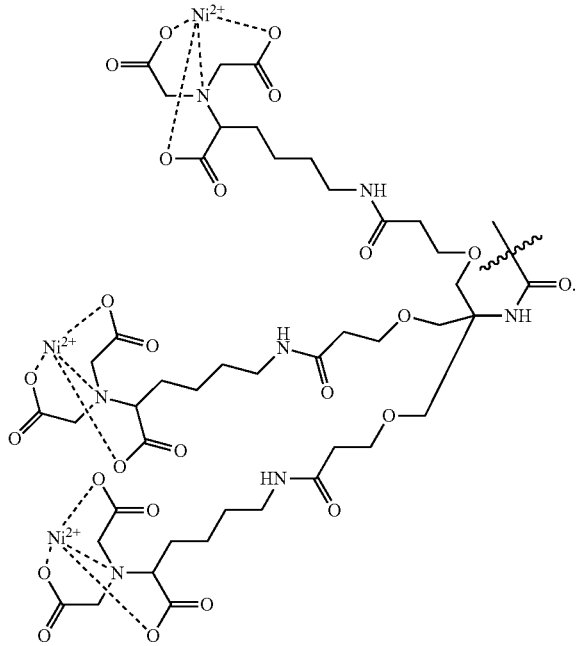

D(b)

In some embodiments, the His-tag binder comprised in the system, the artificial receptor, the recombinant cell, and the methods of the invention comprises a moiety represented by the structure of formula E:

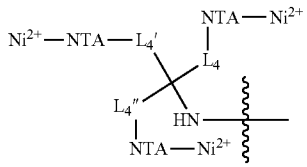

E wherein $L_4$, $L_4'$, and $L_4''$ are each independently a substituted or unsubstituted linear or branched alkyl chain of 1-20 carbon atoms, substituted or unsubstituted linear or branched alkyl ether chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl diamide chain of 1-20 carbon atoms, substituted or unsubstituted linear or branched alkyl amine chain of 1-20 carbon atoms or any combination thereof.

In another embodiment, the His-tag binder comprised in the system, the artificial receptor, the recombinant cell, and the methods of the invention comprises a moiety represented by the structure of formula E(a):

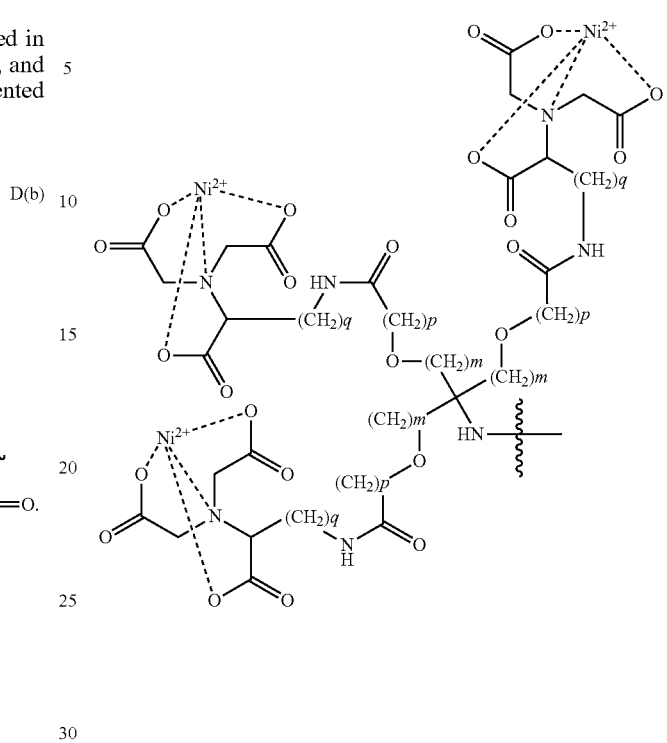

E(a)

wherein m, p and q are each independently an integer number between 1 and 8.

In some embodiments, the His-tag binder comprised in the system, the artificial receptor, the recombinant cell, and the methods of the invention comprises a moiety represented by the structure of formula E(b):

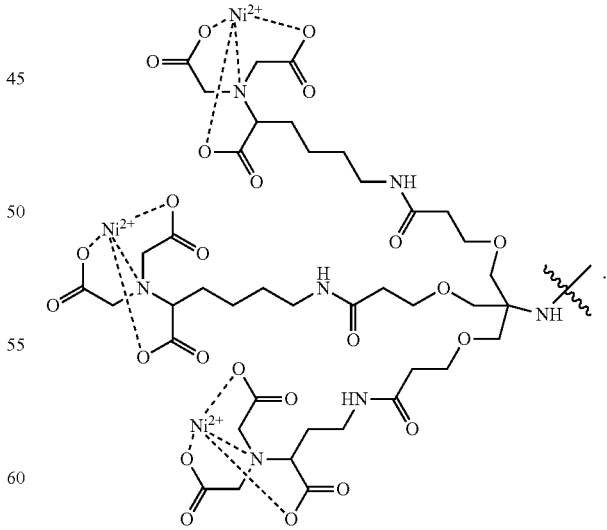

E(b)

In some embodiments, the His-tag binder comprised in the system, the artificial receptor, the recombinant cell, and the methods of the invention comprises a moiety represented by the structure of formula G:

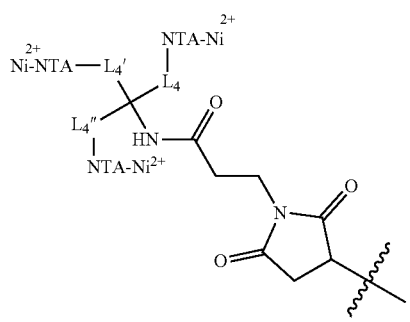

G wherein
L$_4$, L$_4$', and L$_4$" are each independently a substituted or unsubstituted linear or branched alkyl chain of 1-20 carbon atoms, substituted or unsubstituted linear or branched alkyl ether chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl diamide chain of 1-20 carbon atoms, substituted or unsubstituted linear or branched alkyl amine chain of 1-20 carbon atoms or any combination thereof.

In another embodiment, the His-tag binder comprised in the system, the artificial receptor, the recombinant cell, and the methods of the invention comprises a moiety represented by the structure of formula G(a):

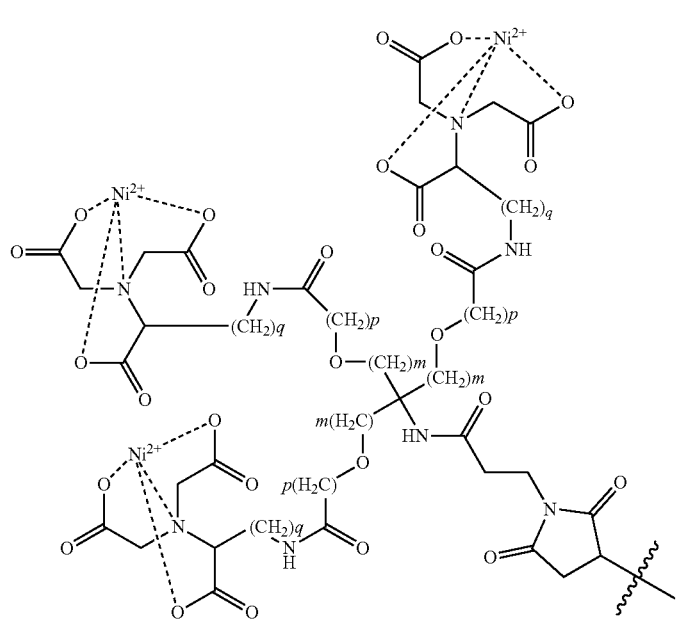

G(a)

wherein
m, p and q are each independently an integer number between 1 and 8.

In some embodiments, the His-tag binder comprised in the system, the artificial receptor, the recombinant cell, and the methods of the invention comprises a moiety represented by the structure of formula G(b):

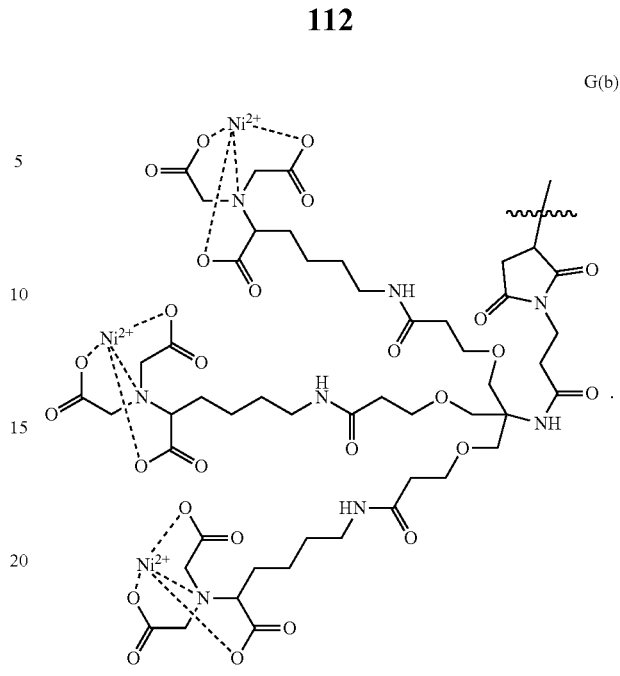

G(b)

In some embodiments, each of L$_4$, L$_4$', and L$_4$" of the structures of formulas D, E, G and/or H, is independently a substituted or unsubstituted linear or branched alkyl chain of 1-20 carbon atoms, substituted or unsubstituted linear or branched alkyl ether chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl diamide chain of 1-20 carbon atoms, substituted or unsubstituted linear or branched alkyl amine chain of 1-20 carbon atoms or any combination thereof; each represents a separate embodiment according to this invention. In some embodiments, each of L$_4$, L$_4$', and L$_4$" is a combination of alkyl ether and alkyl amide (i.e., alkylether-alkylamide). In another embodiment, each of $L_4$, $L_4'$, and $L_4''$ is independently —$(CH_2)_q$—NHCO—$(CH_2)_p$—O—$(CH_2)_m$—, wherein q, p and m are each independently an integer between 1 and 8. In another embodiment, q is 4, p is 2 and m is 1. In another embodiment, each of $L_4$, $L_4'$, and $L_4''$ is —$(CH_2)_4$—NHCO—$(CH_2)_2$—O—$CH_2$—. In another embodiment, each of $L_4$, $L_4'$, and $L_4''$ is represented by the following structure:

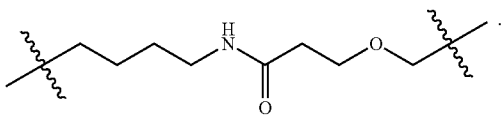 [SMILES: *CCCCNC(=O)CCOC*]

In another embodiment, m of the structures of formulas D(a), E(a), G(a) and/or H(a), is 1. In another embodiment, m is 2. In another embodiment, m is 3. In another embodiment, m is 4.

In another embodiment, p of the structures of formulas D(a), E(a), G(a) and/or H(a) is 1. In another embodiment, p is 2. In another embodiment, p is 3. In another embodiment, p is 4.

In another embodiment, q of the structures of formulas D(a), E(a), G(a) and/or H(a) is 1. In another embodiment, q is 2. In another embodiment, q is 3. In another embodiment, q is 4. In another embodiment, q is 5. In another embodiment, q is 6.

In another embodiment, m is 1, p is 2 and q is 4.

l. ODN Sequences

As used herein, "oligonucleotide sequence," "oligonucleotide" or "nucleic acid sequence" refer to a nucleotide, oligonucleotide, polynucleotide, or any fragment thereof and to naturally occurring or synthetic molecules, such as L-DNA, phosphorothioates, locked nucleic acids, etc.

As used herein, an "oligonucleotide", "ODN" or "oligonucleotide sequence" is understood to be a molecule that has a sequence of bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. A distinction may be made between oligodeoxyribonucleotides, which do not have a hydroxyl group at the 2' position, and oligoribonucleotides, which have a hydroxyl group in this position. Oligonucleotides also may include derivatives, in which the hydrogen of the hydroxyl group is replaced with organic groups, e.g., an allyl group. An oligonucleotide is a nucleic acid that includes at least two nucleotides.

One oligonucleotide sequence may be "complementary" to a second oligonucleotide sequence. As used herein, the terms "complementary" or "complementarity," when used in reference to nucleic acids (i.e., a sequence of nucleotides such as an oligonucleotide or a target nucleic acid), refer to sequences that are related by base-pairing rules. For natural bases, the base pairing rules are those developed by Watson and Crick. As an example, for the sequence "T-G-A", the complementary sequence is "A-C-T." Complementarity can be "partial," in which only some of the bases of the nucleic acids are matched according to the base pairing rules. Alternatively, there can be "complete", "full" or "total" complementarity between the nucleic acids. The degree of complementarity between the oligonucleotide strands has effects on the efficiency and strength of hybridization between the nucleic acid strands.

Oligonucleotides as described herein may be capable of forming hydrogen bonds with oligonucleotides having a complementary base sequence. These bases may include the natural bases such as A, G, C, T and U, as well as artificial bases. An oligonucleotide may include nucleotide substitutions. For example, an artificial or modified base may be used in place of a natural base such that the artificial base exhibits a specific interaction that is similar to the natural base.

An oligonucleotide that is complementary to another nucleic acid will "hybridize" to the nucleic acid under suitable conditions (described below). As used herein, "hybridization" or "hybridizing" refers to the process by which an oligonucleotide single strand anneals with a complementary strand through base pairing under defined hybridization conditions. "Specific hybridization" is an indication that two nucleic acid sequences share a high degree of complementarity. Specific hybridization complexes form under permissive annealing conditions and remain hybridized after any subsequent washing steps. "Hybridizing" sequences which bind under conditions of low stringency are those which bind under non-stringent conditions (6×SSC/50% formamide at room temperature) and remain bound when washed under conditions of low stringency (2×SSC, 42° C.). Hybridizing under high stringency refers to the above conditions in which washing is performed at 2×SSC, 65° C. (where SSC is 0.15 M NaCl, 0.015 M sodium citrate, pH 7.2)

In some embodiments, the oligonucleotide sequences of the system, the artificial receptor, the recombinant cell, and the methods according to the invention may each be at least 4, at least 8, at least 12, at least 16, at least 20, or at least 30 nucleotides in length; each is a separate embodiment according to this invention. In illustrative embodiments, oligonucleotide sequences may each be no more than about 50 nucleotides in length. In illustrative embodiments, oligonucleotide sequences may each be no more than about 200 nucleotides in length. In one embodiment, the oligonucleotide sequences, may be partially complementary to a third oligonucleotide, which binds the at oligonucleotide sequences for the formation of larger molecular assemblies.

m. ODN-1

In some embodiments, the first oligonucleotide (ODN1) of the system, the artificial receptor, the recombinant cell, and the methods according to the invention is at least 4, at least 8, at least 12, at least 16, at least 20, or at least 30 nucleotides in length; each is a separate embodiment according to this invention. In some embodiments, the first oligonucleotide of the system, the artificial receptor, the recombinant cell, and the methods according to the invention is no more than about 50 nucleotides in length. In some embodiments, the first oligonucleotide is at least 2, at least 4, at least 8, at least 12, at least 16, or at least 20 nucleotides shorter than the second oligonucleotide; each is a separate embodiment according to this invention.

In some embodiments, the first oligonucleotide comprises a sequence comprising at least 80/o homology to any of SEQ ID Nos.: 1-5. In some embodiments, the first oligonucleotide sequence is represented by any one of SEQ ID Nos.: 1-5.

n. ODN-2

In some embodiments, the second oligonucleotide (ODN2) of the system, the artificial receptor, the recombinant cell, and the methods according to the invention is at least 4, at least 8, at least 12, at least 16, at least 20, or at least 30 nucleotides in length; each is a separate embodiment according to this invention. In some embodiments, the second oligonucleotide of the system, the artificial receptor, the recombinant cell, and the methods according to the invention is no more than about 50 nucleotides in length. In some embodiments, the second oligonucleotide is at least 2, at least 4, at least 8, at least 12, at least 16, or at least 20 nucleotides longer than the first oligonucleotide; each is a separate embodiment according to this invention. In some embodiments, the second oligonucleotide comprises a toehold region.

In some embodiments, the second oligonucleotide comprises a sequence comprising at least 80% homology to any of SEQ ID Nos.: 6-9. In some embodiments, the second oligonucleotide sequence is represented by any one of SEQ ID Nos.: 6-9.

o. ODN-3

In some embodiments, the system according to this invention, further comprises a third oligonucleotide (ODN-3).

In some embodiments, ODN-3 is capable of detaching ODN-2 from ODN-1, thereby detaching the second compound according to this invention from the cell of the invention. In some embodiments, the third oligonucleotide is fully complementary to the second oligonucleotide.

In some embodiments, the third oligonucleotide (ODN3) of the system according to the invention is at least 4, at least 8, at least 12, at least 16, at least 20, or at least 30 nucleotides in length. In some embodiments, the third oligonucleotide of the system according to the invention is no more than about 50 nucleotides in length. In some embodiments, the third oligonucleotide is at least 2, at least 4, at least 8, at least 12, at least 16, or at least 20 nucleotides longer than the second oligonucleotide; each is a separate embodiment according to this invention. In some embodiments, the third oligonucleotide has the same length as the second oligonucleotide. In some embodiments, the third oligonucleotide is at least 2, at least 4, at least 8, at least 12, at least 16, or at least 20 nucleotides longer than the first oligonucleotide; each is a separate embodiment according to this invention.

In some embodiments, the third oligonucleotide comprises a sequence comprising at least 80% homology to SEQ ID No.: 10. In some embodiments, the third oligonucleotide sequence is represented by SEQ ID No.: 10.

In some embodiments, ODN-3 is capable of detaching ODN-2 from ODN-1 by a toehold mechanism. In some embodiments, ODN-2 comprises a toehold region complementary to a fragment of ODN-3. A "toehold region" refers to an oligonucleotide segment that comprises a single-stranded overhang that allows detaching two complementary oligonucleotides. In some embodiments, ODN-2 is hybridized to ODN-1, and ODN-2 further comprises a toehold region, which is a single-stranded overhang not complementary of ODN-1. In some embodiments. ODN-2's toehold region is complementary to a fragment of ODN-3. Therefore, in some embodiments, when ODN-3 is added, it binds to ODN-2 toehold region. Once ODN-3 is bound to the toehold region, ODN-3 will compete with ODN-1 for binding the rest of ODN-2's bases. As ODN-1 and ODN-3 exchange base pairs with ODN-2, the branch point of the three-stranded complex moves back and forth. This 'three-way branch migration' is an unbiased random walk, as each step causes no net change in base pairing. Eventually, ODN-1 will fully dissociate, and ODN-2 will become fully bound to ODN-3. Thus, in some embodiments, ODN-3 can be used to detach the second compound, ODN-2, or the synthetic agent from the recombinant cell.

p. The Second Compound (Y-ODN-2)

In some embodiments, the system, the artificial receptor, the recombinant cell, and the methods of this invention, comprise a second compound comprising a second oligonucleotide (ODN-2) covalently bound to a synthetic agent, either directly or through a second linker, wherein said second oligonucleotide is complementary to said first oligonucleotide.

In some embodiments, the second compound of the system, the artificial receptor, the recombinant cell, and the methods according to this invention (i.e., Y-ODN-2) comprises:
    a. a second oligonucleotide (ODN-2), which is complementary to said first oligonucleotide;
    b. a synthetic agent,
    c. optionally a second linker which links the second oligonucleotide with the synthetic agent;
    d. optionally a second labeling moiety;
    e. optionally a fourth linker which links the second oligonucleotide with the second labeling moiety.

In some embodiments, the second oligonucleotide is directly bound to the synthetic agent. In other embodiments, the second oligonucleotide is bound to the synthetic agent through a second linker. In some embodiments, the second oligonucleotide is directly bound to the second labeling moiety. In other embodiments, the second oligonucleotide is bound to the second labeling moiety through a fourth linker.

In some embodiments, the second compound according to this invention (i.e., Y-ODN-2) is represented by the structure of formula K:

$$F_2\text{-}L_4\text{-}ODN2\text{-}L_2\text{-}X \tag{K}$$

wherein
X is a synthetic agent;
$L_2$ is a second linker or absent;
ODN2 is a second oligonucleotide sequence;
$L_4$ is a fourth linker or absent; and
$F_2$ is a second labeling moiety or absent.

In some embodiments, the second compound according to this invention (i.e., Y-ODN-2) is represented by the structure of the following compounds:

Compound 200

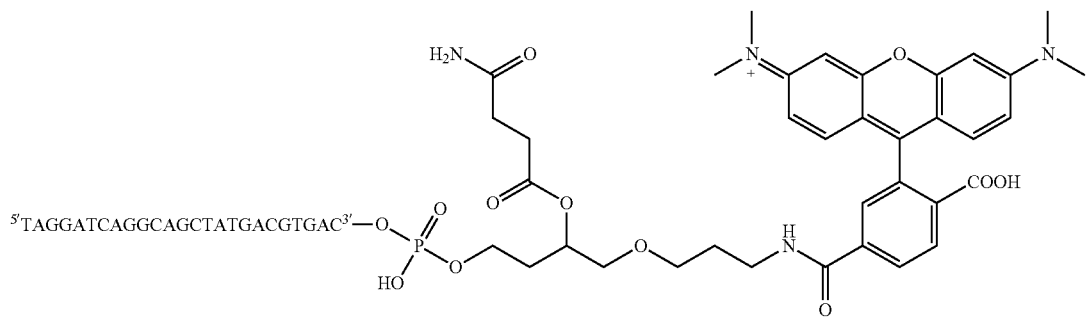

[TAMRA-ODN-2]

Compound 201
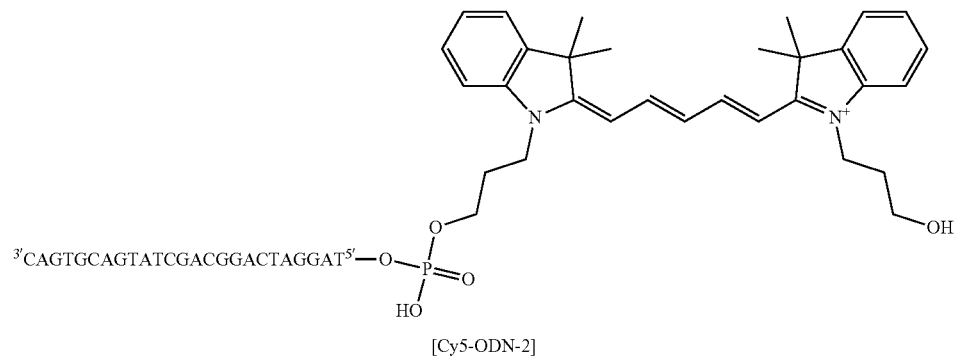
[Cy5-ODN-2]
Compound 202
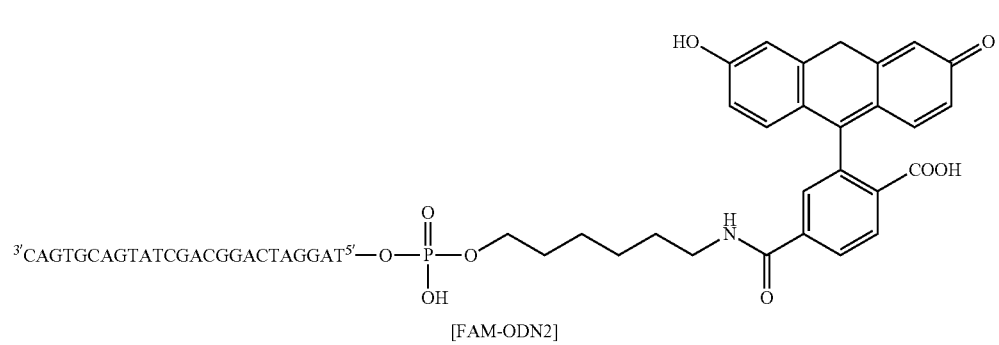
[FAM-ODN2]
Compound 203
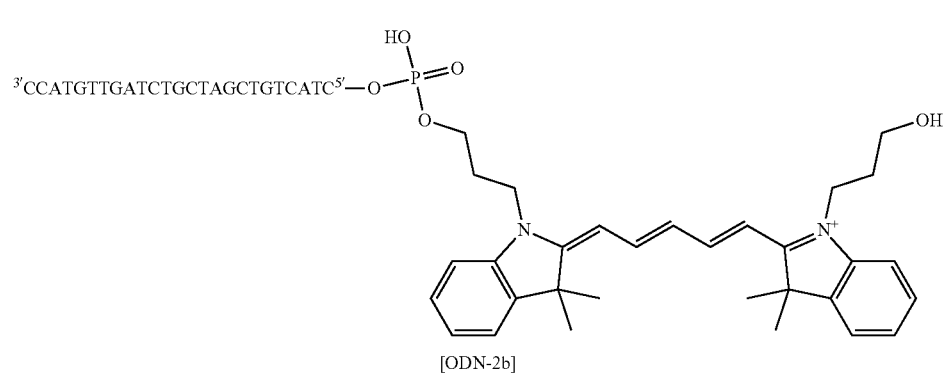
[ODN-2b]
Compound 204
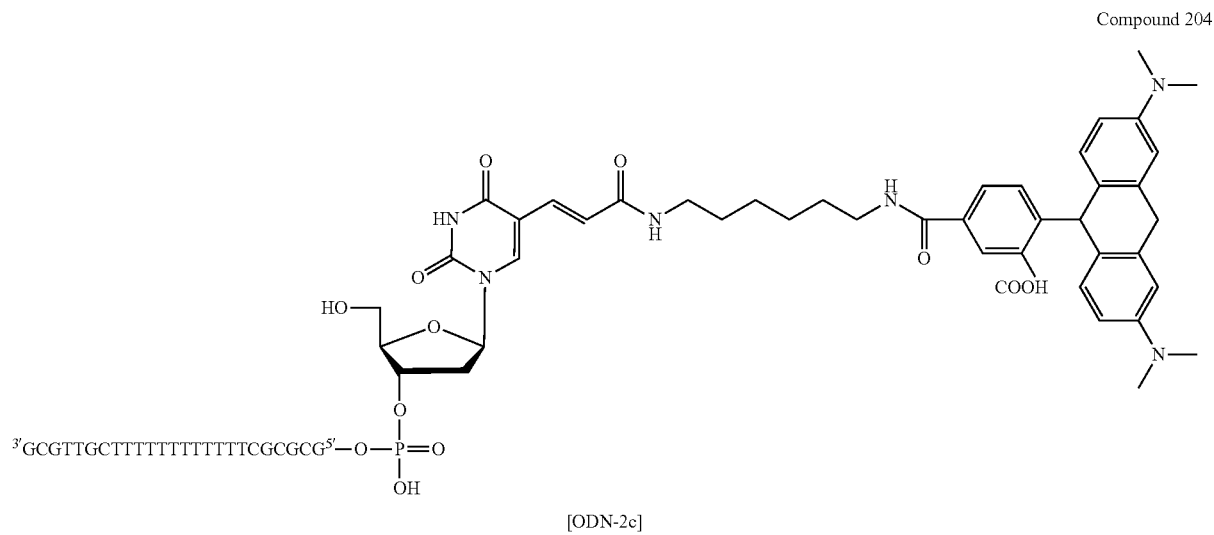
[ODN-2c]

Compound 205

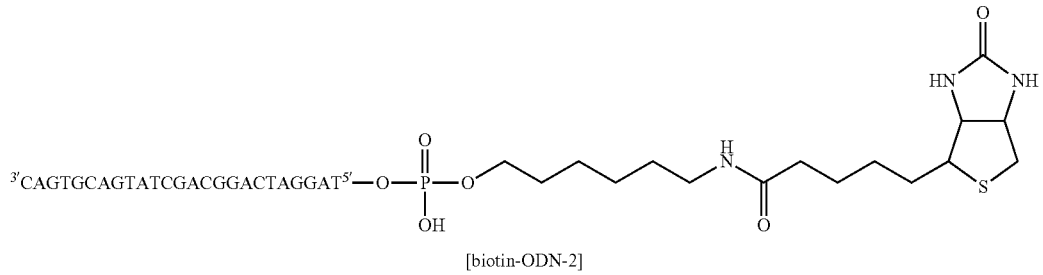

[biotin-ODN-2]

Compound 206

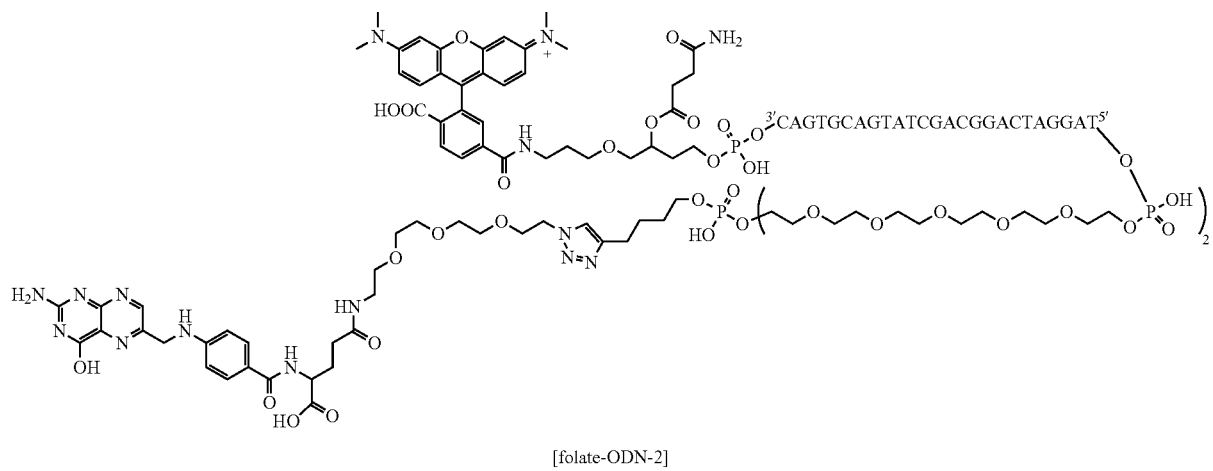

[folate-ODN-2]

Compound 207

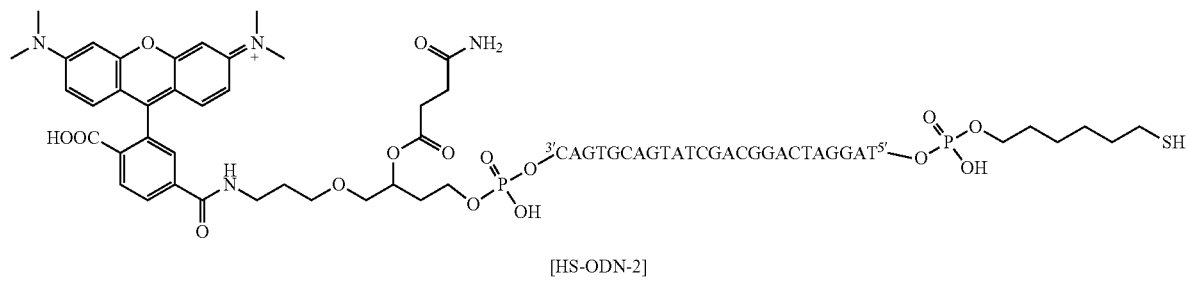

[HS-ODN-2]

In some embodiments, X of formula K is a synthetic agent. In some embodiments, X is a selective protein binder. In some embodiments, X is a folate. In some embodiments, X is a biotin. In some embodiments, X comprises an adhesion molecule. In some embodiments, X comprises a surface binder. In some embodiments, X comprises an abiotic surface binder. In some embodiments, X comprises an —SH functional group. In some embodiments, X is a thioalkyl. In some embodiments, X is a labeling moiety. In some embodiments, X is a dye. In some embodiments, X is a fluorescent dye. Examples of dyes include but are not limited to: dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, TAMRA, BODIPY, FITC or derivative thereof. In some embodiments, X is bound to ODN2 through an amide bond, an ester bond, a phosphate bond, an ether bond, a thiolether bond, each represents a separate embodiment according to this invention. In some embodiments, X is covalently bound to ODN2 through a phosphate moiety. In some embodiments, X is bound to $L_2$ through an amide bond, an ester bond, a phosphate bond, an ether bond, a thioether bond, each represents a separate embodiment according to this invention. In some embodiments, X is as described hereinbelow in the definition of a synthetic agent. In some embodiments, X is a dye derivative. In some embodiments, X is a derivative of a commercially available phosphoramidite dye agent. Non limiting examples of such phosphoramidite dye agents include:

| 121 | 122 |
|---|---|
| 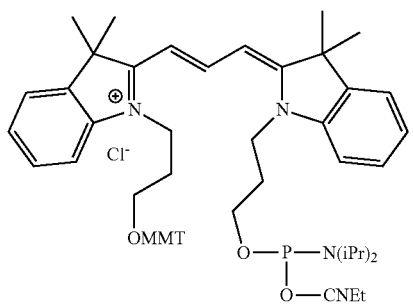 | 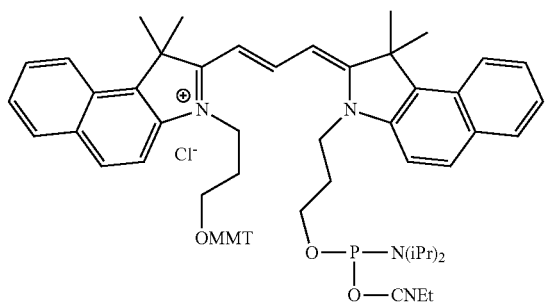 |
| Cyanine 3 Phosphoramidite | Cyanine 3.5 Phosphoramidite |
| 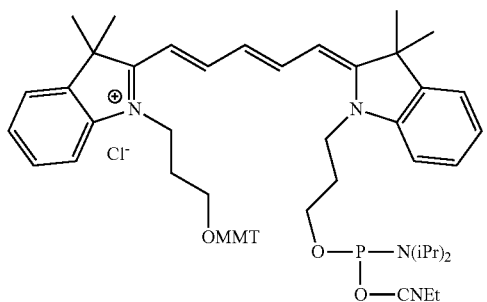 | 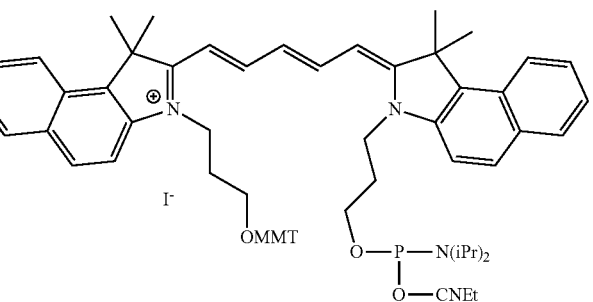 |
| Cyanine 5 Phosphoramidite | Cyanine 5.5 Phosphoramidite |
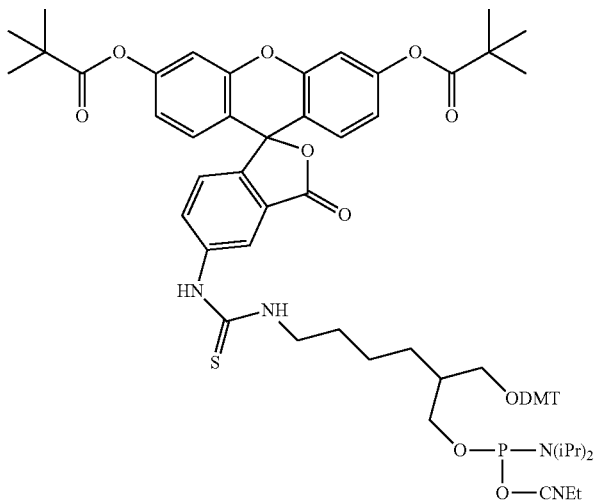
Fluorescein Phosphoramidite

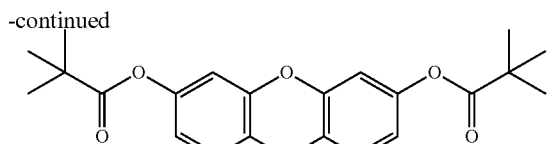
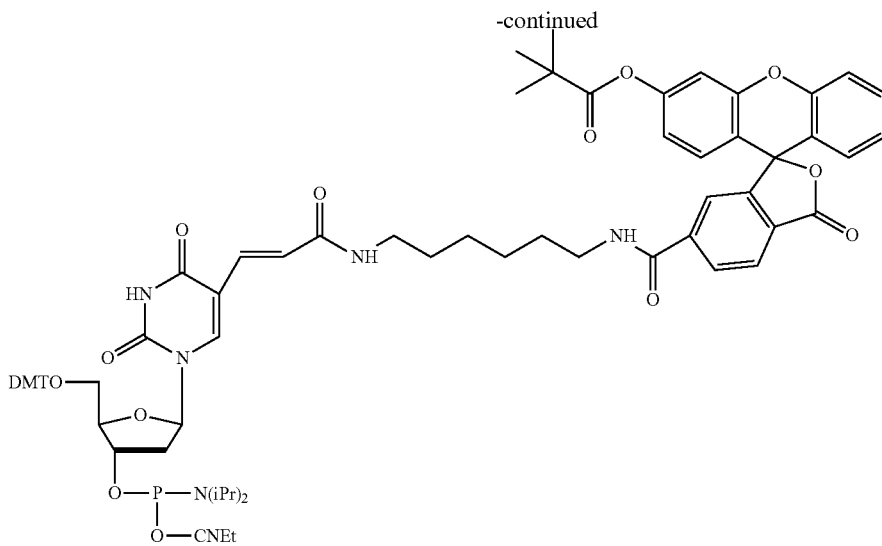

Fluorescein-dT Phosphoramidite

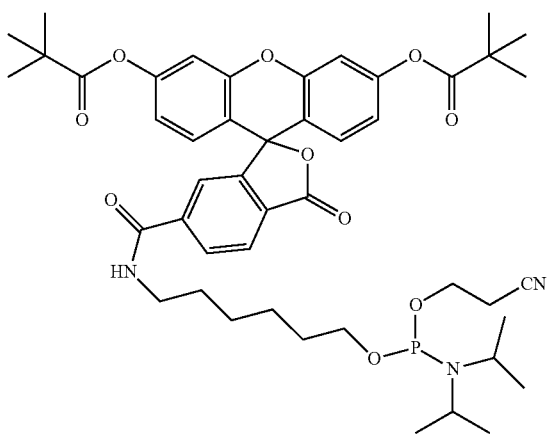

5' Fluorescein Phosphoramidite

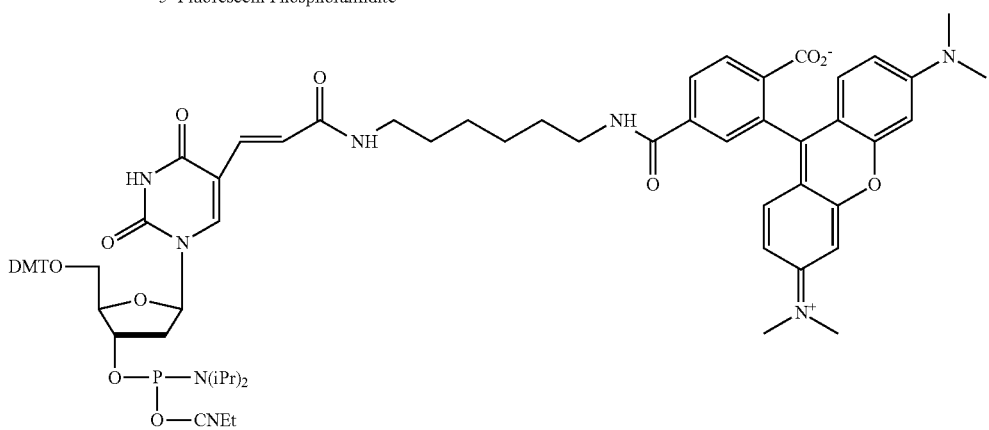

TAMRA dT

In some embodiments, $L_2$ of formula K is a second linker. In some embodiments, $L_2$ is absent. In some embodiments, $L_2$ is bound to the 3' end of ODN2. In some embodiments, $L_2$ is bound to the 5' end of ODN2. In some embodiments, $L_2$ is bound to X through an amide bond, an ester bond, a phosphate bond, an ether bond, a thioether bond, each represents a separate embodiment according to this invention. In some embodiments, $L_2$ is bound to ODN2 through an amide bond, an ester bond, a phosphate bond, an ether bond, a thioether bond, each represents a separate embodiment according to this invention. In some embodiments, $L_2$ is defined for the "second linker" hereinbelow.

In some embodiments, ODN2 of formulas K is a second oligonucleotide sequence. In some embodiments, ODN2 is directly bound to X, through an amide bond, an ester bond, a phosphate bond, an ether bond, a thioether bond, each represents a separate embodiment according to this invention. In some embodiments, ODN2 is directly bound to $F_2$, through an amide bond, an ester bond, a phosphate bond, an ether bond, a thioether bond, each represents a separate embodiment according to this invention. In some embodiments, ODN2 is directly bound to $F_2$, through a phosphate moiety.

In some embodiments, $L_4$ of formulas K is a fourth linker. In some embodiments, $L_4$ is absent. In some embodiments, $L_4$ is bound to the 3' end of ODN2. In some embodiments, $L_4$ is bound to the 5' end of ODN2. In some embodiments, $L_4$ is bound to $F_2$ through an amide bond, an ester bond, a phosphate bond, an ether bond, a thioether bond, each represents a separate embodiment according to this invention. In some embodiments, $L_4$ is bound to ODN2 through an amide bond, an ester bond, a phosphate bond, an ether bond, a thioether bond, each represents a separate embodiment according to this invention. In some embodiments, $L_4$ is bound to ODN2 through a phosphate moiety. In some embodiments, $L_4$ is as defined for the "fourth linker" hereinbelow.

In some embodiments, $F_2$ of formulas K is a second labeling moiety. In some embodiments, $F_2$ is absent. In some embodiments, $F_2$ is a dye. Examples of dyes include but are not limited to: dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, TAMRA, BODIPY, FITC or derivative thereof. In some embodiments, $F_2$ is a dye derivative. In some embodiments, $F_2$ is bound to ODN2 through an amide bond, an ester bond, a phosphate bond, an ether bond, a thiolether bond, each represents a separate embodiment according to this invention. In some embodiments, $F_2$ is bound to $L_4$ through an amide bond, an ester bond, a phosphate bond, an ether bond, a thioether bond, each represents a separate embodiment according to this invention. In some embodiments, $F_2$ is as defined for the "labeling moiety" hereinbelow.

q. Linkers ($L_2$ and $L_4$)

In some embodiments, the second compound of the system, the artificial receptor, the recombinant cell, and the methods according to this invention (i.e., Y-ODN-2) comprises:

a. a second oligonucleotide (ODN-2), which is complementary to said first oligonucleotide;
b. a synthetic agent,
c. optionally a second linker which links the second oligonucleotide with the synthetic agent;
d. optionally a second labeling moiety;
e. optionally a fourth linker which links the second oligonucleotide with the second labeling moiety.

r. A Second Linker ($L_2$)

In some embodiments, the second compound (Y-ODN-2) of the system, the artificial receptor, the recombinant cell, and the methods of this invention, comprises a second linker, which links the second oligonucleotide with the synthetic agent. In some embodiments, the second linker is absent. In some embodiments, the second oligonucleotide is directly bound to the synthetic agent. In some embodiments, the second linker is bound to the 3' end of the second oligonucleotide (ODN2). In some embodiments, the second linker is bound to the 5' end of ODN2. In some embodiments, the second linker is bound to the synthetic agent through an amide bond, an ester bond, a phosphate bond, an ether bond, a thioether bond; each represents a separate embodiment according to this invention. In some embodiments, the second linker is bound to ODN2 through an amide bond, an ester bond, a phosphate bond, an ether bond, a thioether bond; each represents a separate embodiment according to this invention. In some embodiments, the second linker is covalently bound to the second oligonucleotide through a phosphate moiety.

In some embodiments, the second linker of the system, the artificial receptor, the recombinant cell, and the methods according to this invention and/or $L_2$ according to formula K is any chemical fragment which comprises at least one segment of a commercially available phosphoramidite spacer derivative as described hereinabove for the "first linker".

In some embodiments, the second linker of the system, the artificial receptor, the recombinant cell, and the methods according to this invention and/or $L_2$ according to formula K is a substituted or unsubstituted linear or branched alkyl chain of 1-20 carbon atoms, substituted or unsubstituted linear or branched alkyl ether chain of 1-20 carbon atoms, substituted or unsubstituted linear or branched thioalkyl chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl ester of 1-20 carbon atoms, substituted or unsubstituted linear or branched alkyl diamide chain of 1-20 carbon atoms, substituted or unsubstituted linear or branched alkyl triazole of 1-20 carbon atoms, substituted or unsubstituted linear or branched alkyl amine chain of 1-20 carbon atoms or any combination thereof; each is a separate embodiment according to this invention.

In some embodiments, the second linker of the system, the artificial receptor, the recombinant cell, and the methods according to this invention and/or $L_2$ according to formula K comprises the following moieties:

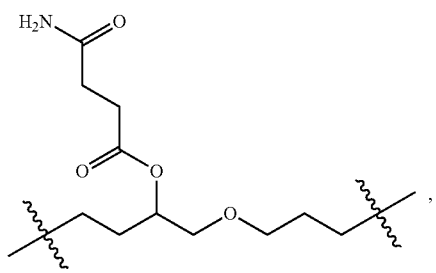

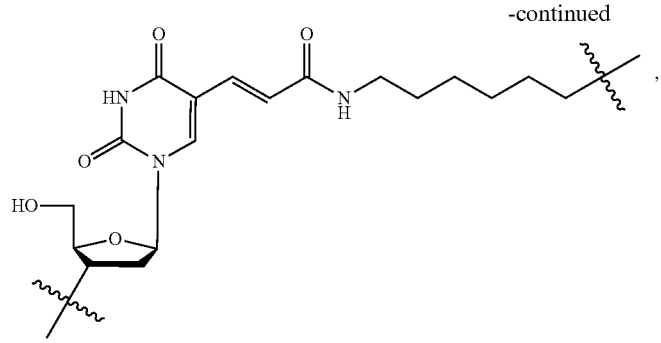

-continued

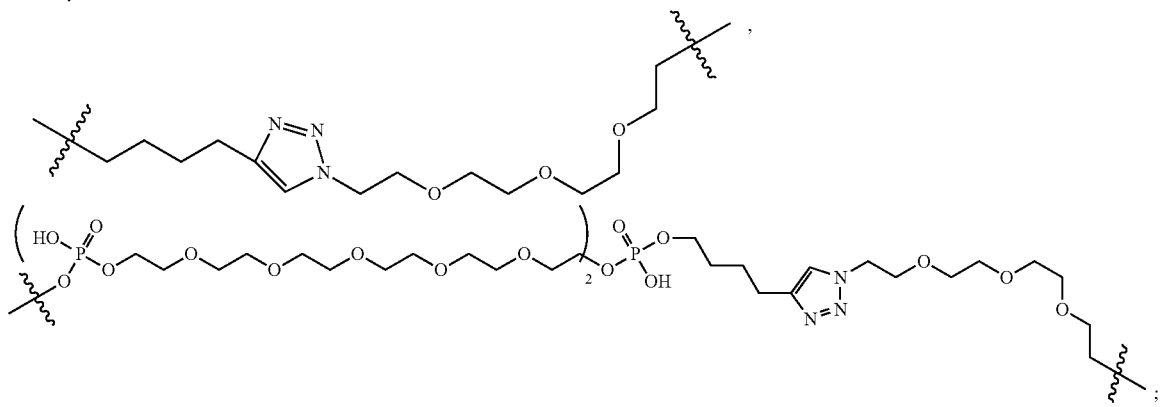

each represent a separate embodiment according to this invention.

In some embodiments, the second linker of the system, the artificial receptor, the recombinant cell, and the methods according to this invention and/or $L_2$ according to formula K comprises at least one polyethyleneglycol (PEG) moiety, at least one phosphate moiety, at least one thioalkyl moiety, each represents a separate embodiment according to this invention. In some embodiments, the second linker and/or $L_2$ comprises at least one polyethyleneglycol (PEG) moiety, at least one phosphate moiety, at least one thioalkyl moiety, or any combination thereof.

In some embodiments, the second linker of the system, the artificial receptor, the recombinant cell, and the methods according to this invention and/or $L_2$ according to formula K is represented by the following formula:

—[(CH$_2$O)$_k$—PO$_3$H]$_l$(CH$_2$)$_w$—S— wherein k and l are each independently an integer number between 0 and 10; and w is an integer number between 1 and 10.

In some embodiments, k is 0. In some embodiments, k is 6. In some embodiments, k is 1, 2, 3, 4, 5, 7, 8, 9, 10; each is a separate embodiment according to this invention.

In some embodiments, l is 0. In some embodiments, l is 1. In some embodiments, l is 5. In some embodiments, l is 2, 3, 4, 6, 7, 8, 9, 10; each is a separate embodiment according to this invention.

In some embodiments, w is 6. In some embodiments, w is 1, 2, 3, 4, 5, 7, 8, 9, 10; each is a separate embodiment according to this invention.

s. A Fourth Linker ($L_4$)

In some embodiments, the second compound (Y-ODN-2) of the system, the artificial receptor, the recombinant cell, and the methods according to this invention, comprises a fourth linker, which links the second oligonucleotide with the second labeling moiety. In some embodiments, the second oligonucleotide is directly (covalently) bound to the second labeling moiety. In other embodiments, the second oligonucleotide is covalently bound to the second labeling moiety through a fourth linker. In some embodiments, the fourth linker is absent. In some embodiments, the fourth linker is covalently bound to the 3' end of ODN-2. In some embodiments, the fourth linker is covalently bound to the 5' end of ODN-2. In some embodiments, the third linker is a part of a commercially available phosphoramidite dye derivative. In some embodiments, the fourth linker is covalently bound to the second labeling moiety through an amide bond, an ester bond, a phosphate bond, an ether bond, a thioether bond; each represents a separate embodiment according to this invention. In some embodiments, the fourth linker is covalently bound to ODN-2 through an amide bond, an ester bond, a phosphate bond, an ether bond, a thioether bond; each represents a separate embodiment according to this invention. In some embodiments, the fourth linker is covalently bound to the second oligonucleotide through a phosphate moiety.

In some embodiments, the fourth linker of the system, the artificial receptor, the recombinant cell, and the methods according to this invention, and/or $L_4$ according to formula K is any chemical fragment which comprises at least one segment of a commercially available phosphoramidite spacer derivative as described hereinabove for the "first linker".

In some embodiments, the fourth linker of the system, the artificial receptor, the recombinant cell, and the methods according to this invention and/or $L_4$ according to formula K is a substituted or unsubstituted linear or branched alkyl chain of 1-20 carbon atoms, substituted or unsubstituted linear or branched alkyl ether chain of 1-20 carbon atoms, substituted or unsubstituted linear or branched thioalkyl chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl ester of 1-20 carbon atoms, substituted or unsubstituted linear or branched alkyl diamide chain of 1-20 carbon atoms, substituted or unsubstituted linear or branched alkyl triazole of 1-20 carbon atoms, substituted or unsubstituted linear or branched alkyl amine chain of 1-20 carbon atoms or any combination thereof; each is a separate embodiment according to this invention.

In some embodiments, the fourth linker of the system, the artificial receptor, the recombinant cell, and the methods according to this invention and/or $L_4$ according to formula K comprises the following moieties:

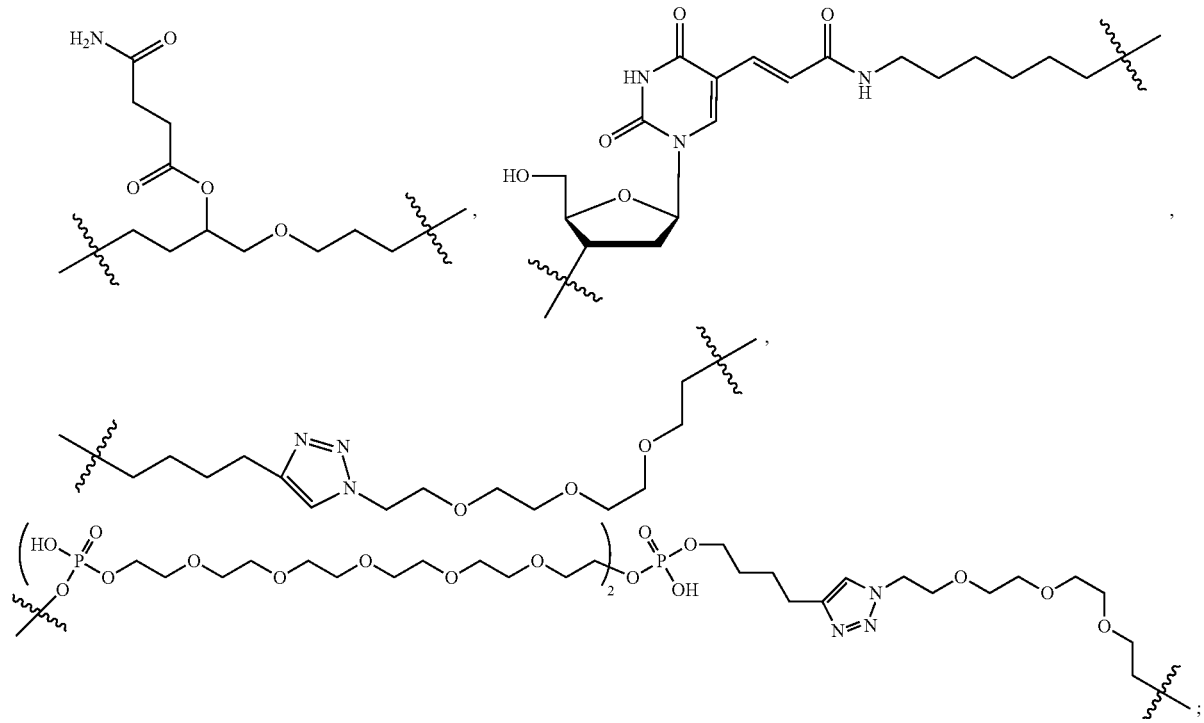

each represent a separate embodiment according to this invention.

In some embodiments, the fourth linker of the system, the artificial receptor, the recombinant cell, and the methods according to this invention and/or $L_4$ according to formula K comprises at least one polyethyleneglycol (PEG) moiety, at least one phosphate moiety, at least one thioalkyl moiety; each represents a separate embodiment according to this invention. In some embodiments, the fourth linker and/or $L_4$ comprises at least one polyethyleneglycol (PEG) moiety, at least one phosphate moiety, at least one thioalkyl moiety, or any combination thereof.

In some embodiments, the fourth linker of the system, the artificial receptor, the recombinant cell, and the methods according to this invention and/or $L_4$ according to formula K is represented by the following formula:

—[(CH$_2$O)$_k$—PO$_3$H]$_l$—(CH$_2$)$_w$—S— wherein k and l are each independently an integer number between 0 and 10; and w is an integer number between 1 and 10.

In some embodiments, k is 0. In some embodiments, k is 6. In some embodiments, k is 1, 2, 3, 4, 5, 7, 8, 9, 10; each is a separate embodiment according to this invention.

In some embodiments, l is 0. In some embodiments, l is 1. In some embodiments, l is 5. In some embodiments, l is 2, 3, 4, 6, 7, 8, 9, 10; each is a separate embodiment according to this invention.

In some embodiments, w is 6. In some embodiments, w is 1, 2, 3, 4, 5, 7, 8, 9, 10; each is a separate embodiment according to this invention.

As used herein, the term "alkyl" can be any straight- or branched-chain alkyl group containing up to about 30 carbons unless otherwise specified. In various embodiments, an alkyl includes $C_1$-$C_5$ carbons. In some embodiments, an alkyl includes $C_1$-$C_6$ carbons. In some embodiments, an alkyl includes $C_1$-$C_8$ carbons. In some embodiments, an alkyl includes $C_1$-$C_{10}$ carbons. In some embodiments, an alkyl is a $C_1$-$C_{12}$ carbons. In some embodiments, an alkyl is a $C_1$-$C_{20}$ carbons. In some embodiments, branched alkyl is an alkyl substituted by alkyl side chains of 1 to 5 carbons. In various embodiments, the alkyl group may be unsubstituted. In some embodiments, the alkyl group may be substituted by a halogen, haloalkyl, hydroxyl, alkoxy, carbonyl, amido, alkylamido, dialkylamido, cyano, nitro, $CO_2H$, amino, alkylamino, dialkylamino, carboxyl, thio, thioalkyl, $C_1$-$C_5$ linear or branched haloalkoxy, $CF_3$, phenyl, halophenyl, (benzyloxy)phenyl, —CH$_2$CN, NH$_2$, NH-alkyl, N(alkyl)$_2$, —OC(O)CF$_3$, —OCH$_2$Ph, —NHCO-alkyl, —C(O)Ph, C(O)O-alkyl, C(O)H, —C(O)NH$_2$ or any combination thereof.

The alkyl group can be a sole substituent or it can be a component of a larger substituent, such as in an alkoxy, alkoxyalkyl, haloalkyl, arylalkyl, alkylamino, dialkylamino, alkylamido, alkylurea, thioalkyl, alkyldiamide, alkylamide, alkylphosphate, alkylether, alkyltriazole, alkylester, etc. Preferred alkyl groups are methyl, ethyl, and propyl, and thus halomethyl, dihalomethyl, trihalomethyl, haloethyl, dihaloethyl, trihaloethyl, halopropyl, dihalopropyl, trihalopropyl, methoxy, ethoxy, propoxy, arylmethyl, arylethyl, arylpropyl, methylamino, ethylamino, propylamino, dimethylamino, diethylamino, methylamido, acetamido, propylamido, halomethylamido, haloethylamido, halopropylamido, methyl-urea, ethyl-urea, propyl-urea, 2, 3, or 4-CH$_2$—C$_6$H$_4$—Cl, C(OH)(CH$_3$)(Ph), etc.

t. Labeling Moiety (F and $F_2$)

In accordance with the system, the artificial receptor, the recombinant cell, and the methods disclosed herein, the compounds may comprise one or more labeling moieties, which are attached to the oligonucleotides. Oligonucleotides can be labeled by incorporating moieties detectable by one or more means including, but not limited to, spectroscopic, photochemical, biochemical, immunochemical, or chemical assays. The method of linking or conjugating the label to the nucleotide or oligonucleotide depends on the type of label(s) used and the position of the label on the nucleotide or oligonucleotide.

As used herein, "labeling moieties" or "labels" are chemical or biochemical moieties useful for labeling a compound. Such labeling moieties include fluorescent agents, chemiluminescent agents, chromogenic agents, quenching agents, radionucleotides, enzymes, substrates, cofactors, inhibitors, nanoparticles, magnetic particles, and other moieties known in the art. Labels are capable of generating a measurable signal and may be covalently or noncovalently joined to an oligonucleotide or nucleotide. In some embodiments, the labeling moieties are covalently bound to the oligonucleotides of the invention. In some embodiments, the labeling moieties are covalently bound to the oligonucleotides of the invention through a linker or a spacer.

In illustrative embodiments, the compounds according to this invention, may be labeled with a "fluorescent dye" or a "fluorophore." As used herein, a "fluorescent dye" or a "fluorophore" is a chemical group that can be excited by light to emit fluorescence. Some fluorophores may be excited by light to emit phosphorescence. Dyes may include acceptor dyes that are capable of quenching a fluorescent signal from a fluorescent donor dye. In some embodiments, the dye is selected from: dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, TAMRA, BODIPY, FITC or a derivative thereof. Non limiting examples of Dyes that may be used in the disclosed compounds, system and methods include, but are not limited to, the following dyes and/or dyes sold under the following trade names: 1,5 IAEDANS; 1,8-ANS; 4-Methylumbelliferone; 5-carboxy-2, 7-dichlorofluorescein; 5-Carboxyfluorescein (5-FAM); 5-Carboxytetramethylrhodamine (5-TAMRA); 5-Hydroxy Tryptamine (HAT); 5-ROX (carboxy-X-rhodamine); 6-Carboxyrhodamine 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™ Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue™; Calcium Crimson™; Calcium Green; Calcium Orange; Calcofluor White; Cascade Blue™; Cascade Yellow; Catecholamine; CCF2 (GeneBlazer); CFDA; CFP-Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.18; Cy3.5™; Cy3™; Cy5.18; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DHR); DiI (DiIC18(3)); Dinitrophenol; DiO (DiOC8(3)); DiR; DiR (DiIC18(7)); DNP; Dopamine: DsRed, DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; NED™; Nitrobenzoxadidole; Noradrenaline; Nuclear Fast Red; Nuclear Yellow; Nylosan Brilliant Iavin EBG; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B;

Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; TET™; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; VIC®; wt GFP; WW 781; X-Rhodamine; XRITC; Xylene Orange; Y66F; Y66H; Y66W; Yellow GFP; YFP; YO-PRO-1; YO-PRO-3; YOYO-1; YOYO-3; and salts thereof; each is a separate embodiment according to this invention.

Fluorescent dyes or fluorophores may include derivatives that have been modified to facilitate conjugation to another reactive molecule. As such, fluorescent dyes or fluorophores may include amine-reactive derivatives such as isothiocyanate derivatives and/or succinimidyl ester derivatives of the fluorophore.

In some embodiments, the labeling moiety on the oligonucleotides and the compounds of the system and methods according to the invention, is a quencher. Quenching may include dynamic quenching (e.g., by FRET), static quenching, or both. Illustrative quenchers may include Dabcyl. Illustrative quenchers may also include dark quenchers, which may include black hole quenchers sold under the tradename "BHQ" (e.g., BHQ-0, BHQ-1, BHQ-2, and BHQ-3, Biosearch Technologies, Novato, Calif.). Dark quenchers also may include quenchers sold under the tradename "QXL™" (Anaspec, San Jose, Calif.). Dark quenchers also may include DNP-type non-fluorophores that include a 2,4-dinitrophenyl group.

In some situations, it may be useful to include interactive labels on two oligonucleotides with due consideration given for maintaining an appropriate spacing of the labels on the oligonucleotides to permit the separation of the labels during conformational changes. One type of interactive label pair is a quencher-dye pair, which may include a fluorophore and a quencher. The ordinarily skilled artisan can select a suitable quencher moiety that will quench the emission of the particular fluorophore. In an illustrative embodiment, the Dabcyl quencher absorbs the emission of fluorescence from the fluorophore moiety.

Alternatively, the proximity of the two labels can be detected using fluorescence resonance energy transfer (FRET) or fluorescence polarization. FRET is a distance-dependent interaction between the electronic excited states of two dye molecules in which excitation is transferred from a donor molecule to an acceptor molecule without emission of a photon. Examples of donor/acceptor dye pairs for FRET are known in the art and may include fluorophores and quenchers described herein such as Fluorescein/Tetramethylrhodamine, IAEDANS/Fluorescein (Molecular Probes, Eugene, Oreg.), EDANS/Dabcyl, Fluorescein/Fluorescein (Molecular Probes, Eugene, Oreg.), BODIPY FL/BODIPY FL (Molecular Probes, Eugene, Oreg.), BODIPY TMR/ALEXA 647, ALEXA-488/ALEXA-647, and Fluorescein/QSY7™.

The labels can be conjugated to the oligonucleotides directly, or indirectly through linkers or spacers, by a variety of techniques. Depending upon the precise type of label used, the label can be located at the 5' or 3' end of the oligonucleotide, located internally in the oligonucleotide's nucleotide sequence, or attached to spacer arms extending from the oligonucleotide and having various sizes and compositions to facilitate signal interactions. According to various embodiments, the labeling moiety is attached to the 5' or 3' end of the first and/or the second oligonucleotide; each is a separate embodiment. Using commercially available phosphoramidite reagents, one can produce oligonucleotides containing functional groups (e.g., thiols or primary amines) at either terminus, for example by the coupling of a phosphoramidite dye to the 5' hydroxyl of the 5' base by the formation of a phosphate bond, or internally, via an appropriately protected phosphoramidite.

Oligonucleotides may also incorporate oligonucleotide functionalizing reagents having one or more sulfhydryl, amino or hydroxyl moieties into the oligonucleotide sequence. For example, biotin can be added to the 5' end by reacting an aminothymidine residue, introduced during synthesis, with an N-hydroxysuccinimide ester of biotin. Labels at the 3' terminus, for example, can employ polynucleotide terminal transferase to add the desired moiety, such as for example, cordycepin, $^{35}$S-dATP, and biotinylated dUTP.

In some embodiments, the first and/or the second compound of the system, the artificial receptor, the recombinant cell, and the methods according to this invention according to this invention, comprises a labeling moiety and/or a second labeling moiety (F of formula H, H(a), H(b) and/or $F_2$ of formula K, respectively). In some embodiments, the first oligonucleotide (ODN-1) is bound to a labeling moiety in its 3' or 5' end. In some embodiments, the labeling moiety is bound to the first oligonucleotide directly. In some embodiments, the labeling moiety is bound to first oligonucleotide through a third linker. In some embodiments, the second oligonucleotide (ODN-2) is bound to a second labeling moiety in its 3' or 5' end. In some embodiments, the second labeling moiety is bound to the second oligonucleotide directly. In some embodiments, the second labeling moiety is bound to second oligonucleotide through a fourth linker.

Synthetic Agent

In some embodiments, the second compound of the system, the artificial receptor, the recombinant cell, and the methods according to this invention, comprises a synthetic agent. In some embodiments, the second oligonucleotide (ODN-2) is bound to a synthetic agent in its 3' or 5' end. In some embodiments, the synthetic agent is bound to ODN-2 directly. In some embodiments, the synthetic agent is bound to ODN-2 through a second linker.

In some embodiments, the second compound comprises a synthetic agent and a second labeling moiety. In some embodiments, the second compound does not comprise a second labeling moiety.

According to this invention, the term "synthetic agent" refers to any chemical moiety, which provides a chemical or biological function to the system, or to the cell, to which it is attached. In some embodiments, synthetic agent refers to any chemical moiety, which is capable of binding to various extracellular signals such as ions, small molecules, proteins, and cells, and can control the response of cells to their surroundings. In some embodiments, a synthetic agent refers to any chemical moiety, which has a chemical, physical or biological effect on the cell to which it is attached. In some embodiments, a synthetic agent refers to any chemical moiety, which has a biological effect on a living organism, a tissue or a cell (also referred herein as "a bioactive moiety"). In some embodiments, a biological effect comprises affecting the growth, the survival, the replication, the differentiation, the transcriptome, the proteome, or the function of a cell. In some embodiments, synthetic agent refers to any chemical moiety, which can bind, either covalently or non-covalently, to a solid support, and/or to an abiotic surface (also referred herein as "a surface binder"). In some embodiments, a synthetic agent refers an artificial receptor appended with a specific functionality. In some embodiments, a synthetic agent refers to any chemical moiety, which provides the cell, system or compound to which it is attached, with a specific functionality (e.g., fluorescence, therapeutic effect, solid surface binding capability, specific cell targeting, etc.).

In some embodiments, the synthetic agent is a labeling moiety as described herein above.

In some embodiments, the synthetic agent is a therapeutically active agent. In some embodiments, the therapeutically active agent is a drug. In some embodiments, the therapeutically active agent is selected from: anticancer agents, DNA-interacting molecules, cholesterol-lowering compounds, antibiotics, anti-AIDS molecules, each represents a separate embodiment according to the invention.

In some embodiments, the synthetic agent is a is an oligonucleotide, a nucleic acid construct, an antisense, a plasmid, a polynucleotide, an amino acid, a peptide, a polypeptide, a hormone, a steroid, an antibody, an antigen, a radioisotope, a chemotherapeutic agent, a toxin, an anti-inflammatory agent, a growth factor or any combination thereof; each represents a separate embodiment according to the invention.

In some embodiments, the synthetic agent is a molecular marker. In some embodiments, the synthetic agent is an adhesion molecule. In some embodiments, synthetic agent is a cancer cell binder. In some embodiments, "cancer cell binder" refers to any chemical moiety capable of interacting with proteins expressed by cancer cells. In some embodiments, "cancer cell binder" refers to a protein binder capable of interacting with proteins expressed by cancer cells. In some embodiments, the synthetic agent is a protein ligand. In some embodiments, the synthetic agent is a protein binder. In some embodiments, the synthetic agent is a protein receptor. In some embodiments, the synthetic agent is a drug. In some embodiments, the synthetic agent is an anticancer agent. In some embodiments, the synthetic agent is a growth factor. In some embodiments, the synthetic agent is a surface binder. In some embodiments, the synthetic agent is an abiotic surface binder. In some embodiments, the surface binder is a functional group capable of binding a solid surface or a solid support.

In some embodiments, the synthetic agent is a protein binder. In some embodiments, a "protein binder" refers to any biological research reagent which binds to a specific target protein. Non limiting examples of protein binders known in the art include: drugs, folate, biotin, marimastat, ethacrynic acid, bisethacrynic acid, Ni-nitrilotriacetic acid (Ni-NTA), bis Ni-NTA, tris-Ni-NTA, PDGF-BB, heparin, FGF aptamer, estrogen, DNA aptamer, RNA aptamer, peptide aldehyde, estrogen, suberoylanilidehydroxamic acid (SAHA), or a peptide binder; each represents a separate embodiment according to this invention.

In some embodiments, the synthetic agent is a cancer cell binder. In some embodiments, the cancer cell binder is a folate.

In some embodiments, the synthetic agent is a molecular marker. In some embodiments, the synthetic agent is an angiogenic factor. In some embodiments, the synthetic agent is a cytokine. In some embodiments, the synthetic agent is a hormone. In some embodiments, the synthetic agent is a DNA molecule. In some embodiments, the synthetic agent is a siRNA molecule. In some embodiments, the synthetic agent is an oligosaccharide.

In some embodiments, the synthetic agent is a protein receptor. In some embodiments, the synthetic agent is an immune activator. In some embodiments, the synthetic agent is an immune suppressor. In some embodiments, the synthetic agent is a small molecule. In some embodiments, the small molecule is a drug.

In some embodiments, the synthetic agent is a labeling moiety as described herein above. In some embodiments, the labeling moiety is a dye. In some embodiments, the dye is a fluorescent dye. In some embodiments, the dye is selected from a group consisting of: dansyl, fluorescein (6-FAM), FAM, cyanine dyes (e.g. Cy3, Cy5), sulfoindocyanine, nile red, rhodamine, perylene, fluorenyl, coumarin, 7-methoxy-coumarin (Mca), dabcyl, NBD, Nile blue, TAMRA, BODIPY, FITC or a derivative thereof.

In some embodiments, the synthetic agent is a protein receptor. In some embodiments, the synthetic agent is a protein binder. In some embodiments, the synthetic agent is a biotin.

In some embodiments, the synthetic agent is a surface binder. In some embodiments, the synthetic agent is an abiotic surface binder. In some embodiments, the synthetic agent is a binder for abiotic surfaces. In some embodiments, the synthetic agent is an agent capable of binding to solid support. In some embodiments, the surface binder is capable of binding a surface. According to this invention, a "surface binder" is any chemical moiety, or functional group, that is capable of binding solid surfaces. In some embodiments, the binding is covalent, electrostatic, van der Waals or any combination thereof; each is a separate embodiment. In some embodiments, attachment of the surface binder to the surface comprises covalent bond, coordination bond, polar bond, van der Waals bond or any combination thereof. In some embodiments, the surface binder comprises a functional moiety capable of binding a surface. According to this aspect and in some embodiments, the surface binder comprises a thiol end group (SH) or an end group comprising a sulfur-sulfur bond (—S—S—). Such bonds are capable of binding to a noble metal. For example, thiol or —S—S— moieties binds strongly to gold surfaces and to other noble metal surface including but not limited to silver, platinum and palladium. Thiols and —S—S— bonds also bind to semiconductor surfaces such as GaAs etc. In some embodiments, the surface binder comprises a thiol group (HS). In some embodiments, the surface binder is a $C_1$-$C_{20}$ thioalkyl. In some embodiments, the surface binder is a $C_2$-$C_8$ thioalkyl. In some embodiments, the surface binder is a thiohexyl. In some embodiments, attachment of the surface binder to a surface comprise silicon chemistry. According to this aspect and in some embodiments, the surface is or comprises silicon. In some embodiments, the surface comprises silicon oxide. In some embodiments, the silicon oxide surface comprises glass or quartz. In some embodiments, the surface comprises silicon coated by a silicon oxide layer. According to this aspect and in some embodiments, the surface binder comprises a functional group capable of binding to silicon oxide. In some embodiments, the functional group comprises silicon atom. In some embodiments, the functional group comprises silicon bonded to a halogen atom. In some embodiments, the halogen atom is Cl, Br, F or I. In one embodiment the silicon-halogen functional group comprise Si-trichloride, Si-tribromide, Si-dichloride, Si dibromide. In some embodiments, the functional group comprises Si bonded to oxygen atom. In some embodiments, the functional group comprises Si bonded to two or three oxygen atoms. In some embodiments, the functional group of the surface binder comprises Si-halogen bond and upon reaction with the surface, the halogen atom is replaced by an oxygen atom, and bonding to the surface occurs. In some embodiments, the surface binder comprises a pyridine moiety.

In some embodiments, the surface is an abiotic surface. In some embodiments, the surface is a passivated. In some embodiments, surfaces of this invention are inorganic (e.g. silicon oxide, gold). In some embodiments, surfaces of this invention are organic (e.g. an organic polymer). In some embodiments, surfaces of this invention are metals (e.g., gold). In some embodiments, surfaces of this invention comprise both organic and inorganic materials. In some embodiments, the surface is a material selected from gold, glass, a doped glass, indium tin oxide (ITO)-coated glass, silicon, a doped silicon, Si(100), Si(111), $SiO_2$, SiH, silicon carbide mirror, quartz, a metal, metal oxide, a mixture of metal and metal oxide, group IV elements, mica, a polymer such as polyacrylamide and polystyrene, a plastic, a zeolite, a clay, wood, a membrane, an optical fiber, a ceramic, a metalized ceramic, an alumina, an electrically-conductive material, a semiconductor, steel or a stainless steel; each is a separate embodiment according to the invention. In some embodiments, the surface is a gold surface. In some embodiments, the surface is a passivated gold surface. In some embodiments, surfaces of this invention are flat. In some embodiments, the surfaces are curved. In some embodiments, the surface is macroscopically flat and microscopically curved or vice-versa. In some embodiments, the surface is the surface of a particle. In some embodiments, the surface is the surface of a nanoparticle.

u. Methods for Decorating a Cell

In some embodiments, this invention is directed to a method for decorating a cell with a synthetic agent, said method comprises:
 a. ectopically expressing in said cell a polypeptide, wherein said polypeptide comprises a membranal anchoring domain and an extracellular binding domain,
 b. incubating the cell of (a) with a first compound comprising a first oligonucleotide (ODN-1) covalently bound to a binder, either directly or through a first linker, said binder comprising affinity to said extracellular binding domain, and
 c. incubating the cell of (b) with a second compound comprising a second oligonucleotide (ODN-2) covalently bound to a synthetic agent, either directly or through a second linker, wherein said second oligonucleotide is complementary to said first oligonucleotide:

thereby decorating said cell with said synthetic agent.

In some embodiments, this invention is directed to a method for modifying a cell with a synthetic agent, said method comprises:
 a. ectopically expressing in said cell a polypeptide, wherein said polypeptide comprises a membranal anchoring domain and an extracellular binding domain,
 b. incubating the cell of (a) with a first compound comprising a first oligonucleotide (ODN-1) covalently bound to a binder, either directly or through a first linker, said binder comprising affinity to said extracellular binding domain, and
 c. incubating the cell of (b) with a second compound comprising a second oligonucleotide (ODN-2) covalently bound to a synthetic agent, either directly or through a second linker, wherein said second oligonucleotide is complementary to said first oligonucleotide;

thereby modifying said cell with said synthetic agent.

A skilled artisan would appreciate that "decorating" a cell with a compound or a molecule comprises attaching a number of such molecules to the cell surface. In some embodiments the cell surface is a cell membrane. In some embodiments, the terms "decorating", "modifying", "attaching", "incorporating", and "binding" are used herein interchangeably, having all the same meanings.

In some embodiments, the methods disclosed herein are applicable to any type of cells. In some embodiments, the cell is an eukaryote cell, a prokaryote cell, a mammalian cell, a plant cell, a human cell, and a bacteria cell. In some embodiments, the cell is E. coli.

In some embodiments, cells are transformed with a construct encoding a polypeptide comprising a membranal anchoring domain and an extracellular binding domain. In some embodiments, said anchoring domain comprises OmpC, and said binding domain comprises a His-tag as described herein above. In some embodiments, transformed cells are cultured to saturation in a growth medium, such as LB supplemented with antibiotics at 30° C. In some embodiments, cells are incubated until the $OD_{600}$ reaches about 0.6, then the expression of the polypeptide is induced by addition of an inducer, such as Rhamnose or isopropyl-b-D-1-thiogalactopyranoside (IPTG), letting cultures to grow further.

Recombinant cells expressing the polypeptide are then collected, in some embodiments, by centrifugation at 6,000 g for 4 min, washed, and resuspended in the same buffer to an $OD_{600}$ of 0.3. A preincubated sample of a first molecule comprising a first oligonucleotide (ODN-1) can be added to a sample of the cell suspension. In some embodiments, 500 nM of ODN-1 and 2.5 µM of $NiCl_2$ can be added to the cells, which can then be incubated in some embodiments for 1 hour.

After a first compound is bound to the cell membrane, cells can be incubated with a second compound comprising a second oligonucleotide (ODN-2), wherein ODN-2 is complementary to ODN-1. Cells ODN-2 can be added in some embodiments at a concentration of 500 nM and incubated in some embodiments for 30 min.

In some embodiments, a second oligonucleotide ODN-2 can be detached from ODN-1 and from the recombinant cells by adding a third compound comprising a third oligonucleotide ODN-3, wherein ODN-3 is complementary to ODN-2. In some embodiments, ODN-3 can be added at a concentration of 2 µM and incubated for 2 h.

In some embodiments, a first, a second, or a third compound comprising a first, a second, or a third oligonucleotide, respectively, is added at a concentration lower than about 5 nM, between about 5 nM and 50 nM, between about 50 nM and 500 nM, between about 500 nM and 5 µM, between about 5 µM and 50 µM, between about 50 µM and 500 µM, or higher than 500 µM.

In some embodiments, the first compound comprising the first oligonucleotide (ODN-1) can in some embodiments be removed from the cell surface by incubating the cells with EDTA. In some embodiments, incubating the cells with about 5 mM or about 10 mM EDTA for 1 hour detaches the first compound from the cell surface. Cells can then be collected by centrifugation and washed.

In some embodiments, the cell is a living cell. In some embodiments, the membranal anchoring domain comprises a transmembranal protein or a part of it, an artificial polypeptide, or a combination thereof. In some embodiments, the transmembranal protein comprises an outer membrane protein C (OmpC); receptor tyrosine kinases (RTKs); Ion channel linked receptors; Enzyme-linked receptors; G protein-coupled receptors or any combination thereof; each represents a separate embodiment according to this invention. In some embodiments, the extracellular domain comprises an affinity tag. In some embodiments, the affinity tag comprises a poly-histidine peptide (6×-His-tag, 10×-His-tag, His-tag), a tetra cysteine peptide (CCPGCC, TC tag), or a combination thereof. In some embodiments, the binder comprises a His-tag specific binder. In some embodiments, the binder comprises a moiety represented by the structure of formula C, D, D(a), D(b), E, E(a), E(b), G, G(a), or G(b). In some embodiments, the first compound is represented by the structure of formula J, H, H(a) and H(b) and compounds 100-104. In some embodiments, the second compound is represented by the structure of formula K and compounds 200-207. In some embodiments, the first linker comprises at least one polyethyleneglycol (PEG) moiety, at least one phosphate moiety, at least one thioalkyl moiety or any combination thereof. In some embodiments, the first compound further comprises a labeling moiety. In some embodiments, the labeling moiety is a fluorescent dye. In some embodiments, the synthetic agent of said second compound comprises a molecular marker, a labeling moiety, a fluorescent dye, an adhesion molecule, a cancer cell binder, a protein binder, a protein ligand, an anticancer agent, a surface binder (e.g., an abiotic surface binder), a growth factor, an angiogenic factor, a cytokine, a hormone, a DNA molecule, a siRNA molecule, an oligosaccharide, a protein receptor, an immune activator, an immune suppressor, a small molecule, a drug, or a derivative therefore, or any combination thereof, each represents a separate embodiment according to this invention. In some embodiments, the second compound further comprises a second labeling moiety. In some embodiments, the second labeling moiety comprises a fluorescent dye.

In some embodiments, the method is for decorating a cell surface. In some embodiments, the method is for decorating a cell membrane. In some embodiments, the method is for modifying a cell surface. In some embodiments, the method is for modifying a cell membrane. In some embodiments, the synthetic agent is a labeling moiety. In some embodiments, the synthetic agent is a fluorescent dye. In some embodiments, the synthetic agent is a surface binder. In some embodiments, the synthetic agent is an abiotic surface binder. In some embodiments, the synthetic agent is a thioalkyl. In some embodiments, the synthetic agent is a protein binder. In some embodiments, the synthetic agent is a biotin. In some embodiments, the synthetic agent is a cancer cell binder. In some embodiments, the synthetic agent is a folate. In some embodiments, the binder is a His-tag binder. In some embodiments, the His-tag binder is represented by the structure of formula C, D, D(a), D(b), E, E(a), E(b), G, G(a), G(b).

v. Methods for Adhering a First Cell to a Second Cell

In some embodiments, this invention is directed to a method for adhering a first cell to a second cell, said method comprises incubating a recombinant cell according to this invention, with a second cell, wherein the synthetic agent is an adhesion molecule.

In some embodiments, this invention is directed to a method for binding a first cell to a second cell, said method comprises incubating a recombinant cell according to this invention, with a second cell, wherein the synthetic agent is an adhesion molecule. In another embodiment, the synthetic agent is a protein binder.

In some embodiments, this invention is directed to a method for adhering a first cell to a second cell, said method comprises incubating a cell ectopically expressing a polypeptide according to this invention, wherein said polypeptide comprises a membranal anchoring domain and an extracellular binding domain, with a first compound according to this invention and with a second compound according to this invention, wherein the synthetic agent is an adhesion molecule, thereby forming a complex according to this invention, following by incubating the formed complex with a second cell, thereby adhering a first cell to a second cell.

In some embodiments, this invention is directed to a method for binding a first cell to a second cell, said method comprises incubating a cell ectopically expressing a polypeptide according to this invention, wherein said polypeptide comprises a membranal anchoring domain and an extracellular binding domain, with a first compound according to this invention and with a second compound according to this invention, wherein the synthetic agent is a protein binder, thereby forming a complex according to this invention, following by incubating the formed complex with a second cell, thereby binding a first cell to a second cell.

In some embodiments, this invention is directed to a method for adhering a first cell to a second cell, said method comprises:
  a. ectopically expressing in the first cell a polypeptide, wherein said polypeptide comprises a membranal anchoring domain and an extracellular binding domain,
  b. incubating the cell of (a) with a first compound according to this invention comprising a first oligonucleotide (ODN-1) covalently bound to a binder, either directly or through a first linker, said binder comprises affinity to said extracellular binding domain, and
  c. incubating the cell of (b) with a second compound according to this invention comprising a second oligonucleotide (ODN-2) covalently bound to an adhesion molecule, either directly or through a second linker, wherein said second oligonucleotide is complementary to said first oligonucleotide, and said adhesion molecule comprises affinity to a compound present on the surface of said second cell,
  d. incubating said first cell with said second cell,
thereby adhering said first cell to said second cell.

In some embodiments, this invention is directed to a method for binding a first cell to a second cell, said method comprises:
  a. ectopically expressing in the first cell a polypeptide, wherein said polypeptide comprises a membranal anchoring domain and an extracellular binding domain,
  b. incubating the cell of (a) with a first compound according to this invention comprising a first oligonucleotide (ODN-1) covalently bound to a binder, either directly or through a first linker, said binder comprises affinity to said extracellular binding domain, and
  c. incubating the cell of (b) with a second compound according to this invention comprising a second oligonucleotide (ODN-2) covalently bound to an adhesion molecule, either directly or through a second linker, wherein said second oligonucleotide is complementary to said first oligonucleotide, and said adhesion molecule comprises affinity to a compound present on the surface of said second cell,
  d. incubating said first cell with said second cell,
thereby binding said first cell to said second cell.

In some embodiments, the adhesion molecule is a protein binder.

In some embodiments, the recombinant cell is selected from a group comprising eukaryotes, prokaryotes, mammalian cells, plant cells, human cells, and bacteria. In some embodiments, a mammalian or a human cell is selected from a group comprising epithelial cells, Brunner's gland cells in duodenum, insulated goblet cells of respiratory and digestive tracts, stomach, foveolar cells, chief cells, parietal cells, pancreatic acinar cells, Paneth cells of small intestine, Type II pneumocyte of lung, club cells of lung, barrier cells, type i pneumocytes, gall bladder epithelial cells, centroacinar cells, intercalated duct cells, intestinal brush border cells, hormone-secreting cells, enteroendocrine cells, K cells, L cells, I cells, G cells, enterochromaffin cells, enterochromaffin-like cells, N cells, S cells, D cells, Mo cells, thyroid gland cells, thyroid epithelial cells, parafollicular cells, parathyroid gland cells, parathyroid chief cells, oxyphil cells, pancreatic islets, alpha cells, beta cells, delta cells, epsilon cells, PP cells, salivary gland mucous cells, salivary gland serous cells, Von Ebner's gland cells in tongue, mammary gland cells, lacrimal gland cells, ceruminous gland cells in ear, eccrine sweat gland dark cells, eccrine sweat gland clear cells, apocrine sweat gland cells, gland of moll cells in eyelid, sebaceous gland cells, Bowman's gland cells in nose, hormone-secreting cells, anterior/intermediate pituitary cells, corticotropes, gonadotropes, lactotropes, melanotropes, somatotropes, thyrotropes, magnocellular neurosecretory cells, parvocellular neurosecretory cells, chromaffin cells, keratinocytes, epidermal basal cells, melanocytes, trichocytes, medullary hair shaft cells, cortical hair shaft cells, cuticular hair shaft cells, huxley's layer hair root sheath cells, Henle's layer hair root sheath cells, outer root sheath hair cells, surface epithelial cells of cornea, tongue, mouth, nasal cavity, distal anal canal, distal urethra, and distal vagina, basal cells, intercalated duct cells, striated duct cells, lactiferous duct cells, ameloblast, auditory inner hair cells of organ of Corti, auditory outer hair cells of organ of Corti, basal cells of olfactory epithelium, primary sensory neurons, Merkel cells of epidermis, olfactory receptor neuron, pain-sensitive primary sensory neurons, photoreceptor cells of retina in eye, proprioceptive primary sensory neurons, touch-sensitive primary sensory neurons, chemoreceptor glomus cells of carotid body cells, outer hair cells of vestibular system of ear, inner hair cells of vestibular system of ear, taste receptor cells of taste bud, neuron cells, interneurons, basket cells, cartwheel cells, Stellate cells, Golgi cells, granule cells, Lugaro cells, unipolar brush cells, Martinotti cells, chandelier cells, Cajal-Retzius cells, double-bouquet cells, neurogliaform cells, retina horizontal cells, amacrine cells, spinal interneuron, renshaw cells, spindle neurons, fork neurons, pyramidal cells, place cells, grid cells, speed cells, head direction cells, Betz cells, stellate cells, boundary cells, bushy cells, Purkinje cells, medium spiny neurons, astrocytes, oligodendrocytes, ependymal cells, tanycytes, pituicytes, adipocytes, white fat cells, brown fat cells, liver lipocytes, cells of the adrenal cortex, cells of the zona glomerulosa, cells of the zona fasciculata, cells of the zona reticularis, theca interna cells of ovarian follicle, granulosa lutein cells, theca lutein cells, leydig cells of testes, seminal vesicle cells, prostate gland cells, bulbourethral gland cells, Bartholin's gland cells, gland of littre cells, uterus endometrium cells, juxtaglomerular cells, macula densa cells of kidney, peripolar cells of kidney, mesangial cells of kidney, parietal epithelial cells, podocytes, proximal tubule brush border cells, loop of Henle thin segment cells, kidney distal tubule cells, kidney collecting duct cells, principal cells, intercalated cells, transitional epithelium, duct cells, efferent ducts cells, epididymal principal cells, epididymal basal cells, endothelial cells, planum semilunatum epithelial cells of vestibular system of ear, organ of Corti interdental epithelial cells, loose connective tissue fibroblasts, corneal fibroblasts, tendon fibroblasts, bone marrow reticular tissue fibroblasts, other nonepithelial fibroblasts, pericytes, hepatic stellate cells, nucleus pulposus cells of intervertebral disc, hyaline cartilage chondrocytes, fibrocartilage chondrocytes, elastic cartilage chondrocytes, osteoblast/osteocytes, osteoprogenitor cells, hyalocyte of vitreous body of eye, stellate cells of perilymphatic space of ear, pancreatic stellate cells, red skeletal muscle cells, white skeletal muscle cells, intermediate skeletal muscle cells, nuclear bag cells of muscle spindle, nuclear chain cells of muscle spindle, myosatellite cells, cardiac muscle cells, cardiac muscle cells, node cells, Purkinje fiber cells, smooth muscle cells, myoepithelial cells of iris, myoepithelial cells of exocrine glands, erythrocytes, megakaryocytes, platelets, monocytes, connective tissue macrophage, epidermal Langerhans cells, osteoclast, dendritic cells, microglial cells, neutrophil granulocytes, eosinophil granulocytes, basophil granulocytes, hybridoma cells, mast cells, helper T cells, suppressor T cells, cytotoxic T cells, natural killer T cells, B cells, natural killer cells, reticulocytes, hematopoietic stem cells and committed progenitors for the blood and immune system, oogonium/oocytes, spermatids, spermatocytes, spermatogonium cells, spermatozoon, and interstitial kidney cells.

In some embodiments, the second cell comprises a cellular pathology. In some embodiments, the second cell is a cancer cell. In some embodiments, the cancer is selected from: a carcinoma, a sarcoma, a lymphoma, leukemia, a germ cell tumor, a blastoma, chondrosarcoma, Ewing's sarcoma, malignant fibrous histiocytoma of bone/osteosarcoma, osteosarcoma, rhabdomyosarcoma, heart cancer, brain cancer, astrocytoma, glioma, medulloblastoma, neuroblastoma, breast cancer, medullary carcinoma, adrenocortical carcinoma, thyroid cancer, Merkel cell carcinoma, eye cancer, gastrointestinal cancer, colon cancer, gallbladder cancer, gastric (stomach) cancer, gastrointestinal carcinoid tumor, hepatocellular cancer, pancreatic cancer, rectal cancer, bladder cancer, cervical cancer, endometrial cancer, ovarian cancer, renal cell carcinoma, prostate cancer, testicular cancer, urethral cancer, uterine sarcoma, vaginal cancer, head cancer, neck cancer, nasopharyngeal carcinoma, hematopoetic cancer, lymphoma, Non-hodgkin lymphoma, skin cancer, basal-cell carcinoma, melanoma, small cell lung cancer, non-small cell lung cancer, or any combination thereof.

In some embodiments, the adhesion molecule is any compound that comprises affinity to a compound present in the membrane of a second cell. In some embodiments, the adhesion molecule is selected according to its binding potency to a molecule known to be expressed in a second cell. In some embodiments, the adhesion molecule is any adhesion molecule known in the art.

In some embodiments, the adhesion molecule is a peptide, a polypeptide, a protein or a part thereof. In some embodiments, the adhesion molecule comprises an integrin or a fragment thereof. In some embodiments, the adhesion molecule comprises an immunoglobulin (Ig) or a fragment thereof. In some embodiments, the adhesion molecule comprises a cadherin, or a fragment thereof. In some embodiments, the adhesion molecule comprises a selectins, or a fragment thereof. In some embodiments, the adhesion molecule comprises a calcium-dependent cell adhesion molecule, or a fragment thereof. In some embodiments, the adhesion molecule comprises a proteoglycan, or a fragment thereof. A skilled artisan would appreciate that adhesion molecule recognizes a different ligand.

In some embodiments an adhesion molecule is selected from a group comprising VLA1, VLA2, VLA3, VLA4, VLA5, VLA6, FLJ25220, RLC, HsT18964, FLJ39841, HUMINAE, LFA1A, MAC-1, VNRA, MSK8, GPIIb, FNRB, MSK12, MDF2, LFA-1, MAC-1, MFI7, GP3A, GPIIIa, FLJ26658, fibronectin receptor, laminin receptor, LFA-1, CR3, fibrinogen receptor; gpIIbIIa, vitronectin receptor, CDH1, CDH2, CDH12, CDH3, DSG1, DSG2, DSG3, DSG4, Desmocollin, DSC1, DSC2, DSC3, Protocadherins, IgSF CAMs, NCAMs, ICAM-1, CD2, CD58, CD48, CD150, CD229, CD244, E-selectin. L-selectin, P-selectin, any fragment thereof, or any combination thereof.

In some embodiments, the cell adhesion molecule comprises a folate. In some embodiments, the second cell expresses an extracellular folate receptor on its surface.

In some embodiments, the first cell is a living cell. In some embodiments, the second cell is a living cell. In some embodiments, the second cell is a cancer cell. In some embodiments, the second cell expresses an extracellular protein receptor on its surface. In some embodiments, the adhesion molecule is a protein binder. In some embodiments, the adhesion molecule is a folate. In some embodiments, the membranal anchoring domain comprises a transmembranal protein or a part of it, an artificial polypeptide, or a combination thereof. In some embodiments, the transmembranal protein comprises an outer membrane protein C (OmpC); receptor tyrosine kinases (RTKs); Ion channel linked receptors; Enzyme-linked receptors; G protein-coupled receptors or any combination thereof; each represents a separate embodiment according to this invention. In some embodiments, the extracellular domain comprises an affinity tag. In some embodiments, the affinity tag comprises a poly-histidine peptide (6×-His-tag, 10×-His-tag, His-tag), a tetra cysteine peptide (CCPGCC, TC tag), or a combination thereof. In some embodiments, the binder comprises a His-tag specific binder. In some embodiments, the binder comprises a moiety represented by the structure of formula C, D, D(a), D(b), E, E(a), E(b), G, G(a), or G(b). In some embodiments, the first compound is represented by the structure of formula J, H, H(a) and H(b) and compounds 100-104. In some embodiments, the second compound is represented by the structure of formula K and compounds 200-207. In some embodiments, the first linker comprises at least one polyethyleneglycol (PEG) moiety, at least one phosphate moiety, at least one thioalkyl moiety or any combination thereof. In some embodiments, the first compound further comprises a labeling moiety. In some embodiments, the labeling moiety is a fluorescent dye. In some embodiments, the second compound further comprises a second labeling moiety. In some embodiments, the second labeling moiety comprises a fluorescent dye.

w. Methods for Adhering a Cell to a Surface

In some embodiments, this invention is directed to a method for adhering a cell to a surface, said method comprises incubating a recombinant cell according to the invention, with a first compound according to the invention, following by incubating the formed cell with a second compound according to this invention, wherein the synthetic agent is a surface binder.

In some embodiments, this invention is directed to a method for adhering a cell to a surface, said method comprises:
a. ectopically expressing in a cell a polypeptide, wherein said polypeptide comprises a membranal anchoring domain and an extracellular binding domain,
b. incubating the cell of (a) with a first compound according to this invention comprising a first oligonucleotide (ODN-1) covalently bound to a binder, either directly or through a first linker, said binder comprises affinity to said extracellular binding domain,
c. incubating the cell of (b) with a second compound according to this invention comprising a second oligonucleotide (ODN-2) covalently bound to a surface binder, either directly or through a second linker, wherein said second oligonucleotide is complementary to said first oligonucleotide, and said surface binder is capable of binding to said surface, and
d. applying said cell to said surface under conditions sufficient for the binding of said surface binder to said surface, thereby adhering said cell to said surface.

In some embodiments, the cell is a living cell. In some embodiments, the cell is a bacteria. In some embodiments, the membranal anchoring domain comprises a transmembranal protein or a part of it, an artificial polypeptide, or a combination thereof. In some embodiments, the transmembranal protein comprises an outer membrane protein C (OmpC); receptor tyrosine kinases (RTKs); Ion channel linked receptors; Enzyme-linked receptors; G protein-coupled receptors or any combination thereof, each represents a separate embodiment according to this invention. In some embodiments, the extracellular domain comprises an affinity tag. In some embodiments, the affinity tag comprises a poly-histidine peptide (6×-His-tag, 10×-His-tag, His-tag), a tetra cysteine peptide (CCPGCC, TC tag), or a combination thereof. In some embodiments, the binder comprises a His-tag specific binder. In some embodiments, the binder comprises a moiety represented by the structure of formula C, D, D(a), D(b), E, E(a), E(b), G, G(a), or G(b). In some embodiments, the first compound is represented by the structure of formula J, H, H(a) and H(b) and compounds 100-104. In some embodiments, the second compound is represented by the structure of formula K and compounds 200-207. In some embodiments, the first linker comprises at least one polyethyleneglycol (PEG) moiety, at least one phosphate moiety, at least one thioalkyl moiety or any combination thereof. In some embodiments, the first compound further comprises a labeling moiety. In some embodiments, the labeling moiety is a fluorescent dye. In some embodiments, the second compound further comprises a second labeling moiety. In some embodiments, the second labeling moiety comprises a fluorescent dye.

In some embodiments, the surface binder is an abiotic surface binder. In some embodiments, the surface is a solid support. In some embodiments, the surface is a passivated. In some embodiments, the surface is a material selected from gold, glass, a doped glass, indium tin oxide (ITO)-coated glass, silicon, a doped silicon, Si(100), Si(111), $SiO_2$, SiH, silicon carbide mirror, quartz, a metal, metal oxide, a mixture of metal and metal oxide, group IV elements, mica, a polymer such as polyacrylamide and polystyrene, a plastic, a zeolite, a clay, wood, a membrane, an optical fiber, a ceramic, a metalized ceramic, an alumina, an electrically-conductive material, a semiconductor, steel or a stainless steel; each is a separate embodiment according to the invention. In some embodiments, the surface is a gold surface. In some embodiments, the surface binder is a $C_1$-$C_{20}$ thioalkyl. In some embodiments, the surface binder is a $C_2$-$C_8$ thioalkyl. In some embodiments, the surface binder is a thiohexyl. In some embodiments, the surface binder is a pyridine-terminated moiety.

x. Methods for Inducing Luminescent in a Cell

In some embodiments, this invention is directed to a method for inducing luminescence in a cell, said method comprises incubating a recombinant cell according to the invention, with a first compound according to the invention, following by incubating the formed cell with a second compound according to this invention, wherein the synthetic agent is a luminescent moiety.

In some embodiments, this invention is directed to a method for inducing luminescence in a cell, said method comprises:
a. ectopically expressing in a cell a first polypeptide, wherein said polypeptide comprises a membranal anchoring domain and an extracellular binding domain,
b. incubating the cell of (a) with a first compound according to this invention, comprising a first oligonucleotide (ODN-1) covalently bound to a binder, either directly or through a first linker, said binder comprises affinity to said extracellular binding domain, and
c. incubating the cell of (b) with a second compound according to this invention, comprising a second oligonucleotide (ODN-2) covalently bound to a luminescent molecule, either directly or through a second linker, wherein the second oligonucleotide is complementary to the first oligonucleotide, thereby inducing luminescence in said cell.

Any luminescent molecule can be used in the methods disclosed herein. In some embodiments, the luminescent molecule is as described for a "labeling moiety" herein above. In some embodiments, the luminescent molecule is a fluorescent dye. Examples of fluorescent dyes are given herein above. In some embodiments, the dye is selected from: dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, TAMRA, BODIPY, FITC and derivatives thereof.

In some embodiments, the cell is a living cell. In some embodiments, the cell is a bacteria. In some embodiments, the membranal anchoring domain comprises a transmembranal protein or a part of it, an artificial polypeptide, or a combination thereof. In some embodiments, the transmembranal protein comprises an outer membrane protein C (OmpC); receptor tyrosine kinases (RTKs); Ion channel linked receptors; Enzyme-linked receptors; G protein-coupled receptors or any combination thereof; each represents a separate embodiment according to this invention. In some embodiments, the extracellular domain comprises an affinity tag. In some embodiments, the affinity tag comprises a poly-histidine peptide (6×-His-tag, 10×-His-tag, His-tag), a tetra cysteine peptide (CCPGCC, TC tag), or a combination thereof. In some embodiments, the binder comprises a His-tag specific binder. In some embodiments, the binder comprises a moiety represented by the structure of formula C, D, D(a), D(b), E, E(a), E(b), G, G(a), or G(b). In some embodiments, the first compound is represented by the structure of formula J, H, H(a) and H(b) and compounds 100-104. In some embodiments, the second compound is represented by the structure of formula K and compounds 200-207. In some embodiments, the first linker comprises at least one polyethyleneglycol (PEG) moiety, at least one phosphate moiety, at least one thioalkyl moiety or any combination thereof. In some embodiments, the first compound further comprises a labeling moiety. In some embodiments, the labeling moiety is a fluorescent dye. In some embodiments, the second compound further comprises a second labeling moiety. In some embodiments, the second labeling moiety comprises a fluorescent dye.

y. Methods for Binding a Cell to a Protein

In some embodiments, this invention is directed to a method for binding a cell to a protein of interest (POI), said method comprises incubating a recombinant cell according to this invention, with said POI, wherein the synthetic agent is a protein binder.

In some embodiments, this invention is directed to a method for binding a cell to a protein of interest (POI), said method comprises incubating a cell ectopically expressing a polypeptide according to this invention, wherein said polypeptide comprises a membranal anchoring domain and an extracellular binding domain, with a first compound according to this invention and with a second compound according to this invention, thereby forming a complex according to this invention, following by incubating the formed complex with a POI, wherein the synthetic agent is a protein binder, thereby binding a cell to a protein of interest (POI).

In some embodiments, this invention is directed to a method for binding a cell to a protein of interest (POI), said method comprises:
  a. ectopically expressing in a cell a polypeptide, wherein said polypeptide comprises a membranal anchoring domain and an extracellular binding domain,
  b. incubating the cell of (a) with a first compound according to this invention, comprising a first oligonucleotide (ODN-1) covalently bound to a binder, either directly or through a first linker, said binder comprises affinity to said extracellular binding domain, and
  c. incubating the cell of (b) with a second compound according to this invention, comprising a second oligonucleotide (ODN-2) covalently bound to a protein binder, either directly or through a second linker, wherein said second oligonucleotide is complementary to said first oligonucleotide, and said protein binder is selective to said POI, and
  d. incubating said cell with said POI,
thereby binding said cell to said POI.

In some embodiments, the cell is a living cell. In some embodiments, the cell is a bacteria. In some embodiments, the membranal anchoring domain comprises a transmembranal protein or a part of it, an artificial polypeptide, or a combination thereof. In some embodiments, the transmembranal protein comprises an outer membrane protein C (OmpC); receptor tyrosine kinases (RTKs); Ion channel linked receptors; Enzyme-linked receptors; G protein-coupled receptors or any combination thereof; each represents a separate embodiment according to this invention. In some embodiments, the extracellular domain comprises an affinity tag. In some embodiments, the affinity tag comprises a poly-histidine peptide (6×-His-tag, 10×-His-tag, His-tag), a tetra cysteine peptide (CCPGCC, TC tag), or a combination thereof. In some embodiments, the binder comprises a His-tag specific binder. In some embodiments, the binder comprises a moiety represented by the structure of formula C, D, D(a), D(b), E, E(a), E(b), G, G(a), or G(b). In some embodiments, the first compound is represented by the structure of formula J, H, H(a) and H(b) and compounds 100-104. In some embodiments, the second compound is represented by the structure of formula K and compounds 200-207. In some embodiments, the first linker comprises at least one polyethyleneglycol (PEG) moiety, at least one phosphate moiety, at least one thioalkyl moiety or any combination thereof. In some embodiments, the first compound further comprises a labeling moiety. In some embodiments, the labeling moiety is a fluorescent dye. In some embodiments, the second compound further comprises a second labeling moiety. In some embodiments, the second labeling moiety comprises a fluorescent dye.

In some embodiments, the protein binder is a small molecule ligand. In some embodiments, the protein binder is a peptide, polypeptide a protein, or a part thereof; each is a separate embodiment. In some embodiments, the protein binder is a biotin. In some embodiments, the protein binder is a folate.

z. Methods for Treating a Disease

In some embodiments, the recombinant cells disclosed herein comprise a therapeutic effect and are delivered to a patient in need thereof. When used therapeutically, the recombinant cells are referred to herein as "therapeutics". Methods of administration of therapeutics include, but are not limited to, intravenal, intradermal, intraperitoneal, or surgical routes. The therapeutics of the disclosure presented herein may be administered by any convenient route, for example by infusion, by bolus injection, by surgical implantation and may be administered together with other biologically-active agents. Administration can be systemic or local. It may also be desirable to administer the therapeutic locally to the area in need of treatment; this may be achieved by, for example, and not by way of limitation, local infusion during surgery, by injection, by means of a catheter, or by means of an implant.

A skilled artisan would appreciate that a therapeutically effective amount of the cells may encompass total the amount of cells that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the a therapeutically effective amount refers to that ingredient alone. When applied to a combination, the term refers to combined amounts of the active ingredients that result in the therapeutic effect, whether administered in combination, serially or simultaneously.

In some embodiments, suitable dosage ranges of the therapeutics of the disclosure presented herein are generally between 1 million and 2 million recombinant cells. In some embodiments, suitable doses are between 2 million and 5 million recombinant cells. In some embodiments, suitable doses are between 5 million and 10 million recombinant cells. In some embodiments, suitable doses are between 10 million and 25 million recombinant cells. In some embodiments, suitable doses are between 25 million and 50 million recombinant cells. In some embodiments, suitable doses are between 50 million and 100 million recombinant cells. In some embodiments, suitable doses are between 100 million and 200 million recombinant cells. In some embodiments, suitable doses are between 200 million and 300 million recombinant cells. In some embodiments, suitable doses are between 300 million and 400 million recombinant cells. In some embodiments, suitable doses are between 400 million and 500 million recombinant cells. In some embodiments, suitable doses are between 500 million and 600 million recombinant cells. In some embodiments, suitable doses are between 600 million and 700 million recombinant cells. In some embodiments, suitable doses are between 700 million and 800 million recombinant cells. In some embodiments, suitable doses are between 800 million and 900 million recombinant cells. In some embodiments, suitable doses are between 900 million and 1 billion recombinant cells. In some embodiments, suitable doses are between 1 billion and 2 billion recombinant cells. In some embodiments, suitable doses are between 2 billion and 3 billion recombinant cells. In some embodiments, suitable doses are between 3 billion and 4 billion recombinant cells. In some embodiments, suitable doses are between 4 billion and 5 billion recombinant cells.

One skilled in the art would appreciate that effective doses may be extrapolated from dose-response curves derived from in vitro or animal model test systems.

In some embodiments, recombinant cells are decorated in vitro before delivering to a patient. In some embodiments, recombinant cells are decorated in vivo. In some embodiments, cells are decorated in vivo by first delivering to a patient the recombinant cells, then delivering a first compound that binds the extracellular binding domain of the cells, and then delivering a second compound that binds the first compound. In some embodiments, recombinant cells can proliferate after being delivered to a patient.

The herein-described recombinant cells, either decorated or not, can be incorporated into pharmaceutical compositions suitable for administration. Such compositions typically comprise a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Some examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition disclosed here is formulated to be compatible with its intended route of administration. Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents are included, for example, sugars, polyalcohols such as mannitol, sorbitol or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

In some embodiments, the recombinant cells are prepared with carriers that will protect them against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers.

In some embodiments, this invention is directed to a kit comprising:

a. a recombinant cell ectopically expressing a polypeptide according to this invention, wherein said polypeptide comprises a membranal anchoring domain and an extracellular binding domain, said extracellular binding domain bound to b. a first compound according to this invention, comprising a first oligonucleotide (ODN-1) covalently bound to a binder according to this invention, either directly or through a first linker, said binder comprises affinity to said extracellular binding domain, c. a second compound according to this invention, comprising a second oligonucleotide (ODN-2) covalently bound to a synthetic agent, either directly or through a second linker, wherein said second oligonucleotide is complementary to said first oligonucleotide.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

The following examples are presented in order to more fully illustrate the preferred embodiments of the invention. They should in no way be construed, however, as limiting the broad scope of the invention.

EXAMPLES

Materials and Methods

All solvents and reagents were obtained from commercial suppliers and used without further purification. Dry solvents were purchased from Sigma Aldrich with the exception of dry DMSO, which was purchased from Arcos.

IgG from human serum, IgA from human serum, human serum albumin (HSA), human $\alpha_1$ acid glycoprotein (AGP) and calmodulin (CaM) from bovine testes were purchased from Sigma Aldrich. Human recombinant GST-P1-1, mouse recombinant His-calmodulin, human recombinant Drp1 (DAPK-related protein 1), and human recombinant CaMKII were obtained from the Israel Structural Proteomics Center (Weizmann Institute of Science). M13 and Bax BH3 peptide (55-74) wild type were purchased from Anaspec (Fremont, Calif.). Protein G protein fragment His-Tag was purchased from abcam. Recombinant human insulin from yeast, recombinant human B-cell lymphoma protein 2 alpha His-Tag (Bcl-2), recombinant streptavidin from *Streptomyces avidinii*, and avidin from hen's egg white were all purchased from ProSpec-Tany TechnoGene Ltd. (Ness Ziona, Israel). Bovine serum albumin (BSA) was purchased from MP biomedicals (Santa Ana, Calif.). Fmoc-L-2,3-diaminopropionic acid, cholesterol and paclitaxel were purchased from Chem-Impex International (Wood Dale, Ill.). $H_2N$-$PEG_3$-tBu, 4-Azidobutyric acid and tolbutamide were purchased from Chem-Impex International (Wood Dale, Ill.), ChemPep, Inc. (Wellington, Fla.), and Chiralix (Nijmegen, The Netherlands), respectively. Calmidazolium, Mastoparan, sodium salicylate, andrographolide, pioglitazone, DPC (fenamic acid), apigenin, aspirin, carbimazole, α-D-glucose-6-phosphate monosodium salt (α-G6P), angiotensin II human, 1,3-PB-ITU dihydrobromide, irsogladine maleate, and PP2 (4-amino-5-(4-chlorophenyl)-7-(t-butyl)pyrazolo[3,4-d]pyrimidine) were purchased from Santa Cruz Biotechnology. Dopamine, histamine dihydrochloride, ouabain octahydrate, naringin, amikacin, biotin, digitoxin, estrone, glucose pentaacetate, podophyllotoxin, colchicine, neocuproine hydrate, and erythromycin were purchased from Sigma Aldrich. λ-protein phosphatase and CaMKII (phospho Thr305) antibody were purchased from New England Biolabs (UK) Ltd, and GeneTex (Irvine, Calif.), respectively. Anti-flag-tag antibody was purchased from Pierce thermo scientific (Rockford, Ill.). The $^1$H NMR spectra were recorded on a Bruker Avance 300 MHz NMR instrument. Electrospray mass spectrometry was performed either with a Micromass Platform LCZ-4000 instrument at the Weizmann Institute of Science mass spectrometry facility or by using the LTQ Orbitrap Discovery hybrid FT mass spectrometer (Thermo Fisher Scientific, Inc.) equipped with an electrospray ionization ion source at the Faculty of Agriculture, Hebrew University of Jerusalem. The exact masses from elemental compositions were calculated using ChemDraw Ultra 12.0. Analytical reversed phase high-performance liquid chromatography (RP-HPLC) analysis was performed either on a Waters liquid chromatography system equipped with a 2487 dual wavelength UV detector, 600 gradient pump, and a 717 plus autosampler or an Agilent 1260 infinity quaternary pump LC system, maximum pressure 400 bar, equipped with a diode-array detector with max-light high-sensitivity cartridge cell.

Peptides were either synthesized manually (peptide P1, Table 1) or purchased from Synpeptide Co., Ltd. Shanghai, China (peptides P2 and P3, Table 1) or using an automated synthesizer (Advanced ChemTech, Apex 396) (peptides P4 and P5, Table 1). The azido-modified peptides (Table 1) and compounds C10-C19 (Table 1) were purified by RP-HPLC using a ThermoSeparation instrument (P200 pump, UV 100 detector), and a pre-packed Vydac $C_{18}$ column. Protein structures were produced using Discovery Studio Visualizer, version 2.5 (Accelrys, San Diego, Calif.). Structures of CaM, CaM($Ca^{+2}$), CaM-M13, CaMKII, and CaMKII/CaM ($Ca^{+2}$) were taken from the Protein Databank codes ICFD, 1CLL, 2BBM, 2VN9, 2WEL, respectively.

Fluorescence was measured using a BioTek synergy H4 hybrid multiwell plate reader, in black flat-bottom polystyrene NBS 384-well microplates (Corning). The same machine was used to calculate the concentration of the final sensors using clear flat-bottom polystyrene 384 well microplates (Corning). The concentrations of compounds 1-5 were determined by measuring the absorbance of dansyl at 330 nm and using an extinction coefficient $\varepsilon=4300$ $M^{-1}$ $cm^{-1}$. Protein concentrations were determined using a Nano-Drop ND-1000 spectrophotometer (Thermo Scientific).

Example 1

Synthetic Details for Various Compounds of the Invention

Fluorescent Molecular Sensor for Targeting Changes in Protein Surfaces

Synthesis of Tri-Nitrilotriacetic Acid (C3) (FIG. 3)

Compounds C1 and C2 were synthesized according to published procedures. The synthetic details of compounds C1 and C2 are described in Example 3 below.

Compound C1 (615 mg, 1.3 mmol), compound C2 (1.8 g, 4.18 mmol), EDC (996.8 mg, 5.2 mmol), HOBt (175.63 mg, 1.3 mmol), and triethyl amine (725.2 µL, 5.2 mmol) were mixed under argon in dry THF (40 mL) for 36 hours. The solvent was evaporated and the mixture was re-dissolved in diethyl ether and washed with HCl (0.5 M) and brine. After drying with $Na_2SO_4$, the product was purified by combiflash silica column chromatography using a gradient of 0-7% MeOH in DCM to afford the pure material (1.16 g, 52% yield).

$^1$H NMR (300 MHz, $CDCl_3$): δ=1.43 (s, 54H), 1.44 (s, 27H), 1.50-1.56 (m, 12H), 1.63-1.65 (m, 6H), 2.40 (t, J=5.7 Hz, 6H), 3.15-3.22 (m, 6H), 3.32 (t, J=7.4 Hz, 3H), 3.40-3.54 (m, 12H), 3.62 (s, 6H), 3.67 (t, J=5.6 Hz, 6H), 5.01 (s, 2H), 5.40 (s, 1H), 6.78-6.79 (m, 2H), 7.32-7.33 (m, 5H).

$ESI^+$-MS (m/z): calcd. for $[M+Na]^+$ 1732.04, found 1732.42, calcd. for $[M+2Na]^{+2}$ 877.01, found 877.40, calcd. for $[M+3Na]^{+3}$ 592.34, found 592.84.

This product was then hydrogenated using 10% Pd/C (86 mg) in methanol (20 mL) under $H_2$ atmosphere (1 atm) overnight. After complete removal of the benzyl group, as determined by TLC and ninhydrin staining, the palladium catalyst was filtered through cotton to afford a viscous oily product (925 mg, 87% yield).

$^1$H NMR (300 MHz, $CDCl_3$): δ=1.44 (s, 54H), 1.45 (s, 27H), 1.52-1.58 (m, 12H), 1.63-1.64 (m, 6H), 2.42-2.50 (m, 6H), 3.22-3.24 (m, 6H), 3.27-3.32 (m, 3H), 3.36-3.47 (m, 12H), 3.50-3.62 (m, 6H), 3.72-3.75 (m, 6H), 6.65-6.68 (m, 1H), 7.17 (br-s, 2H).

$ESI^+$-MS (m/z): calcd. for $[M+H]^+$ 1575.03 found 1575.29, calcd. for $[M+2H]^{+2}$ 788.01, found 788.40.

Synthesis of Compound C9 (FIG. 4)

C4, C7 were synthesized according to previously published procedures.

Compound C6 (FIG. 4)

C4 (1.64 g, 2.9 mmol), C5 (805 mg, 2.9 mmol), DIPEA (1 mL, 5.8 mmol), and HATU (1.1 g, 2.9 mmol) were stirred in dry THF (50 mL) under argon at room temperature overnight. The reaction mixture was evaporated and then purified by combiflash silica column chromatography using a gradient of 0-8% MeOH in DCM to afford the Fmoc protected product (2.13 g, 89% yield).

$^1$H NMR (300 MHz, $CDCl_3$): δ=1.42 (s, 9H), 2.45 (t, J=6.6 Hz, 2H), 2.86 (s, 6H), 3.10-3.33 (m, 2H), 3.38-3.45

(m, 2H), 3.54-3.60 (m, 10H), 3.65 (t, J=6.5 Hz, 2H), 4.17-4.21 (m, 1H), 4.27 (m, 1H), 4.31-4.33 (m, 2H), 5.99-6.06 (m, 2H), 6.97 (br-s, 1H), 7.16 (d, J=7.5 Hz, 1H), 7.29-7.34 (m, 2H), 7.37-7.42 (m, 2H), 7.49-7.60 (m, 4H), 7.76 (d, J=7.5 Hz, 2H), 8.25-8.28 (m, 2H), 8.54 (d, J=8.4 Hz, 1H).

ESI$^+$-MS (m/z): calcd. for [M+Na]+841.34, found 841.39.

Next, the Fmoc group of the residue (321 mg, 0.39 mmol) was deprotected by 20% piperidine in dry DMF (15 mL) for 1 hour. The solvent was then evaporated and the residue was further placed under high vacuum for 6 h. The product was purified by combiflash silica column chromatography using a gradient of 0-3.5% MeOH in DCM to afford C6 (170 mg, 65% yield).

$^1$H NMR (300 MHz, CDCl$_3$): δ=1.42 (s, 9H), 2.50 (t, J=6 Hz, 2H), 2.88 (s, 6H), 3.09 (dd, J=4.8, 13.5 Hz, 1H), 3.18-3.24 (m, 2H), 3.40-3.45 (m, 2H), 3.50 (t, J=5.3 Hz, 1H), 3.54-3.57 (m, 2H), 3.60-3.62 (m, 8H), 3.69 (t, J=6.2 Hz, 2H), 7.18 (d, J=7.5 Hz, 1H), 7.49-7.60 (m, 2H), 7.64-7.65 (m, 1H), 8.18-8.26 (m, 2H), 8.54 (d, J=8.4 Hz, 1H).

ESI$^+$-MS (m/z): calcd. for [M+H]$^+$ 597.29, found 597.40, calcd. for [M+Na]$^+$ 619.27, found 619.40.

Compound C8 (FIG. 4)

C6 (168 mg, 0.281 mmol), C7 (88.04 mg, 0.309 mmol), N,N-Diisopropylethylamine (DIPEA) (97.88 μL, 0.56 mmol), and HCTU (290.6 mg, 0.70 mmol) were stirred in 10 mL dry THF under argon at room temperature overnight. Then the solvent was evaporated and the residue was purified by combiflash silica column chromatography using a gradient of 0-5% MeOH in DCM. The fractions containing the product were collected, dissolved with ethyl acetate, and washed with 0.5 M HCl, 0.5 M NaOH and brine, and then the organic layer was dried with Na$_2$SO$_4$. The tert-butyl protected product (130 mg) was obtained with a 53% yield.

$^1$H NMR (300 MHz, CDCl$_3$): δ=1.42 (s, 9H), 2.44-2.49 (m, 2H), 2.58-2.59 (m, 1H), 2.79 (s, 2H), 2.89 (s, 6H), 3.15-3.24 (m, 1H), 3.42-3.46 (m, 3H), 3.56 (br-s 6H), 3.60 (br-s 4H) 3.66 (t, J=6.5 Hz, 2H), 4.59-4.61 (m, 1H), 4.82-4.84 (m, 6H), 6.39-6.43 (m, 1H), 7.19 (d, J=7.5 Hz, 1H), 7.31 (t, J=5.3 Hz, 1H), 7.36 (s, 2H), 7.48-7.57 (m, 2H), 7.82 (d, J=6.9 Hz, 1H), 8.23-8.27 (m, 2H), 8.56 (d, J=8.4 Hz, 1H).

ESI$^+$-MS (m/z): calcd. for [M+Na]$^+$ 885.33, found 885.19, calcd. for [2 M+Na]$^{+1}$ 1747.68, found 1747.50.

The tert-butyl protected product (120 mg) was then dissolved in a mixture of TFA/DCM (6 mL; 1:1) and stirred for 2 h. The reaction mixture was diluted with chloroform (50 mL) and evaporated 5 times and placed under high vacuum overnight to afford C8 in a quantitative yield.

$^1$H NMR (300 MHz, CDCl$_3$): δ=2.47 (t, J=2.1 Hz, 1H), 2.55-2.58 (m, 4H), 2.95 (s, 6H), 3.24-3.34 (m, 2H), 3.43-3.47 (m, 2H), 3.58-3.70 (m, 10H), 3.73-3.80 (m, 2H), 4.79-4.81 (m, 7H), 6.82 (t, J=6.2 Hz, 1H), 7.21-7.24 (m, 1H), 7.28 (s, 2H), 7.48-7.56 (m, 2H), 7.77-7.82 (m, 1H), 7.91 (d, J=7.5 Hz, 1H), 8.25 (d, J=7.2 Hz, 1H), 8.36 (d, J=8.7 Hz, 1H), 8.58 (d, J=8.4 Hz, 1H).

ESI$^+$-MS (m/z): calcd. for [M+Na]$^+$829.27, found 829.35, calculated for [M−H+2Na]$^+$ 851.25, found 851.41. ESI$^-$-MS (m/z): calcd. for [M−H]$^-$ 805.27, found 805.39.

Compound C9 (FIG. 4)

A solution of C8 (40 mg, 49.5 μmol), C3 (186 mg, 118 μmol), HCTU (56.29 mg, 136 μmol), and DIPEA (23.6 μL, 135.5 μmol) in 3 mL dry THF was stirred overnight under argon. The solvent was evaporated and the reaction was purified by combiflash silica column chromatography using a gradient of 0-4.8% MeOH in EtOAc to afford C9 (74 mg, 63% yield). $^1$H NMR (300 MHz, CD$_3$CN): δ=1.40-1.42 (m, 81H), 1.56-1.61 (m, 18H), 2.29-2.31 (m, 11H), 2.82-2.84 (m, 6H), 2.90 (br-s, 1H), 3.09-3.11 (m, 6H), 3.25-3.32 (m, 8H), 3.36-3.41 (m, 10H), 3.45-3.48 (m, 11H), 3.58 (br-s, 13H), 4.42-4.46 (m, 1H), 4.74-4.76 (m, 2H), 4.80-4.81 (m, 4H), 6.66-6.67 (m, 1H), 6.83-6.85 (m, 3H), 7.16-7.21 (m, 3H), 7.49-7.58 (m, 2H), 7.68-7.70 (m, 1H), 8.17-8.24 (m, 2H), 8.47-8.52 (m, 1H).

ESI$^+$-MS (m/z): calcd. for [M+3Na]$^{+3}$ 810.75, found 810.84 calcd. for [M+2Na]$^2$ 1204.63, found 1204.67.

Synthesis of Compounds 1-5. (FIGS. 5, 14)

TABLE 1

The sequences of the peptides used in this study.

| Compound | peptide | Peptide sequence |
| --- | --- | --- |
| C10, C15 | P1 | N$_3$-(CH$_2$)$_3$-I-L-S-G-CONH$_2$ |
| C11, C16 | P2 | N$_3$-(CH$_2$)$_3$-G-E-S-E-COOH |
| C12, C17 | P3 | N$_3$-(CH$_2$)$_3$-S-G-S-S-COOH |
| C13, C18 | P4 | N$_3$-(CH$_2$)$_3$-S-K-S-K-CONH$_2$ |
| C14, C19 | P5 | N$_3$-(CH$_2$)$_3$-I-L-K-S-I-K-CONH$_2$ |

TABLE 1A

SEQ ID Nos. of the peptides used in this study.

| Peptide sequence | SEQ ID No. |
| --- | --- |
| I-L-S-G | SEQ ID No. 22 |
| G-E-S-E | SEQ ID No. 23 |
| S-G-S-S | SEQ ID No. 24 |
| S-K-S-K | SEQ ID No. 25 |
| I-L-K-S-I-K | SEQ ID No. 26 |

Compound C10 (FIG. 5)

C9 (6.52 mg, 2.76 μmol) and P1 (Table 1, 8.25 mg, 16.5 μmol) were dissolved in 200 μL DMSO and 2 mL acetonitrile under argon. Then 2,6-lutidine (3.82 μL, 33 μmol), DIPEA (5.75 μL, 33 μmol), and CuI (1.84 mg, 9.65 μmol) were sequentially added under argon. The reaction mixture was stirred overnight. The solvents were removed and the residue was purified using RP-HPLC. Yield: 22.5%.

HRMS-ESI$^+$ (m/z) calcd. for [M+2Na]$^{+2}$, 1952.5753 found, 1952.5712, calcd. for [M+3Na]$^{+3}$, 1309.3800 found 1309.3784.

Compound C11 (FIG. 5)

C9 (5.18 mg, 2.19 μmol) and P2 (7 mg, 13.1 μmol) were dissolved in 100 μL DMSO under argon. Then 2,6-lutidine (3.07 μL, 26.3 μmol), DIPEA (4.58 μL, 26.3 μmol), and CuI (5 mg, 26.3 μmol) were sequentially added under argon. The reaction mixture was stirred overnight. The reaction was purified using RP-HPLC. Yield 23%. C11 was used directly for the next step.

Compound C12 (FIG. 5)

C9 (3.64 mg, 1.54 μmol) and P3 (4.14 mg, 9.255 μmol) were dissolved in 100 μL DMSO under argon. Then 2,6-lutidine (2.15 μL, 18.5 μmol), DIPEA (3.22 μL, 18.5 μmol), and CuI (3.52 mg, 18.5 μmol) were sequentially added under argon. The reaction mixture was stirred overnight. The reaction was purified using RP-HPLC. Yield 52.6%.

HRMS-ESI$^-$ (m/z) calcd. for [M−2H]$^{-2}$, 1851.8987 found 1851.8998, calcd. for [M−3H]$^{-3}$, 1234.2634, found 1234.2618.

Compound C13 (FIG. 5)

C9 (6.13 mg, 2.59 µmol) and P4 (8.7 mg, 15.6 µmol) were dissolved in 100 µL DMSO under argon. Then 2,6-lutidine (3.62 µL, 31.1 µmol), DIPEA (5.42 µL, 31.1 µmol), and CuI (5.93 mg, 31.1 µmol) were sequentially added under argon. The reaction mixture was stirred overnight. The reaction was purified using RP-HPLC. Yield 42%.

HRMS-ESI$^+$ (m/z) calcd. for $[M+3H]^{+3}$ 1347.4304, found 1347.4290, calcd. for $[M+4H]^{+4}$ 1010.8246, found 1010.8240, calcd. for $[M+5H]^{+5}$ 808.8611, found 808.8604.

Compound C14 (FIG. 5)

C9 (3.93 mg, 1.66 µmol) and P5 (8.1 mg, 9.98 µmol) were dissolved in 100 µL DMSO under argon. Then 2,6-lutidine (2.32 µL, 19.9 µmol), DIPEA (3.46 µL, 19.9 µmol), and CuI (3.79 mg, 19.9 µmol) were sequentially added under argon. The reaction mixture was stirred overnight. The reaction was purified using RP-HPLC. Yield 37%.

HRMS-ESI$^-$ (m/z) calcd. for $[M-3H]^{-3}$ 1597.6360, found 1597.6362

Compounds C15-C19 (FIG. 5)

Compounds C10-C14 were deprotected using 50% TFA in DCM (1 mL) for 6 h. The solvent and TFA were removed and the products were purified using RP-HPLC.

Compound C15: yield 40%, HRMS-ESI$^-$ (m/z) calcd. for $[M-3H+Na]^2$ 1686.7864, found 1686.7852, calcd. for $[M-3H]^{-3}$ 1116.8612, found 1116.8598.

Compound C16: yield 32%, HRMS-ESI$^-$ (m/z) calcd. for $[M-2H]^{-2}$ 1725.1470, found 1725.1455, calcd. for $[M-3H]^{-3}$ 1149.7623, found 1149.7610.

Compound C17: yield 290/%, HRMS-ESI$^-$ (m/z) calcd. for $[M-2H]^{-2}$ 1599.1153, found 1599.1142, calcd. for $[M-3H]^{-3}$ 1065.7411, found 1065.7411.

Compound C18: yield 38%, HRMS-ESI$^-$ (m/z) calcd. for $[M-2H]^{-2}$ 1766.3456, found 1766.3456, calcd. for $[M-3H]^3$ 1177.2280, found 1177.2273.

Compound C19: yield 64%, HRMS-ESI$^-$ (m/z) calcd. for $[M-3H]^{-3}$ 1429.4482, found 1429.4482.

General Procedure for Peptide Synthesis

Peptide 1 (P1, Table 1) was synthesized manually on Rink amide resin using standard solid phase Fmoc method. Coupling reactions were run on a 0.2-mmol scale. The coupling was carried out using a twofold excess of each amino acid (coupling for 1 hour), PyBOP/NMM as the coupling reagents, and 25% piperdine in NMP for Fmoc deprotection. 4-azidobutyric acid (1.2 equiv.) was coupled overnight using the HOAT/DIC (1.2 equiv.) coupling reagents.

Peptides 2 and 3 (P2 and P3, Table 1), synthesized on Wang resin were purchased from Synpeptide Co., Ltd. Shanghai, China.

Peptides 4 and 5 (P4 and P5, Table 1) were synthesized using an automated synthesizer (Advanced ChemTech, Apex 396) on Rink amide resin. The coupling was carried out using a sixfold excess of each amino acid (coupling for 2×45 min), HCTU/DIPEA as coupling reagents, and 25% piperdine in NMP for Fmoc deprotection. 4-azidobutyric acid (1.2 equiv.) was coupled overnight using HOAT/DIC (1.2 equiv.) coupling reagents. The peptides were cleaved from resin by TFA/H$_2$O/triisopropylsilane (95:2.5:2.5) for 2 h. The peptides were purified using preparative RP-HPLC on a C$_{18}$ column and characterized by electrospray mass spectrometry.

P1: ESI$^+$-MS (m/z): calcd. for $[M+H]^+$ 499.29, found 499.32, calcd. for $[M+Na]^+$ 521.28, found 521.26.

P2: ESI$^-$-MS (m/z): calcd. for $[M-H]^-$ 530.18, found 530.20.

P3: ESI$^-$-MS (m/z): calcd. for $[M-H]^-$ 446.16, found 446.13.

P4: ESI$^+$-MS (m/z): calcd. for $[M+H]^+$ 559.33, found 559.43 calcd. for $[M+Na]^+$ 581.31, found 581.36.

P5: ESI$^+$-MS (m/z): calcd. for $[M+H]^+$ 811.55, found 811.60.

Compounds 1-5 (FIG. 5).

An aqueous solution of NiCl$_2$ (final concentration, 79.2 µM) was added to a solution of compounds 1-5 (12 µM) in PBS buffer (4.1 mM, pH=7.3) and incubated for either 30 minutes or overnight.

Example 2

Synthetic Routes for Preparing Universal His-Tag Binding Compounds (Compound 10u) (FIGS. 6-10)

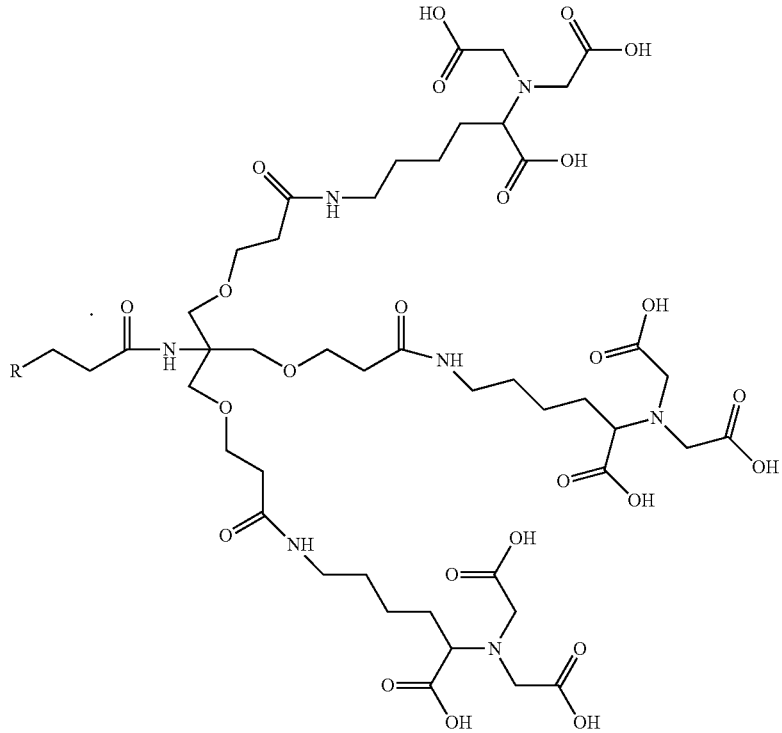

10u

The synthesis of 10u begins with N-alkylation of N-benzyloxycarbonyl-L-lysine tert-butyl ester (1u) with tert-butyl bromoacetate (2u), followed by benzyl deprotection to obtain an amino-modified NTA (C2), according to a literature procedure. A tripodal precursor molecule (9u) was also synthesized according to a reported procedure by 1,4-addition of 2-amino-2-hydroxymethyl-propane-1,3-diol (5u) to tert-butyl acrylate (6u), followed by coupling to a modified carboxylic acid (8u) and TFA deprotection. The final product (10u), whose complex with Nickel (II) can tightly bind His-tags, was obtained by coupling 9u to C2 using EDC and deprotecting the t-butyl groups by TFA.

Figure 7:
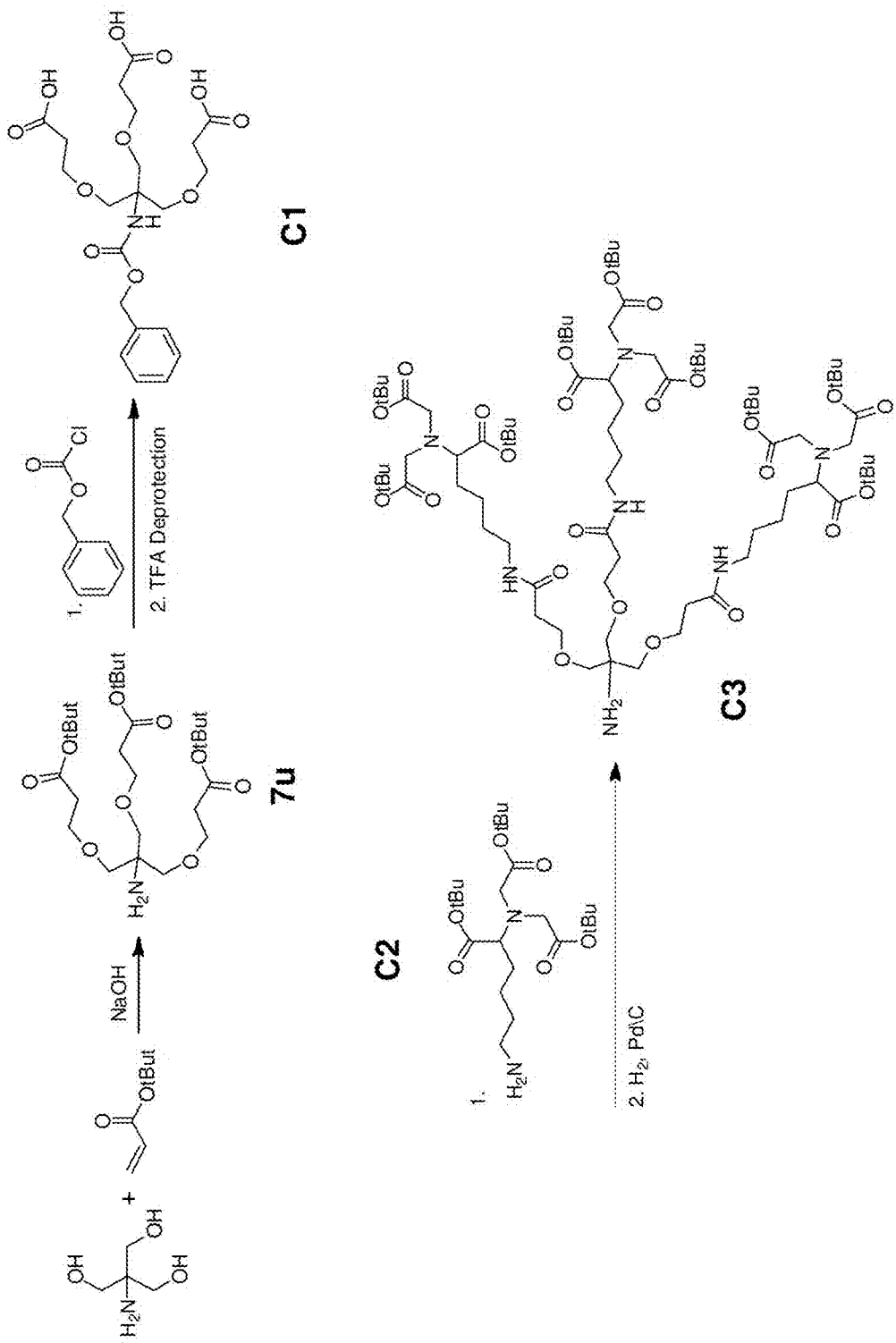
FIG. 7 depicts a synthetic scheme for preparing compound C3.

In order to afford an amine-modified and t-Bu-protected tri-NTA (C3), compound 7u can also be protected by Benzyl chloroformate followed by coupling to C2 and benzyl deprotection to afford compound C3 (FIG. 7).

Figure 8:
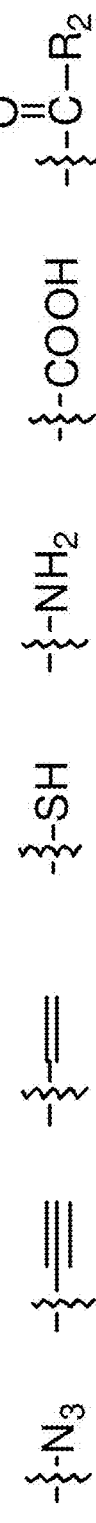
FIG. 8 depicts examples of various possible R groups for compound 8u [R(CH$_2$)$_x$COOH].
Figure 8:
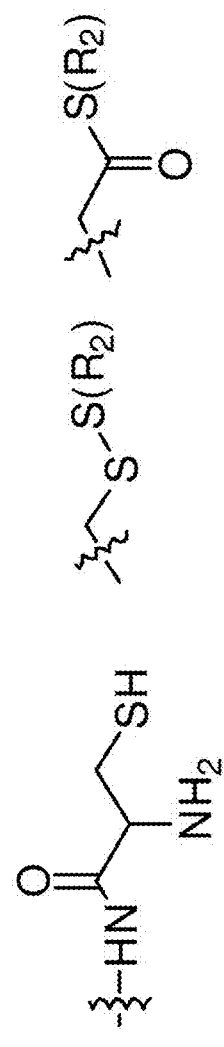
Figure 8:
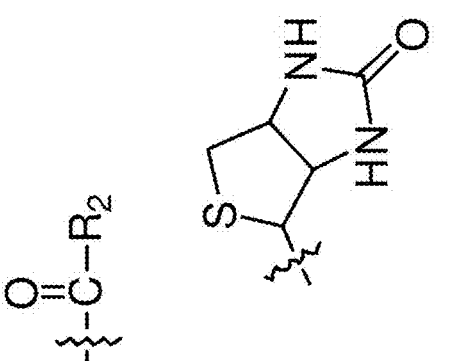
Figure 8:
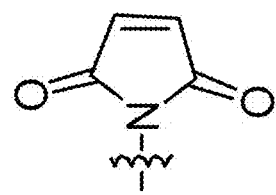

The modified carboxylic acid of compound 8u (FIG. 6) can be any R(CH$_2$)x COOH, where x represents the number of carbons and the R groups can consist of various functionalities, such as an azide, alkyne, thioester, disulfide, maleimide, and biotin (FIG. 8).

Figure 9:
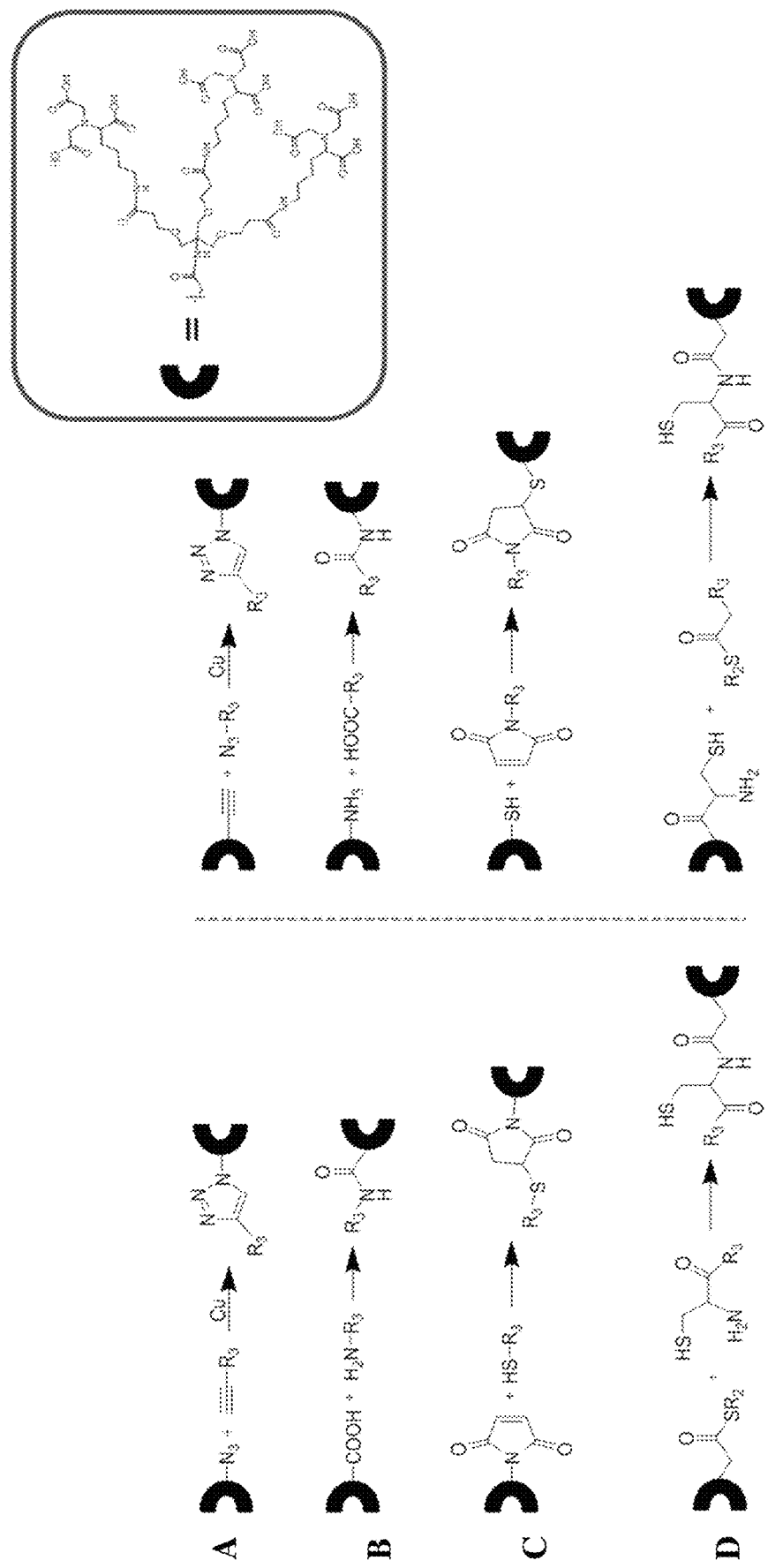
FIG. 9 depicts examples of different reactions that can be utilized to modify the His-tag binding compounds of the invention (the insert shows a specific His-tag binder) for a variety of linkers and compounds.

These functionalities, as well as various other functionalities, can be used to attach compound 10u (FIG. 6, and the insert in FIG. 9), as well as its t-Bu-protected precursor or compound C3 (FIG. 7) to a variety of compounds using the click reaction (FIG. 9A), carboxylic acid-amine coupling (FIG. 9B), thiol-malemide coupling (FIG. 9C), or native chemical ligation (FIG. 9D).

FIG. 10 shows specific examples of how modified tri-NTA compounds can be attached to DNA, small molecules, and peptides.

Figure 39:
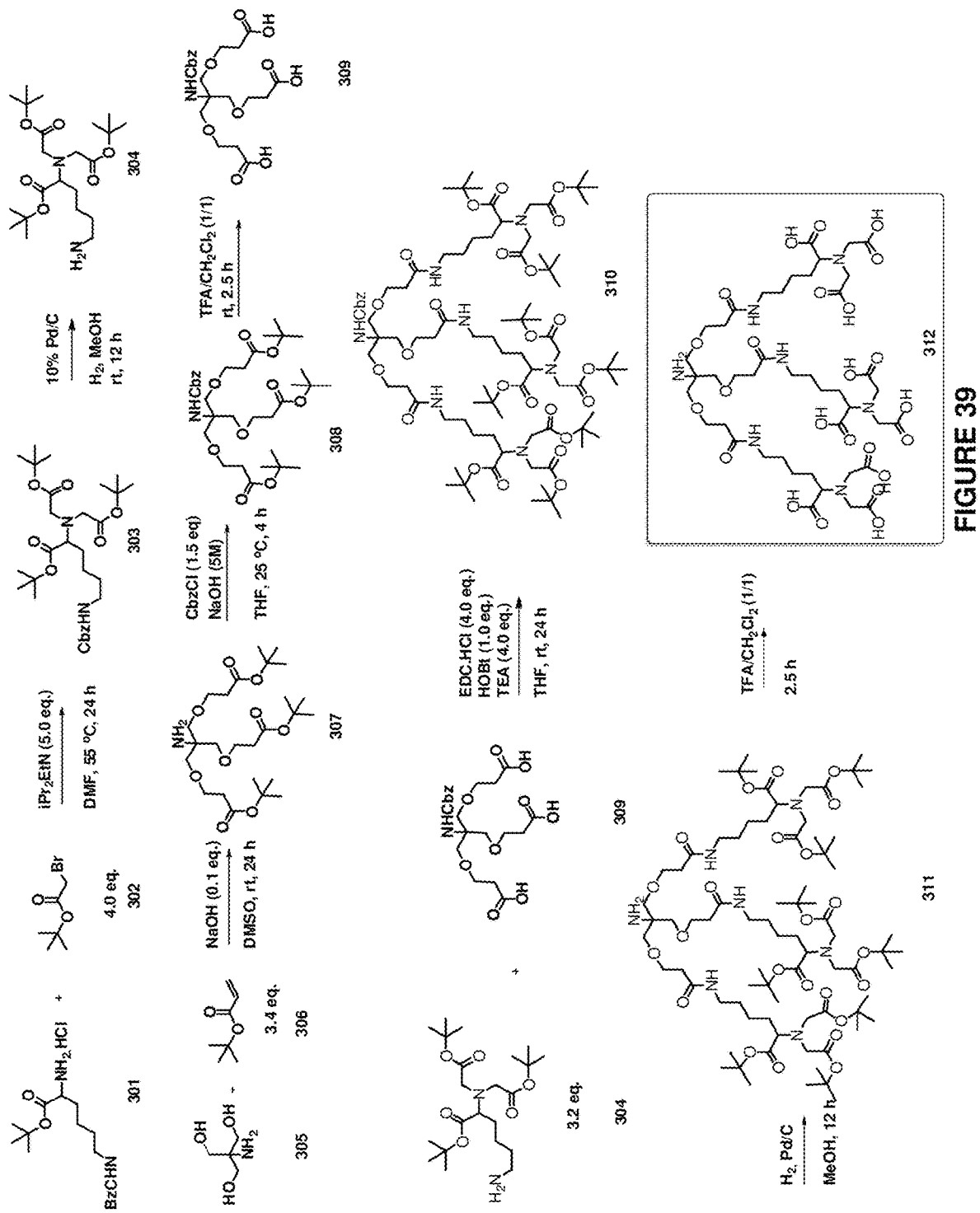
FIG. 39 shows the synthesis of a His-tag binding compound according to this invention.

Example 13 below, and FIGS. 39 and 40 describe alternative synthetic routes for the preparation of His-tag binding compounds (Compound 312, 313, 314, 315) and precursors (Compound 311) according to this invention.

Example 3

Figure 12:
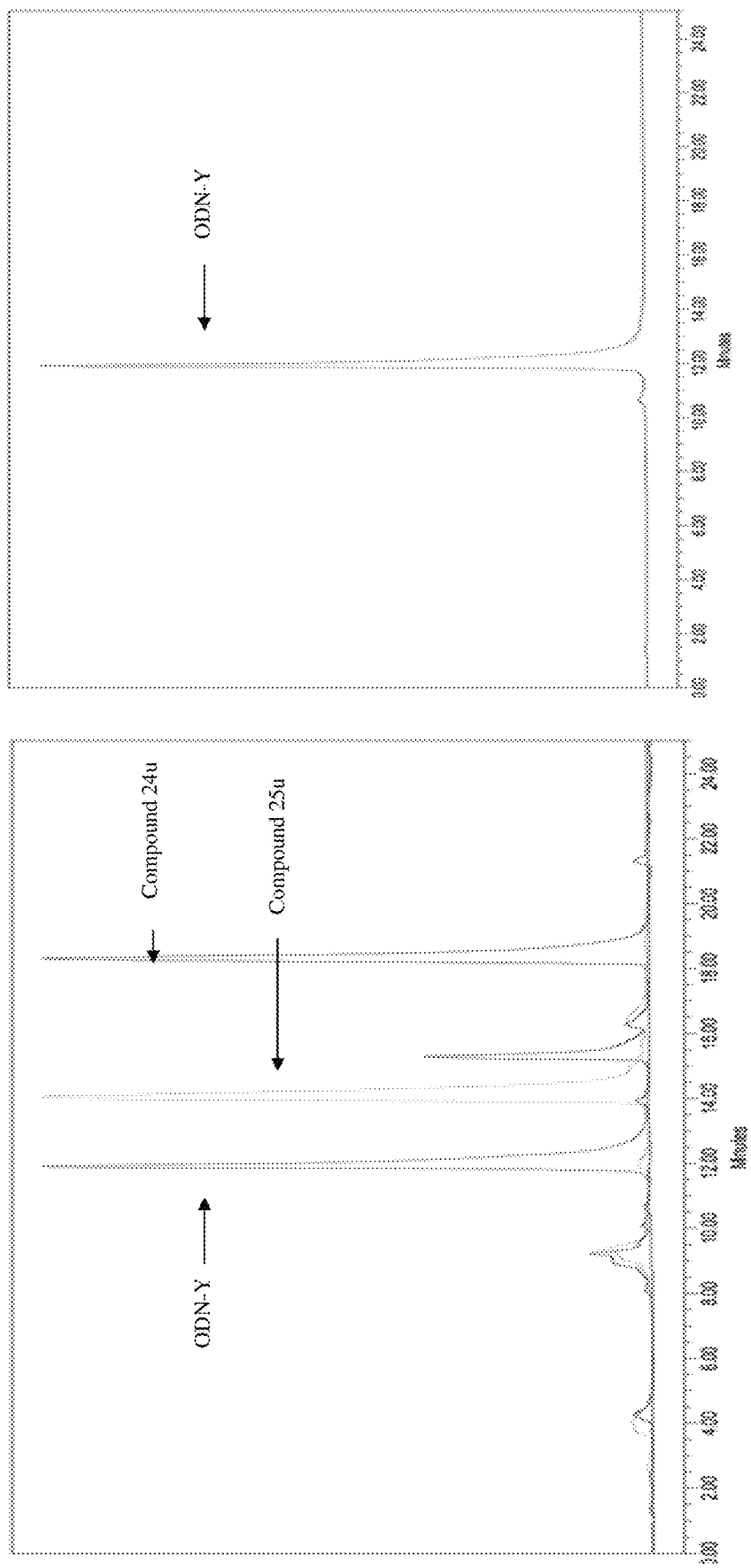
FIG. 12 depicts HPLC chromatogram of the reaction mixture (left) for preparing ODN-Y and of the pure product (ODN-Y, right).

Synthetic Procedures, Characterization, and Binding Studies of ODN Bound His-Tag Binders of the Invention An oligonucleotide (ODN) modified with a tri NTA group (FIG. 11, ODN-Y) was prepared by reducing a dithiol-modified ODN (24u) with DTT and reacting the resulting product (25u) with 10u via Michael addition. ODN-Y was purified using HPLC (FIG. 12) and characterized by MALDI-TOFF. Compound 10u was prepared according to the scheme presented in FIG. 6, where compound 8u is a Maleimidopropionic acid.

The synthesis procedures and the $^1$H-NMR and MS characterization of the various products are described below:

di-tert-butyl-2,2'-((6-(((benzyloxy)carbonyl)amino)-1-(tert-butoxy)-1-oxohexan-2-yl)azanediyl)diacetate (C1)

t-butyl bromo acetate (2.39 ml, 16 mmol) and DIPEA (3.5 ml, 20 mmol) were added to a solution of N-benzyloxycarbonyl-L-lysine tert-butyl ester (1.5 g, 4.02 mmol) in 25 ml DMF. The reaction was purged with argon and then heated to 55° C. and stirred overnight. The excess solvent was removed under high vacuum and 15 ml hexane:ethyl acetate 3:1 was added to the solidified mixture. The mixture was filtered over sinter glass and washed with the same solvent (3×10 ml). The filtrate was concentrated under reduced pressure and the residue was purified by column chromatography (80:20 hexane/EtOAc) to yield the purified product (2.2 g, 97% yield).

$^1$H NMR (CDCl$_3$, 300 MHz): δ 1.44 (s, 18H); 1.47 (s, 9H); 1.50 (m, 2H); 1.54 (m, 2H); 1.65 (m, 2H); 3.21 (m, 2H); 3.31 (t, J=6 Hz, 1H); 3.46 (dd, 4H); 5.09 (s, 2H); 7.33 (s, 5H).

ES-MS (m/z): Calcd: 564.34; Found: 587.32 (M+Na).

di-tert-butyl 2,2'-((6-amino-1-(tert-butoxy))-1-oxo-hexan-2-yl)azanediyl)diacetate (C2)

C1 (2.2 g, 3.92 mmol) was dissolved in 50 ml MeOH and purged with argon. 10% Pd/C (44 mg) was added and the reaction was stirred vigorously overnight under H$_2$. The mixture was filtered over colite and the solvents from the filtrate were removed under reduced pressure. Yield: 1.6 g, (3.8 mmol), 96%.

$^1$H NMR (CDCl$_3$, 300 MHz): δ 1.44 (s, 27H); 1.65 (m, 4H); 1.81 (m, 2H); 2.99 (t, J=9 Hz, 2H); 3.31 (t, J=6 Hz, 1H); 3.43 (dd, 4H).

ES-MS (m/z): Calcd: 430.3; Found: 431.35 (MH+), 453.42 (M+Na).

di-tert-butyl 3,3'-((2-amino-2-((3-(tert-butoxy)-3-oxopropoxy)methyl)propane-1,3-diyl)bis(oxy)) dipropanoate (7u)

2-Amino-2-hydroxy ethyl-propane-1,3-diol (1.21 g, 10.0 mmol) was dissolved in 2.0 mL of DMSO and cooled to 15° C. under argon. Then, 0.2 mL 5.0 M NaOH was injected, followed by dropwise addition of tert-butyl acrylate (5.0 mL, 34 mmol). The reaction mixture was brought to room temperature and stirred overnight. The excess regents and solvents were removed under high vacuum and the residue was purified by column chromatography (70:30 EtOAc/hexane+0.05% v/v NH$_4$OH) to yield colorless oil (1.01 g, 20% yield).

$^1$H NMR (CDCl$_3$, 300 MHz): δ 1.44 (s, 27H); 2.46 (t, J=6.0 Hz, 6H); 3.39 (s, 6H); 3.66 (t, J=6 Hz, 6H).

ES-MS (m/z): Calcd: 505.33; Found: 506.36 (MH+), 528.36 (M+Na).

di-tert-butyl 3,3'-((2-((3-(tert-butoxy)-3-oxo-propoxy)methyl)-2-(3-(2,5-dioxo-2, S5-dihydro-1H-pyrrol-1-yl)propanamido)propane-1,3-diyl)bis(oxy)) dipropanoate (intermediate product, 9u Wherein R is Maleimide)

600 mg (1.18 mmol) of 7u was dissolved in 30 ml dry DCM under argon and cooled to 0° C. in an ice bath. Thereafter, EDC (339 mg, 1.7 mmol, 1.5 eq) and DIPEA (413.7 µL, 2.32 mmol, 2 eq) were added and the reaction mixture was stirred for 30 min. 3-Maleimidopropionic acid (240.1 mg, 1.4 mmol, 1.2 eq) was added, and the solution was stirred overnight. Then 40 mL DCM was added and the solution was washed with water (10 mL) and brine (10 mL). The organic layer was dried with Na$_2$SO$_4$, filtered, and concentrated at high vacuum. Finally, the crude product was purified by column chromatography (97:3 DCM/MeOH) to yield a yellow oil (501.6 mg, 64%).

$^1$H NMR (CDCl$_3$, 300 MHz): δ 1.44 (s, 27H); 2.44 (t, J=6 Hz, 6H); 2.51 (t, J=6 Hz, 2H); 3.63 (t, J=6 Hz, 6H); 3.67 (s, 6H); 3.80 (t, J=6 Hz, 6H); 6.69 (s, 2H). ES-MS (m/z): Calcd: 656.35; Found: 657.44 (MH+), 679.31 (M+Na).

3,3'-((2-((2-carboxyethoxy)methyl)-2-(3-(2,5-dioxo-2, S-dihydro-1H-pyrrol-1-yl)propanamido)propane-1,3-diyl)bis(oxy))dipropanoic Acid (9u)

Deprotection of the tert-butyl group was done with 50% trifluoroacetic acid in DCM (v/v) for 2.5 h. The product was washed repeatedly with DCM and then dried under high vacuum.

¹H NMR (D₂O, 300 MHz): 2.47 (t, J=6 Hz, 2H); 2.59 (t, J=6 Hz, 6H); 3.61 (s, 6H); 3.67-3.75 (m, 8H); 6.83 (s, 2H).

ES-MS (m/z): Calcd: 488.16; Found: 489.18 (MH+), 511.12 (M+Na) 977.03 (2 M+H) 999.15 (2 M+Na).

Tert-Butyl Protected Tri-NTA (Intermediate Product).

A solution of compound 9u (160 mg, 304.8 µmol) in 10 ml dry DCM was cooled to 0° C. in an ice bath and DIPEA (212 µL, 1.2 mmol, 4 eq), EDC (191 mg, 1 mmol, 3.3 eq), and HOBt (41 mg, 304.8 µmol, leg) were added consecutively. After 15 min, compound C2 (433 mg, 1 mmol, 3.3 eq) was added and the reaction was stirred overnight. Then 40 mL DCM was added and the solution was washed with water (10 mL). The organic layer was dried with Na₂SO₄, filtered, and concentrated at high vacuum. Finally, the crude product was purified by column chromatography (96:4 DCM/MeOH) to yield a colorless oil (96.6 mg, 18.3%).

¹H NMR (MeOD, 300 MHz): δ 1.50 (s, 54H); 1.55 (s, 27H); 1.71 (m, 18H); 2.42 (t, 6H); 2.49 (m, 2H); 3.20 (t, 6H); 3.31 (m, 12H); 3.55-3.74 (m, 17H); 6.84 (s, 2H).

ES-MS (m/z): Calcd: 656.35; Found: 657.44 (MH+), 679.31 (M+Na).

Maleimide-modified tri-NTA (10u)

Deprotection of the tri-NTA t-butly groups was done with 50% trifluoroacetic acid in DCM (v/v) for 2.5 h. The product was washed repeatedly with DCM and then dried under high vacuum.

¹H NMR (MeOD, 300 MHz): δ 1.47 (m, 6H): 1.53 (m, 6H); 1.91 (m, 6H); 2.43 (m, 8H); 3.17 (m, 6H); 3.58-3.65 (m, 15H); 4.1 (m, 14H); 6.82 (s, 2H). ES-MS (m/z): Calcd: 1220.48; Found: 1221.53 (MH+), 1243.39 (M+Na).

Following the successful preparation of 10u, a His-tag binding strand (ODN-Y, FIG. 11) was also prepared by reducing a dithiol-modified ODN (24u) with DTT and reacting the resulting product (25u) with 10u via Michael addition. ODN-Y was purified using HPLC (FIG. 12) and characterized by MALDI-TOFF.

Example 4

Determination of the Dissociation Constant for the His-Tag-ODN-Y Interaction

Figure 13:
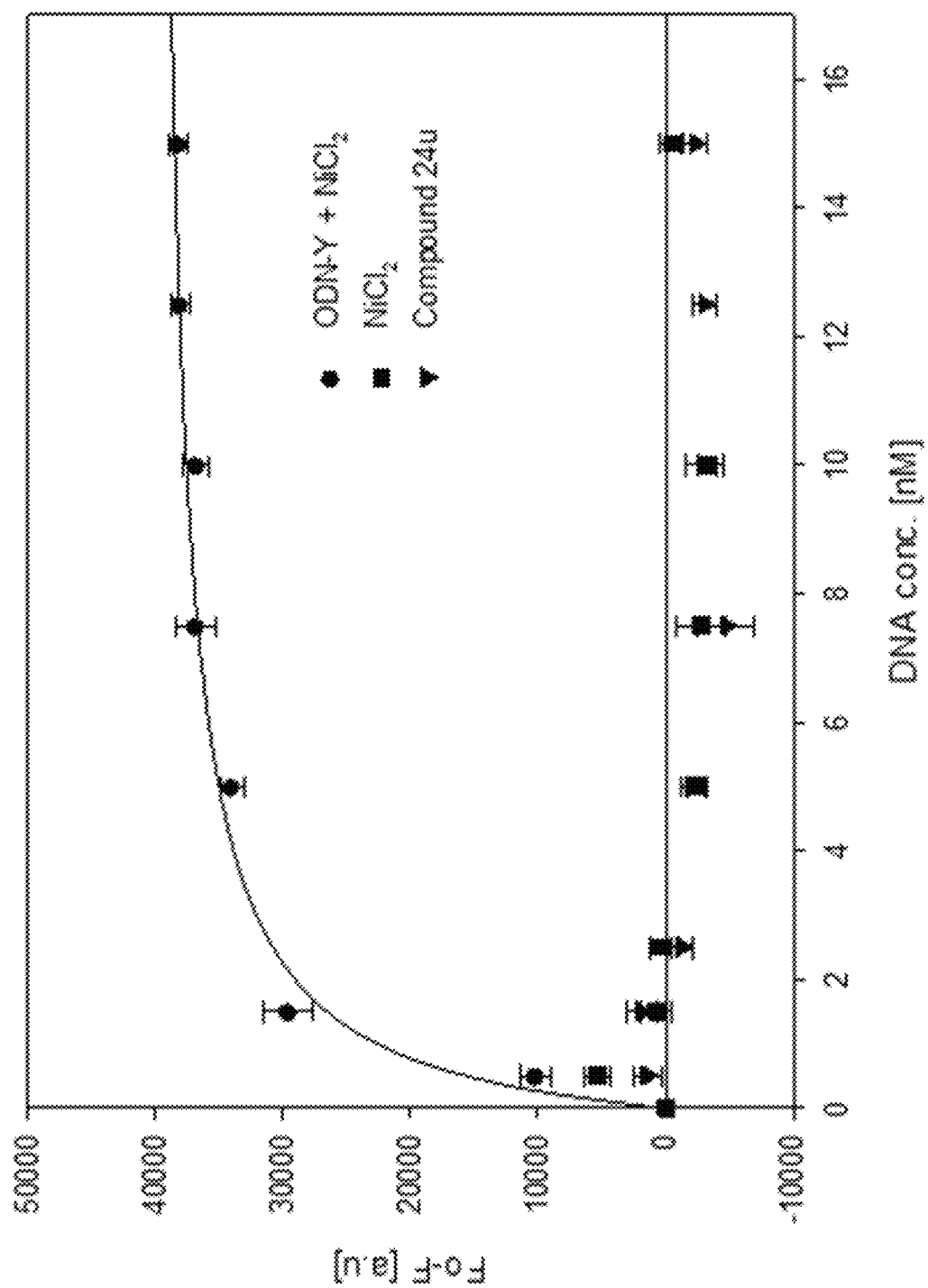
FIG. 13 depicts His-tag compound binding assay. Changes in the fluorescence of a fluorescein-labeled His-tag peptide (5 nM) upon the addition of increasing concentrations of ODN—Y—Ni(II) in PBS. Compound 24u (FIG. 11) and $NiCl_2$ were tested as negative controls.

ODN Y was incubated with nickel chloride and the binding of the resulting complex to His-tag was confirmed by following the decrease in the emission signal of a fluorescein-labeled His6 peptide upon incremental addition of ODN—Y—Ni⁻² (FIG. 13). The dissociation constant ($K_d$) was determined by subtracting the fluorescence signal of the complex from the signal of the His6 peptide alone. The binding curve fitting and $K_d$ calculation were done using SigmaPlot software. The Kd value was found to be 3.2±0.4 nM.

Example 5

Binding Measurements of Sensors of the Invention to His-Tagged Protein

His-tagged calmodulin (His-CaM) (FIG. 2, state a) was selected as the first protein of interest (POI) for testing this approach because, upon binding to Ca² ions, this calcium-binding protein exposes a large hydrophobic cleft that can potentially accommodate a complementary synthetic receptor (FIG. 2, state b). In addition, this hydrophobic patch is involved in various binding interactions, which should enable testing the suitability of the technique for identifying binding partners (FIG. 2, state c).

Five compounds were prepared, which share the same His-tag binder and fluorophore, but differ in their appended receptors (FIG. 14). Compound 1, which possesses a hydrophobic receptor, was designed to interact with the hydrophobic surface of His-CaM($Ca^{+2}$) (FIG. 2, State b). In contrast, the other compounds, which possess negatively charged (2), polar (3), positively charged (4), as well as positively charged and hydrophobic (5) receptors were designed to serve as control compounds, which would not respond to changes in the surface of His-CaM.

In principle, compounds 2-5 could also be used to sense changes in the surfaces of other His-tag-labeled proteins. In all compounds (1-5), complexation of tri-nitrilotriacetic acid (tri-NTA) ligand (I) with nickel ions forms the His tag binder, which is connected via a tri-ethylene glycol spacer to a tripodal peptide (II) and a dansyl group (III), which serve as a protein surface receptor, and a solvatochromic probe, respectively.

Figure 15:
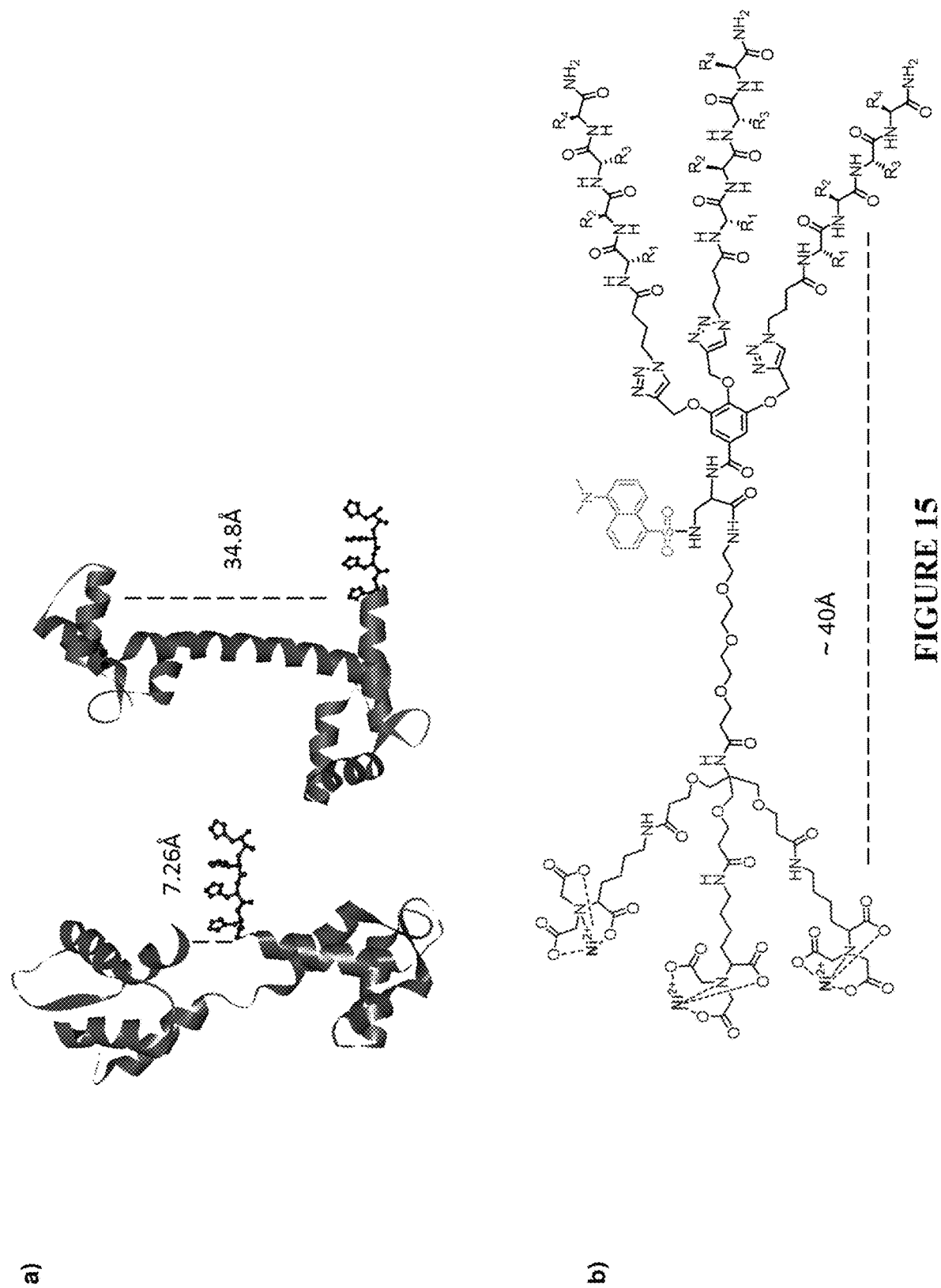
FIG. 15 depicts (a) Visualization of CaM in the calcium-free (left panel) and calcium-bound (right panel) conformations, showing the distance between the N' and C' termini. The proteins' images were generated with Discovery Studio Visualizer 2.5, which was also used to calculate the distance. (b) Approximate length of the sensor 1.

A modeling program showed that the length of the spacer is sufficient to bind various locations of CaM's surface and, in particular, to allow simultaneous binding of the sensor to both the His-tag and the hydrophobic patch on His-CaM ($Ca^{+2}$) (FIG. 15).

Prior to measuring the sensor's performance, it was confirmed that 1 can bind to His-CaM in each of its states, namely, before (FIG. 2a) and after the subsequent binding to $Ca^{2+}$ (FIG. 2b) and binding partners (FIG. 2c). Fluorescence binding studies were performed first, to confirm that 1 can bind His-tag with nanomolar affinity ($K_d$ (approx)=157 nM±21, FIG. 17), akin to other multivalent NTA ligands.

Figure 16:
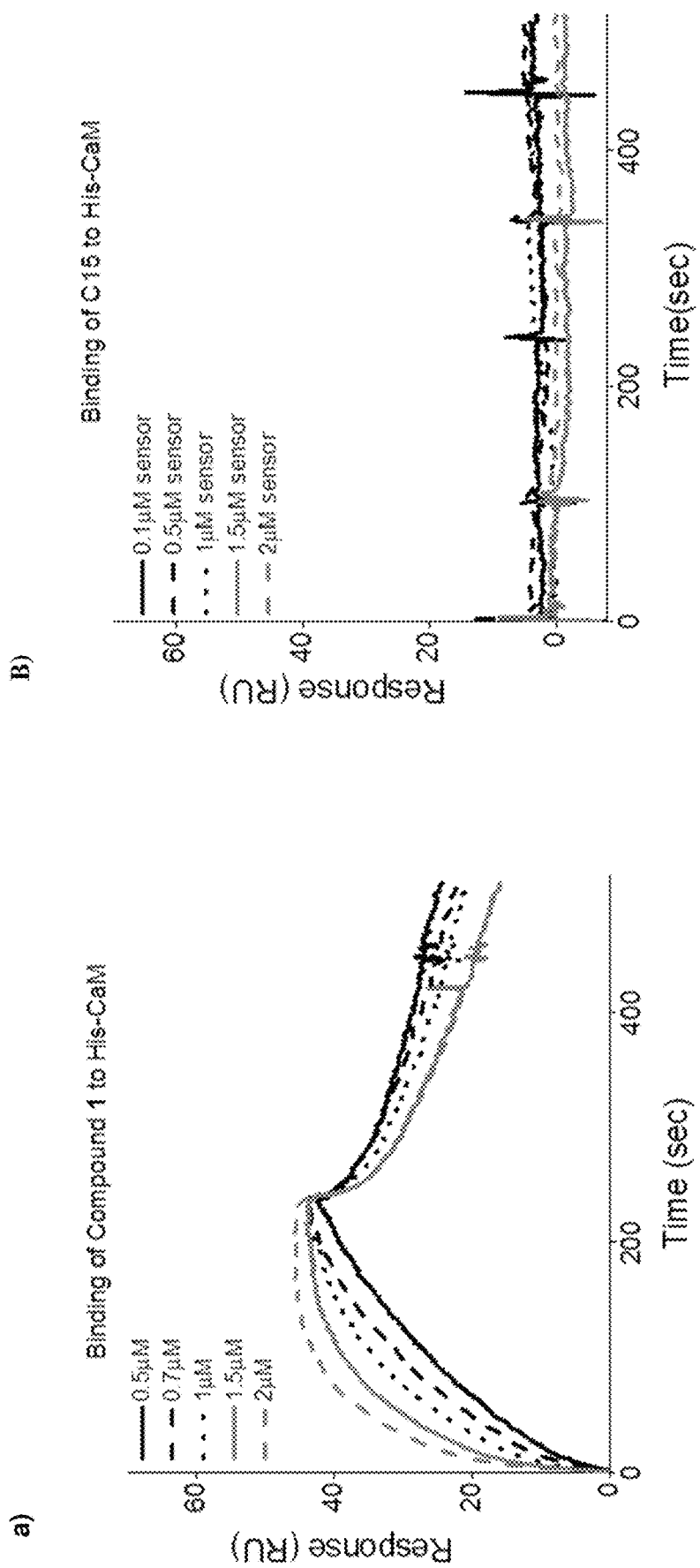
FIG. 16 depicts SPR sensorgrams recorded for the (a) 1-His-CaM and (b) C15-His-CaM interactions.
Figure 18:
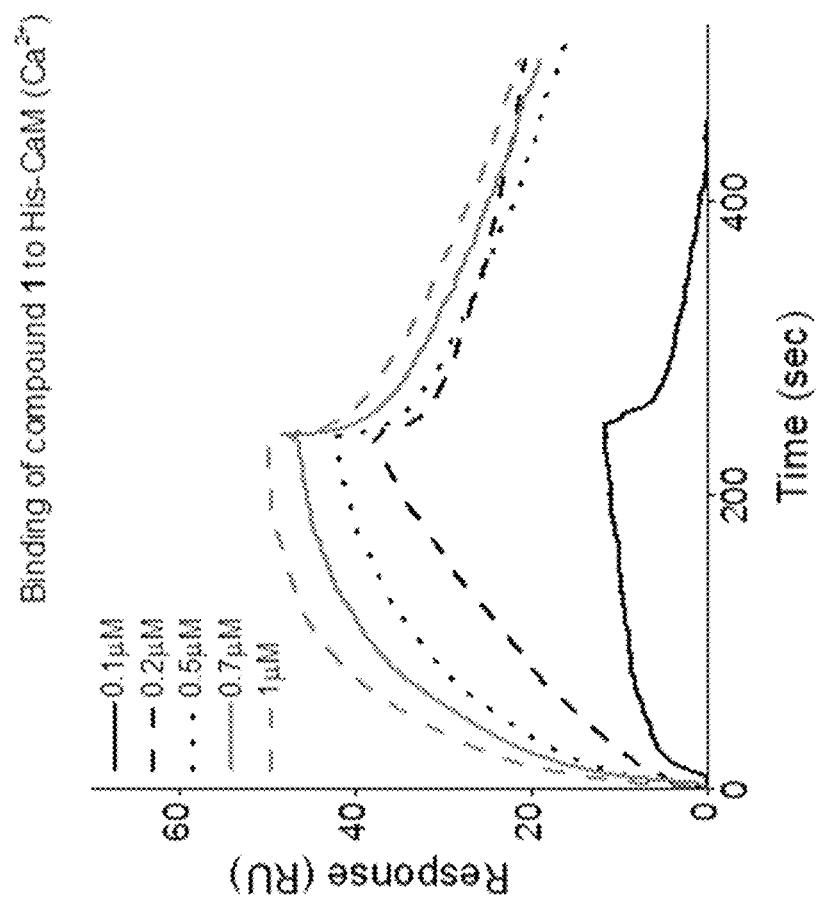
FIG. 18 depicts SPR sensorgrams recorded for the 1-His-CaM($Ca^{2+}$) interaction.
Figure 19:
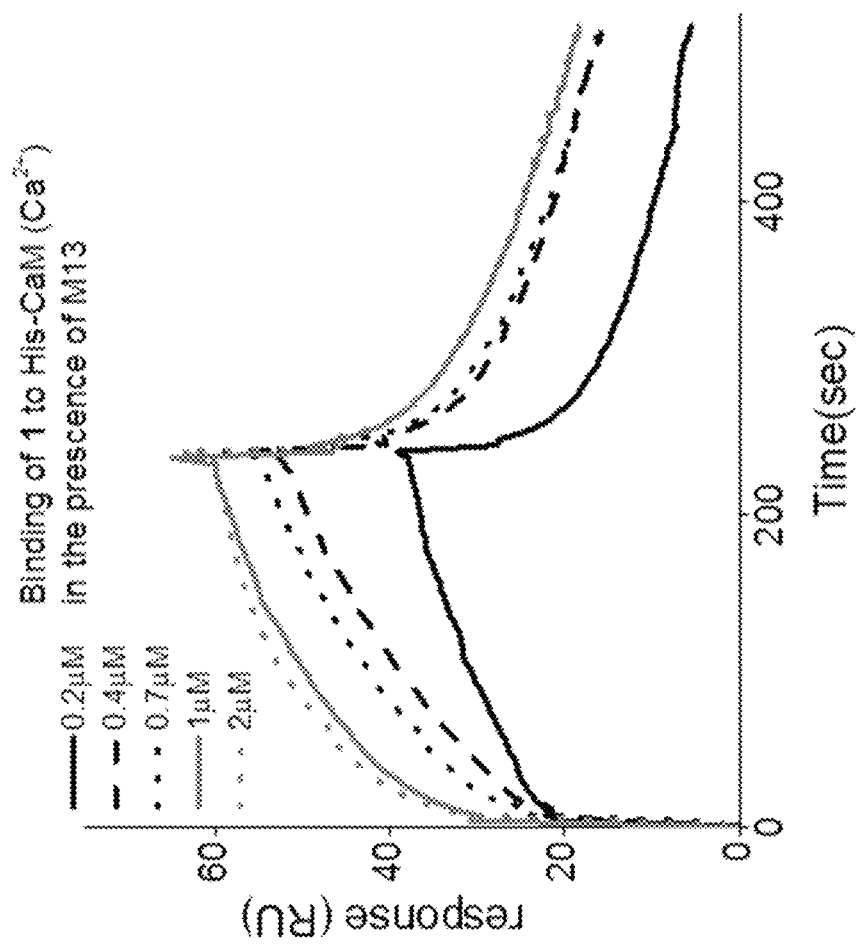
FIG. 19 depicts SPR sensorgrams recorded for the 1-His-CaM($Ca^{2+}$) interaction in the presence of excess M13.

In the next step, surface plasmon resonance (SPR) measurements were performed (FIG. 16) to ensure that 1 also binds His-CaM ($K_d$ (approx)=176 nM, FIG. 16, left panel) and His-CaM($Ca^{2+}$) ($K_d$ (approx)=134 nM, FIG. 18) with similar affinities. SPR also showed 1 also binds His-CaM ($Ca^{2+}$) in the presence of excess of known binding partner M13 (FIG. 19), which bind to His-CaM($Ca^{2+}$) with low nanomolar affinity. Similar measurements performed in the absence of nickel ions confirmed that apo 1 does not interact with His-CaM (FIG. 16, left panel) indicating the weak affinity of the tripodal receptor toward the surface of His-CaM. Taken together (FIGS. 16 and 18, 19, and Table 2) the SPR studies show that possible interactions between tripodal receptor of 1 and the CaM's surface (FIG. 2, state b) could only be induced by the strong interactions between the tri-NTA-Ni²⁺ complex and the His tag of CaM.

TABLE 2

Summary of dissociation constants that were obtained using SPR experiments.

| Entry | Analyte | Dissociation constant (µM) |
|---|---|---|
| 1 | 1-His CaM | 176 |
| 2 | 1-His CaM ($Ca^{2+}$) | 134 |
| 3 | 1-His CaM ($Ca^{2+}$)-M13 | 231 |
| 4 | 1-His CaM ($Ca^{2+}$)-Mastoparan | 244 |
| 5 | C15- His CaM | — |
| 6 | M13-His CaM ($Ca^{2+}$) | 0.0088 |
| 7 | Mastoparan- His CaM ($Ca^{2+}$) | 0.0012 |

Example 6

Fluorescence Measurements: Sensing Protein Surface Changes with Compounds 1-5

The ability of sensor 1 (200 nM) to detect the $Ca^{+2}$-induced conformational change of His-CaM was tested (FIG. 20a), by following the change in the emission upon the sequential addition of 1) His-CaM (200 nM), 2) CaCl₂ (0.3 mM), and 3) EGTA (1.2 mM). As expected from the design, a strong enhancement in dansyl's emission was observed only when calcium ions were added to the solution and this fluorescence was immediately decreased upon the addition of EGTA. Similar fluorescence responses were observed with higher concentrations of sensor and protein, however, the concentrations, which were used in these measurements, were selected after screening for various different conditions (FIG. 21) and selecting the minimal concentrations (200 nM) that can provide strong and reproducible emission signals.

Figure 20:
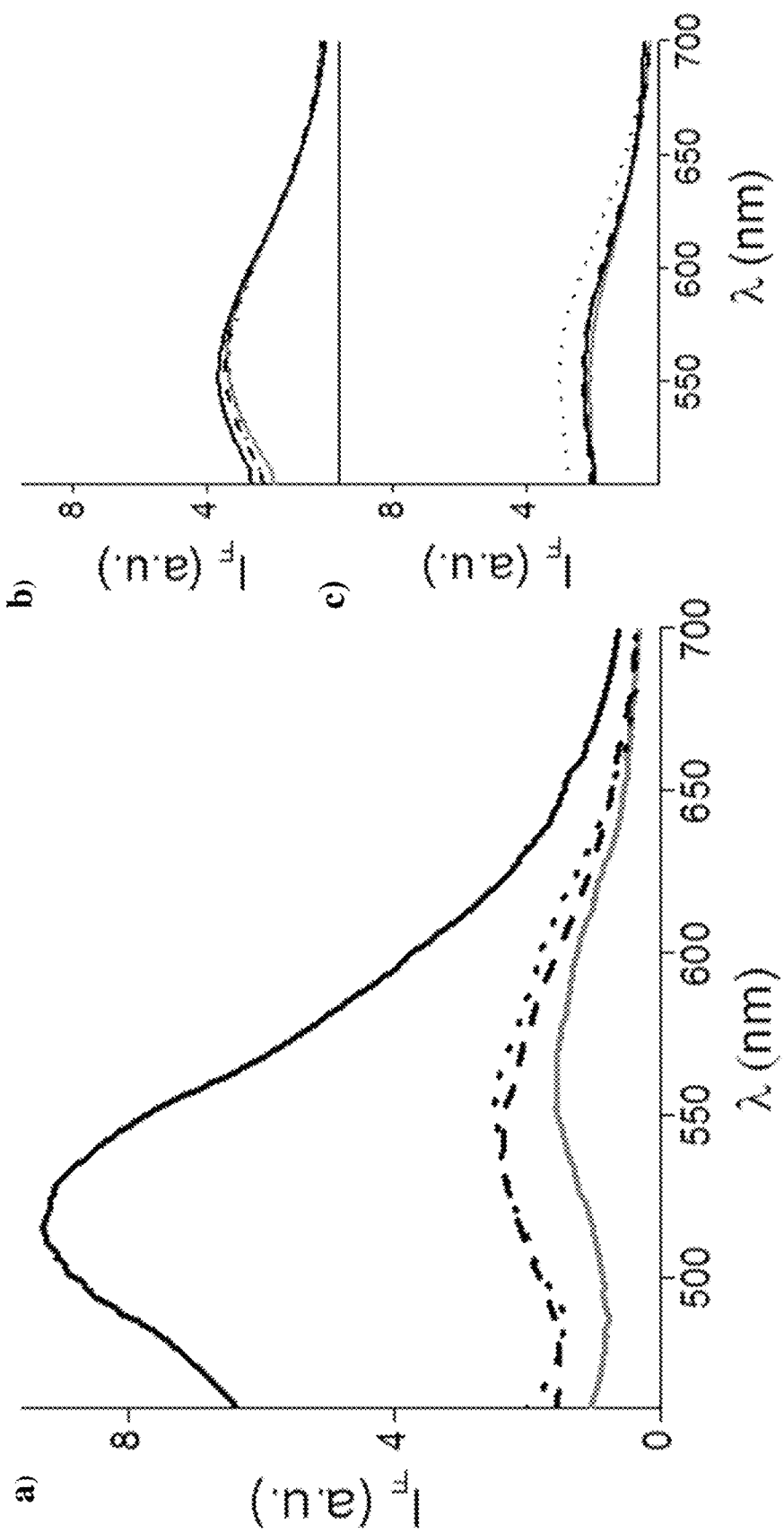
FIG. 20 depicts (a) Fluorescence spectra of 1 (200 nM) before (solid grey line) and after the sequential addition of 200 nM His-CaM (dashed line), 0.3 mM $CaCl_2$) (solid black line), and 1.2 mM EGTA (dotted line). (b) A similar experiment performed in the absence of $Ni^{+2}$ ions. (c) A similar experiment performed with CaM lacking a His-tag. Excitation: 330 nm.
Figure 22:
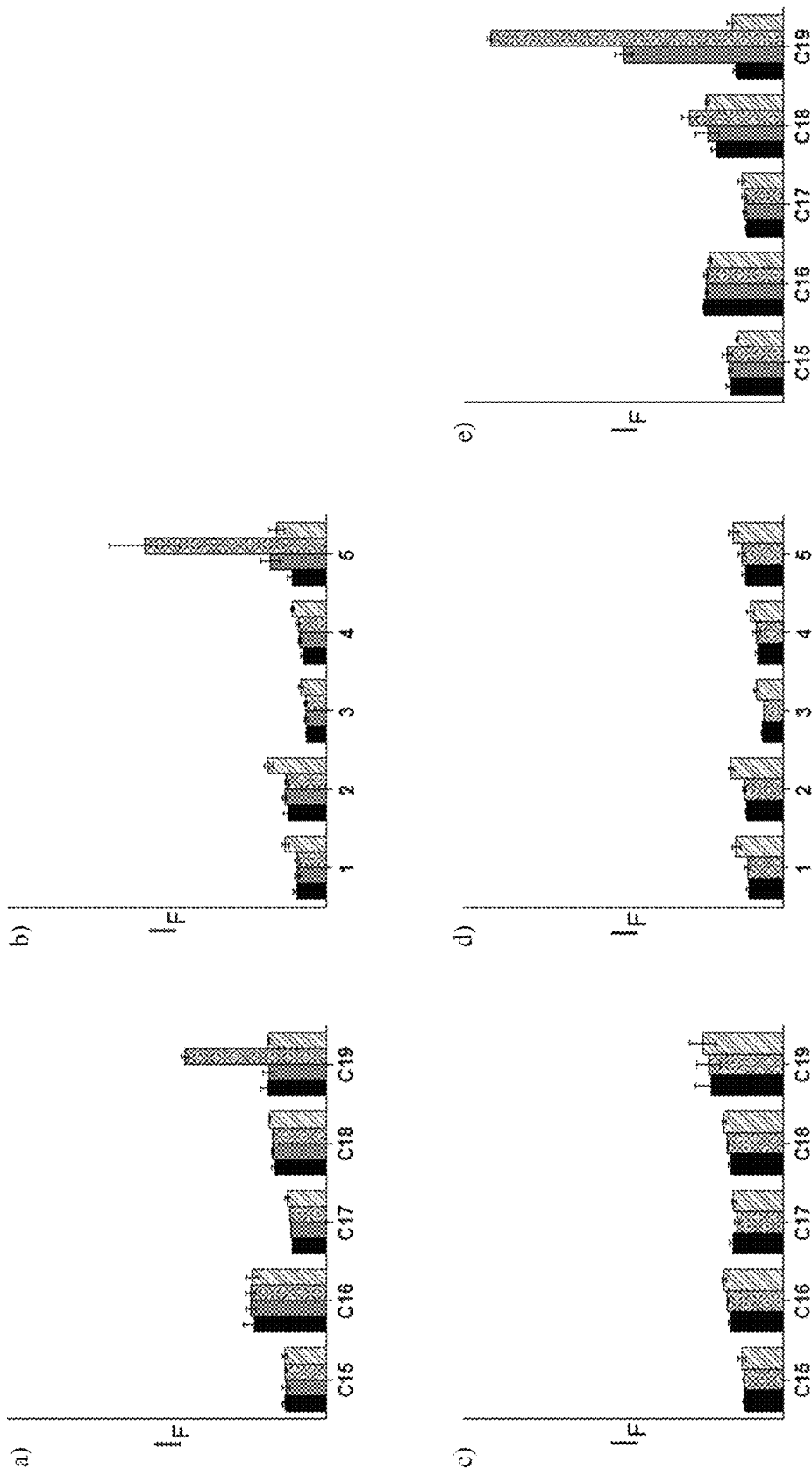
FIG. 22 depicts the fluorescence response of (a) (■) compounds C15-C19 (200 nM) and (b) (■) compounds 1-5 (200 nM) to the sequential addition of (※) CaM (200 nM), (▨) $Ca^{2+}$ (0.3 mM), and (▨) EGTA (1.2 mM). (c) Fluorescence response of (■) compounds C15-C19 (200 nM) and (d) (■) compounds 1-5 to the sequential addition of (※) $Ca^{2+}$ (0.3 mM) and (▨) EGTA (1.2 mM) (e) Fluorescence response of (■) compounds C15-C19 (200 nM) to the sequential addition of (※) His-CaM (200 nM), (▨) $Ca^{2+}$ (0.3 mM), and (▨) EGTA (1.2 mM).

To further confirm that the fluorescence enhancement did not result from non-specific interactions between His-CaM ($Ca^{+2}$) and the tripodal receptor, or from the presence of excess of calcium ions in the medium, several control experiments were performed (FIGS. 20 and 22). For example, no change in the emission signal was observed when the experiment was repeated in the absence of nickel ions (FIG. 20b), or with CaM that lacks the His-tag (FIG. 20c). Similarly, sensor 1 did not respond to the addition of $Ca^{+2}$ only (FIG. 22). Taken together with the SPR measurements (FIG. 16, right panel), these control experiments confirm the proposed sensing mechanism, in which the simultaneous binding of sensor 1 to both the His-tag and the hydrophobic surface of His-CaM($Ca^{+2}$) (FIG. 2, state b) is crucial for obtaining the observed effect.

Example 7

Figure 23:
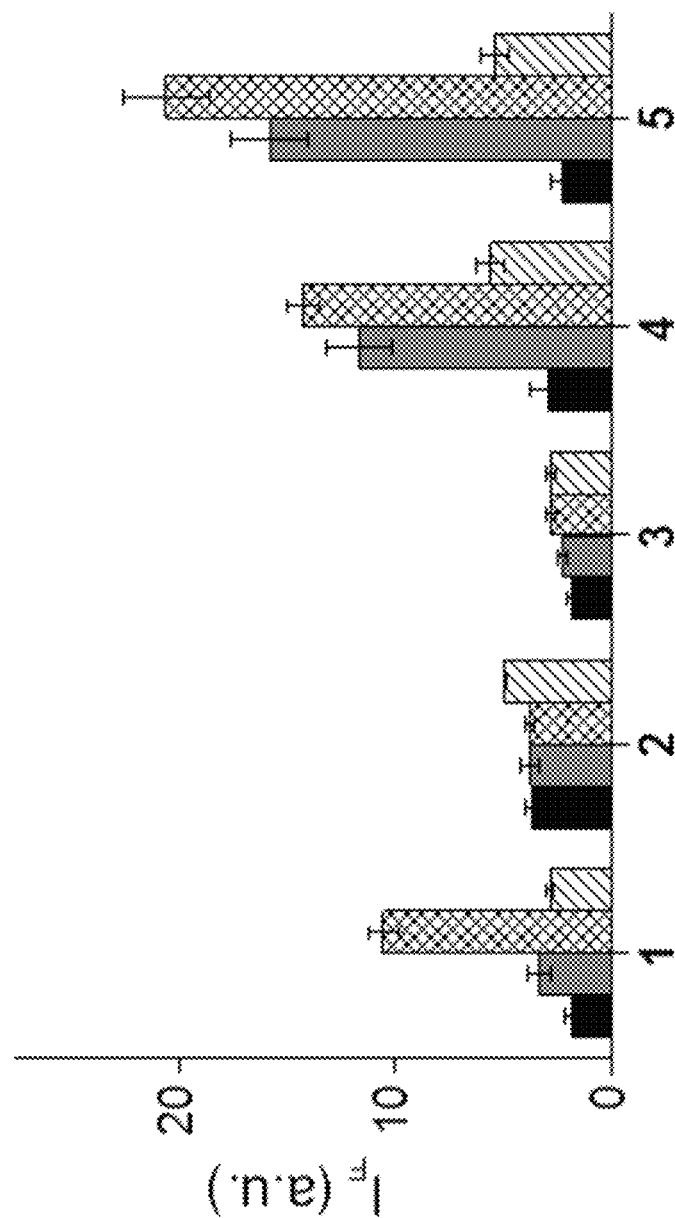
FIG. 23 depicts a Fluorescence response of compounds 1-5 (■) to the sequential addition of His-CaM (※), $Ca^{+2}$ (▨), and EGTA (▨).

The Effect of the Peptide Character on the Fluorescence Response of Sensors of the Invention As noted before, an important aspect of the proposed approach is the ability to "tune" the properties of the tripodal peptide, in such a way that would enable the receptor to interact primarily with a specific region (or a modification) on the protein's surface (FIG. 2, state b). This principle was validated by repeating the above experiments with the four additional control compounds (2-5, FIG. 23), which do not contain hydrophobic receptors. As shown in FIG. 23, a simple alteration in the sequence of the appended peptides had a dramatic effect on the fluorescence response. Specifically, the emission of compounds with negatively charged (2) or polar (3) receptors was not enhanced by the sequential addition of His-CaM and calcium ions, indicating that these sensors do not interact with the surface of His-CaM or His-CaM($Ca^{+2}$). In contrast, sensors with positively charged (4) or hydrophobic and positively charged (5) receptors generated high fluorescence signals both in the presence and absence of calcium ions, which most likely result from electrostatic interactions with negatively charged side chains on the surface of this acidic protein (pI=3.9-4.3). This experiment also indicates that structural activity relationship (SAR) studies could be used to further improve the efficiency of such systems.

Example 8

Figure 24:
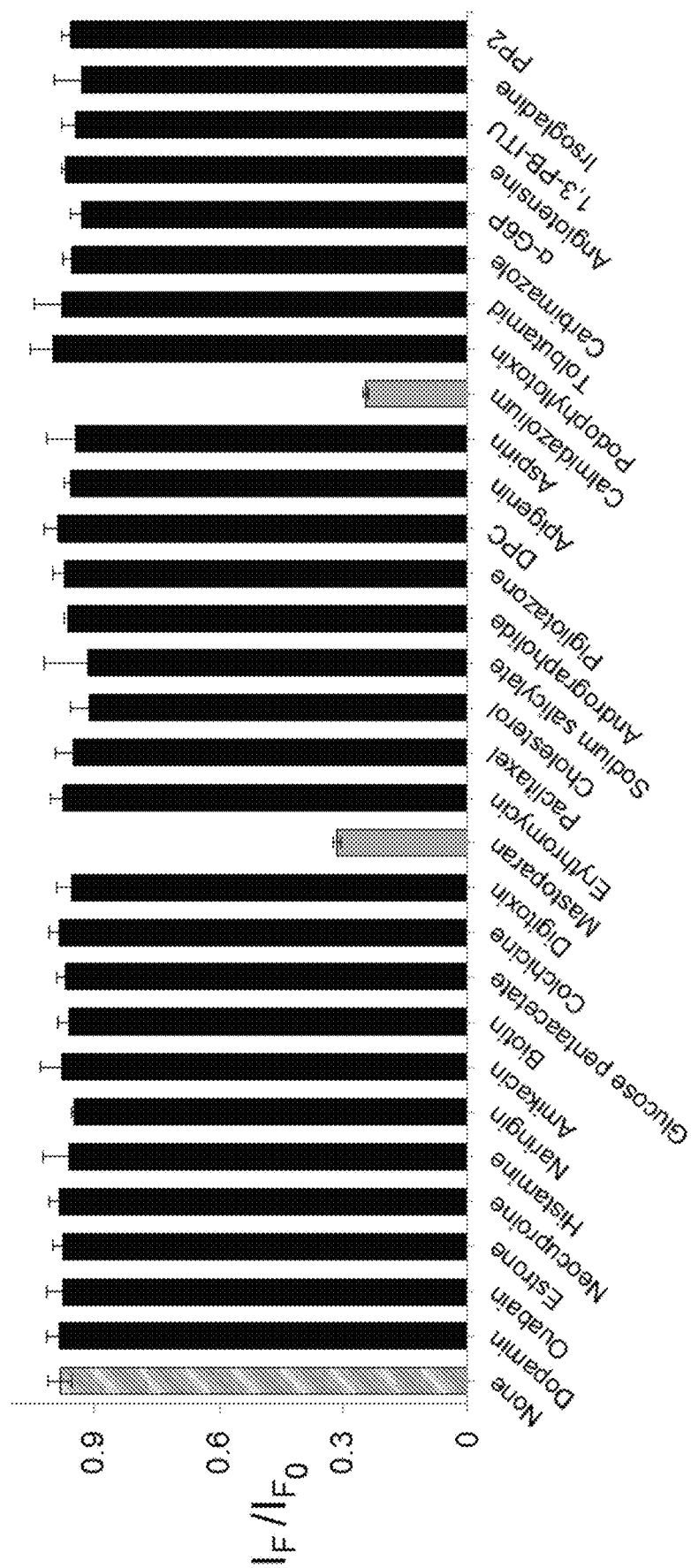
FIG. 24 depicts Fluorescence emission generated by the His-CaM($Ca^{+2}$)-1-complex (200 nM) in the absence (▨) and presence of 1.6 μM of randomly selected drugs (■), and known CaM inhibitors calmidazolium and mastoparan (※).

The Fluorescence Response of Sensor of the Invention to the Addition of a Variety of Randomly Selected Drugs The ability to detect changes in protein surfaces opens up new possibilities for using such sensors to identify binding partners (FIG. 2, state c). Unlike enzyme inhibitors that can be readily detected by enzymatic assays, identifying molecules that interact with protein surfaces is generally complicated by the need to use antibodies and stepwise protocols, or special techniques such as fluorescence anisotropy or surface plasmon resonance (SPR) (FIG. 16). To determine whether synthetic molecules that bind to the CaM surface can be identified by our system, we followed the fluorescence response of the His-CaM($Ca^{+2}$)-1 complex (FIG. 2, state b) to the addition of a variety of randomly selected drugs, as well as the known CaM inhibitors calmidazolium and mastoparan (FIG. 24). A decrease in the fluorescence emission was observed only in the presence of the CaM inhibitors, which is expected from the release of the protein-bound receptor upon the formation of the His-CaM($Ca^{+2}$)-drug complex (FIG. 2, state c).

Example 9

The Fluorescence Response of Sensor of the Invention to the Addition of Natural Binding Partners The ability of sensor 1 to detect natural binding partners was tested. This is a more challenging goal to achieve because the sensor must be inert to the presence of large proteins that may also possess hydrophobic patches on their surfaces and/or proteins that tend to engage in non-specific interactions such as serum albumin (e.g., BSA and HSA). Accordingly, the His-CaM($Ca^{+2}$)-1 complex was incubated with 12 different proteins (FIG. 25), among which CaMKII and Drp1 are known to be CaM binding partners, whereas M13 is the binding fragment (26 aa peptide) of the skeletal muscle myosin light chain kinase (sk-MLCK). The response of the system to the known binding partners and, most importantly, the recovery of emission by the addition of a competing CaM (that lacks His-tag) provide evidence for the ability of the system to identify specific protein partners.

Example 10

Figure 26:
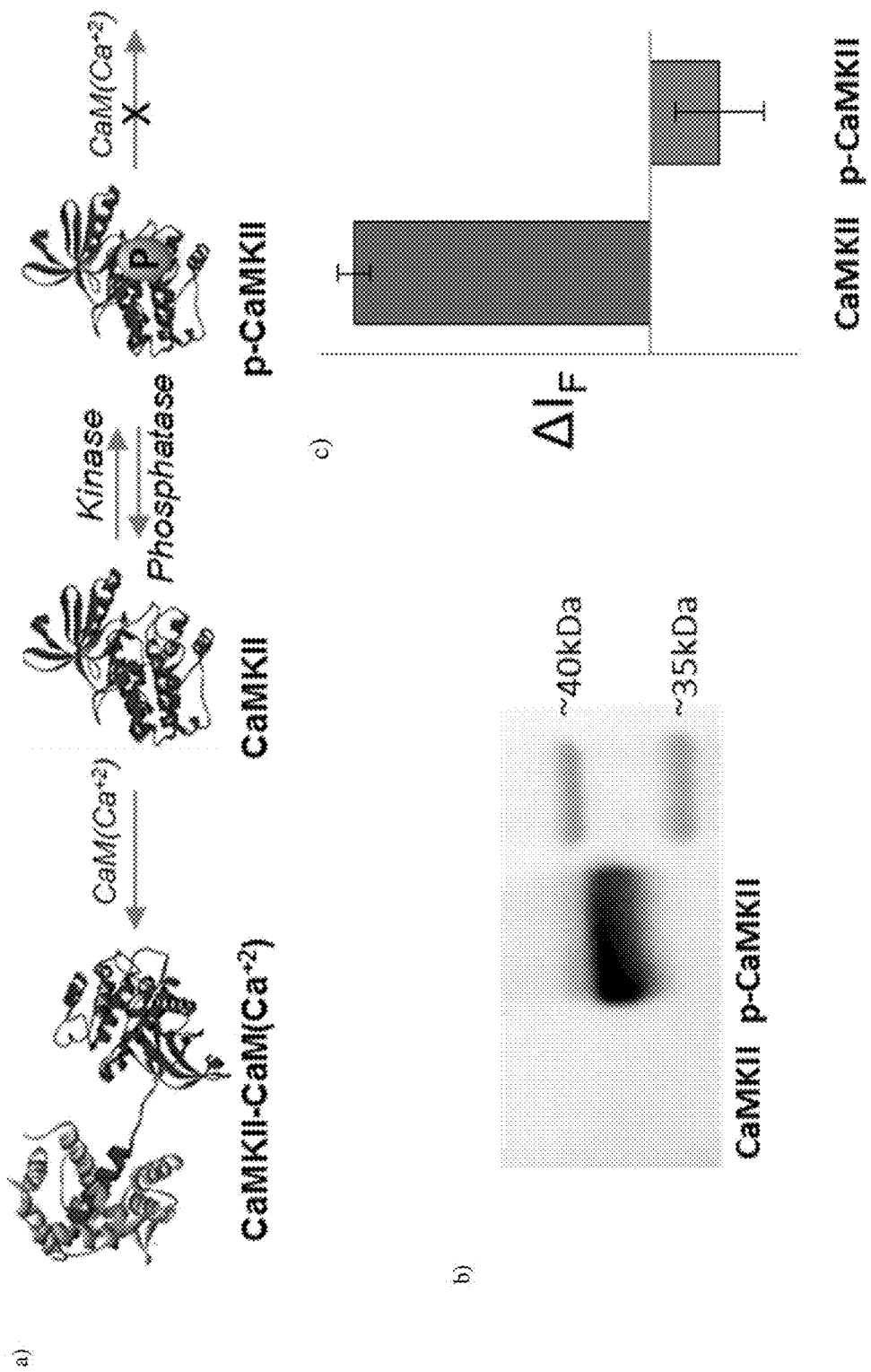
FIG. 26 depicts (a) Schematic illustration showing the preferential binding of CaM($Ca^{+2}$) to a non-phosphorylated CaMKII. The phosphate group on p-CaMKII is denoted as Ⓟ (b) Determining the phosphorylation state of CaMKII by a conventional western blot technique. (c) Determining the phosphorylation state of CaMKII (800 nM) by recording the fluorescence response of His-CaM($Ca^{+2}$)-1 (200 nM) to addition of CaMKII and p-CaMKII.

Detection of Surface Modifications in Unlabeled Proteins by Sensors of the Invention The system was also probed to detect surface modifications of unlabeled proteins. As a proof-of-principle, the phosphorylation state of calmodulin-dependent protein kinase II was determined (CaMKII, FIG. 26) using the His-CaM($Ca^{+2}$)-1 complex. CaM($Ca^{+2}$) is known to bind only the dephosphorylated state of this enzyme (FIG. 26a) and hence, it was expected that a decrease in the fluorescence signal will be observed only in response to a dephosphorylated CaMKII. Accordingly, p-CaMKII was treated with phosphatase to obtain CaMKII (see experimental details in Example 19 below) and the phosphorylation state of samples containing p-CaMKII or CaMKII was initially determined by conventional western blot analysis (FIG. 26b). Although this technique can be used to distinguish between the samples, it is a laborious process that normally takes 1-2 days, in which proteins are separated using SDS-PAGE and transferred to a membrane to allow the binding of primary and secondary antibodies. This approach also requires multiple incubation and washing steps, and a specific antibody for each modification. In contrast, this system could determine the phosphorylation state of each sample within seconds, simply by incubating the protein with a solution containing the His-CaM($Ca^{+2}$)-1 complex (FIG. 26c).

Example 11

Detection of Binding Interactions Between Bcl-2 and BAX by Sensors of the Invention The sensing of His-CaM's surface by the tripodal receptor of 1 supports previous studies, in which it was shown that bringing a non-specific synthetic receptor in the vicinity of a protein, is likely to promote interactions between this receptor and the surface of the protein target. It was therefore expected that even a small sensor library, consisting of only five different receptors (FIG. 23, compounds 1-5), would be sufficient for identifying sensors that can detect surface modifications of His-tag labelled proteins, which are not related to CaM. The ability of compounds 1-5 to detect the interactions between Bcl-2 and Bax was tested. These proteins belong to Bcl-2 family, which plays an important role in regulating apoptosis. The interaction between Bcl-2 and an amphipathic alpha helical peptide of Bax (Bax-BH3), in particular, prevents Bax from triggering apoptosis. As shown in FIG. 27a, of the different compounds tested, the emission of the amphipathic sensor 5, was most significantly enhanced upon binding to His-Bcl-2 and this emission was decreased when the Bax-BH3 peptide was added. Other proteins, as well as M13 and mastoparan that were previously detected by the His-CaM($Ca^{+2}$)-1-complex (FIG. 24), did not change the emission signal generated by the His-Bcl-2-5 complex. In addition, no change in the emission signal was observed in the absence of nickel ions (FIG. 28), which further demonstrate the selectivity and binding mechanism of such sensors.

Example 12

Experimental Details

Fluorescence Response of Compounds 1-5 to CaM Surface Modifications

Figure 21:
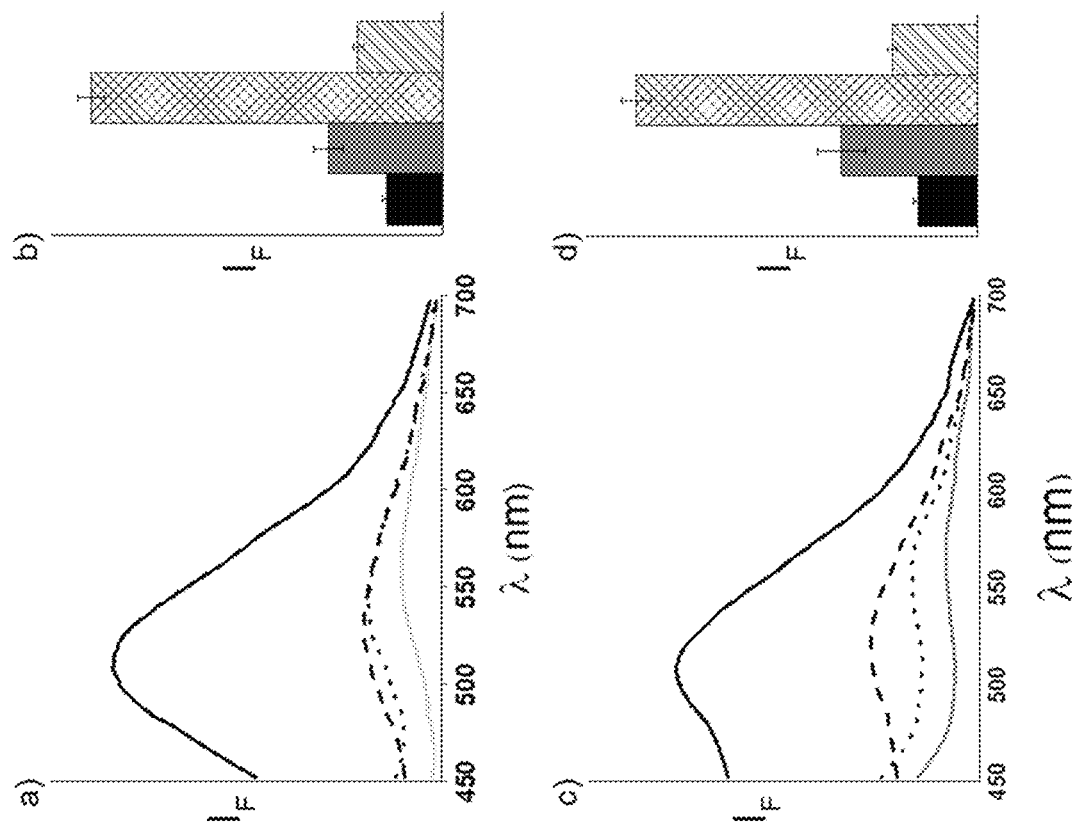
FIG. 21 depicts the fluorescence spectra of 1 (200 nM) before (solid grey line) and after the sequential addition of (a) 400 nM His-CaM (dashed line) or (c) 600 nM His-CaM (dashed line), 0.3 mM $CaCl_2$ (solid black line), and 1.2 mM EGTA (dotted line). The fluorescence response of (■) compound 1 (200 nM) to the sequential addition of (b) (※) His-CaM (400 nM) or (d) (※) His-CaM (600 nM), (▨) $Ca^{2+}$ (0.3 mM), and (▤) EGTA (1.2 mM).

Compounds 1-5 (50 µL, 12 µM) in phosphate buffer (4.1 mM, pH=7.3) were dispensed into a 384-well plate and fluorescence intensities were recorded with an excitation wavelength of 330 nm. His-CaM (final concentration, 200 nM), $CaCl_2$ (final concentration, 0.3 mM), and EGTA (final concentration, 1.2 mM) were subsequently added to each well and the fluorescence intensity values were recorded again (FIGS. 22 and 20). The emission values correspond to the maximal intensities recorded either at $\lambda_{em}$=510 nm or at $\lambda_{em}$=560 nm. Fluorescence was measured in triplicate. Data shown in FIGS. 20 and 22 are the average of the triplicates and error bars represent standard deviation. Control experiments were performed in a similar manner (FIGS. 22a-e) and with higher His-CaM concentrations (FIG. 21).

Fluorescence Response of Compounds 1-5 to Protein G Surface Modifications

Compounds 1-5 (50 µL, 10 µM) in phosphate buffer (4.1 mM, pH=7.3) are dispensed into a 384-well plate and fluorescence intensities are recorded with an excitation wavelength of 330 nm. His-Protein G (final concentration, 200 nM) and IgG (final concentration, 800 nM) are subsequently added to each well and the fluorescence intensity values are recorded again. The emission values obtained, correspond to the maximal intensities recorded either at $\lambda_{em}$=530 nm or at $\lambda_{em}$=560 nm. Fluorescence is measured in triplicate. Control experiments are performed in a similar manner.

Fluorescence Response of Compounds 1-5 to Bcl-2 Surface Modifications

Figure 27:
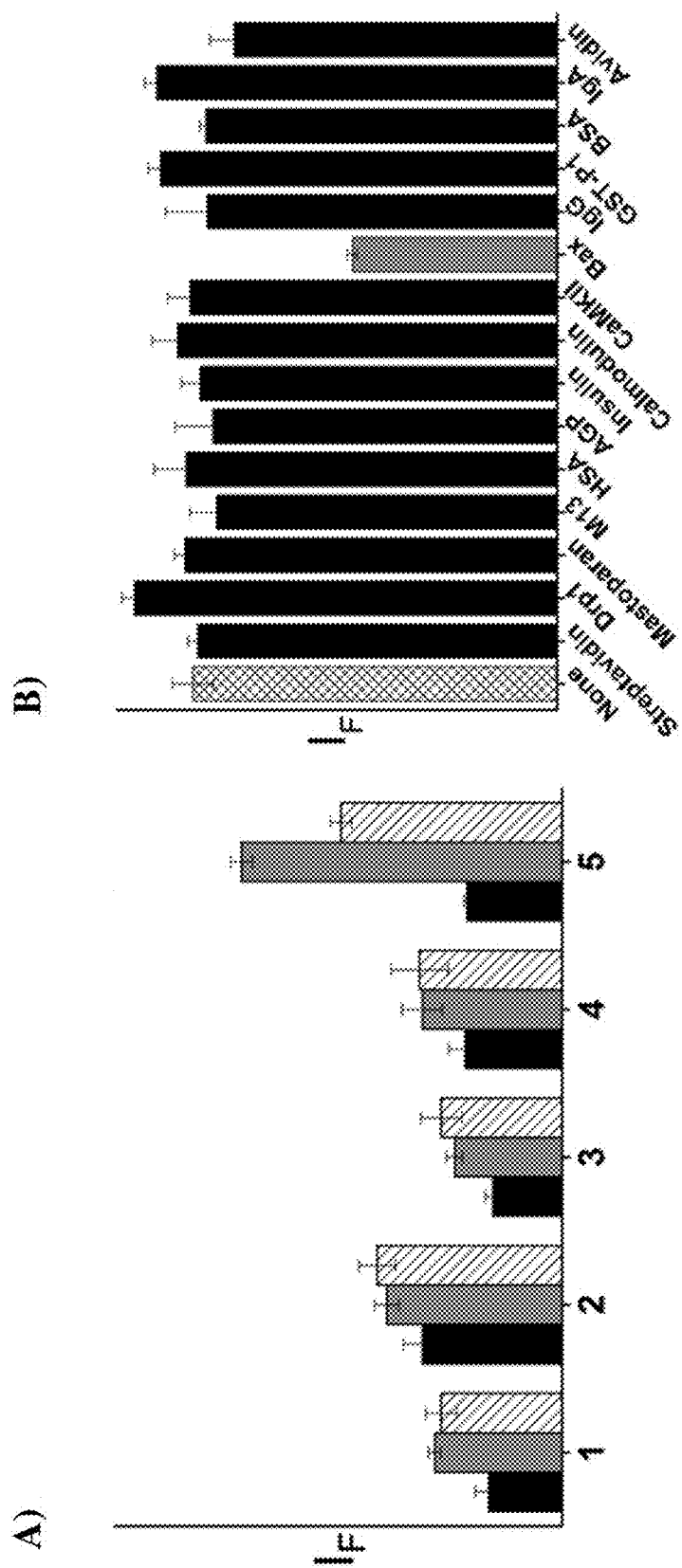
FIG. 27 depicts fluorescence response of a) (■) compounds 1-5 (200 nM) to the sequential addition of (※) His-Bcl-2 (200 nM) (▨) Bax-BH3 (1.6 mM). b) Fluorescence of the His-Bcl-2-5 complex (200 nM) before (▨) and ter the addition of 800 nM of randomly selected proteins (■), as well as the known Bcl-2 binding partner: Bax BH3 (※).
Figure 28:
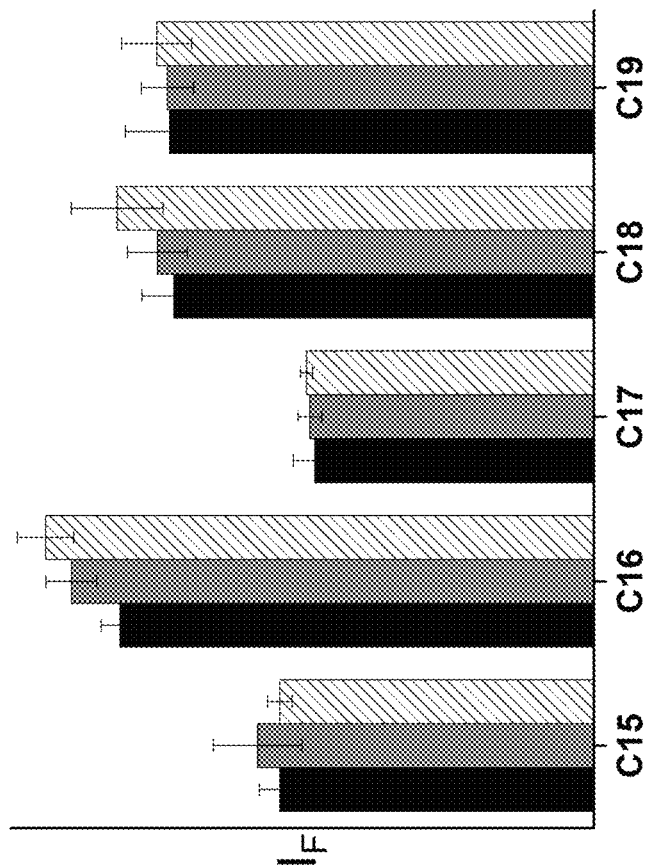
FIG. 28 depicts fluorescence response of (■) compounds C15-19 (200 nM) to the sequential addition of (※) His-Bcl-2 (200 nM) (▨) Bax BH3 (1.6 mM).

Compounds 1-5 (50 µL, 10 µM) in phosphate buffer (4.1 mM, pH=7.3) were dispensed into a 384-well plate and fluorescence intensities were recorded with an excitation wavelength of 330 nm. His-Bcl-2 (final concentration, 200 nM) and Bax BH3 (final concentration, 1.6 µM) were subsequently added to each well and the fluorescence intensity values were recorded again. The emission values correspond to the maximal intensities recorded either at $\lambda_{em}$=530 nm or at $\lambda_{em}$=560 nm. Fluorescence was measured in triplicate. Data shown in FIG. 27 is the average of the triplicates and error bars represent standard deviation. Control experiments were performed in a similar manner (FIG. 28).

Screening Assay with Different Small Molecules and Peptide Inhibitors

A mixture of compound 1 (200 nM), His-CaM (400 nM), and $CaCl_2$ (0.3 mM) in PBS buffer (4.1 mM, pH=7.3) was dispensed into a 384-well microplate, and fluorescence emission spectra were recorded. Then various drugs (1.6 µM) and peptides (1.6 µM) were added and the fluorescence emission was again recorded. Fluorescence measurements were performed in triplicate and the emission intensities before the addition of each drug were normalized to 100% (FIG. 24).

Screening Assay for Protein Protein Interactions Using Surface Sensors.

Probing Protein Protein Interactions for Calmodulin

Figure 25:
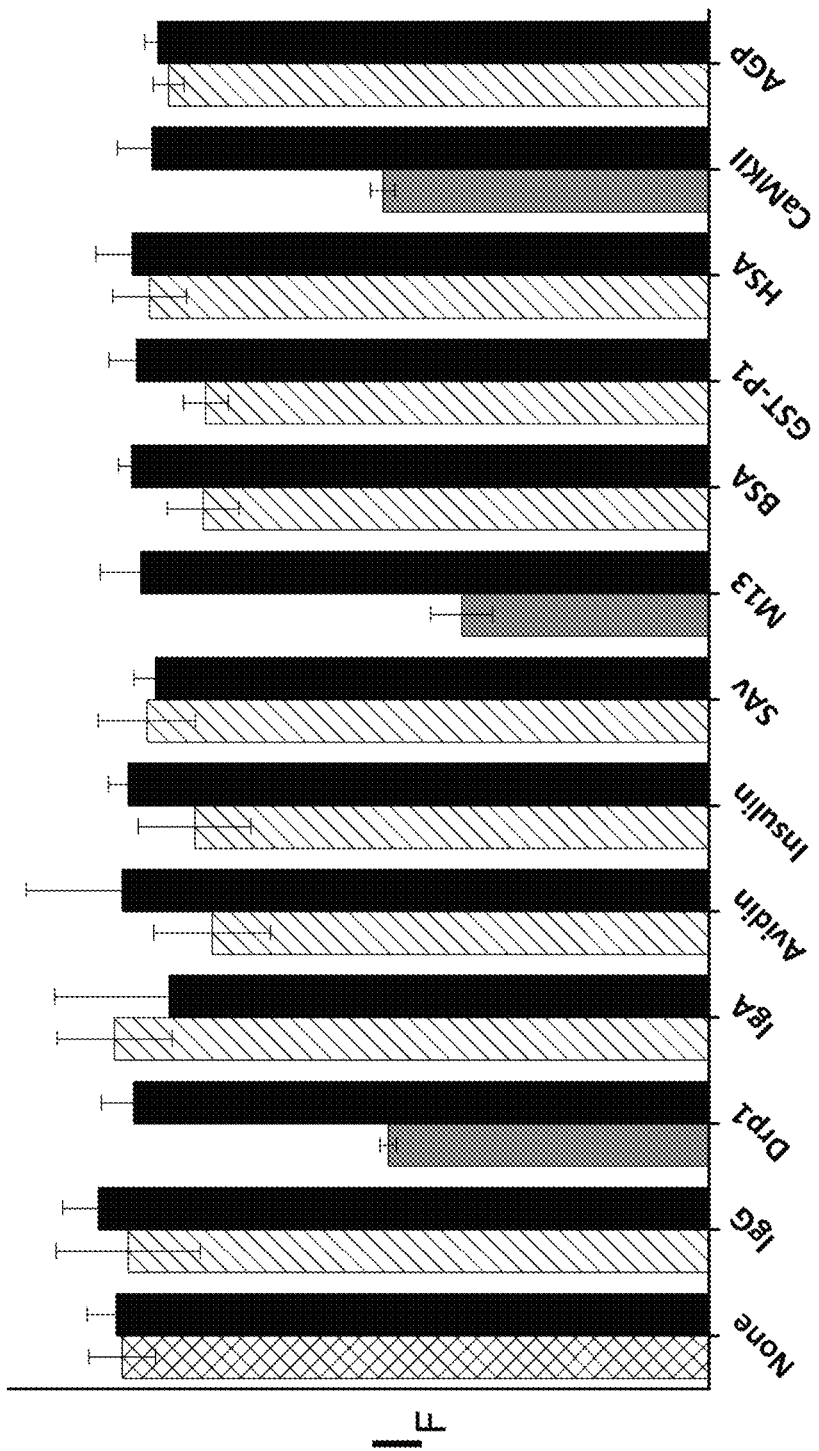
FIG. 25 presents the fluorescence of the His-CaM($Ca^{+2}$)-1-complex (200 nM) before (※) and after the addition of 800 nM of randomly selected proteins (▨), as well as known CaM binding partners: CaMK-II, M13, and Drp1 (※). The black bars correspond to emissions recorded in the presence of a competing CaM, which lacks a His-tag (1.6 μM).

A mixture of compound 1 (200 nM), His-CaM (200 nM), and $CaCl_2$ (0.3 mM) in PBS buffer (4.1 mM, pH=7.3) was dispensed into a 384-well microplate, and the fluorescence emission spectra were recorded. Various proteins (0.8 µM) and M13 peptide (0.8 µM) were added and the fluorescence emission was again recorded. As a competing binding partner CaM (1.6 µM) was added. Fluorescence measurements were performed in triplicate. The emission intensities before the addition of each protein were normalized to 100% (FIG. 25).

Probing Protein Protein Interactions for Protein G

A mixture of compound 5 (200 nM) and His-protein G (200 nM) in PBS buffer (4.1 mM, pH=7.3) is dispensed into a 384-well microplate, and the fluorescence emission spectra are recorded. Various proteins (0.8 µM) and IgG (0.8 µM) are added and the fluorescence emission is again recorded. Fluorescence measurements are performed in triplicate. The emission intensities before the addition of each protein are normalized to 100%.

Probing Protein Protein Interactions for Bcl-2

A mixture of compound 5 (200 nM) and His-Bcl-2 (200 nM) in PBS buffer (4.1 mM, pH=7.3) was dispensed into a 384-well microplate, and the fluorescence emission spectra were recorded. Various proteins (0.8 µM) and Bax BH3 peptide (0.8 µM) were added and the fluorescence emission was again recorded. Fluorescence measurements were performed in triplicate. The emission intensities before the addition of each protein were normalized to 100% (FIG. 27b).

Dissociation Constant.

The approximate dissociation constant for the sensor 1-His tag interaction was determined using a carboxyfluorescein-labeled hexa-histidine peptide. Carboxyfluorescein-labeled hexa-histidine peptide (60 µL, 10 nM) in PBS buffer (4.1 mM, pH=7.3) was dispensed into a 384-well microplate and the fluorescence data were recorded using excitation and emission filters of 485/20 and 580/20, respectively, and a 510 nm cut-off mirror. Then, various concentrations of 1 (final concentrations ranging from 0-650 nM) were added to the wells and the fluorescent intensities were recorded again. The complexation of the labeled peptide with compound 1 leads to strong fluorescence quenching, by the chelated transition $Ni^{+2}$ ions. Fluorescence data were collected in triplicate. The data was normalized to 100% for labeled peptide before the addition of sensor 1 and the relative quenching percentages were plotted against the sensor's concentration. The data was then analyzed by fitting to a non-linear regression for single-site saturation ligand binding $$\left( y = \frac{B_{max} x}{K_d + x}, \right.$$

Figure 17:
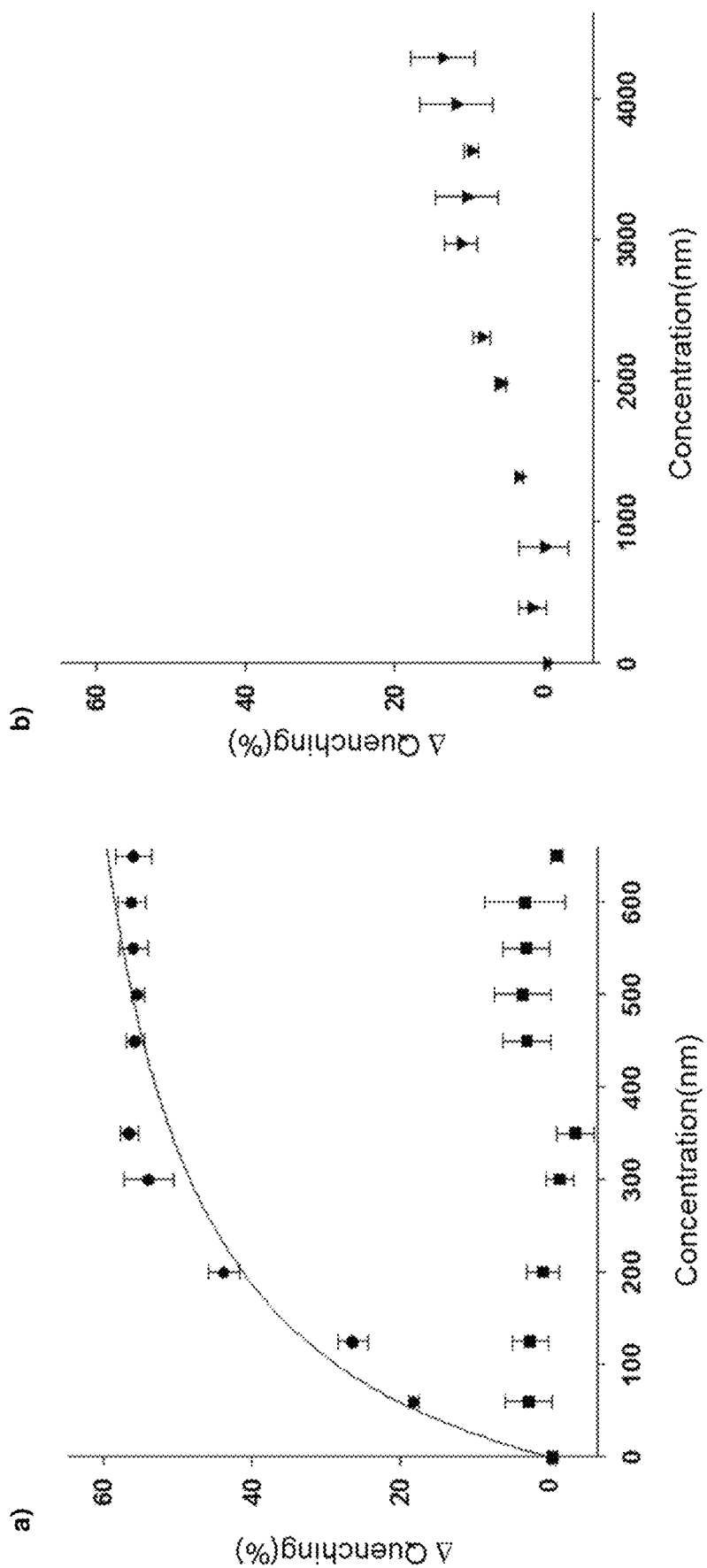
FIG. 17 depicts (a) Binding curves obtained for compound 1 (•) by the addition of increasing amounts of compound 1 to a carboxyfluorescein-labeled hexa-histidine peptide ($K_d$=157±21 nM, $R^2$=0.96). Control experiments (a,b) were performed with C15 (■) and $NiCl_2$(▼).

$B_{max}$=maximum specific binding is 73.82±3) using SigmaPlot 9.0, which resulted in a $K_d$ value of 157±21 nM. The control experiments were performed with C15 and only $NiCl_2$ (FIG. 17).

Surface Plasmon Resonance Experiments.

SPR experiments were performed to assess the dissociation constant between His-CaM and the compound 1 in the presence/absence of $Ca^{2+}$ ions and other ligands. His-CaM was diluted in 180 μL PBS buffer (4.1 mM, pH=7.3) and 20 μL sodium acetate (1 M, pH=3) to reach a final concentration of 20 μg/mL and then immobilized on a Biacore sensor chip CM5 through EDC/NHS chemistry. Flow cells were activated for 5 min by injecting 50 μL mixture of 50 mM NHS:200 mM EDC. Then 50 μL of His-CaM (20 μg/mL) was injected at a rate of 10 μL/min followed by injection of ethanolamine (1 M) to block the remaining surface-activated groups. Various analytes (Table 1) were injected in different concentrations, ranging from 0.1-2 μM for (20 μL/min, 80 μL injection with a delay of 180 s wash) (Table 1). Between consecutive analyte injections, the surface was regenerated with 2 mM NaOH (20 μL at 10 μL/min) followed by PBS buffer (60 μL at 10 μL/min). Non-derivatized dextran matrix flow cells served as reference cells. For determination of dissociation constants in the presence of M13 or Mastoparan (entries 3 and 4), first 80 μL M13 or Mastoparan (3 μM, 20 μL/min) were injected and after dissociation began 80 μL compound 1 (concentration range of 0.2-2 μM, 20 μL/min) was injected. $CaCl_2$ (0.3 mM) was pre-incubated with the analyte before injections. For the control compound C15 (entry 5), prior to each injection, the chip was washed with 20 μL EDTA (50 mM, 20 μL/min) followed by PBS buffer (20 μL at 20 μL/min) to remove any traces of $Ni^{2+}$. The data were globally fitted using BiaEvaluation software 3.2.

CaMKII Assays.

CaMKII Dephosphorylation

CaMKII was dephosphorylated according to a previously published procedure. 0.787 nmol p-CaMKII was incubated with λ-phosphatase (600 U) and $MnCl_2$ (50 mM) at 4° C. overnight. Then the mixture was buffer exchanged into HEPES buffer (20 mM, 0.3 M NaCl, 1 mM $CaCl_2$, pH=7.5) using a 3 kDa cutoff centrifugal filter (Amicon Ultra, Millipore) at 4° C.

CaMKII Western Blot Analysis

Figure 29:
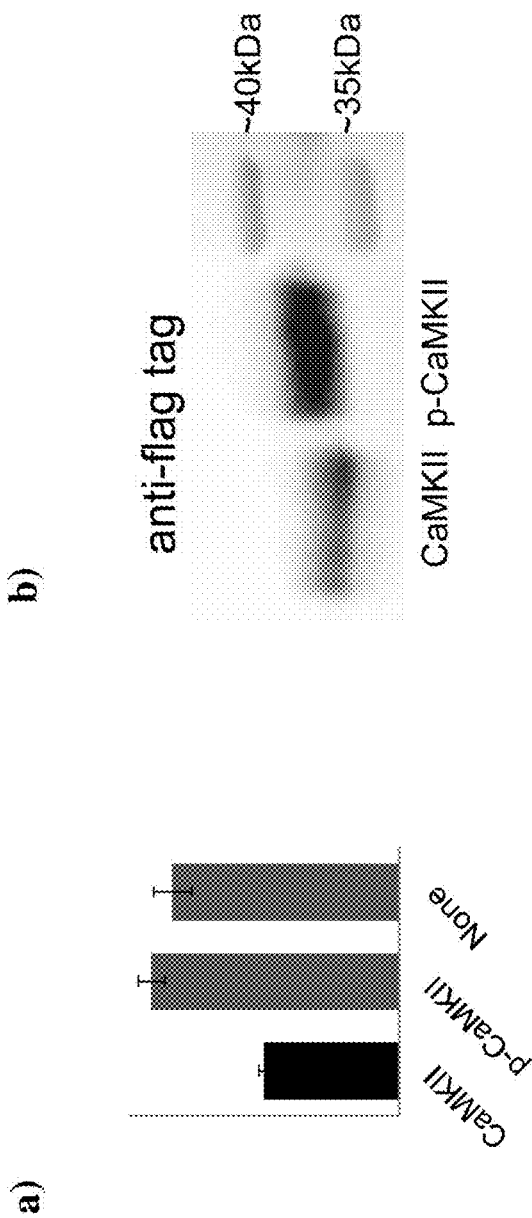
FIG. 29 depicts (a) Fluorescence of the His-CaM ($Ca^{+2}$)-1 complex (200 nM) before (none) and after the addition of 0.8 μM CaMKII and p-CaMKII. (b) Western blot detection of CaMKII and p-CaMKII with anti-flag-tag antibody. Both CaMKII and p-CaMKII are detected by an anti-flag tag antibody whereas only p-CaMKII is detected by phospho-specific antibody, as shown in (b).
Figure 30:
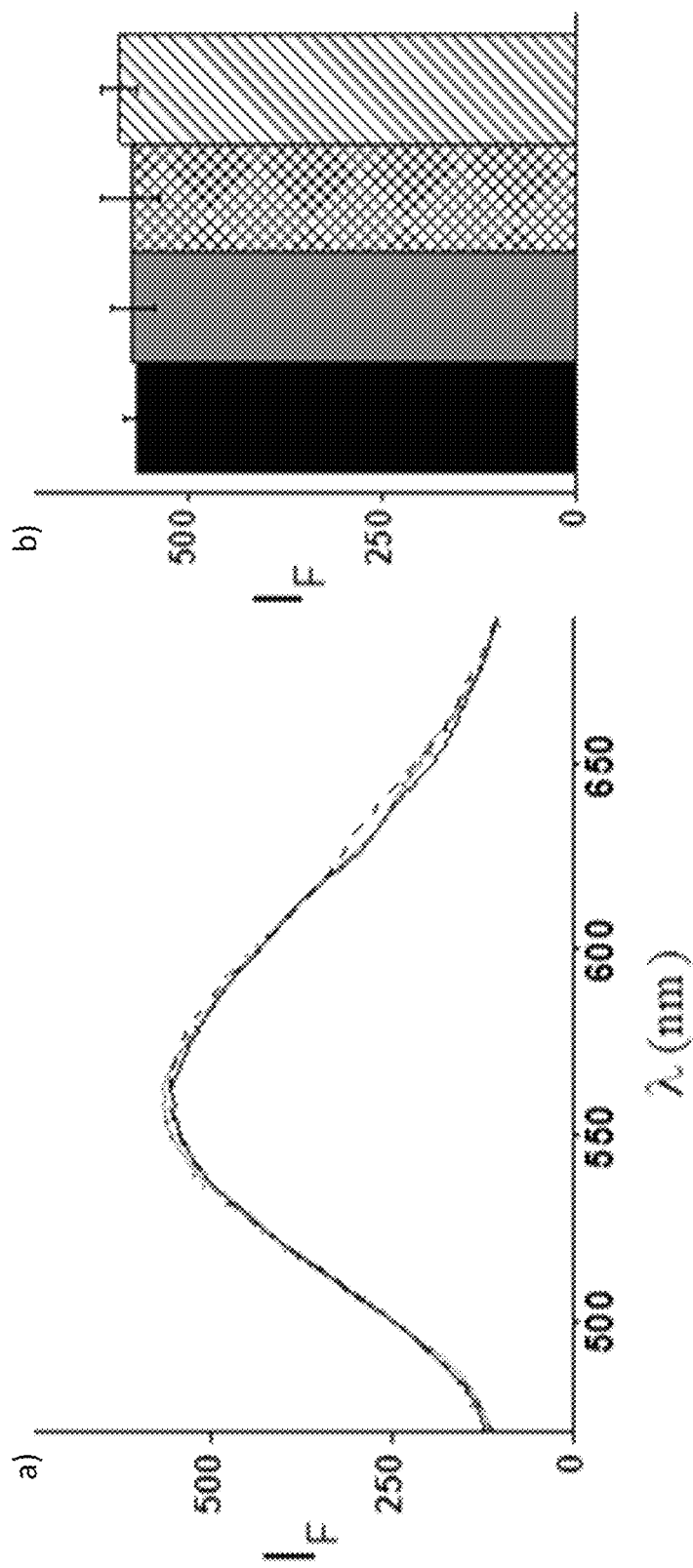
FIG. 30 depicts a-b) Fluorescence response of (■) compounds C15 (2 μM) to the sequential addition of (※) His-CaM (200 nM), (▨) $Ca^{2+}$ (0.3 mM), and (▨) EGTA (1.2 mM).
Figure 31:
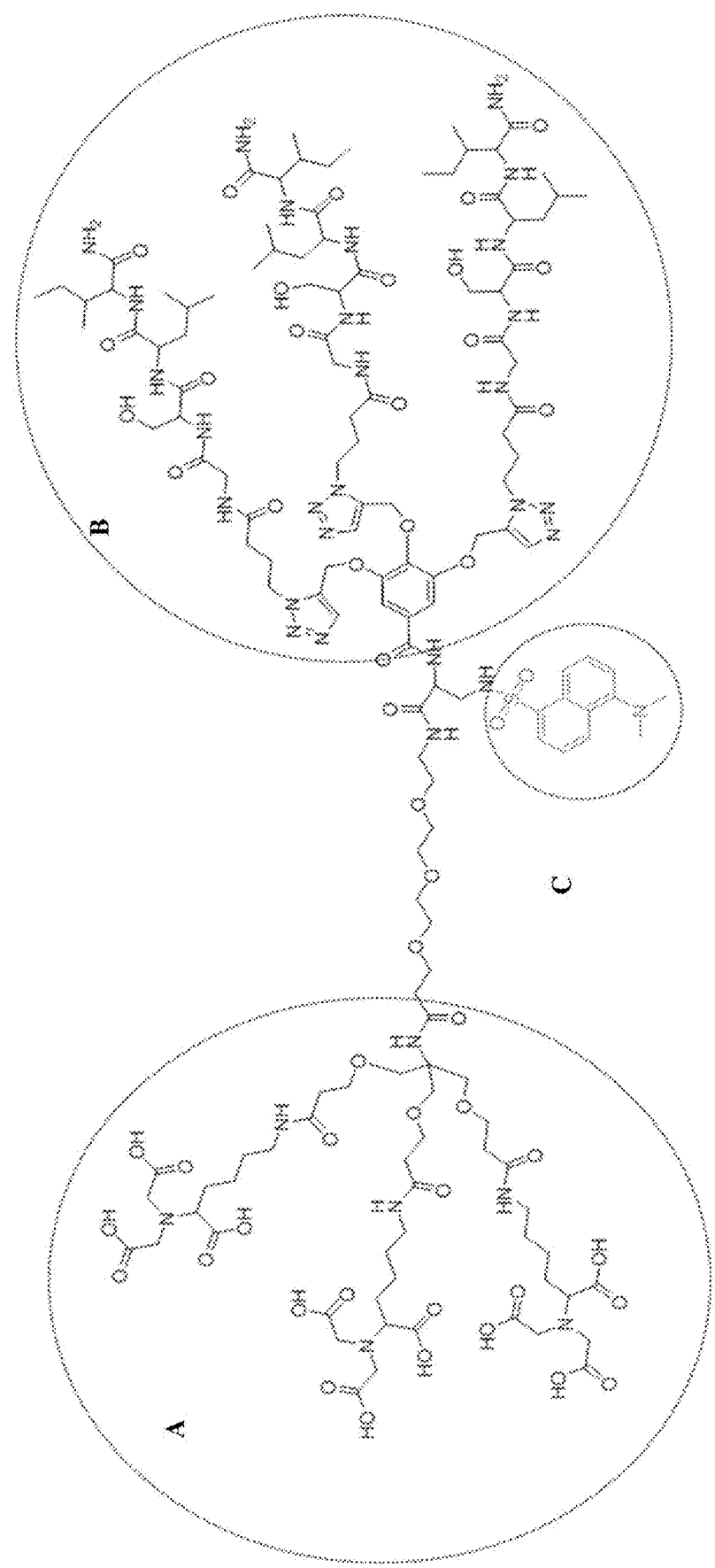
FIG. 31 depicts the protein surface sensor consists of three components. A: A bis-NTA unit for specific His-tag binding. B: A tripodal hydrophobic peptide that serves as a non-selective protein surface receptor. C: A Dansyl group as the solvatochromic fluorophore.

Approximately 2 μg of p-CaMKII and 1 g of CaMKII were loaded in each western blot run. Proteins were resolved on a 10% SDS-PAGE gel and transferred to a membrane, blocked with 5% BSA in PBST buffer (0.1% Tween), and probed with either antibody specific for p-CaMKII (at a dilution of 1:1000) or anti-flag tag (at a dilution of 1:1000 dilution) as primary antibodies. Intermediate washing between steps was done with PBST buffer. HRP-conjugated goat anti-rabbit was used as secondary antibody (at a dilution of 1:10000). CaMKII is expressed with anti-flag tag, which permits performing loading control analysis. Using the primary antibody that is specific for flag tag, a signal for both p-CaMKII and CaMKII (phosphatase treated) was obtained using BIORAD ChemiDoc™ XRD+ (FIGS. 26 and 29).

Example 13

Synthetic Details of ODN Bound His-Tag Binders of the Invention

Materials and Methods

All reagents and solvents were obtained from commercial suppliers. Oligonucleotides were obtained from W. M. Keck Foundation Biotechnology at Yale University, which were synthesized using standard automated solid-phase synthesis. Aluminum-backed silica plates (Merck silica gel 60 F254) were used for thin layer chromatography (TLC) to monitor solution-phase reactions. The $^1$H-NMR spectra were recorded using a 300 MHz Bruker Avance NMR spectrometer. Chemical shifts are reported in ppm on the δ scale down field from TMS as the internal standard. The following abbreviations were used to describe the peaks: s-singlet, d-doublet, t-triplet, q-quartet, quin-quintet, and m-multiplet. Electronspray mass spectrometry was performed with a Micromass Platform LCZ-4000 instrument at the Weizmann Institute of Science mass spectrometry facility. Matrix-assisted laser desorption ionization time-of-flight (MALDI-TOF) mass spectrometry was performed on an AB SCIEX 5800 system, equipped with an Nd:YAG (355 nm) laser with a 1 KHz pulse (Applied Biosystems), at the Weizmann Institute of Science mass spectrometry facility. The purification of oligonucleotides was carried out on a Waters 2695 separation module HPLC system with a 2994 photodiode array detector using either a Waters XBridge™ OST C18 column (2.5 μM, 4.6 mm×50 mm) or an XBridge™ OST C18 column (2.5 μM, 10 mm×50 mm). Oligonucleotide samples were desalted using illustra MicroSpin G-25 Columns (GE Healthcare) according to the supplier's instructions. Concentrations of the oligonucleotides were quantified based on their respective electronic absorption at 260 nm and the molar extinction coefficient of the oligonucleotide at this wavelength. Cell images were acquired using an Olympus IX51 fluorescent microscope equipped with a U-MNIBA3 fluorescence filter cube (excitation and emission filters of 470-495 nm, and 510-550 nm, respectively), a U-MNG2 fluorescence filter cube narrow-band (excitation and emission filters of 530-550 nm, and 590 nm, respectively) and a U-MF2 fluorescence filter cube (excitation and emission filters of 620-660 nm, and 700-775 nm, respectively).

Synthetic Procedures

Scheme 1

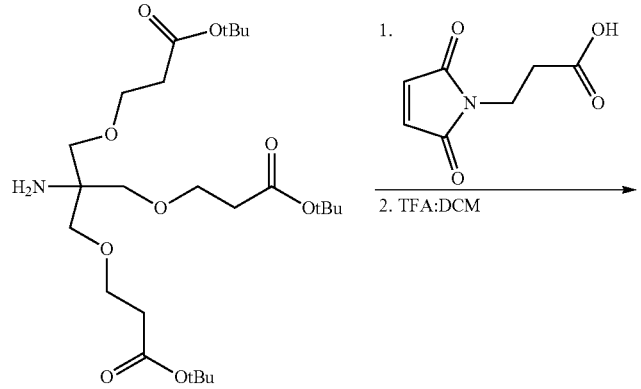

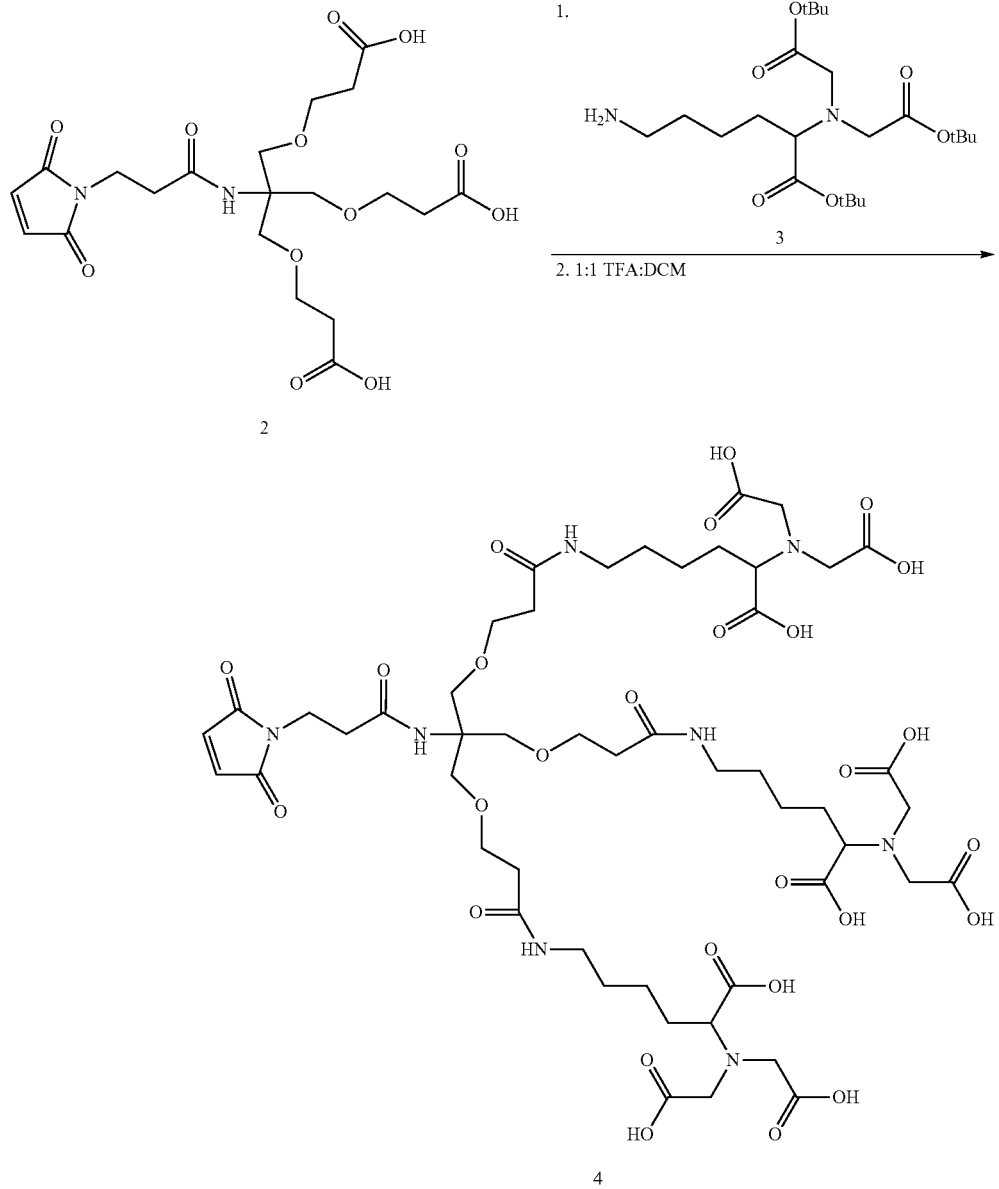

Compounds 1 and 3 of scheme 1 were synthesized according to previously reported procedures (Cardona, C. M. An improved synthesis of a trifurcated newkome-type monomer and orthogonally protected two-generation dendrons. J. Org. Chem. 67, 1411-1413 (2002); Huang, Z. Facile synthesis of multivalent nitrilotriacetic acid (nta) and nta conjugates for analytical and drug delivery applications. Bioconjugate Chem. 17, 1592-1600 (2006).

Compound 2 of scheme 1: Compound 1 (600 mg, 1.18 mmol) was dissolved in dry DCM (30 ml) under argon and cooled to 0° C. Then, EDC (339 mg, 1.7 mmol) and DIPEA (413.7 µl, 2.32 mmol) were added and the reaction mixture was stirred for 30 min at room temperature. 3-Maleimidopropionic acid (240.1 mg, 1.4 mmol) was added, and the solution was stirred overnight. Then 40 ml DCM was added, and the solution was washed with water (10 ml), and brine (10 ml). The organic layer was dried with $Na_2SO_4$, filtered, and concentrated under high vacuum. Finally, the crude product was purified by column chromatography (DCM/MeOH, 97:3) to yield a yellow oil (501.6 mg, 64%).

$^1$H NMR ($CDCl_3$, 300 MHz): δ 1.44 (s, 27H); 2.44 (t, J=6 Hz, 6H); 2.51 (t, J=6 Hz, 2H); 3.63 (t, J=6 Hz, 6H); 3.67 (s, 6H); 3.80 (t, J=6 Hz, 6H); 6.69 (s, 2H). ESI-MS (m/z): calcd. for (M+H): 657.35, found 657.44; calcd. for (M+Na): 679.35, found 679.31.

The tert-butyl groups were then deprotected using a 1:1 (v/v) mixture of TFA:DCM for 2.5 h. After removing the solvents, the excess of TFA was co-evaporated 4 times with DCM and then the product was dried under high vacuum.

$^1$H NMR ($D_2O$, 300 MHz): δ 2.47 (t, J=6 Hz, 2H); 2.59 (t, J=6 Hz, 6H); 3.61 (s, 6H); 3.67-3.75 (m, 8H); 6.83 (s, 2H). ESI-MS (m/z): calcd. for (M+H): 489.16, found 489.18; calcd. for (M+Na): 511.16, found 511.12; calcd. for (2 M+H): 977.32, found 977.03; calcd. for (2 M+Na): 999.32, found 999.15 (2 M+Na).

Compound 4 of scheme 1: A solution of compound 2 (160 mg, 304.8 µmol) in dry DCM (10 ml) was cooled to 0° C. in an ice bath and DIPEA (212 µl, 1.2 mmol), EDC (191 mg, 1 mmol), and HOBt (41 mg, 304.8 µmol) were added consecutively. After 15 min, compound 3 (433 mg, 1 mmol) was added and the reaction was stirred overnight. Then DCM (40 ml) was added and the solution was washed with water (10 ml). The organic layer was dried with $Na_2SO_4$, filtered, and concentrated at high vacuum. Finally, the crude product was purified by column chromatography (DCM/MeOH, 96:4) to yield a colorless oil (96.6 mg, 18.3%). $^1$H NMR (MeOD, 300 MHz): δ 1.50 (s, 54H); 1.55 (s, 27H); 1.71 (m, 18H); 2.42 (t, J=6 Hz, 6H); 2.49 (m, 2H); 3.20 (t, J=6 Hz, 6H); 3.31 (m, 12H); 3.55-3.74 (m, 17H); 6.84 (s, 2H). ESI-MS (m/z): calcd. for (M+Na): 1749.13, found 1748.72; calcd. for (M+2Na): 886.06, found 886.27; calcd. for (M+3Na): 598.37, found 598.52. The tert-butyl groups were then deprotected using a 1:1 (v/v) mixture of TFA:DCM for 2.5 h. After removing the solvents, the excess of TFA was co-evaporated 4 times with DCM and then the product was dried under high vacuum $^1$H NMR (MeOD, 300 MHz): δ 1.47 (m, 6H); 1.53 (m, 6H); 1.91 (m, 6H); 2.43 (m, 8H); 3.17 (m, 6H), 3.58-3.65 (m, 15H), 4.1 (m, 14H); 6.82 (s, 2H). ESI-MS (m/z): calcd. for (M+H): 1221.48, found 1221.53; calcd. for (M+Na): 1243.48, found 1243.39. HRMS.

General Procedure for the Synthesis of the ODN-1 Strands:

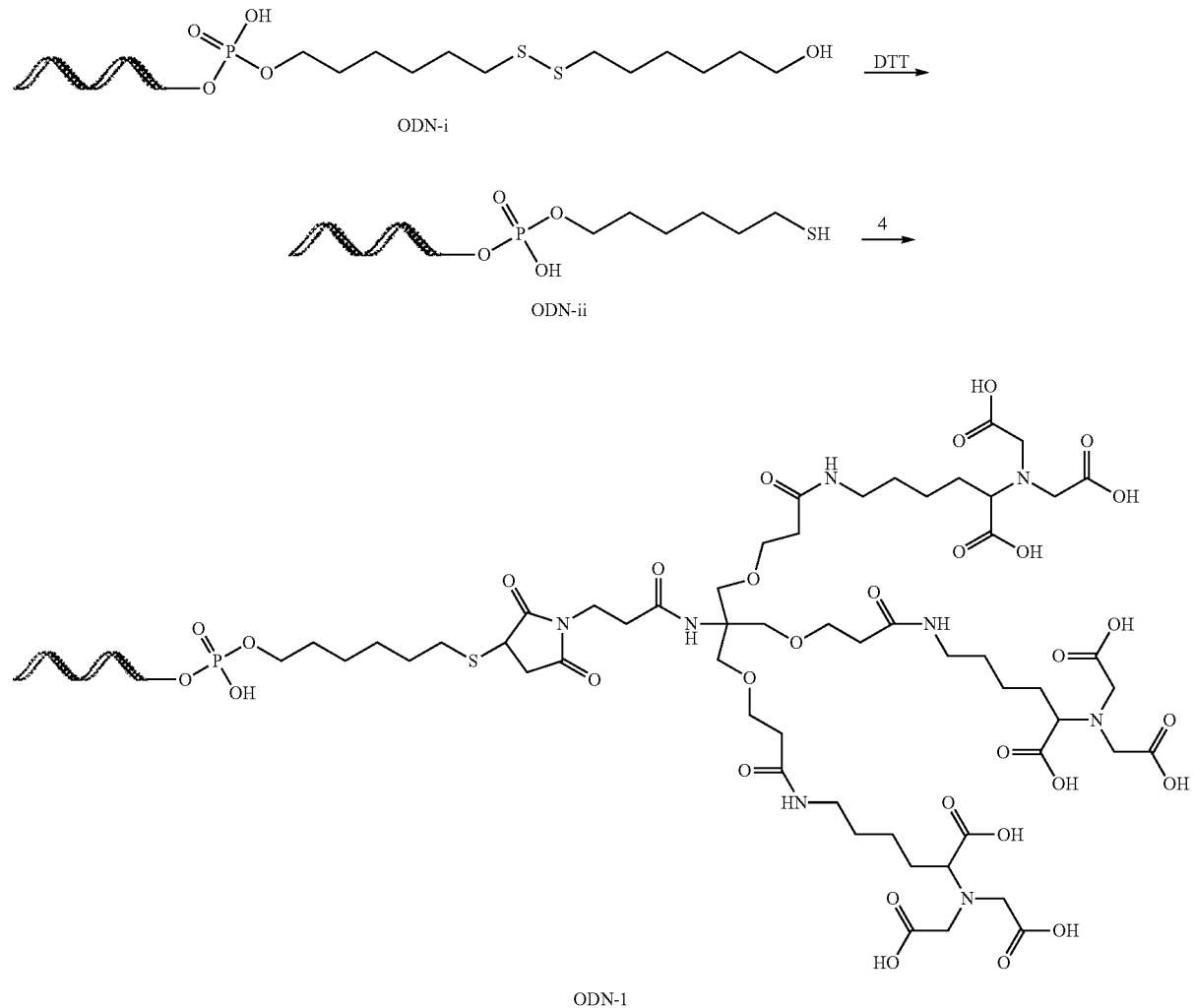

ODN-i of scheme 2 (200 nmol) was treated with 400 μl of a DTT solution (50 mM DTT in 50 mM Tris buffer, pH 8.3) for 1 hour. The reduced oligonucleotide (ODN-ii) was then desalted on Sephadex™ G-25 and dried under reduced pressure. ODN-ii was added to a solution of 4 (8 mg) in concentrated PBS×10, pH 7. The reaction was stirred overnight. The product was purified using RP-HPLC. MALDI-TOF MS (m/z): X-ODN-1: calcd. 6319.6, found 6334.2; ODN-1: calcd. 8876.1, found 8893.3; Compound 101: calcd. 11453.6, found 11454.3; Compound 103: calcd. 9139.8, found 9139.2; Compound 104: calcd. 9119.9, found 9115.9.

Compounds 100-104 where synthesized according to the general synthesis described hereinabove.

Synthesis of Folate-ODN-2 (Compound 206):

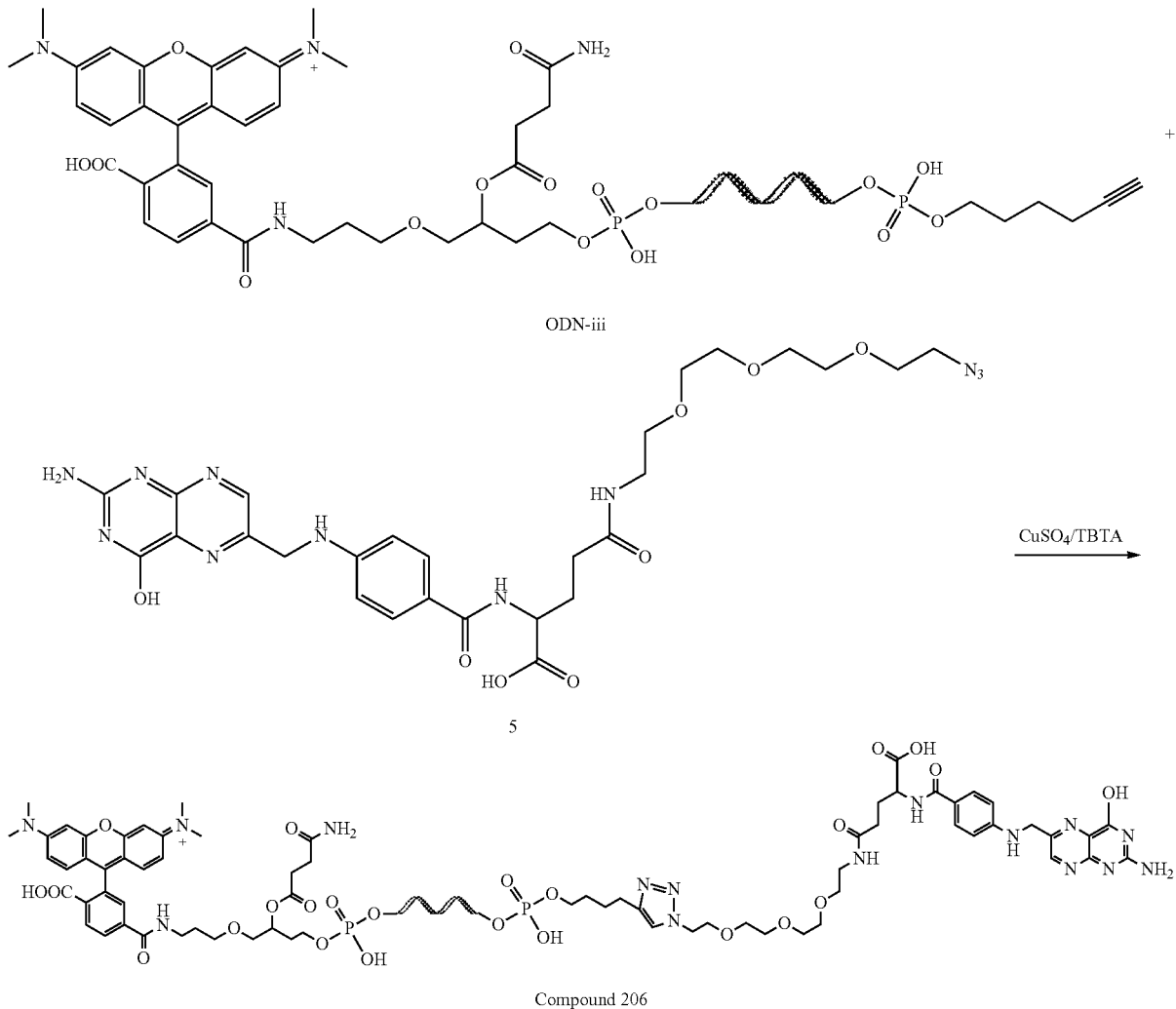

Folate azide 5 of scheme 3, was prepared according to a previously published procedure. ODN-iii of scheme 3 (150 nmol) was dissolved in 160 µl MQ water, followed by the addition of compound 5 (1.5 µmol), ascorbic acid (20 µl, 0.9 µmol), TEAA buffer (40 µl, 2 M, pH=7), and DMSO (200 µL). After degassing with argon, Cu-TBTA (80 µL, 0.9 µmol) was added, and the mixture was stirred for 12 h. The product was purified using RP-HPLC to afford Compound 206. MALDI-TOF MS (m/z): calcd. 9940, found 9941.

OmpC Construction and Expression

OmpC construction. E. coli outer membrane protein C (OmpC) was isolated by PCR, amplified from E. coli ASKA library and cloned into pET21 using RF cloning OmpC_F-pET21: TTTGTTTAACTTTAAGAAGGAGATATA-CATATGAAAGTTAAAGTACTGTCCCTC (SEQ ID No.: 11) and OmpC_RpET21: TTCCTTTCGGGCTTTGT-TAGCAGCCGG ATCTTAGAACTGGTAAACCAGACCC (SEQ ID No.: 12). The resulting plasmid was a His-tag less construct. Polyhistidine-linker sequences were inserted in the predicted $7^{th}$ loop of the OmpC. OmpC-(6His)$_1$ contains 11 amino acid (Aa) sequence: SAGHHHHHHGT (SEQ ID No.: 13) was constructed by Inverse PCR using the following 2 primers: OmpC_His1 F:CATCATCAC-CATGGTACCTCTAAAGGTAAAAACCTGGGTCGTGGC-TAC (SEQ ID No.: 14), and OmpC_His1R: ATGGTGATGATGATGATGACCCGCGGAGGTAC CATGGTGATGATGGTGATGACCCGCGGA (SEQ ID No.: 15). The resulting plasmid served as a template for introducing a second His-linker to obtain OmpC-(6His)$_2$ 22 Aa sequence: SAGHHHHHHGTSAGHHHHHHGT (SEQ ID No.: 16) by using the following 2 primers: OmpC_His2FInverse: CACCAT-CACGGTACCTCTAAAGGTAAAAAC CTGGGTCGTG (SEQ ID No.: 17) and OmpC_His2RInverse: GTGATGGTGACCC GCGGAGGTACCATGGTGAT-GATGGTGATG (SEQ ID No.: 18). An additional third His-linker was introduced to OmpC-(6His)$_2$ by using the following 2 primers: OmpC_His3FInverse: CATCAT-CATGGTACCTCTAAAGGTAAAAACCTGGGTCGTG (SEQ ID No.: 19) and OmpC_His3RInverse: ATGAT-GATGACCCGCG GAGGTACCGTGATGGTGGT-GATGGTG (SEQ ID No.: 20). The resulting construct OmpC-(6His)$_3$ contains 33 Aa His-linker: SAGHHHHHHGTSAGHHHHHHGT SAGHHHHHHGT (SEQ ID No.: 21) in the same position at the predicted $7^{th}$ loop of OmpC. For the Inverse PCR cloning reactions one primer of each set of primers had to be phosphorylated.

Purification of OmpC. The expression of OmpC was tested in the whole cell extracts (WCE) and in the membrane fraction. Cultures expressing OmpC, and His-OmpC were harvested, resuspended in $Na_2HPO_4$ (10 mM, pH 7.3) and lyzed by sonication. A sample from each culture was analyzed by SDS-PAGE for the expression of OmpC in the WCE. Following sonication, the supernatant was separated by centrifugation at 13800 g for 10 min. The membrane fraction was recovered by centrifugation of the supernatant at 13800 g for 30 min., resuspended in 10 mM $Na_2HPO_4$, pH 7.3, 2% Triton X-100 and incubated at 37° C. for 30 min. The insoluble fraction was recovered by centrifugation at 13800 g for 30 min., washed and resuspended in 10 mM $Na_2HPO4$ pH 7.3. Proteins from the membrane fractions were analyzed by SDS-PAGE.

Oligonucleotides

The oligonucleotides used in the experiments are detailed in Table 1.

TABLE 1

Oligonucleotides (ODNs)

| Description | Sequence | SEQ ID No. |
|---|---|---|
| Compound 100 | 5' GCGGCGAGGCAGC 3' | 1 |
| Compound 101 | 3' ATCCTAGTCCGTCGAT ACTGCACTG 5' | 2 |
| ODN-1 and Compound 102 | 3' ATCCTAGTCCGTCGAT ACT 5' | 3 |
| Compound 103 | 3' GATGACAGCTAGCAGA TCAACATGG 5' | 4 |
| Compound 104 | 3' CGCGCGAAAAAAAAAA AAGCAACGC 5' | 5 |
| Compound 200 | 5' TAGGATCAGGCAGCTA TGACGTGAC 3' | 6 |
| Compound 201 | 3' CAGTGCAGTATCGACG GACTAGGAT 5' | 7 |
| Compound 202 and FAM-ODN-2 | 3' CAGTGCAGTATCGACG GACTAGGAT 5' | 7 |
| Compound 203 | 3' CCATGTTGATCTGCTA GCTGTCATC 5' | 8 |
| Compound 204 | 3' GCGTTGCTTTTTTTTT TTTCGCGCG 5' | 9 |
| Compound 205 | 3' CAGTGCAGTATCGACG GACTAGGAT 5' | 7 |
| Compound 206 | 3' CAGTGCAGTATCGACG GACTAGGAT 5' | 7 |
| Compound 207 | 3' CAGTGCAGTATCGACG GACTAGGAT 5' | 7 |
| ODN-3 | 5' GTCACGTCATAGCTGC CTGATCCTA 3' | 10 |

Bacterial Strains and Growth Conditions

*E. coli* K-12 strain KRX (Promega) was used for protein expression.

Transformed bacteria with the different OmpC constructs (OmpC or His-OmpC) were cultured to saturation in LB medium supplemented with 100 μg/ml of ampicillin at 30° C. 40 μl of the pre-cultured cells were then diluted into 4 ml of fresh LB medium supplemented with ampicillin and incubated until the $OD_{600}$ reaches ~0.6. Protein expression was then induced by the addition of 0.1% Rhamnose and 20 μM isopropyl-b-D-1-thiogalactopyranoside (IPTG) and cultures were allowed to grow at 30° C. for 18 h.

General Procedure for Decorating Bacteria with the Oligonucleotides

The bacterial cells (OmpC or His-OmpC) were collected by centrifugation at 6000 g for 4 min. The pellet was washed twice with PBS×1 buffer and resuspended in the same buffer to an $OD_{600}$ of 0.3. To a 100 μl sample of the bacteria suspension, a preincubated sample of DNA (500 nM) and $NiCl_2$ (2.5 μM) was added, and the cells were incubated at room temperature for 1 h. Then the bacterial sample were washed twice with PBS, resuspended in 100 μl PBS and placed on a glass-bottom dish (P35G-1.5-14-C; MatTek) precoated with poly-1-lysine (Sigma Aldrich) and left to adhere for 1 h. Finally, the wells were washed vigorously with PBS three times and imaged using an Olympus IX51 fluorescent microscope. The samples were imaged using 60× or 100× objective lenses.

Treatment of the Modified Bacteria with EDTA

Bacterial samples decorated with Compound 100 were incubated with various concentration of EDTA (0, 5, 10 mM) for 1 h. Cells were then collected (6,000 g, 4 min) and washed twice with 200 μl PBS buffer. Cells were resuspended in 100 μl PBS buffer and added to poly-1-lysine-coated slides for imaging.

Flow Cytometry

Bacteria were decorated with Compound 101 according to the procedure described above. The samples were analyzed using BD FACS Aria Fusion instrument (BD Biosciences, San Jose, Calif. USA) equipped with 488 nm (blue), 561 nm (green), and 640 nm (red) lasers. Sorting was performed using a 100-μm nozzle equipped with BD FACS Diva software v8.0.1 (BD Biosciences). Data was analyzed using FlowJo software.

Bacterial Cell Growth

His-OmpC bacteria decorated with Compound 101 was incubated for 30 min in M9 minimal medium containing 2% glucose. The sample was spun down at 6,000 g for 2 min and the supernatant was discarded. After washing the pellet with M9 minimal medium, the cells were diluted to $OD_{600}$=0.05 in M9 medium in a 96-well plate. Growth kinetics was monitored by recording $OD_{600}$ under shaking at 30° C. for 24 h. Bacteria expressing His-OmpC was used as a control. The ability of the modified His-tagged bacteria to grow and divide was also demonstrated using fluorescence microscopy. For these experiments, the bacteria were prepared using a similar procedure. After diluting the sample to $OD_{600}$=0.3, it was allowed to grow at 30° C. 100 μl samples were withdrawn at different time intervals and plated on poly-1-lysine-coated glass bottom dishes and imaged by fluorescent microscopy.

Introducing 'Posttranslational Modifications' to the Bacteria

Bacterial cells were decorated with ODN-1 according to the procedure described above. After washing the sample with PBS, the following ODNs were added sequentially: Compound 200, ODN-3, Compound 201, ODN-3, Compound 202, and ODN-3. After each incubation step, cells were washed twice with PBS and a sample was taken for imaging before the addition of the subsequent strand. Fluorescently labeled ODN-2 strands were added at a concentration of 500 nM and incubated for 30 min, while ODN-3 strand was added at a concentration of 2 μM and incubated for 2 h.

Mixed Population of Bacteria

Three samples of His-OmpC bacteria (100 μl each) were separately labeled with Compound 102, Compound 103, or Compound 104. Each sample was washed twice with PBS.

Then, an equal ratio (30 μl each) of the three samples were combined and Compound 202, Compound 203 and Compound 204 (500 nM) were added to the mixture and incubated for 10 min. The bacterial cells were centrifuged at 6,000 g for 2 min, washed twice with PBS and imaged by fluorescent microscopy using 488, 561, and 647 nm excitation lasers and 488/50, 610/60, and 685/50 emission filters. For flow cytometry analysis, the samples were not washed after addition of ODN-2 strands.

Bacteria-Streptavidin Interaction

His-tagged bacterial cells were decorated with a duplex consisting of ODN-1 and Compound 205 duplex according to a similar procedure described above. For binding with streptavidin, cells were incubated with Alexa-647 streptavidin conjugate (500 nM) in PBS×1 for 1 h, and after washing twice with PBS were imaged by fluorescent microscopy. The fluorescent signal was abolished when bacterial cells were treated with ODN-3 (3 μM) for 1 h. The control experiment was performed similarly using bacteria decorated with a duplex containing ODN-1 and the complementary strand.

Bacteria-KB Cell Interaction

KB cells were maintained in folate-depleted RPMI supplemented with 10% fetal bovine serum (FBS), 1% L-glutamine, and 1% penicillin/streptomycin. Cells (12,500 cells/well) were seeded onto glass bottom culture dishes (Mattek) and allowed to adhere overnight. Cells were then washed twice with PBS and incubated with 100 μl His-tagged bacteria decorated with ODN-1: Compound 206 duplex for 30 min. The medium was removed and cells were rinsed three times with PBS. Cells were then imaged using a fluorescence microscope and a 60× objective lens. A control experiment was performed similarly using bacteria decorated with a duplex lacking the folate moiety (ODN-1 and ODN-iii). To show the reversibility of interaction, the bacteria bound KB cells were incubated with ODN-3 (5 μM) for 15 min. After washing twice with PBS buffer, cells were imaged again.

Adhesion to the Solid Support

The gold substrates were prepared by electron-beam evaporation of an adhesion layer of chromium (3 nm), followed by a 20 nm layer of gold (99.99% purity) onto high precision cover glasses (170±5 μm, Marienfeld-Superior, Germany). A solution of (11-mercaptoundecyl)tetra(ethylene glycol)$^9$ (2 mM in ethanol) were added to the gold coated substrates and incubated for 2 h. After removing the solution, the slides were washed four times with ethanol. Bacteria samples decorated with a duplex consisting of Compound 102 and Compound 207 were washed twice with PBS, resuspended in 100 μl phosphate buffer (pH=3.8), and then incubated on gold surfaces for 15 min. The solution containing bacteria was removed, and the slides were rinsed three times with PBS, and twice with water. Finally, they were imaged using an Olympus IX51 microscope.

Super-Resolution Microscopy

Super-resolution images were collected on a Vutara SR200 STORM (Bruker) microscope based on the single-molecule localization biplane technology. His-tagged bacteria was decorated with ODN-1:Compound 201 duplex according to the procedure described in above. The bacteria were imaged using 647 nm excitation laser and 405 nm activation laser in an imaging buffer composed of 5 mM cystamine, oxygen scavengers (7 μM glucose oxidase and 56 nM catalase) in 50 mM Tris, 10 mM NaCl and 10% glucose at pH 8.0. Images were recorded using a 60×NA 1.2 water immersion objective (Olympus) and Evolve 512 EMCCD camera (Photometrics) with gain set at 50, frame rate at 50 Hz, and maximal power of 647 and 405 nm lasers set at 6 and 0.05 kW/cm$^2$, respectively. Total number of frames acquired was 8000. Data was analyzed by the Vutara SRX software.

Example 14

Design Principles of a Dynamic Artificial Receptor System

Objective: To produce an artificial receptor fulfilling the following requirements: (1) the artificial receptor is easily modifiable by molecular signals in their environment, (2) the artificial receptor is capable of attaching different bioactive molecules, labeling molecules, and synthetic agents, (3) the artificial receptor does not perturb desirable cell functions, (4) the artificial receptor can be reversibly modified.

Figure 32A:
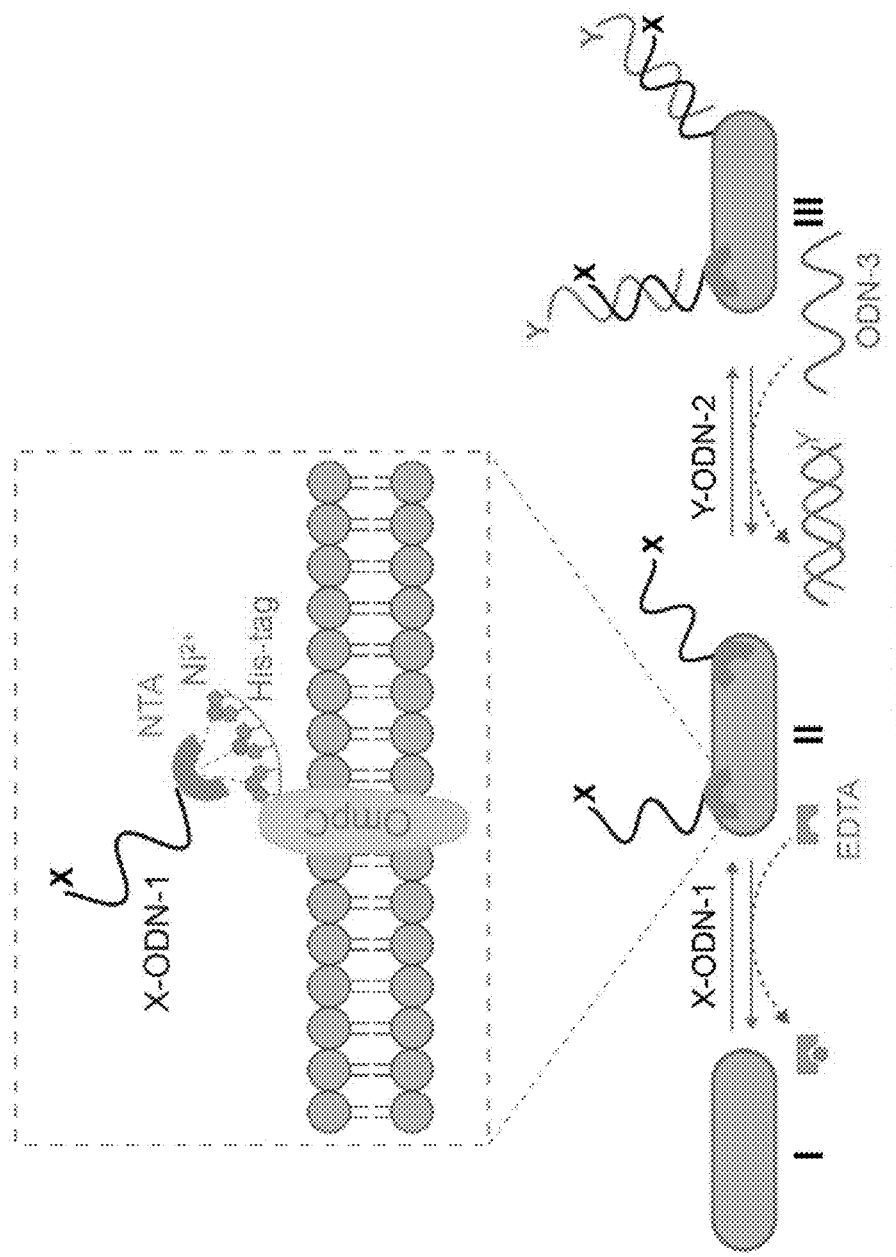
FIGS. 32A-32B show the design of an artificial receptors system.

FIG. 32A shows the design and operation principles of an embodiment of the synthetic receptor system presented herein. The system comprises: A first polypeptide, said polypeptide comprising a membranal anchoring domain and an extracellular binding domain. In the examples shown herein, the membranal anchoring domain used is outer membrane protein C (OmpC) and the extracellular binding domain is hexa-histidine tag (His-tag). The first compound is sometimes termed His-OmpC in the Examples.

Figure 32B:
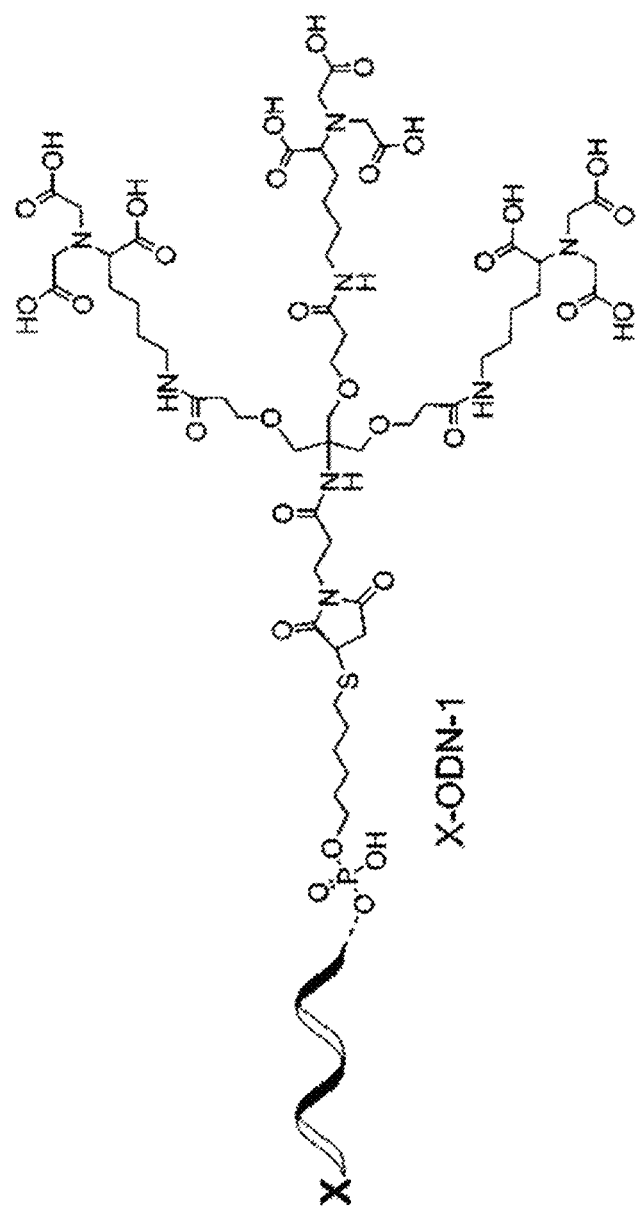

The first compound, comprises a first oligonucleotide (ODN-1) bound to a binder, said binder comprises affinity to said extracellular binding domain. The first compound is sometimes termed X-ODN-1 in the Examples, wherein ODN-1 denotes the first oligonucleotide, and X denotes an optional labeling moiety. In the examples shown herein, the binder is a three nitrilo acetic acid (Tri-NTA) conjugate, which binds His-tag. FIG. 32B shows an embodiment of X-ODN-1.

The second compound comprises a second oligonucleotide (ODN-2) bound to a synthetic agent on its end. The second compound is sometimes termed Y-ODN-2 in the Examples, wherein ODN-2 denotes the second oligonucleotide, and Y denotes the synthetic agent on its end. The oligonucleotide ODN-2 is complementary to the first oligonucleotide ODN-1. However, Y-ODN-2 bears also a short overhang region, termed a toe-hold region. Such toe-hold region can be used to initiate strand displacement and detachment of Y-ODN-2 from X-ODN-1 by an oligonucleotide complementary to the whole ODN-2 oligonucleotide.

The system optionally comprises a third compound, comprising a third oligonucleotide (ODN-3). The oligonucleotide ODN-3 is complementary to the whole ODN-2 sequence, i.e., both to the toe-hold region and to the region bound to ODN-1. Cells can be optionally incubated with ODN-3, which produces strand displacement. In a first step, ODN-3 binds to Y-ODN-2 toe hold region. In a second step, ODN-3 competes with ODN-1 for binding with ODN-2, until eventually it detaches Y-ODN-2 from X-ODN-1.

The artificial receptor system described above was used for decorating a cell surface according to at least two approaches. In the first approach, cells expressing His-OmpC were incubated with X-ODN-1 in the presence of Ni (II) (FIG. 1, steps I and II). X-ODN-1 was efficiently bound to His-OmpC in such conditions. The effect of the synthetic agent was terminated by detaching X-ODN-1 from His-OmpC, for example by incubating the cells with a Ni (II) chelator as EDTA.

In the second approach, cells expressing His-OmpC were first incubated with X-ODN-1 in the presence of Ni (II) (FIG. 1, steps I and II). Then, cells were incubated with Y-ODN-2, which bound to X-ODN-1 (FIG. 1, steps III). Optionally, addition of ODN-3 terminated the effect of the synthetic agent of Y-ODN-2 (FIG. 1, steps III and II).

The artificial receptor system developed and disclosed herein present a number of advantages. First, the receptors are non-covalently anchored to the cellular membrane. Such non-covalent anchoring allows controlling the number of receptors on the cell membrane and surface by external molecular signals (e.g., X-ODN-1, EDTA, Y-ODN-2, and ODN-3). Second, the anchoring domain of the receptors is stably inserted into the cell membrane, and an extracellular domain can bind different synthetic agents. Thus, different synthetic agents can be bound to the extracellular domain without re-engineering the cells. Third, the anchoring domain has a minimal size and is present only at specific locations on the bacteria membrane. Thus, the anchoring domain does not perturb cellular function. Fourth, the synthetic receptors can be to reversible modified. This allows dynamically altering their structure while they are attached to the bacterial membrane, resembling post-translational modifications that occur on natural receptors.

Example 15

Decorating Bacteria with Artificial Receptors and Controlling the Receptors Functioning Objective: To decorate bacterial membranes with an artificial receptor.

Methods: His-tagged OmpC was expressed in *E. coli*, which was then incubated with an X-ODN-1 appended either with a Cy5 dye or TAMRA (Compounds 100-101) in the presence of nickel ions and EDTA. Methods and protocols are detailed in Example 1.

Figure 33A:
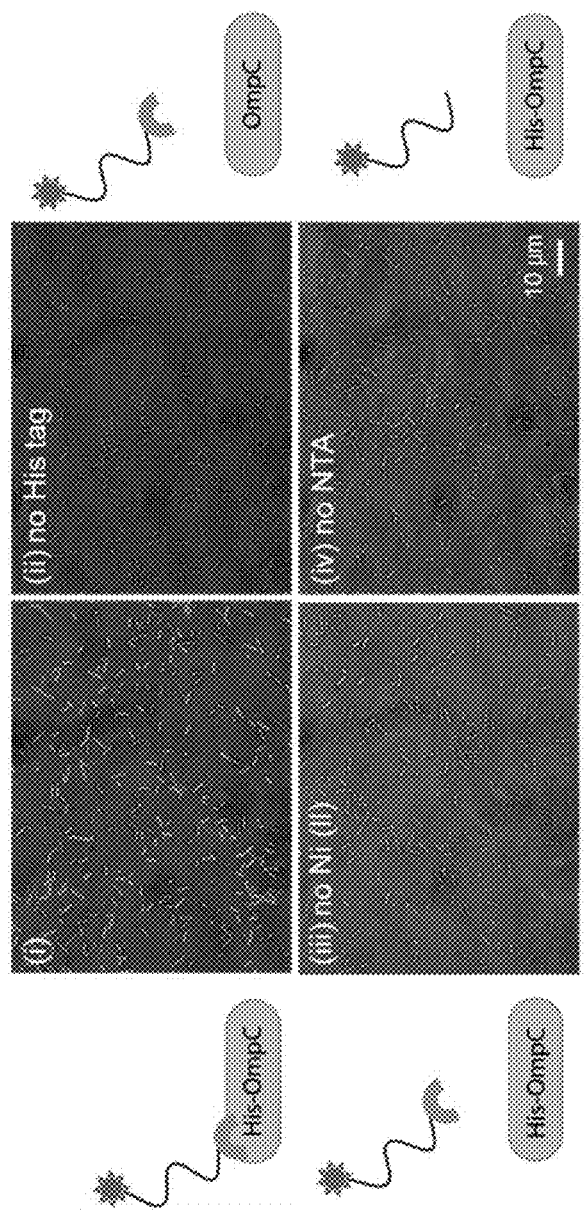
FIGS. 33A-33E show reversible, non-covalent modification of bacterial membrane with a synthetic receptor.

Results: Fluorescence imaging revealed that His-tagged OmpC engineered bacteria incubated with Compound 100 were successfully decorated with the Cy5 fluorophore (FIG. 33A, i). To confirm that the labeling did not result from a non-specific interaction between Compound 100 and the bacteria surface, Compound 100 was also incubated with native bacteria lacking His-OmpC (FIG. 33A, ii), as well as with the His-tagged bacteria in the absence of nickel ions (FIG. 33A, iii). Additionally, His-tagged bacteria was incubated with a Cy5-labeled ODN lacking a tri-NTA group (FIG. 33A, iv). No fluorescence was observed in any of these controls, confirming the selectivity of ODN-1 to membrane bound His-tags.

Figure 33B:
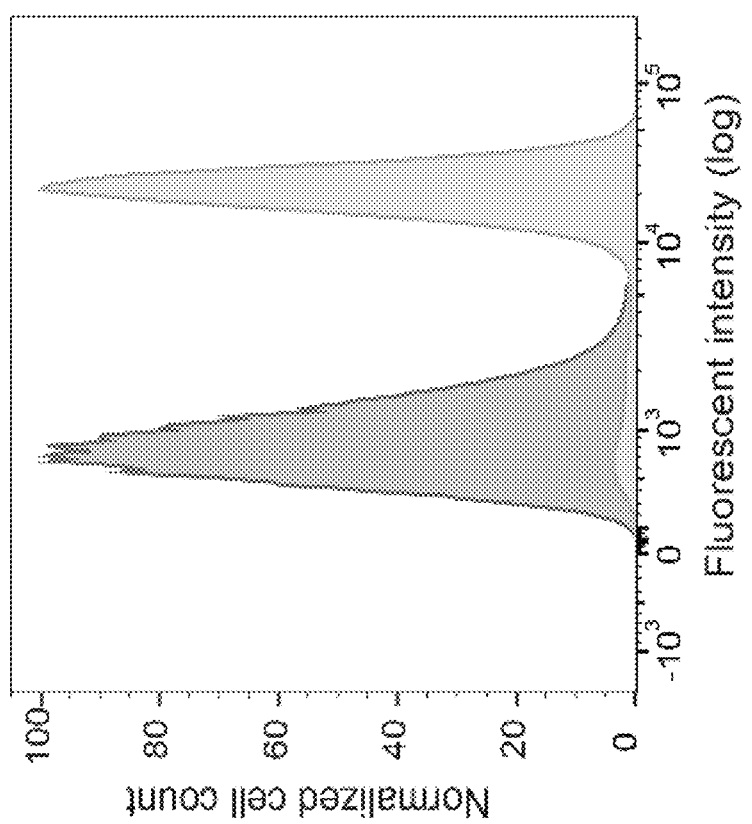

The selectivity and degree of labeling were further analyzed by flow cytometry. 90.9% of His-tagged modified bacteria and 1% of native bacteria were labeled by Cy5 (FIG. 33B).

Figure 33C:
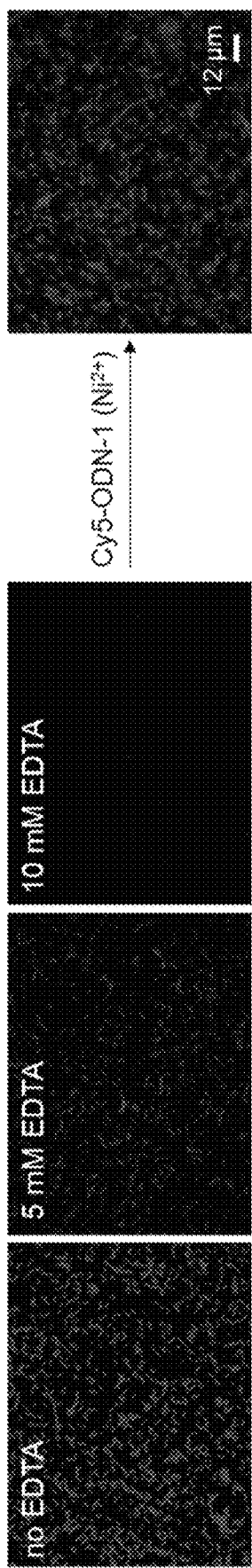

The ability of the system to control the activity levels of the artificial receptors by external signals was further tested. Bacteria were exposed to increased concentrations of EDTA, which resulted in a decrease in surface coverage with Compound 100. 10 mM of EDTA completely removed Compound 100 from the cell surface. Detached Compound 100 could be washed from the medium and bacteria could be re-decorated with other molecules (FIG. 33C).

Figure 33D:
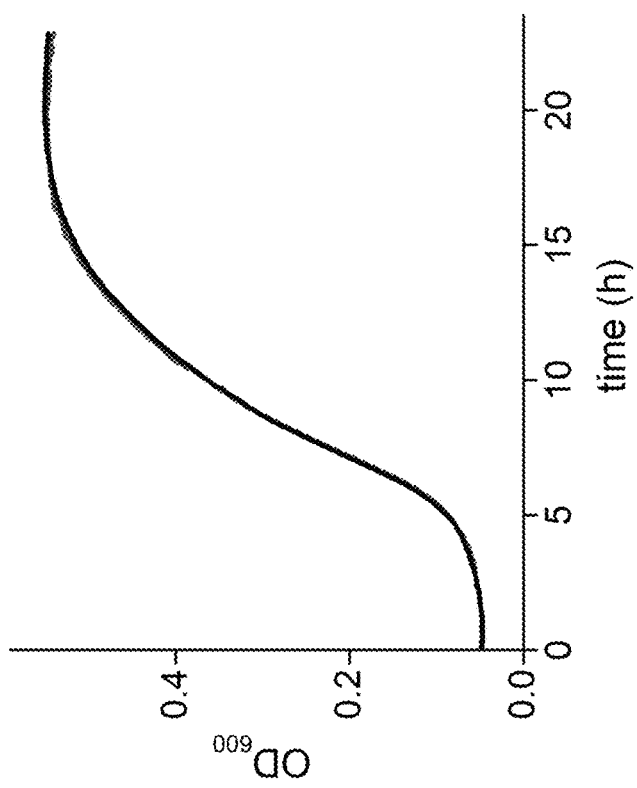

To confirm that attachment of X-ODN-1 does not affect the ability of the bacteria to grow and divide, the growth of TAMRA-ODN-1 (Compound 101) decorated bacteria was measured by optical density (OD) and compared to that of bare His-tagged bacteria. The growth kinetic curves were not affected by Compound 101 binding (FIG. 33D) indicating that the biomimetic cellular surface protein system does not affect cell division and survival.

Figure 33E:
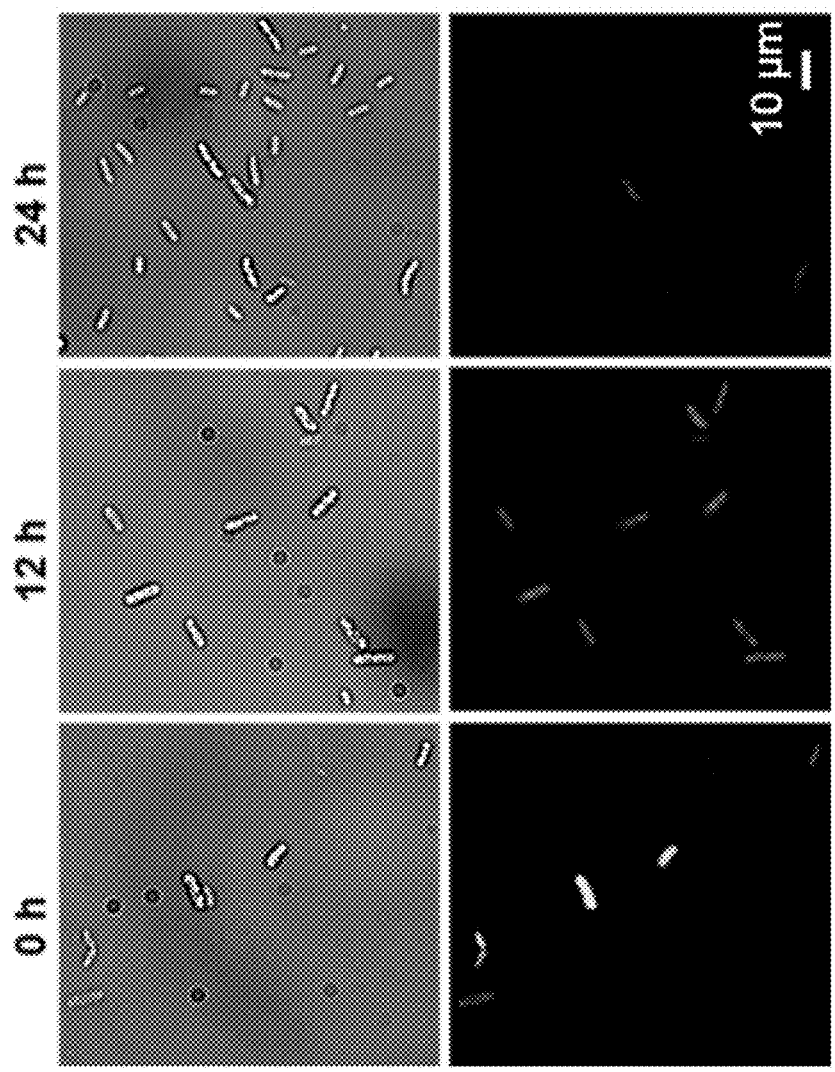

The ability of Compound 101 decorated bacteria to grow and divide was further demonstrated using fluorescence microscopy. Fluorescence microscopy revealed that the number of Compound 101 labeled cells increased with time, but that the fluorescence recorded in each cell decreased (FIG. 33E). These results were interpreted as a consequence of the Compound 101 molecules being divided between the daughter cells in each division.

Example 16

Reversible Modification of Membrane-Bound Synthetic Receptors Using Complementary Strands Objective: To reversibly modify the synthetic receptors by external molecules.

Figure 34A:
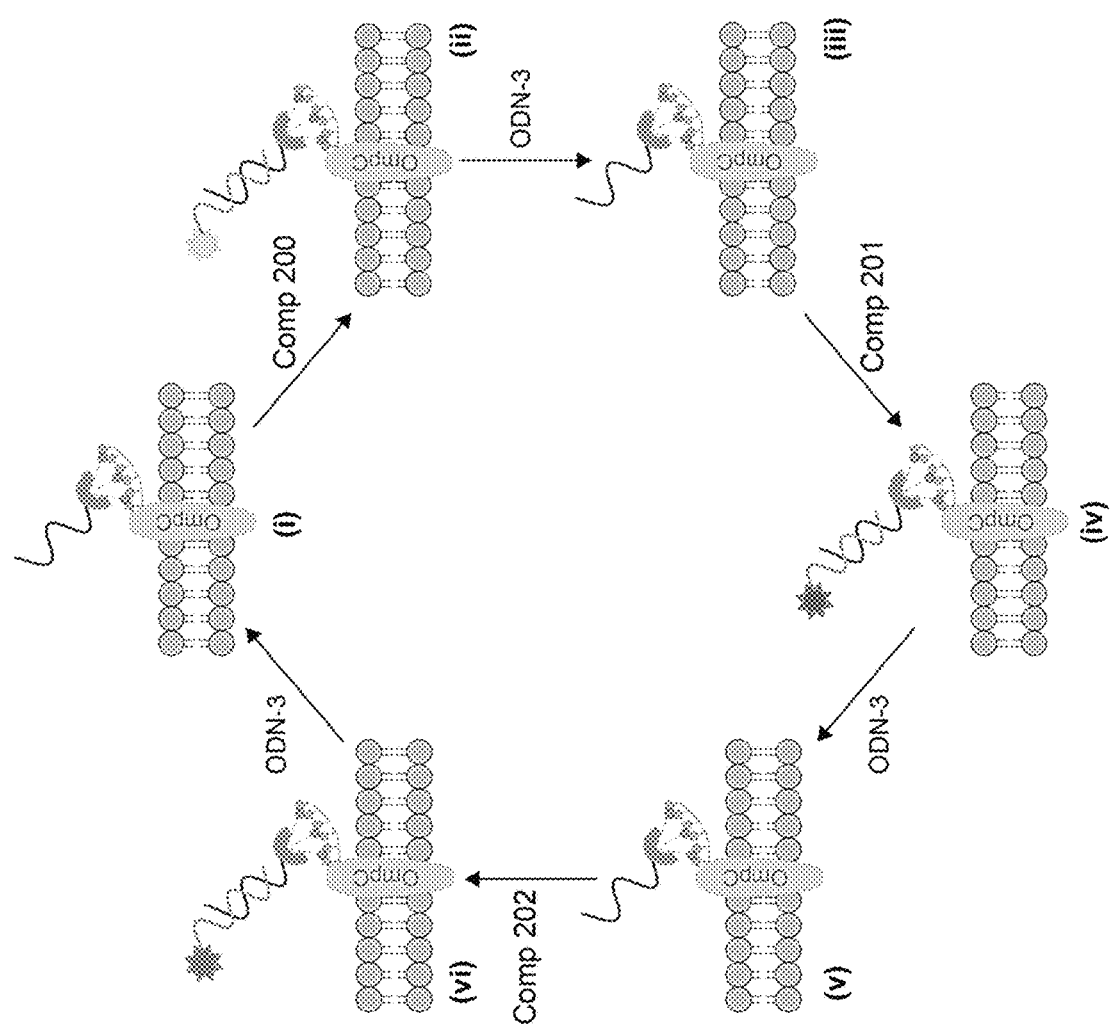
FIGS. 34A-34B show the reversible modification of membrane-bound synthetic receptor using complementary strands.

Methods: FIG. 34A schematically illustrates the experiments detailed herein. *E. Coli* ectopically expressing His-OmpC were first incubated with oligonucleotide X-ODN-1 (FIG. 34A, step (i)). Afterwards cells were incubated with a Compound 200, wherein ODN-2 is an oligonucleotide complementary to ODN-1 (FIG. 34A, step (ii)). Cells were then incubated with an ODN-3 oligonucleotide complementary to ODN-2 (FIG. 34A, step (iii)). Then cells were incubated with a Compound 201 (FIG. 34A, step (iv)). Next, cells were again incubated with an ODN-3 oligonucleotide (FIG. 34A, step (v)). Cells were finally incubated with a Compound 202 (FIG. 34A, step (vi)). Fluorescence was measured in all steps assessing the binding of TAMRA, Cy5, and FAM to the cell membranes.

Figure 34B:
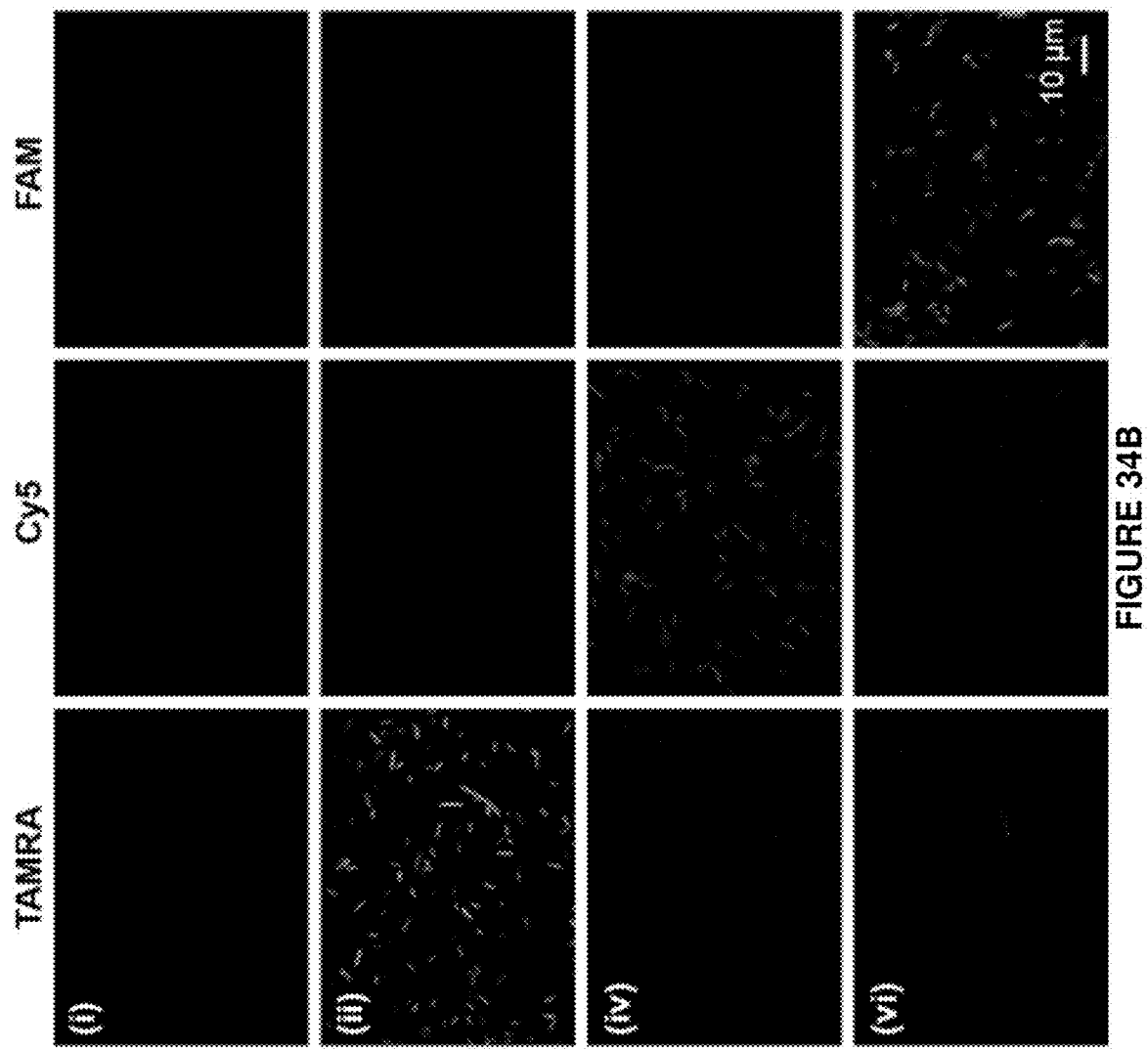

Results: Fluorescence microscopy revealed the presence of the corresponding dye (TAMRA, Cy5, and FAM) after bacteria were incubated with it. Further, the fluorescent emission disappeared after each time bacteria were incubated ODN-3 (FIG. 34B).

Example 17

Decorating Populations of Heterogenous Bacteria with Different Artificial Receptors Objective: To create a mixed population of bacteria, where each subpopulation bears a different sequences of ODN-1 and is modified by a different X-ODN-2 molecule.

Figure 35A:
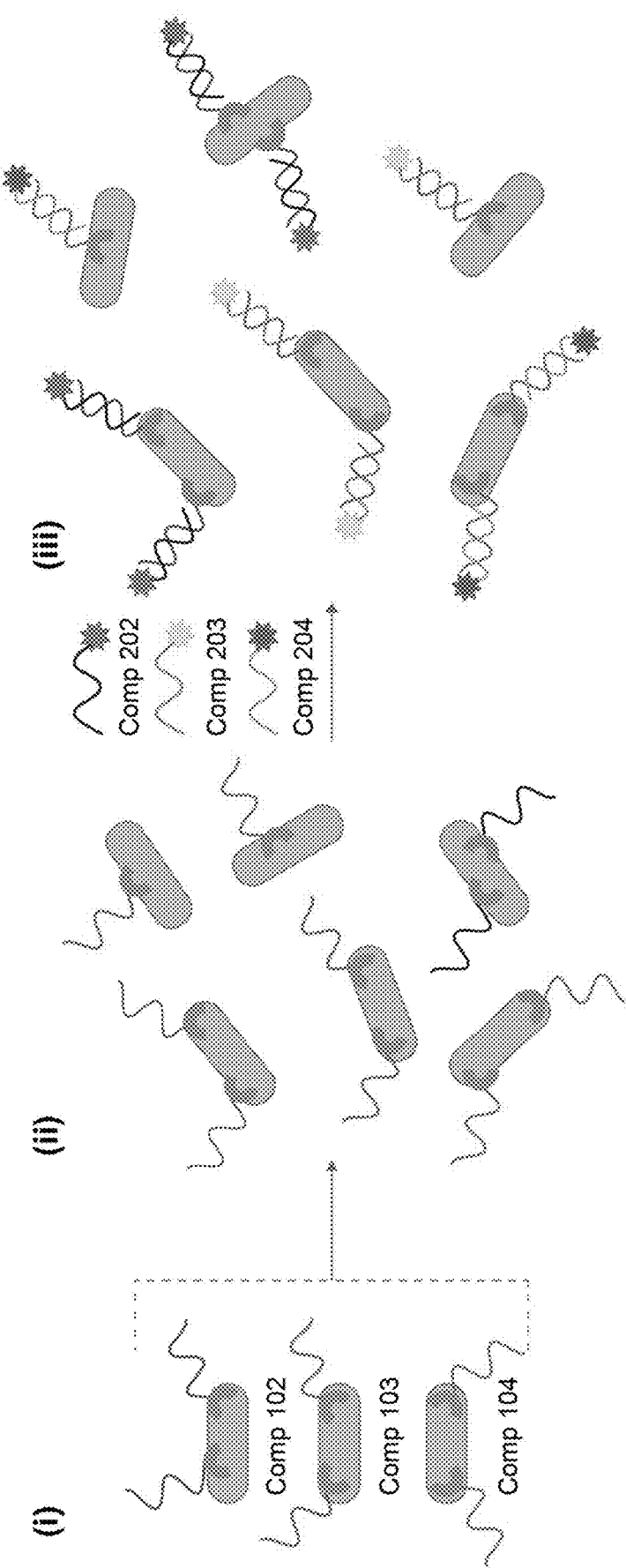
FIGS. 35A-35D show experimental modifications of bacterial cell surface luminescence.

Methods: Three populations of His-tagged *E. coli* were incubated with three different types of ODN-1 (Compound 102, Compound 103, and Compound 104; Compound 102, 103 and 104 respectively), which bared the same tri-NTA types but differed in their oligonucleotide sequences. Then, the three samples were combined and incubated with a mixture of three types of dye-labeled ODN-2 (Compound 202, Compound 200, and Compound 201 respectively); each of which was complementary to only one of the bacteria-bound ODN-1s (FIG. 35A). Bacteria were then analyzed by fluorescent microscopy and FACS.

Figure 35B:
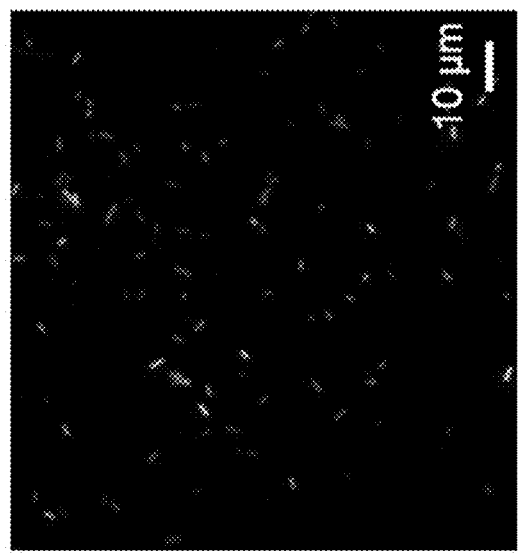
Figure 35C:
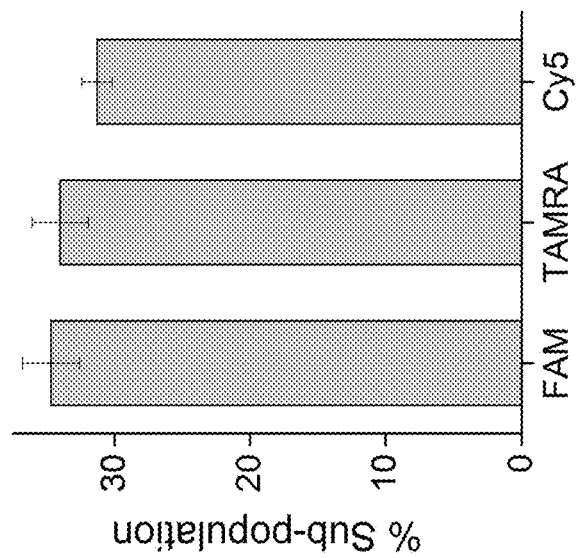
Figure 35D:
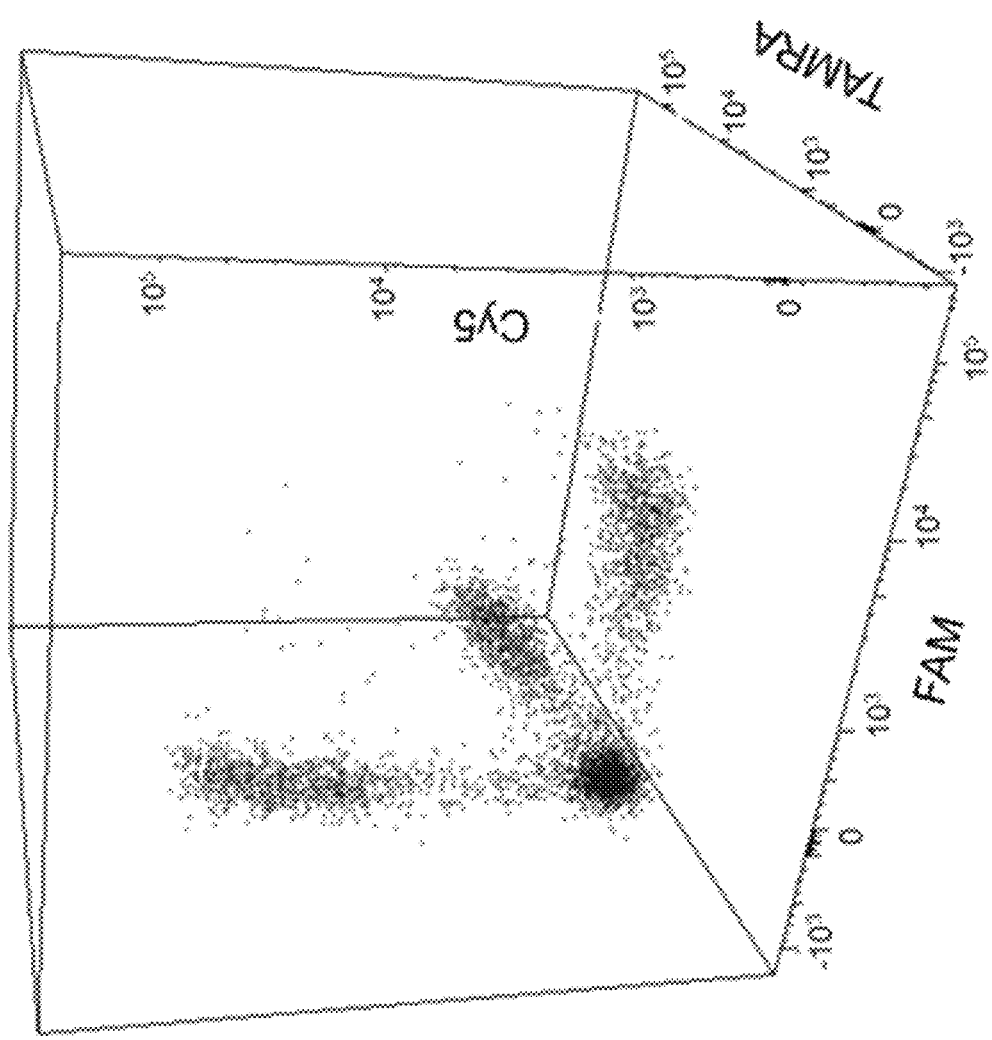

Results: Fluorescence microscopy (FIG. 35B) and FACS analysis (FIG. 35C) revealed the presence of three distinct groups of bacteria, each labeled with only one dye. Calculating the percentage of each population out of the total number of bacteria revealed a 1:1:1 ratio between the three sub-populations. (FIG. 35D) indicating that there is no strand swap between the three populations and that the sub-population modification occurs with very high selectivity.

Discussion: This experiment demonstrates a means to selectively label His-tagged proteins with different colors. Hence, one practical application that can be achieved with this approach is using the synthetic receptors to image specific proteins or cellular compartments in living cells. The advantage of using this method, over using other fluorescent probes that can bind and label short fusion peptides in living cells is the simplicity by which the fluorescent dye can be changed. Specifically, when DNA duplex-based fluorescent probes are used for live cell imaging there is no need to synthetize a new probe for each application. Instead, various different fluorescent dyes can be used for imaging, simply by preparing a wide range of fluorescently labeled ODN-2s from commercially available phosphoramidites and by using an automated DNA synthesizer.

Example 18

Endowment of New Properties to Bacteria by Artificial Receptors

Objective: To endow bacteria with unnatural and potentially useful properties by using the artificial receptor system.

Figures 36A, 36B, 36C:
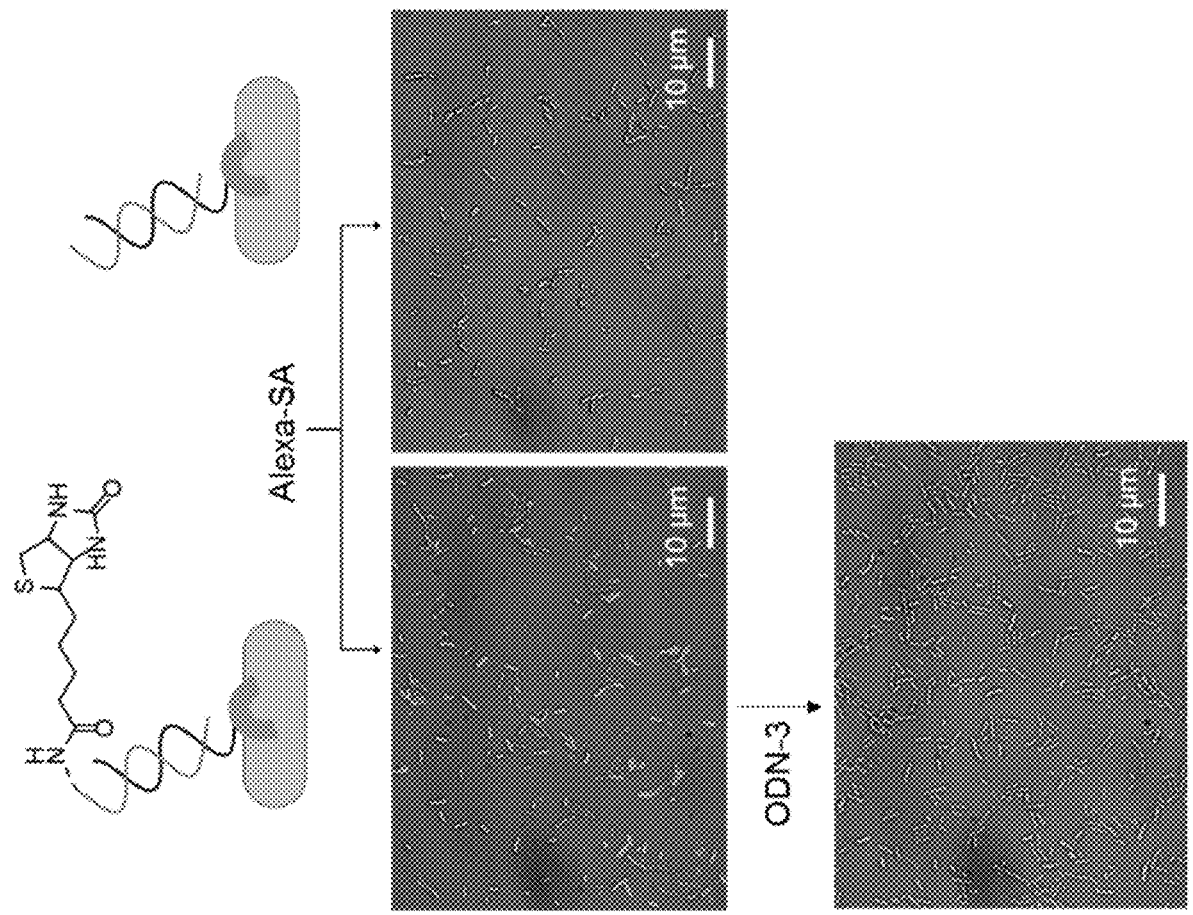
FIGS. 36A-36G show bacteria decorated to interact with proteins and cancer cells.

Methods: His-tagged *E. coli* were incubated with an ODN-1 molecule and afterwards with a biotin-ODN-2 molecule (Compound 205). Then, the cells were incubated with an Alexa 647-modified streptavidin (FIG. 36A). To verify specificity, the same experiment was performed with an ODN-2 molecule lacking biotin (FIG. 36A). Cells were then incubated with ODN-3 to detach ODN-2 from the cell membranes.

Results: Fluorescent microscopy revealed that bacteria became fluorescent only when Compound 205 was incorporated in the synthetic receptor (FIG. 36B), indicating specific binding of the protein to the bacterial membrane. The fluorescent signal disappeared when ODN-3 was added (FIG. 36C), indicating the reversibility of this process, and suggesting the possibility of regulating unnatural cell-protein-interactions using synthetic molecular signals as Compound 205 and ODN-3.

Example 19

Induction of Unnatural Cell-Cell Interactions by Artificial Receptors

Objective: To test whether synthetic receptor-protein interactions can mediate unnatural cell-cell interactions in general, and interactions resembling bacterial-mammalian cell interactions in particular.

Figures 36D, 36E, 36F:
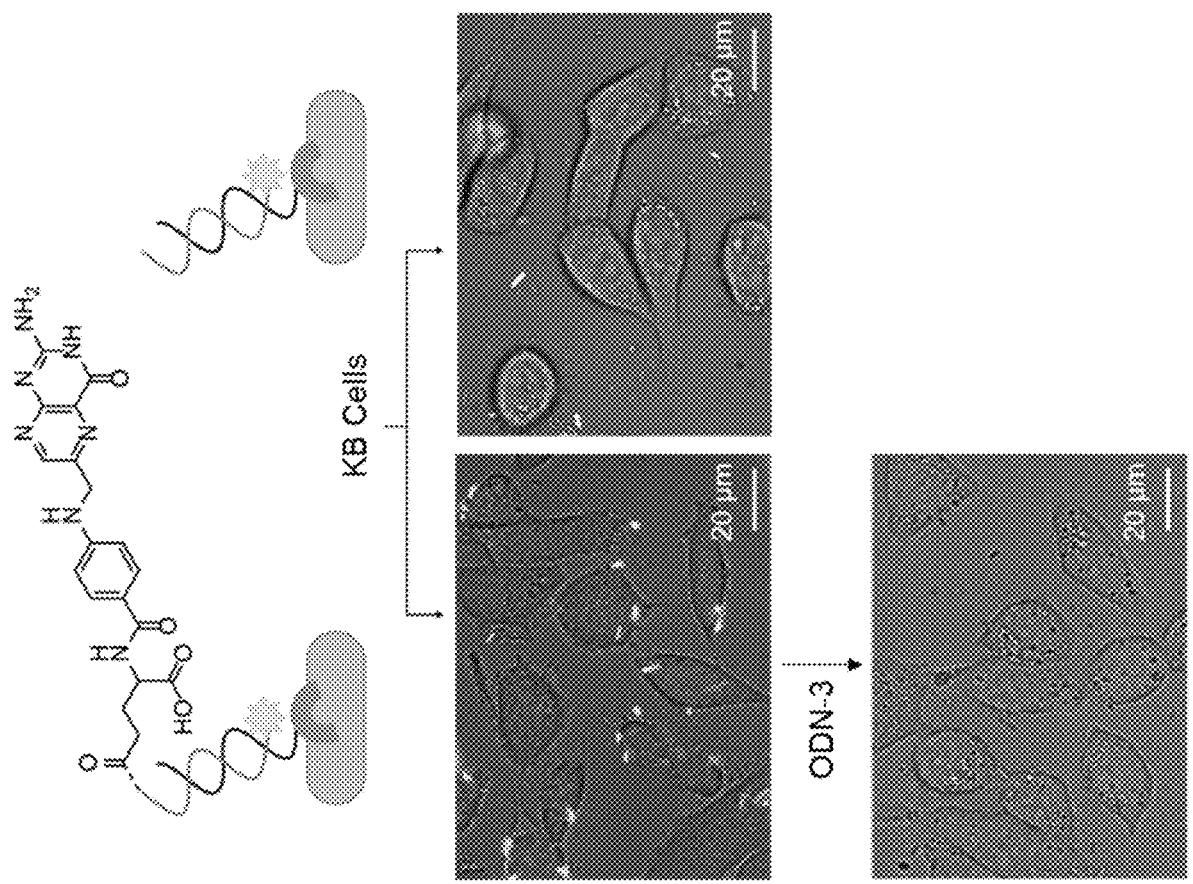

Methods: His-tagged bacteria were decorated with a DNA duplex containing Compound 101 and a folate-modified ODN-2 (compound 206). Then, bacteria were incubated with human epidermoid carcinoma KB cells overexpressing an extracellular folate receptor (FIG. 36D). As a control, KB cells were incubated with bacteria decorated with a similar TAMRA-labeled DNA duplex lacking the folate group (FIG. 36D). Cells were then incubated with ODN-3 to detach compound 206 from bacteria membranes.

Results: Fluorescent imaging revealed KB cells were labeled with glowing bacteria when incubated with compound 206 bound bacteria, but not with control bacteria (FIG. 36E). Incubation with ODN-3 fully detached compound 206 from the bacteria, thus releasing the bacteria from the KB cells (FIG. 36F).

Figure 36G:
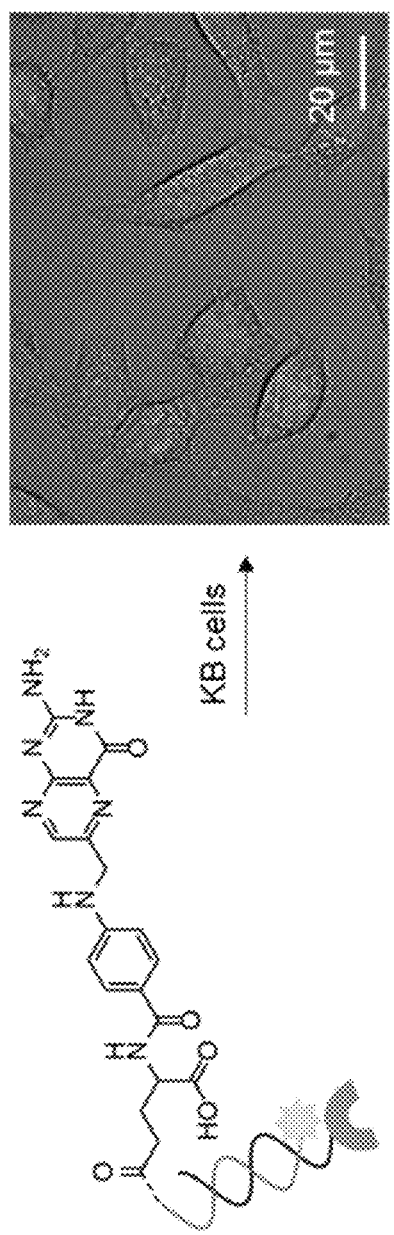

Incubation of KB cells with the DNA duplex alone (without His-tagged bacteria) did not result in fluorescent cancer cell labeling (FIG. 36G). This observation indicates that the bacteria scaffold itself plays a critical role in the interaction of folate with the folate receptor. One contribution of the bacteria to effective cell labeling is an increased avidity, which results from multivalent interactions between natural folate receptors on the KB cell and the folate-modified DNA duplexes on the surface of *E. Coli*. The second contribution is that each bacterial cell is decorated with multiple fluorophores, leading to a bright fluorescent labeling and consequently, to sensitive detection.

Discussion: These experiments provide evidence that unnatural cell-cell interactions can be both induced and disrupted using a biomimetic receptor system that responds to external molecular signals, such as compound 206 and ODN-3, respectively.

These experiments also demonstrate the relevance of this study to cell-based therapy. Here it is shown the ability to program bacterial cells to target cancer cells with increased avidity and selectively, by using synthetic cell-surface receptors to guide therapeutic cells to their targets. Further, the disruption of bacteria-cancer cell interactions with ODN-3 suggests that this approach can be used as an antidote to this class of therapeutics.

Example 20

Induction of Bacterial Adhesion to Abiotic Surfaces by Artificial Receptors

Objective: To test whether synthetic receptor can provide bacteria with the ability to interact selectively with solid substrates.

Figure 37A:
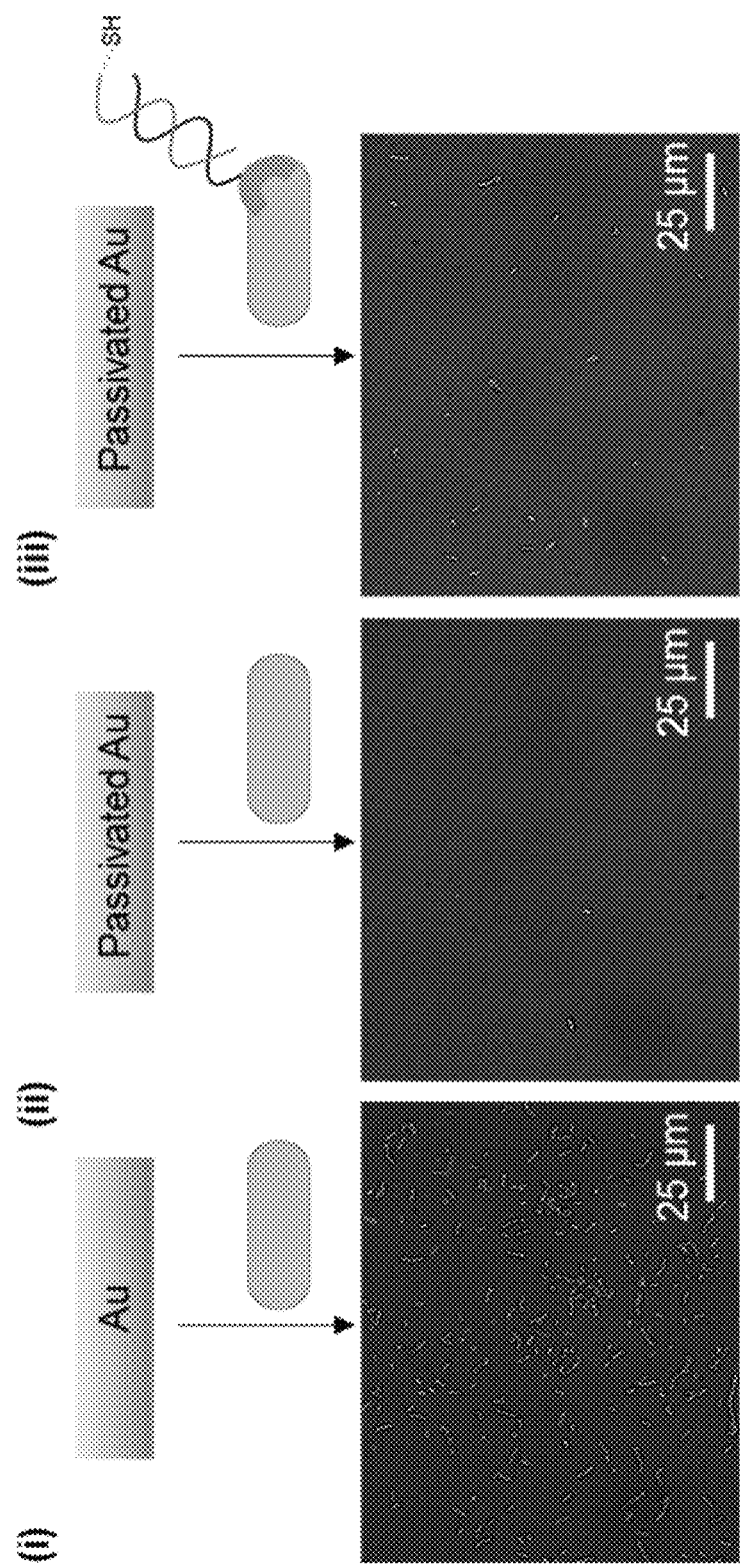
FIGS. 37A-37B show bacteria decorated to interact to a non-biological surface.

Methods: His-tagged bacteria were decorated with a duplex assembled from ODN-1 and HS-ODN-2 (Compound 207), namely, an ODN-2 that is appended with a thiol group. HS is known to have high affinity to gold. In the following step, unmodified His-tagged bacteria and thiol-modified His-tagged bacteria (FIG. 37A) were incubated with a gold substrate that was previously passivated with (11-mercaptoundecyl)tetra(ethylene glycol) to prevent non-specific bacterial adhesion. Gold surfaces were observed after 15 min incubation. Cells were then incubated with ODN-3 to detach Compound 207 from bacteria membranes.

Figure 37B:
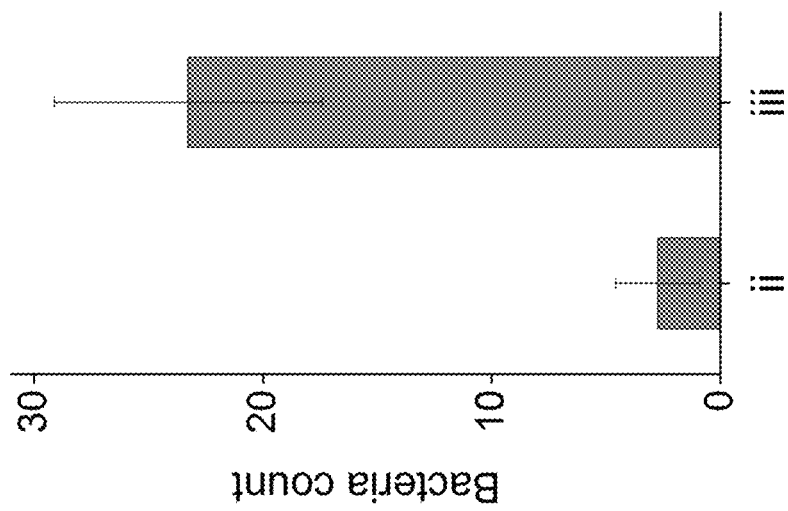

Results: Microscopy revealed an increase of about 8.5-fold in the attachment of thiol-modified bacteria to the gold substrate compared with the control (FIG. 37B). This indicates that the ODN-1:Compound 207 duplex acts as an unnatural adhesin that can mediate specific binding of bacteria to solid support. The selectivity of these synthetic adhesin to gold was further demonstrated by incubating the thiol-modified bacteria with the gold substrate in the presence of ODN-3, which led to a significant decrease in the number of surface-bound His-tagged bacteria.

Discussion: In the context of biomimicry, disruption of adhesion owing to changes that occur on the synthetic receptors resembles the way post-translational modification of natural adhesins are used by bacteria to disrupt adhesion processes. The unnatural adhesins presented herein can be used to have a precise control of the way bacteria are attached to solid supports. For example, changing the length of the DNA linkers or attaching the modified bacteria to more complex DNA architectures (such as DNA Origami/nanotechnology type structures) on the surface may alter the binding properties of the bacteria. Further, the approach presented herein can be used to generate engineered living materials (ELMs) made of controlled bacterial assemblies.

Example 21

Induction of Luminescence in Bacteria by Artificial Receptors

Background: Reversible switching of luminescence in response to the binding of cell surface proteins to extracellular molecular signals is a fundamental property of serval bacterial strains. A key principle underlying natural bacterial luminescence processes is the selective interaction between peptide autoinducers (AI) and their protein receptors, which enables them to trigger the emission of specific bacterial strains in complex biological mixtures. According to this invention, the ability to selectively label specific bacteria (modified with a unique ODN-1) in complex mixtures is described.

Objective: To control bacterial cell luminescence using biomimetic receptor systems (using super resolution microscopy).

Figure 38B:
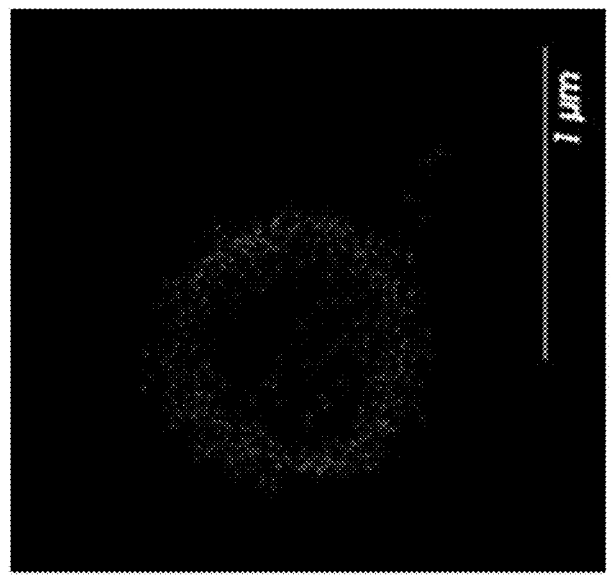
FIGS. 38A-38B show super-resolution images of His-tagged bacteria decorated with an ODN-1:Compound 201 duplex.
Figure 38A:
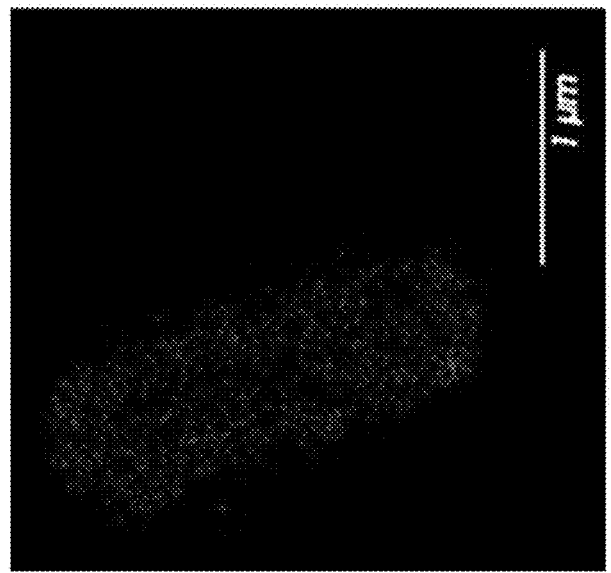

Methods: Due to the small size of bacteria, super resolution (SR) microscopy was used to visualize *E. Coli*'s membrane with super resolution (SR). This was achieved by combining ODN-1 with a commercially available ODN-2 (Cy5-ODN-2; Compound 201) bearing a Cy5 dye, which is compatible with stochastic optical reconstruction microscopy (STORM). SR images of individual bacteria revealed that DNA duplex-based label clearly outlines the bacterial cell's borders (FIG. 38A). Imaging of the transverse cut of the bacteria confirms that only the outer membrane of the bacteria is labeled, namely, that the synthetic receptors are exposed on the bacterial surface and are not internalized (FIG. 38B).

Example 22

Discussion

The Examples disclosed above show a number of unexpected advantages as shown in the following examples: 1) The His-OmpC molecule can be stably expressed in *E. coli*. 2) The hexa-histidine moiety does not perturb the function of cell or of the synthetic agent due to its small size. 3) The His-tag can be efficiently targeted by NTA-Ni (II) complexes, including complexes of ODN-NTA conjugates. 4) The binding of His-OmpC to X-ODN-1 can be efficiently released by incubating the cells with a Ni (II) chelator, as EDTA. 5) The use of Y-ODN-2 circumvents the complexity of synthesizing the oligonucleotide X-ODN-1 which is attached on one end to the Tri-NTA moiety, and on the other to a synthetic agent. 6) The activity of the synthetic agent of Y-ODN-2 can be effectively terminated by incubating the cells with ODN-3.

The advantages of using ODN-small molecule conjugates as synthetic protein binders include the ability to precisely control the orientation, distances and valency of their binding units, as well as the ability to dynamically change their structure, which provides a means to regulate protein functions in real time. The Examples provided herein show that when synthetic proteins binders of this class are attached to cell's surfaces, their regulatory effect can be extended from the protein level to the cellular level. Specifically, on the cell' membrane such systems can act as artificial cell surface receptors that can be reversibly modified and hence, can provide the cells with 'programmable' properties. In this model system, metal coordination and DNA-hybridization were used to direct the formation of artificial receptors on a short peptide tag fused to an outer membrane protein on the surface of *E. coli*. Owing to the high selectivity and reversibility of the self-assembly processes, a biomimetic cell surface receptor system with unique features was obtained. For example, the ability to control reversibly the type of membrane-bound receptors and their local concentration levels with external molecular signals demonstrates the possibility of imitating dynamic processes that occur of cell surface proteins, such as changes in their expression level or post-translational modification. It was also shown that these changes can provide the bacteria with new properties such as an ability to glow with different colors, adhere to surfaces, and interact with proteins or cells; properties that may eventually be used in developing cell imaging methods, living materials and devices, or cell-based therapeutics, respectively. In light of these potential applications, the studies presented herein guide the development of additional biomimetic cell surface receptors, with which living cells could be 'programmed' to preform diverse sets of functions.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A compound, represented by the structure of formula XI:

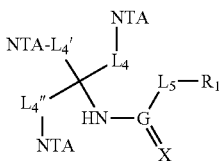

XI wherein
R₁ is selected from: H, azide, amine, $C_2$-$C_6$ alkynyl, $C_2$-$C_6$ alkenyl, thioester, disulfide, maleimide, biotin, carboxyl, thiol, triazole, alkylamide, ketone, aldehyde and carbamate;

G=X is absent, or is $CH_2$, C=O, C(O)NH, C=S, C(S)NH, C(O)O, S=O or $SO_2$;

$L_4$, $L_4'$, and $L_4''$ are identical, and each is represented by the structure

**—$(CH_2)_n$—NHCO—$(CH_2)_m$—O—$(CH_2)_l$—*;

wherein n, m and l are each independently an integer between 1-6; and wherein * indicates point of attachment to the tertiary carbon moiety and ** indicates a point of attachment to NTA;

$L_5$ is absent, or is a substituted or unsubstituted linear or branched alkyl chain of 1-50 carbon atoms (e.g. ethylene: —$CH_2$—$CH_2$—), substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms or any combination thereof; and NTA is nitrilotriacetic acid or a protected derivative thereof.

2. The compound of claim 1, wherein
R₁ is H or is selected from the group consisting of:

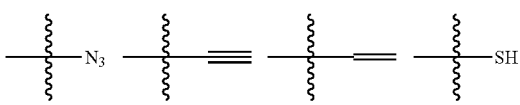

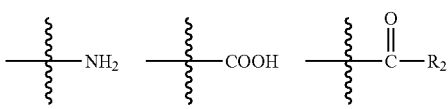

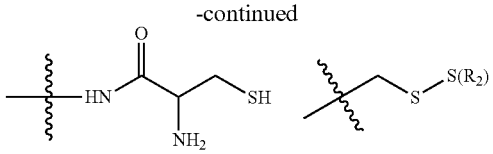

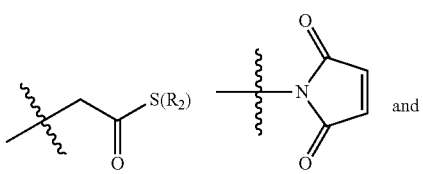

and

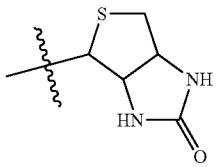

and wherein
R₂ is hydrogen, substituted or unsubstituted linear or branched $C_1$-$C_{12}$ alkyl, substituted or unsubstituted linear or branched $C_1$-$C_{12}$ arylalkyl or benzyl.

3. The compound of claim 1, wherein said protected derivative of nitrilotriacetic acid is represented by the structure of fragment (B):

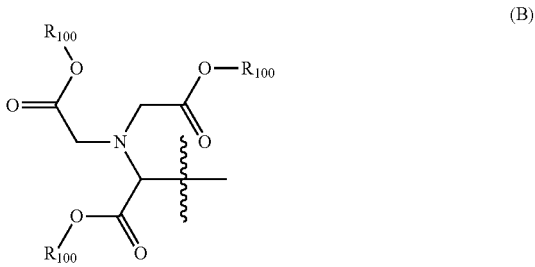

(B)

wherein $R_{100}$ is a substituted or unsubstituted linear, branched or cyclic $C_1$-$C_{10}$ alkyl, including: tert-butyl, ethyl, methyl, neo-pentyl, cyclopropyl, and cyclohexyl; benzyl or a substituted or unsubstituted aryl.

4. The compound of claim 1, complexed with at least one metal ion.

5. The compound of claim 4, wherein the metal ion is Ni(II), Co(II), Co(III) or any combination thereof.

6. The compound of claim 5, complexed with three Ni(II) ions.

7. The compound of claim 1, represented by the structure of formula XIII:

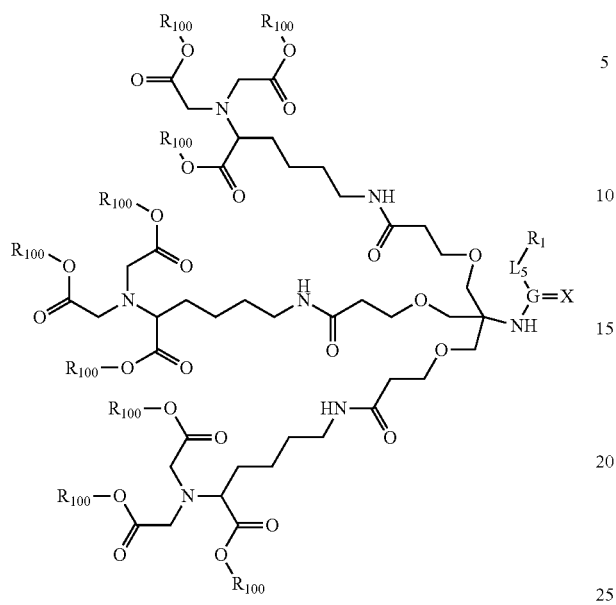

XIII wherein

R_{100} is H or a protecting group.

8. The compound of claim 7, wherein $R_{100}$ is H or a substituted or unsubstituted linear, branched or cyclic $C_1$-$C_{10}$ alkyl.

9. The compound of claim 7, wherein $R_{100}$ is tert-Bu or H; G=X is absent or C=O; $L_5$ is absent or ethylene; $R_1$ is H or maleimide; or any combination thereof.

10. The compound of claim 1, represented by the following structure:

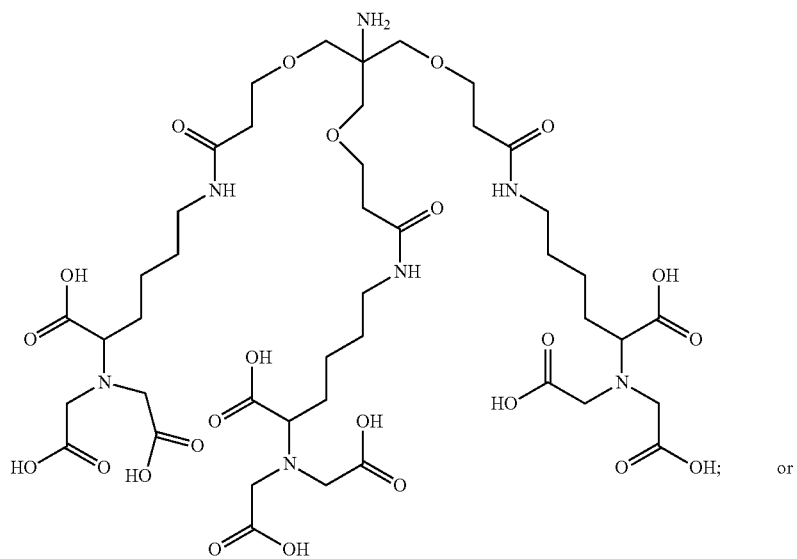

Compound 312 or

Compound 311

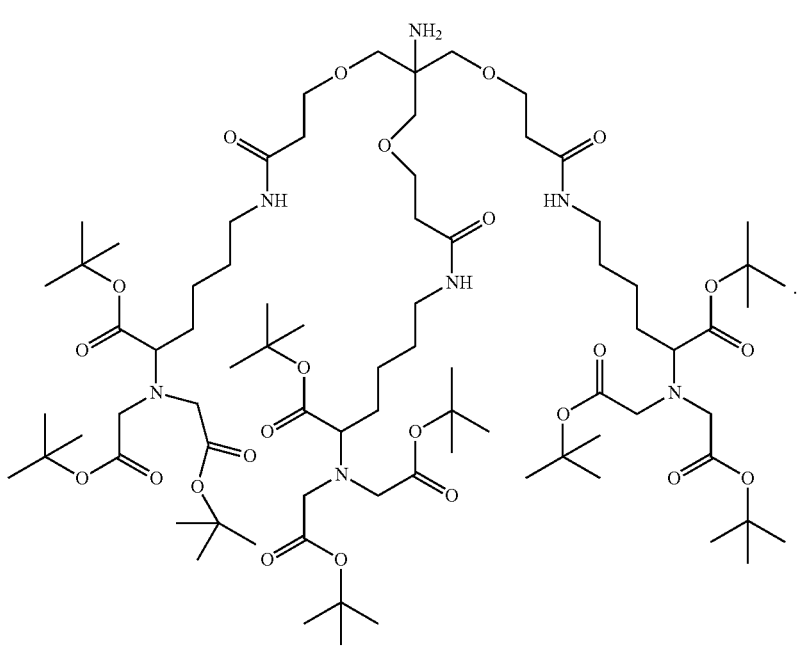

11. The compound of claim 1, represented by the structure of formula XV:

XV

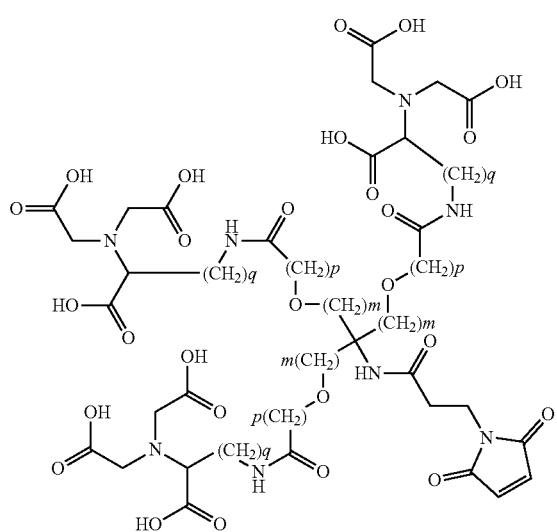

wherein m, p and q are each independently an integer number between 1 and 6.

12. The compound of claim 1, wherein the compound is further coupled via the $R_1$ moiety to an oligonucleotide, a labeling moiety, a peptide, a protein, a small molecule, a solid support, directly or via a first linker.

13. The compound of claim 12, wherein the first linker comprises a phosphate moiety, a PEG moiety, an alkyl moiety, a thioalkyl moiety or any combination thereof.

14. The compound of claim 12, complexed with at least one metal ion selected from: Ni(II), Co(II) and Co(III).

15. The compound of claim 14, wherein said oligonucleotide is DNA or RNA, and said labeling moiety is a fluorescent dye.

16. The compound of claim 14, wherein $R_1$ is an oligonucleotide and is further bound to a labeling moiety, directly or via a third linker.

17. The compound of claim 16, wherein the third linker comprises a phosphate moiety, a PEG moiety, an alkyl moiety, a thioalkyl moiety or any combination thereof.

18. The compound of claim 16, wherein the compound is represented by the structure of formula H:

H

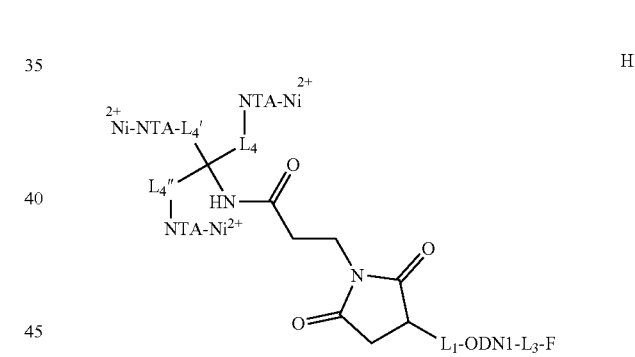

wherein
F is the labeling moiety or is absent and said labeling moiety is a dye or a dye derivative;
$L_3$ is the third linker or is absent;
ODN1 is the oligonucleotide; and
$L_1$ is the first linker or is absent; and
NTA is nitrilotriacetic acid or a protected derivative thereof; and
$L_4$, $L_4'$ and $L_4''$ are as defined in claim 1.

19. The compound of claim 18, wherein F is a fluorescent dye.

20. The compound of claim 18, wherein F is selected from a group comprising dansyl, fluorescein (6-FAM), FAM, cyanine dyes (e.g. Cy3, Cy5, SCy3, SCy5), sulfoindocyanine, nile red, rhodamine, perylene, fluorenyl, coumarin, 7-methoxycoumarin (Mca), dabcyl, NBD, Nile blue, TAMRA, BODIPY, FITC, Thiazole orange, Quinoline blue, Thiazole red, or derivative thereof and $L_1$ and $L_3$ each independently comprises a phosphate moiety, a PEG moiety, an alkyl moiety, a thioalkyl moiety or any combination thereof.

21. The compound of claim 18, represented by the following structures:
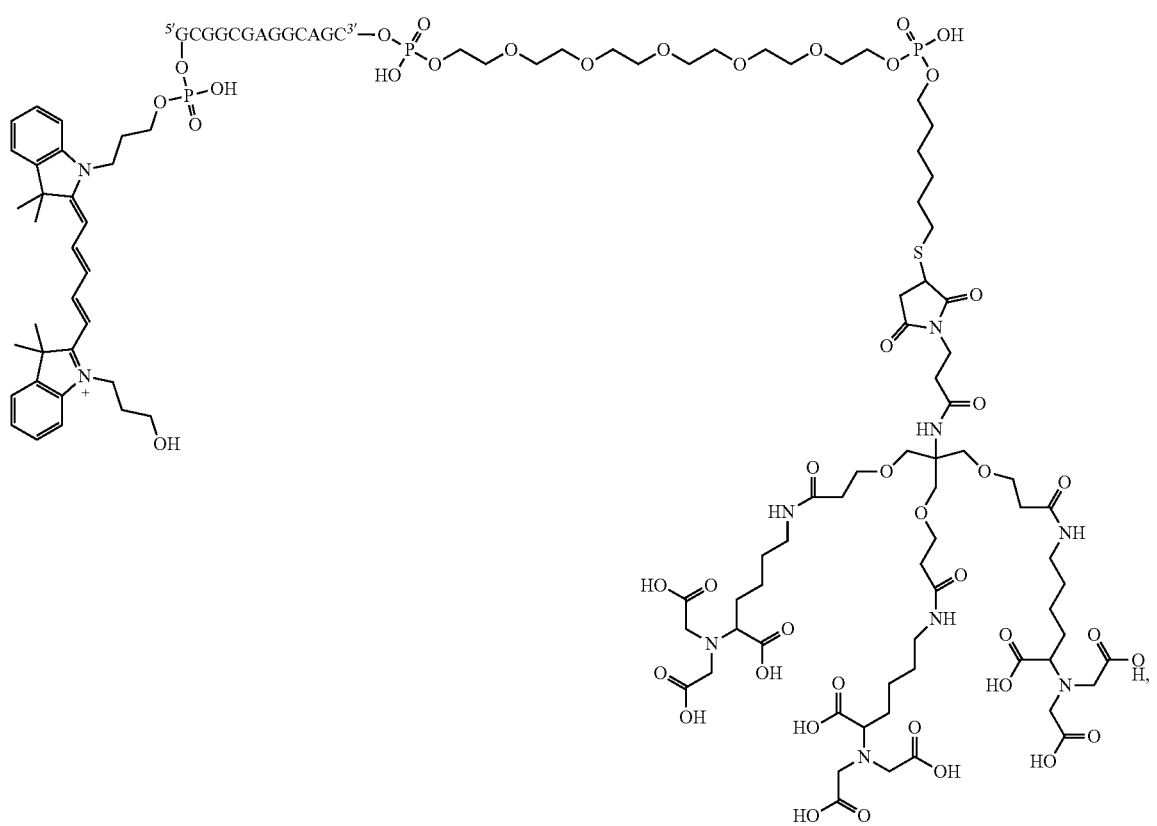
Compound 100
[CY5-ODN-1]

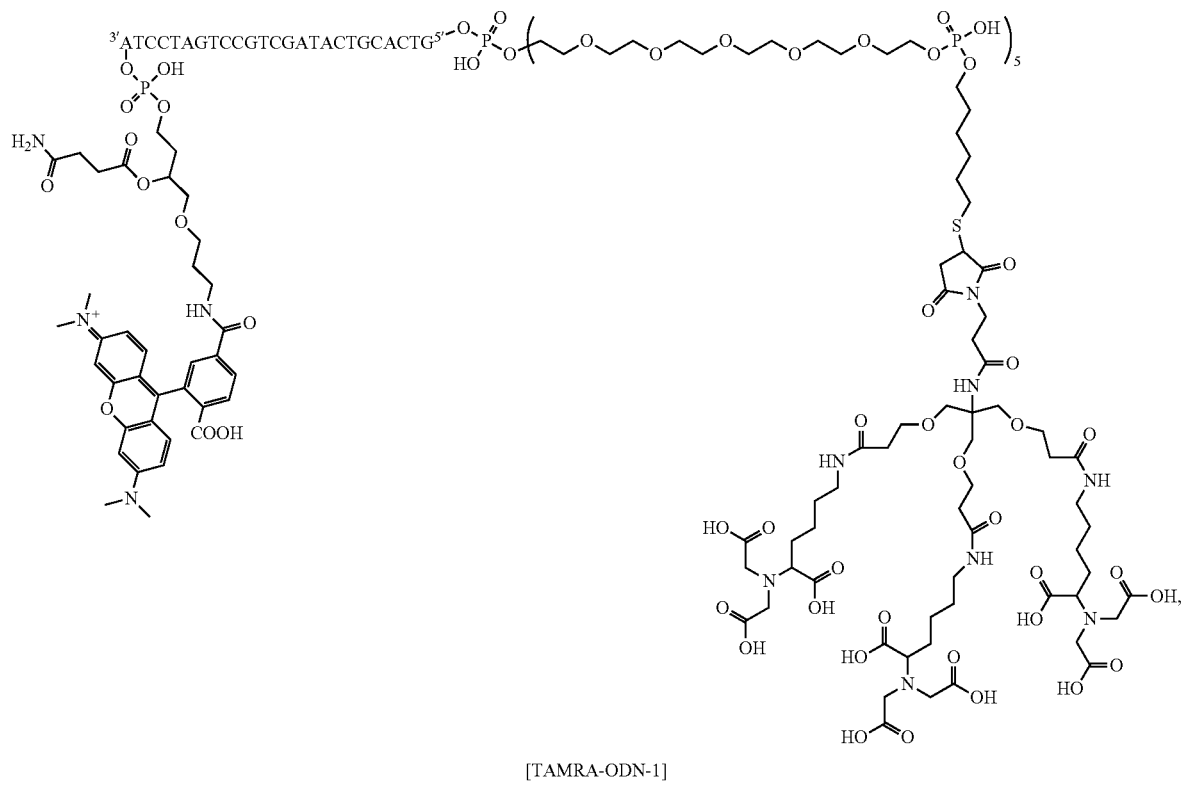
[TAMRA-ODN-1]
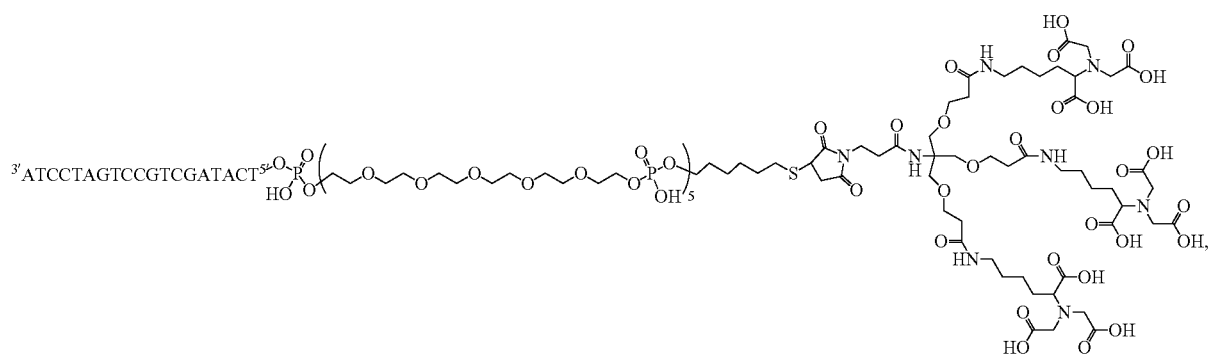
[ODN-1a]

-continued
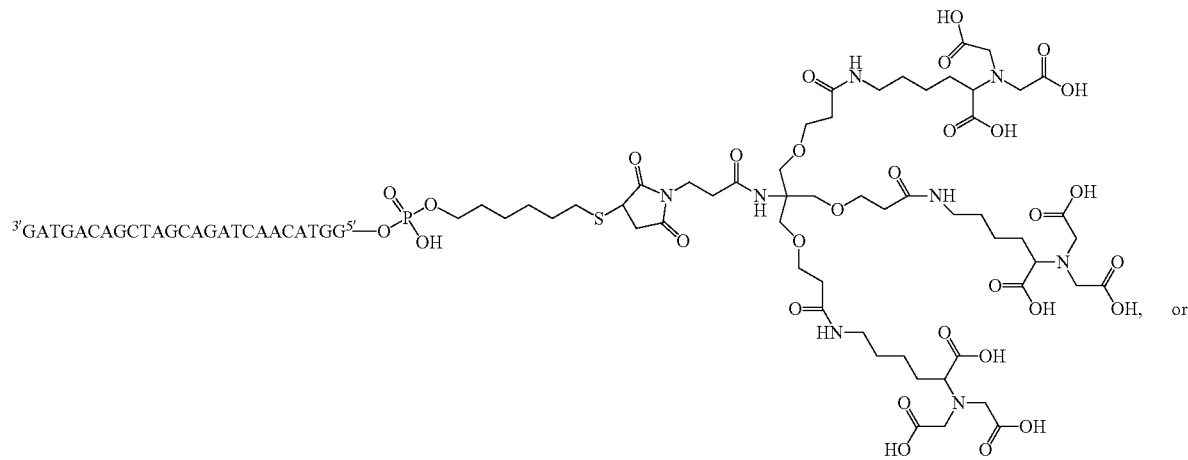
Compound 103
[ODN-1b]
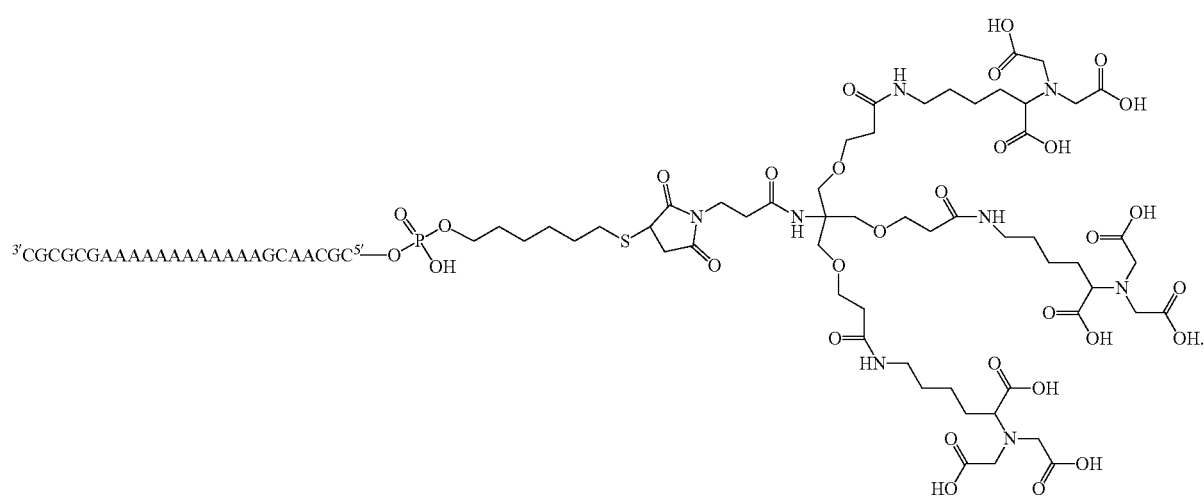
Compound 104
[ODN-1c]

22. The compound of claim 12, wherein the compound is coupled via the $R_1$ moiety with a labeling moiety directly.

23. The compound of claim 22, wherein the compound is represented by the structure of formula XXI:

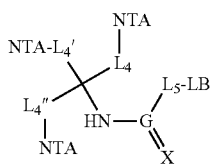

XXI wherein

LB is a labeling moiety; and $L_4$, $L_4'$, and $L_4''$, $L_5$, G=X, and NTA are as defined in claim 1.

24. The compound of claim 23, represented by the structure of formula XXIII:

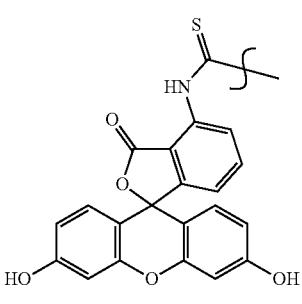

XXIII

25. The compound of claim 22, wherein LB is a fluorescent agent, fluorescent dye, fluorophore, solvatochromic dye, chemiluminescent agent, chromogenic agent, quenching agent, radionucleotide, or a magnetic particle.

26. The compound of claim 25, wherein the fluorescent dye is selected from: dansyl, fluorescein (6-FAM), FAM, cyanine dyes (e.g. Cy3, Cy5, SCy3, SCy5), sulfoindocyanine, nile red, rhodamine, perylene, fluorenyl, coumarin, 7-methoxycoumarin (Mca), dabcyl, NBD, Nile blue, TAMRA, BODIPY, FITC, Thiazole orange, Quinoline blue, Thiazole red, or derivative thereof or a derivative thereof.

27. The compound of claim 26, wherein the compound is represented by the structure of the following compounds:

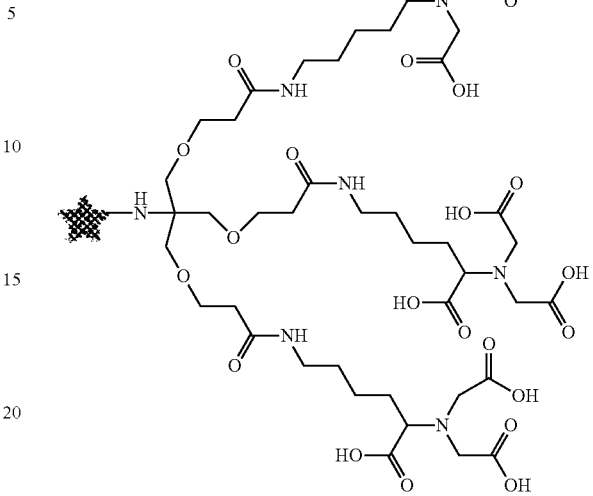

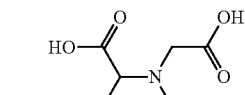

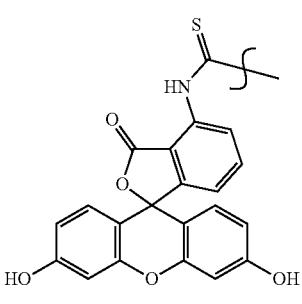

314

FITC (485/520 nm)

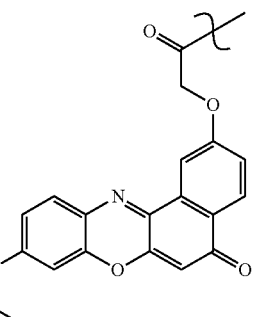

315

Nile Red (560/630 nm)

-continued

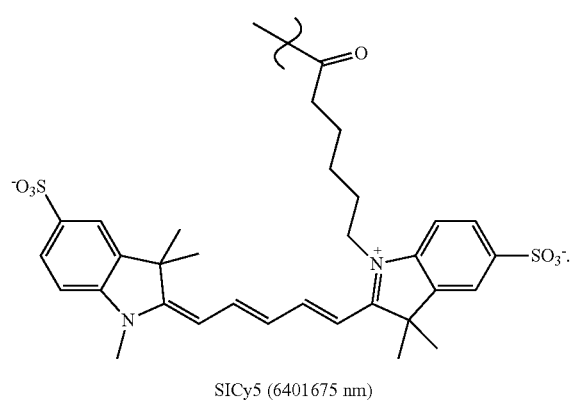

SICy5 (640/675 nm)

28. A fluorescent probe that can selectively label a His-tagged polypeptide, said fluorescent probe comprising the compound of claim 22 complexed to at least one metal ion selected from the group consisting of Ni(II), Co(II) and Co(III).

29. The fluorescent probe of claim 28, wherein the compound is complexed to three Ni(II) ions, wherein the labeling moiety is a fluorescent dye, or combination thereof.

30. The fluorescent probe of claim 29, wherein said fluorescent dye is selected from a group comprising dansyl, fluorescein (6-FAM), FAM, cyanine dyes (e.g. Cy3, Cy5, SCy3, SCy5), sulfoindocyanine, nile red, rhodamine, perylene, fluorenyl, coumarin, 7-methoxycoumarin (Mca), dabcyl, NBD, Nile blue, TAMRA, BODIPY, FITC, Thiazole orange, Quinoline blue, Thiazole red, or derivative thereof.

31. The compound of claim 14, wherein said compound specifically binds to an oligohistidine sequence (His-tag) of a His-tagged polypeptide to generate a fluorescent signal.

32. The compound of claim 31, wherein the His-tag sequence consists of at least 6 histidines.

33. A method for imaging a His-tagged polypeptide of interest within a cell, said method comprises:
   a. expressing said His-tagged polypeptide in a recombinant cell;
   b. incubating said recombinant cell with a fluorescent probe according to claim 28; and
   c. visualizing the fluorescence emission of said fluorescent probe.

34. A method for measuring gene expression of a His-tagged polypeptide of interest in a cell, said method comprises the steps of:
   a. expressing a His-tagged polypeptide in a cell;
   b. incubating said cell with a fluorescent probe according to claim 28; and
   c. measuring the fluorescence of said cell;
   wherein detection of a fluorescent signal is dependent on the formation of a His-tagged polypeptide:fluorescent probe complex.

* * * * *

SEQUENCE LISTING

<160> NUMBER OF SEQ ID NOS: 26

<210> SEQ ID NO 1
<211> LENGTH: 13
<212> TYPE: DNA
<213> ORGANISM: Artificial Sequence
<220> FEATURE:
<223> OTHER INFORMATION: CY5-ODN-1

<400> SEQUENCE: 1
gcggcgaggc agc                                                      13

<210> SEQ ID NO 2
<211> LENGTH: 25
<212> TYPE: DNA
<213> ORGANISM: Artificial Sequence
<220> FEATURE:
<223> OTHER INFORMATION: TAMRA-ODN-1

<400> SEQUENCE: 2
gtcacgtcat agctgcctga tccta                                         25

<210> SEQ ID NO 3
<211> LENGTH: 19
<212> TYPE: DNA
<213> ORGANISM: Artificial Sequence
<220> FEATURE:
<223> OTHER INFORMATION: ODN-1 and ODN-1a

<400> SEQUENCE: 3
tcatagctgc ctgatccta                                                19

-continued

```
<210> SEQ ID NO 4
<211> LENGTH: 25
<212> TYPE: DNA
<213> ORGANISM: Artificial Sequence
<220> FEATURE:
<223> OTHER INFORMATION: ODN-1b

<400> SEQUENCE: 4
ggtacaacta gacgatcgac agtag                                              25

<210> SEQ ID NO 5
<211> LENGTH: 25
<212> TYPE: DNA
<213> ORGANISM: Artificial Sequence
<220> FEATURE:
<223> OTHER INFORMATION: ODN-1c

<400> SEQUENCE: 5
cgcaacgaaa aaaaaaaaag cgcgc                                              25

<210> SEQ ID NO 6
<211> LENGTH: 25
<212> TYPE: DNA
<213> ORGANISM: Artificial Sequence
<220> FEATURE:
<223> OTHER INFORMATION: TAMRA-ODN-2

<400> SEQUENCE: 6
taggatcagg cagctatgac gtgac                                              25

<210> SEQ ID NO 7
<211> LENGTH: 25
<212> TYPE: DNA
<213> ORGANISM: Artificial Sequence
<220> FEATURE:
<223> OTHER INFORMATION: ODN-2 or ODN-2a

<400> SEQUENCE: 7
taggatcagg cagctatgac gtgac                                              25

<210> SEQ ID NO 8
<211> LENGTH: 24
<212> TYPE: DNA
<213> ORGANISM: Artificial Sequence
<220> FEATURE:
<223> OTHER INFORMATION: ODN-2b

<400> SEQUENCE: 8
tactgtcgat cgtctagttg tacc                                               24

<210> SEQ ID NO 9
<211> LENGTH: 25
<212> TYPE: DNA
<213> ORGANISM: Artificial Sequence
<220> FEATURE:
<223> OTHER INFORMATION: ODN-2c

<400> SEQUENCE: 9
gcgcgctttt tttttttcg ttgcg                                               25

<210> SEQ ID NO 10
<211> LENGTH: 25
<212> TYPE: DNA
<213> ORGANISM: Artificial Sequence
<220> FEATURE:
<223> OTHER INFORMATION: ODN-3
```

-continued

<400> SEQUENCE: 10
gtcacgtcat agctgcctga tccta                                              25

<210> SEQ ID NO 11
<211> LENGTH: 54
<212> TYPE: DNA
<213> ORGANISM: Artificial Sequence
<220> FEATURE:
<223> OTHER INFORMATION: OmpC_FpET21

<400> SEQUENCE: 11
tttgtttaac tttaagaagg agatatacat atgaaagtta agtactgtc cctc               54

<210> SEQ ID NO 12
<211> LENGTH: 52
<212> TYPE: DNA
<213> ORGANISM: Artificial Sequence
<220> FEATURE:
<223> OTHER INFORMATION: OmpC_RpET21

<400> SEQUENCE: 12
ttcctttcgg gctttgttag cagccggatc ttagaactgg taaaccagac cc                52

<210> SEQ ID NO 13
<211> LENGTH: 11
<212> TYPE: PRT
<213> ORGANISM: Artificial Sequence
<220> FEATURE:
<223> OTHER INFORMATION: OmpC-(6His)1

<400> SEQUENCE: 13

Ser Ala Gly His His His His His His Gly Thr
1               5                   10

<210> SEQ ID NO 14
<211> LENGTH: 48
<212> TYPE: DNA
<213> ORGANISM: Artificial Sequence
<220> FEATURE:
<223> OTHER INFORMATION: OmpC_His1

<400> SEQUENCE: 14
catcatcacc atggtacctc taaaggtaaa aacctgggtc gtggctac                     48

<210> SEQ ID NO 15
<211> LENGTH: 60
<212> TYPE: DNA
<213> ORGANISM: Artificial Sequence
<220> FEATURE:
<223> OTHER INFORMATION: OmpC_His1R

<400> SEQUENCE: 15
atggtgatga tgatgatgac ccgcggaggt accatggtga tgatggtgat gacccgcgga        60

<210> SEQ ID NO 16
<211> LENGTH: 22
<212> TYPE: PRT
<213> ORGANISM: Artificial Sequence
<220> FEATURE:
<223> OTHER INFORMATION: OmpC-(6His)2

<400> SEQUENCE: 16

Ser Ala Gly His His His His His His Gly Thr Ser Ala Gly His His
1               5                   10                  15

His His His His Gly Thr

<210> SEQ ID NO 17
<211> LENGTH: 40
<212> TYPE: DNA
<213> ORGANISM: Artificial Sequence
<220> FEATURE:
<223> OTHER INFORMATION: OmpC_His2FInverse

<400> SEQUENCE: 17
caccatcacg gtacctctaa aggtaaaaac ctgggtcgtg          40

<210> SEQ ID NO 18
<211> LENGTH: 42
<212> TYPE: DNA
<213> ORGANISM: Artificial Sequence
<220> FEATURE:
<223> OTHER INFORMATION: OmpC_His2RInverse

<400> SEQUENCE: 18
gtgatggtga cccgcggagg taccatggtg atgatggtga tg          42

<210> SEQ ID NO 19
<211> LENGTH: 40
<212> TYPE: DNA
<213> ORGANISM: Artificial Sequence
<220> FEATURE:
<223> OTHER INFORMATION: OmpC_His3FInverse

<400> SEQUENCE: 19
catcatcatg gtacctctaa aggtaaaaac ctgggtcgtg          40

<210> SEQ ID NO 20
<211> LENGTH: 42
<212> TYPE: DNA
<213> ORGANISM: Artificial Sequence
<220> FEATURE:
<223> OTHER INFORMATION: OmpC_His3RInverse

<400> SEQUENCE: 20
atgatgatga cccgcggagg taccgtgatg gtggtgatgg tg          42

<210> SEQ ID NO 21
<211> LENGTH: 33
<212> TYPE: PRT
<213> ORGANISM: Artificial Sequence
<220> FEATURE:
<223> OTHER INFORMATION: OmpC-(6His)3

<400> SEQUENCE: 21

Ser Ala Gly His His His His His His Gly Thr Ser Ala Gly His His
 1               5                  10                  15

```
His His His His Gly Thr Ser Ala Gly His His His His His Gly
            20                  25                  30
Thr

<210> SEQ ID NO 22
<211> LENGTH: 4
<212> TYPE: PRT
<213> ORGANISM: Artificial Sequence
<220> FEATURE:
<223> OTHER INFORMATION: Artificial Peptide Sequence

<400> SEQUENCE: 22

Ile Leu Ser Gly
1

<210> SEQ ID NO 23
<211> LENGTH: 4
<212> TYPE: PRT
<213> ORGANISM: Artificial Sequence
<220> FEATURE:
<223> OTHER INFORMATION: Artificial Peptide Sequence

<400> SEQUENCE: 23

Gly Glu Ser Glu
1

<210> SEQ ID NO 24
<211> LENGTH: 4
<212> TYPE: PRT
<213> ORGANISM: Artificial Sequence
<220> FEATURE:
<223> OTHER INFORMATION: Artificial Peptide Sequence

<400> SEQUENCE: 24

Ser Gly Ser Ser
1

<210> SEQ ID NO 25
<211> LENGTH: 4
<212> TYPE: PRT
<213> ORGANISM: Artificial Sequence
<220> FEATURE:
<223> OTHER INFORMATION: Artificial Peptide Sequence

<400> SEQUENCE: 25

Ser Lys Ser Lys
1

<210> SEQ ID NO 26
<211> LENGTH: 6
<212> TYPE: PRT
<213> ORGANISM: Artificial Sequence
<220> FEATURE:
<223> OTHER INFORMATION: Artificial Peptide Sequence

<400> SEQUENCE: 26

Ile Leu Lys Ser Ile Lys
1               5
```